US012596122B2

(12) United States Patent
An et al.

(10) Patent No.: US 12,596,122 B2
(45) Date of Patent: Apr. 7, 2026

(54) LILRB2 ANTIBODIES AND USES THEREOF

(71) Applicants: IMMUNE-ONC THERAPEUTICS, INC., Palo Alto, CA (US); THE BOARD OF REGENTS OF THE UNIVERSITY OF TEXAS SYSTEM, Austin, TX (US)

(72) Inventors: Zhiqiang An, Houston, TX (US); Ningyan Zhang, Houston, TX (US); Zhiqiang Ku, Houston, TX (US); Chengcheng Zhang, Southlake, TX (US); Xiaoye Liu, Dallas, TX (US); Heyu Chen, Dallas, TX (US); JingJing Xie, Plano, TX (US); Maria Jose Costa, Palo Alto, TX (US); An Song, Palo Alto, TX (US); X. Charlene Liao, Palo Alto, CA (US)

(73) Assignees: THE BOARD OF REGENTS OF THE UNIVERSITY OF TEXAS SYSTEM, Austin, TX (US); IMMUNE-ONC THERAPEUTICS, INC., Palo Alto, CA (US)

( * ) Notice: Subject to any disclaimer, the term of this patent is extended or adjusted under 35 U.S.C. 154(b) by 846 days.

(21) Appl. No.: 17/759,800

(22) PCT Filed: Jan. 28, 2021

(86) PCT No.: PCT/US2021/015362
§ 371 (c)(1),
(2) Date: Jul. 29, 2022

(87) PCT Pub. No.: WO2021/158413
PCT Pub. Date: Aug. 12, 2021

(65) Prior Publication Data
US 2023/0068663 A1     Mar. 2, 2023

Related U.S. Application Data

(60) Provisional application No. 62/970,496, filed on Feb. 5, 2020.

(51) Int. Cl.

| | |
|---|---|
| *A61K 39/395* | (2006.01) |
| *A61K 45/06* | (2006.01) |
| *A61K 47/68* | (2017.01) |
| *A61P 35/02* | (2006.01) |
| *C07K 16/28* | (2006.01) |
| *G01N 33/574* | (2006.01) |
| *A61K 39/00* | (2006.01) |

(52) U.S. Cl.
CPC ... *G01N 33/57492* (2013.01); *A61K 39/3955* (2013.01); *A61K 45/06* (2013.01); *A61K 47/6849* (2017.08); *A61P 35/02* (2018.01); *C07K 16/2803* (2013.01); *A61K 2039/505* (2013.01); *C07K 2317/76* (2013.01); *C07K 2317/92* (2013.01)

(58) Field of Classification Search
CPC ............................ A61K 47/6849; A61P 35/00
See application file for complete search history.

(56) References Cited

U.S. PATENT DOCUMENTS

| | | | |
|---|---|---|---|
| 6,140,470 A | 10/2000 | Garen et al. | |
| 2018/0177847 A1 | 6/2018 | Chen et al. | |
| 2018/0298096 A1 | 10/2018 | Joyce-Shaikh | |
| 2019/0194327 A1* | 6/2019 | Cohen | C07K 16/3061 |

FOREIGN PATENT DOCUMENTS

| | | |
|---|---|---|
| WO | WO 2016/134358 | 8/2016 |
| WO | WO 2018/138297 | 8/2018 |
| WO | WO 2018/187518 | 10/2018 |
| WO | WO 2019/126514 | 6/2019 |
| WO | WO 2020/014132 | 1/2020 |

OTHER PUBLICATIONS

Li, T., Xia, J., Yun, H. et al. A novel autoantibody signatures for enhanced clinical diagnosis of pancreatic ductal adenocarcinoma. Cancer Cell Int 23, 273 (2023). (Year: 2023).*
Almagro JC, Fransson J. Humanization of antibodies. Front Biosci. Jan. 1, 2008;13:1619-33. (Year: 2008).*
Chen et al., Enhancement and destruction of antibody function by somatic mutation: unequal occurrence is controlled by V gene combinatorial associations. EMBO J. Jun. 15, 1995;14(12):2784-94. (Year: 1995).*
Edwards et al. The remarkable flexibility of the human antibody repertoire; isolation of over one thousand different antibodies to a single protein,BLyS. J Mol Biol Nov. 14, 2003;334(1):103-18. (Year: 2003).*
Koenig et al. Mutational landscape of antibody variable domains reveals a switch modulating the interdomain conformational dynamics and antigen binding.PNAS Jan. 24, 2017 114(4)E486-E495;firstpublished Jan. 5, 2017. (Year: 2017).*
Kussie et al. A single engineered amino acid substitution changes antibody fine specificity. J Immunol. Jan. 1, 1994; 152(1):146-52. (Year: 1994).*
Umiker et al. Inhibition of LILRB2 by a Novel Blocking Antibody Designed to Reprogram Immunosuppressive Macrophages to Drive T-Cell Activation in Tumors. Mol Cancer Ther. Apr. 3, 2023;22(4):471-484. (Year: 2023).*
Redondo-García S, Barritt C, Papagregoriou C, Yeboah M, Frendeus B, Cragg MS, Roghanian A. Human leukocyte immunoglobulin-like receptors in health and disease. Front Immunol. Nov. 13, 2023;14:1282874. (Year: 2023).*

(Continued)

*Primary Examiner* — Aurora M Fontainhas
*Assistant Examiner* — Jennifer A Benavides
(74) *Attorney, Agent, or Firm* — pH IP Law

(57) ABSTRACT

Provided herein are antibodies binding to LILRB2 and the uses of the antibodies in detecting and treating cancer and autoimmune diseases.

26 Claims, 65 Drawing Sheets
Specification includes a Sequence Listing.

(56) References Cited

OTHER PUBLICATIONS

"Immunoglobulin heavy chain junction region, partial [*Homo sapiens*]", GenBank Accession No. MOL17124.1, dated Jan. 17, 2019. Retrieved on May 20, 2021, from https://www.ncbi.nlm.nih.gov/protein/MOL_17124.1, Austin, J.W. et al.

International Preliminary Report on Patentability issued in International Application No. PCT/US2021/015362, dated Aug. 18, 2022.

International Search Report and Written Opinion issued in International Application No. PCT/US2021/015362, dated Jun. 21, 2021.

Invitation to Pay Additional Fees issued in International Application No. PCT/US2021/015362, dated Apr. 6, 2021.

Bang, Lyone M., and Gillian M. Keating. "Adalimumab: a review of its use in rheumatoid arthritis." *BioDrugs* 18.2 (2004): 121-139.

Curran, Kevin J., et al. "Toxicity and response after CD19-specific CAR T-cell therapy in pediatric/young adult relapsed/refractory B-ALL." *Blood, The Journal of the American Society of Hematology* 134.26 (2019): 2361-2368.

Gremel G, Bergman J, Djureinovic D, Edqvist PH, Maindad V, Bharambe BM, Khan WA, Navani S, Elebro J, Jirström K, Hellberg D, Uhlén M, Micke P, Pontén F. A systematic analysis of commonly used antibodies in cancer diagnostics. Histopathology. Jan. 2014;64(2):293-305. doi: 10.1111/his.12255. Epub Nov. 5, 2013.

Jayaraman J, Mellody MP, Hou AJ, Desai RP, Fung AW, Pham AHT, Chen YY, Zhao W. CAR-T design: Elements and their synergistic function. EBioMedicine. Aug. 2020;58:102931. doi: 10.1016/j.ebiom.2020.102931. Epub Jul. 30, 2020.

Kulemzin SV, Kuznetsova VV, Mamonkin M, Taranin AV, Gorchakov AA. Engineering Chimeric Antigen Receptors. Acta Naturae. Jan.-Mar. 2017;9(1):6-14.

Search Report issued in European Application No. 21750682.3, dated Feb. 8, 2024.

Sterner RC, Sterner RM. CAR-T cell therapy: current limitations and potential strategies. Blood Cancer J. Apr. 6, 2021;11(4):69. doi: 10.1038/s41408-021-00459-7.

Office Communication issued in corresponding Japanese Application No. 2022-547675, dated on Feb. 17, 2025. English Translation.

* cited by examiner

A

From FIG. 1A-1 anti-hIgG APC

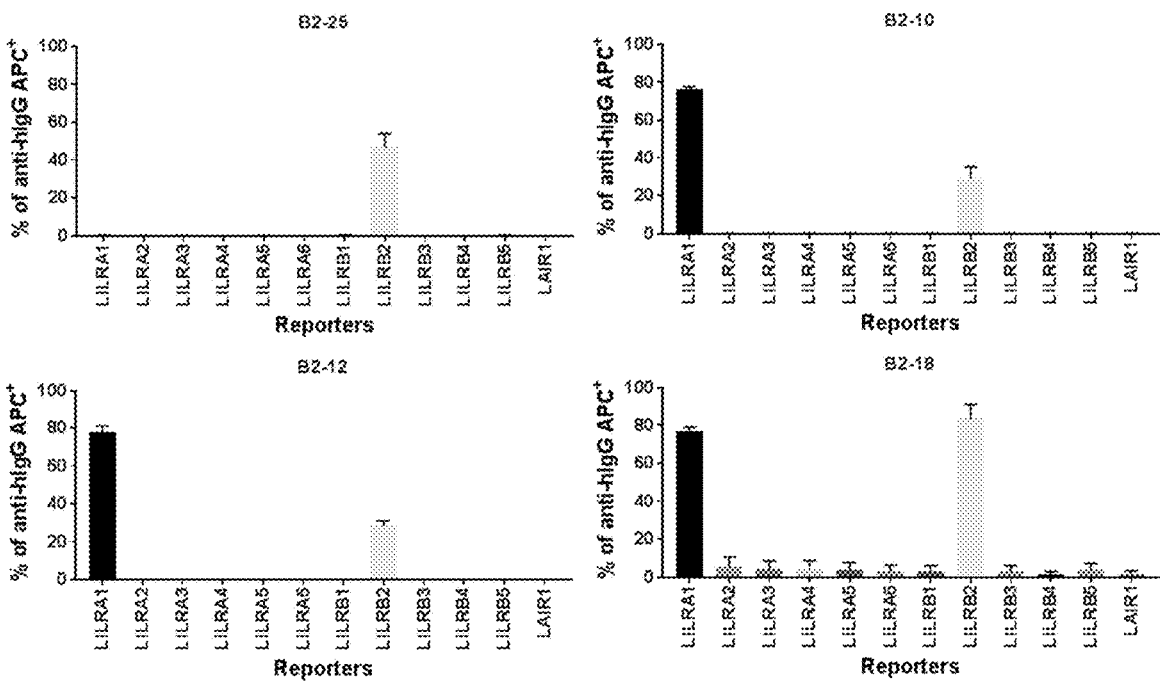
FIG. 1D
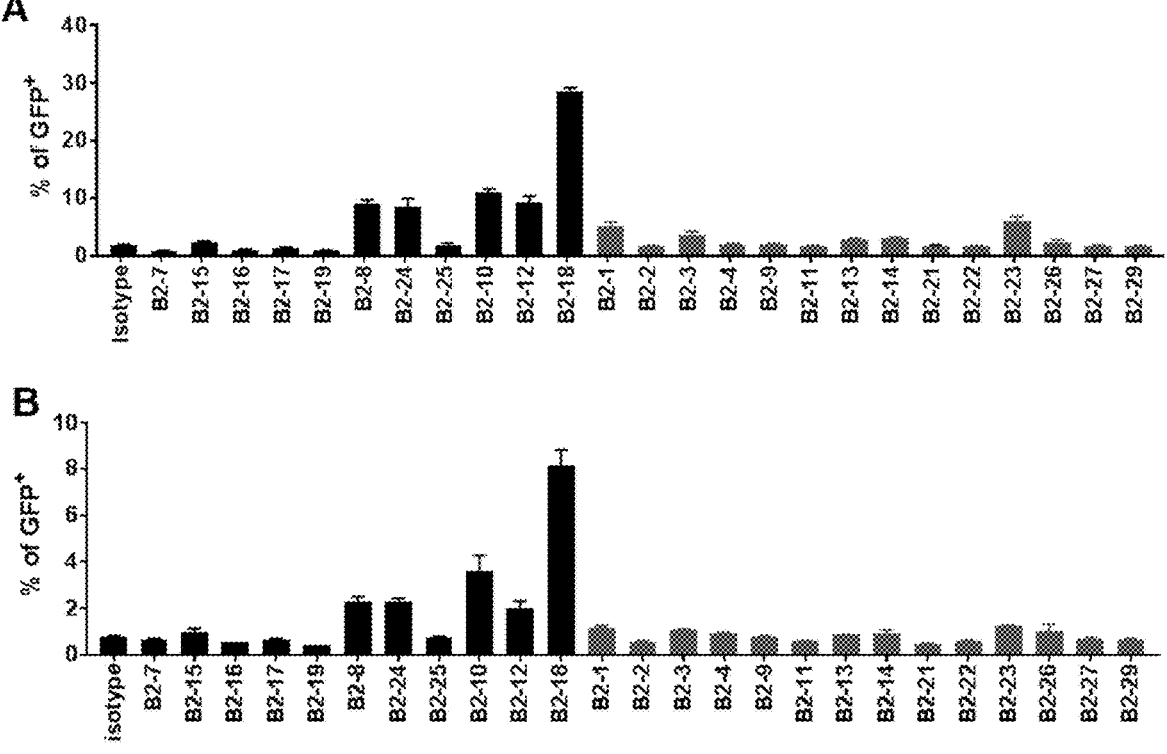
FIGS. 2A-B

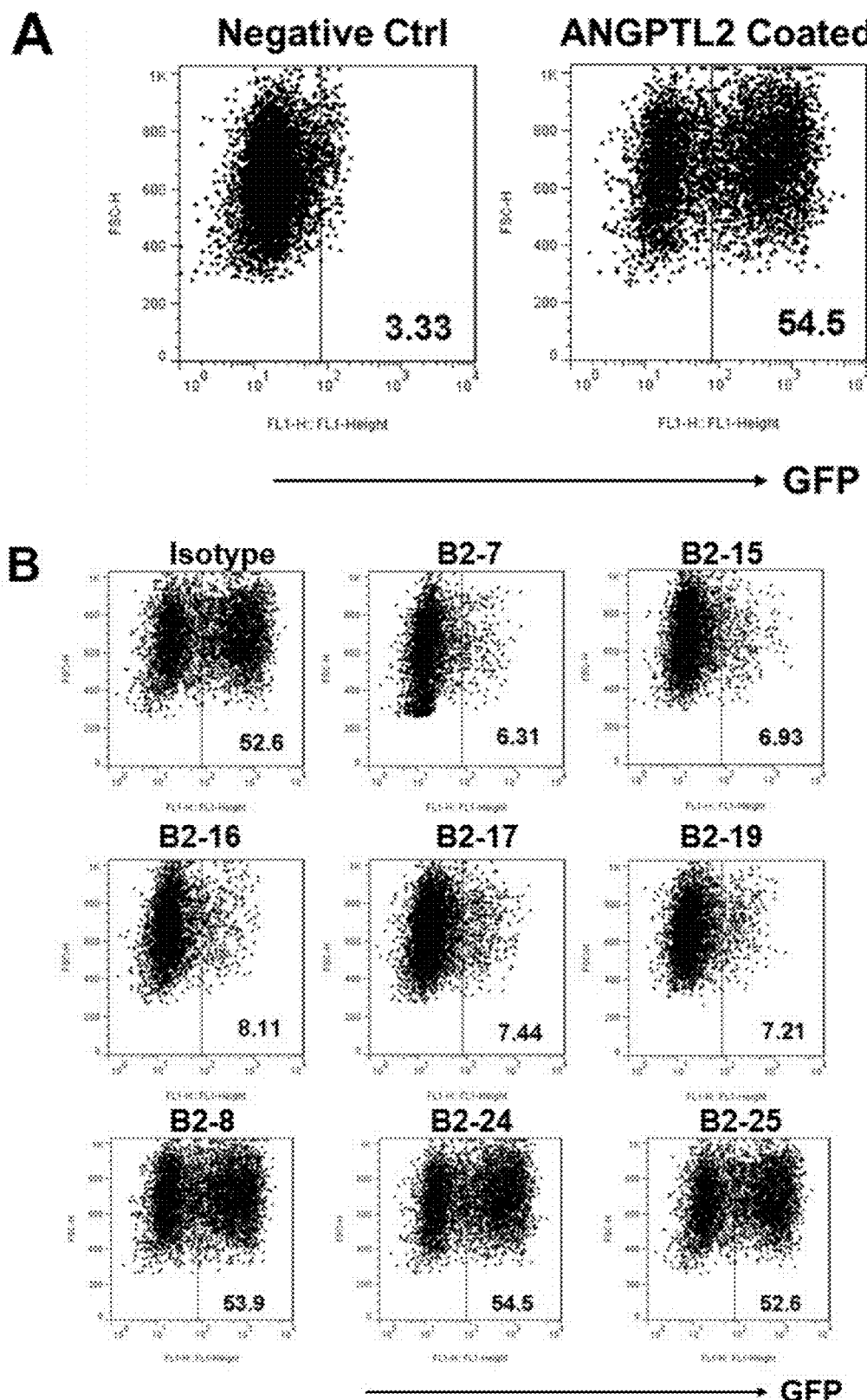
FIGS. 3A-B

C

A
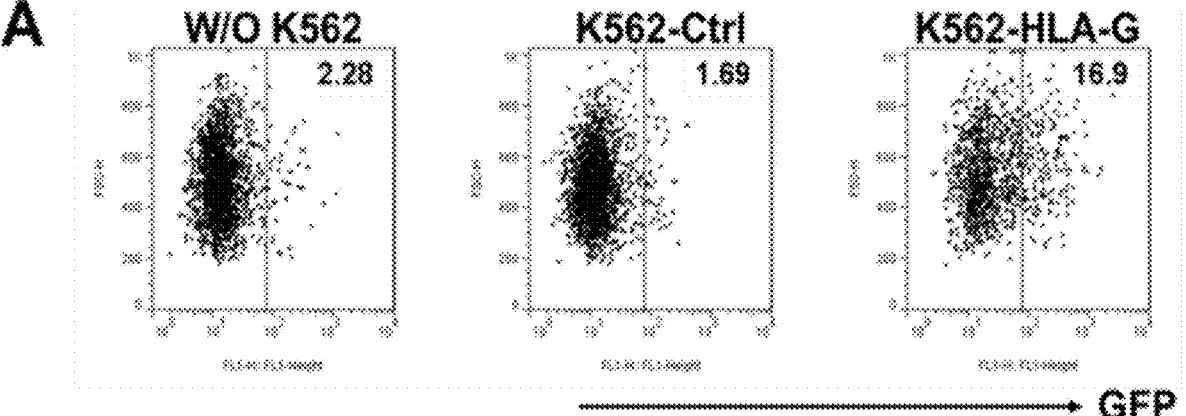
B
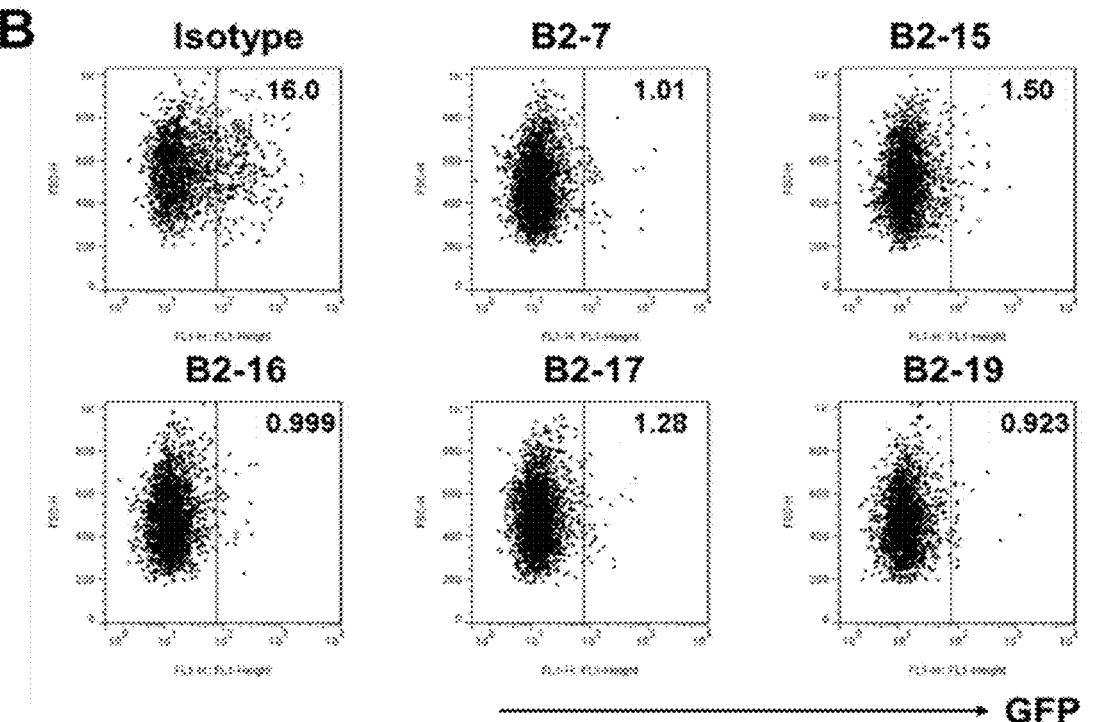
FIGS. 5A-B

B
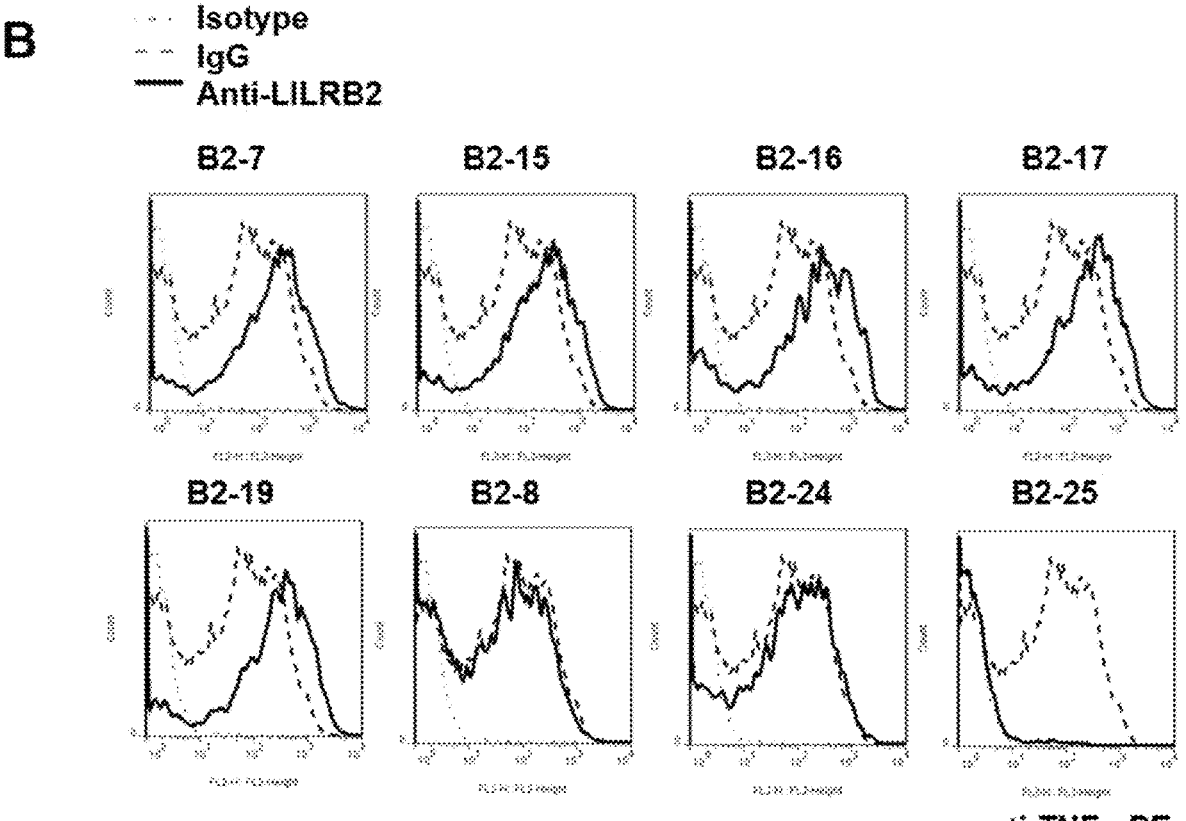
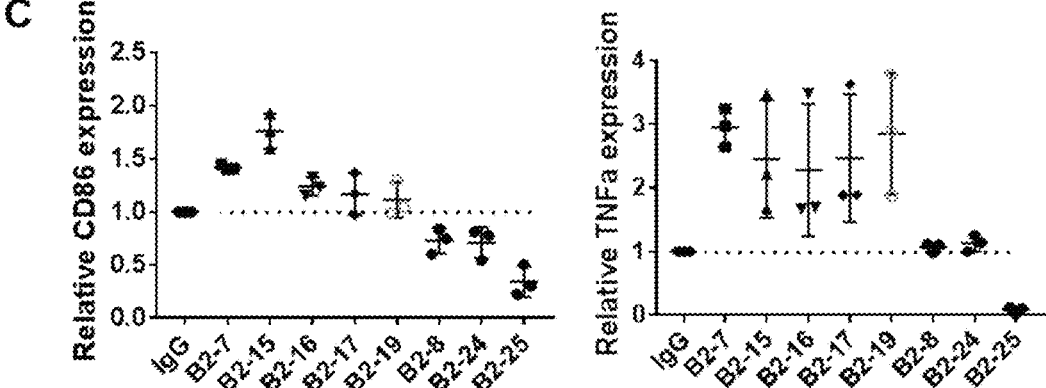
FIGS. 6B-C

A

B

E

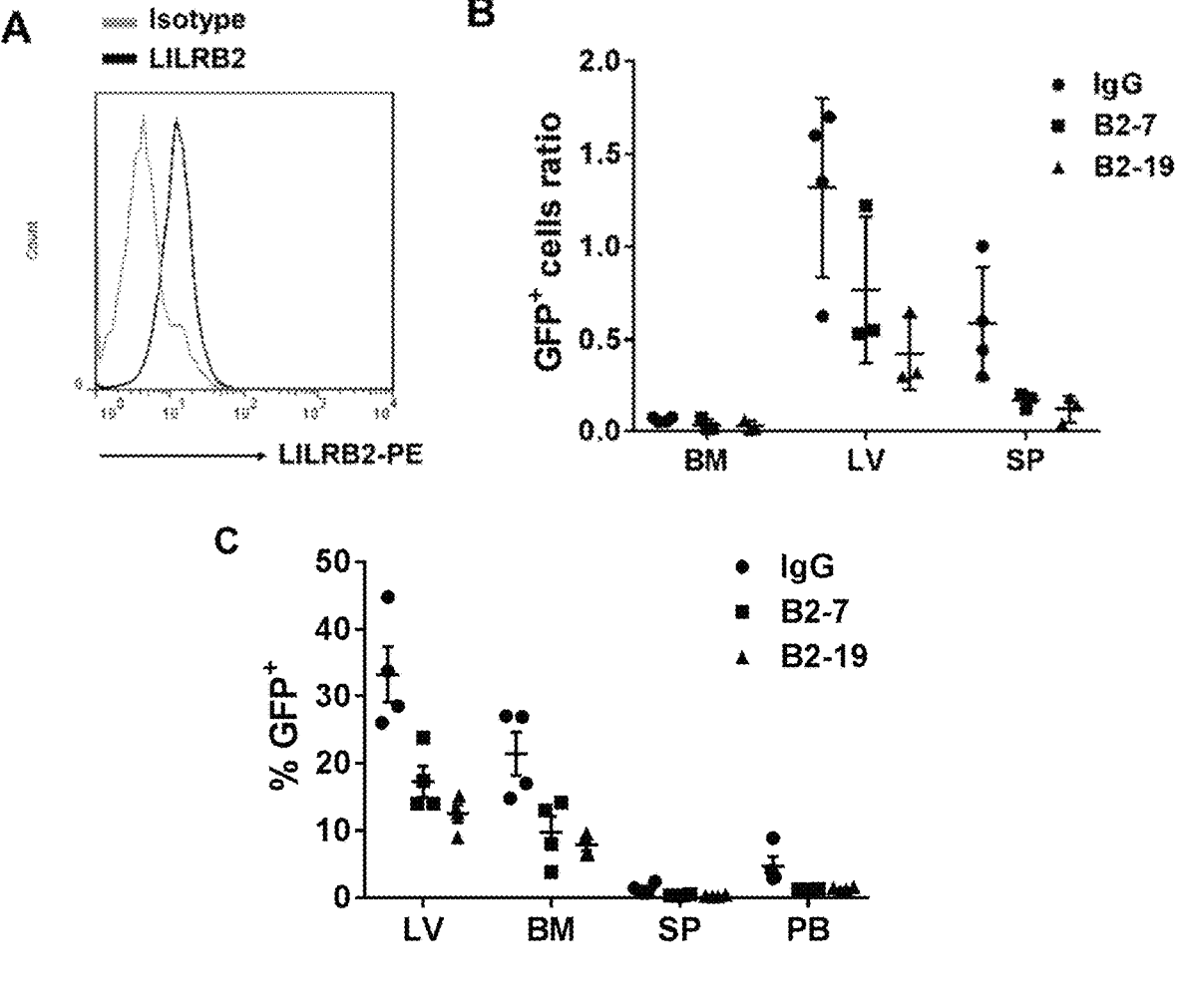
FIGS. 9A-C

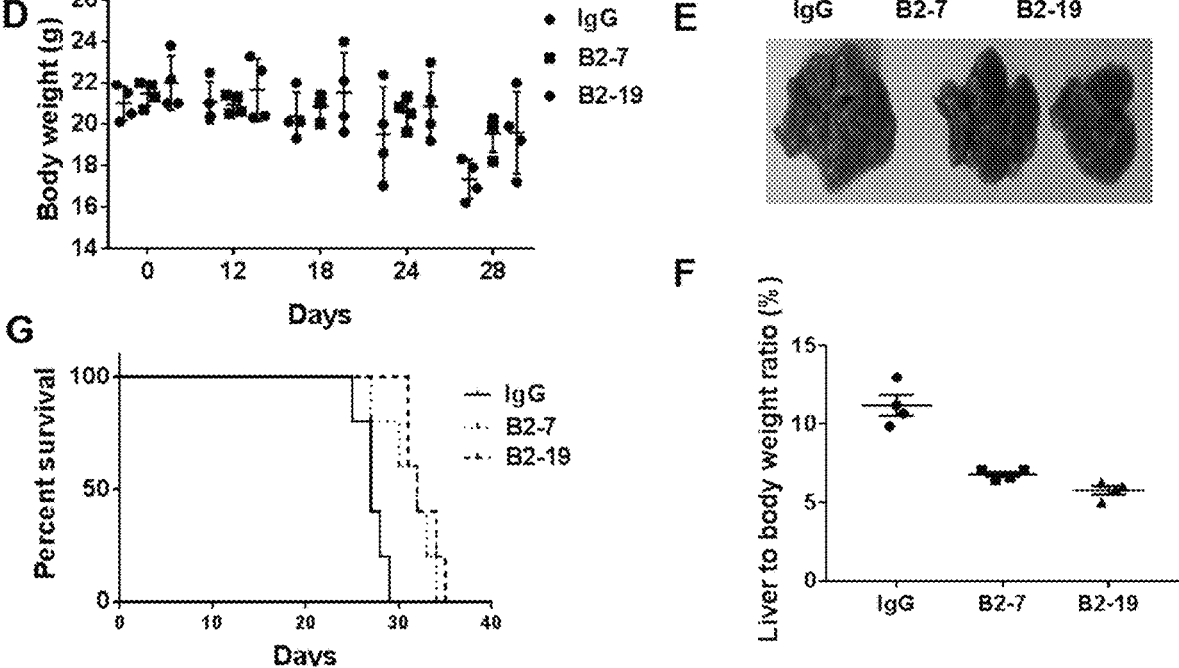
FIGS. 9D-G

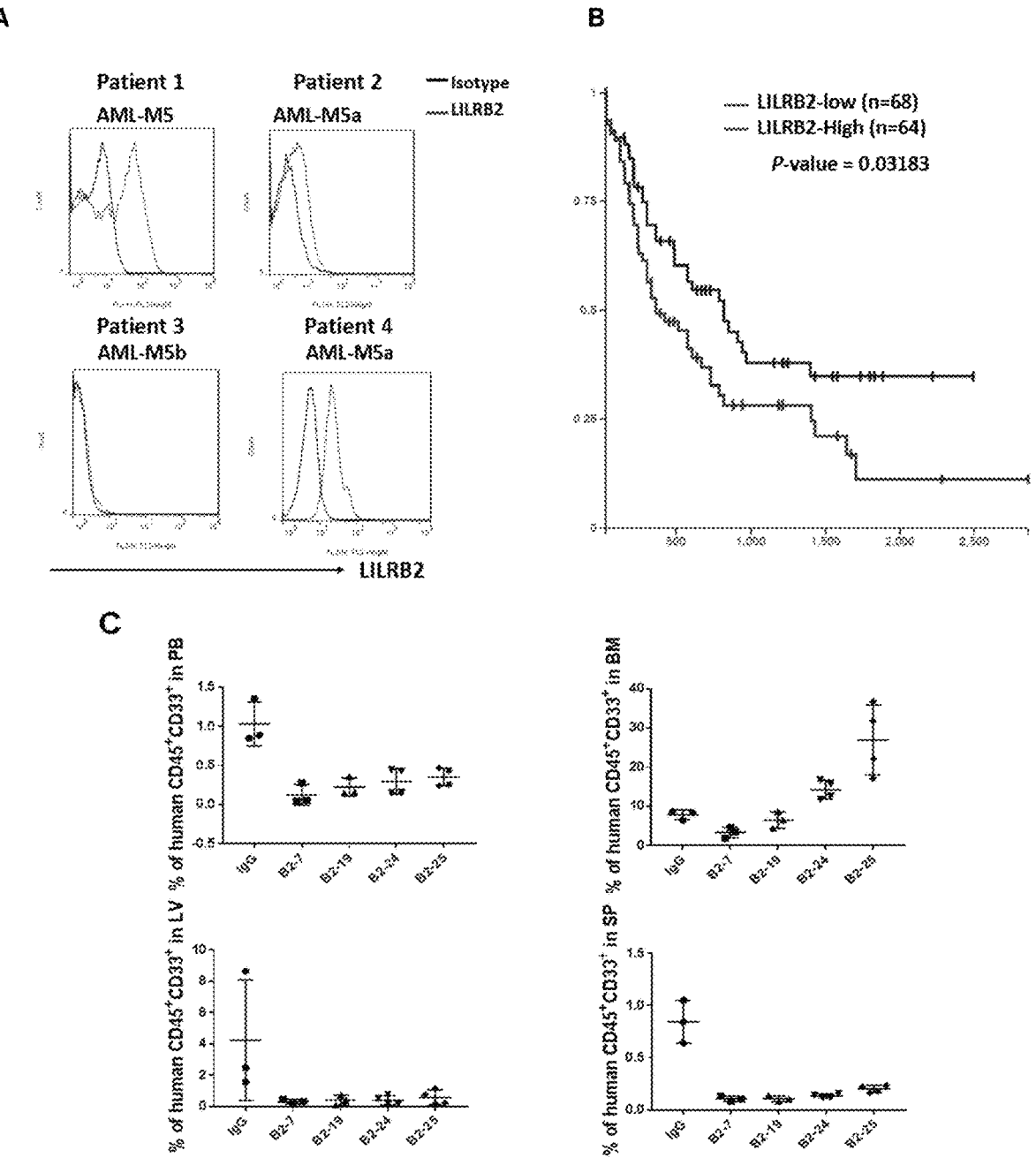
FIGS. 10A-C

D
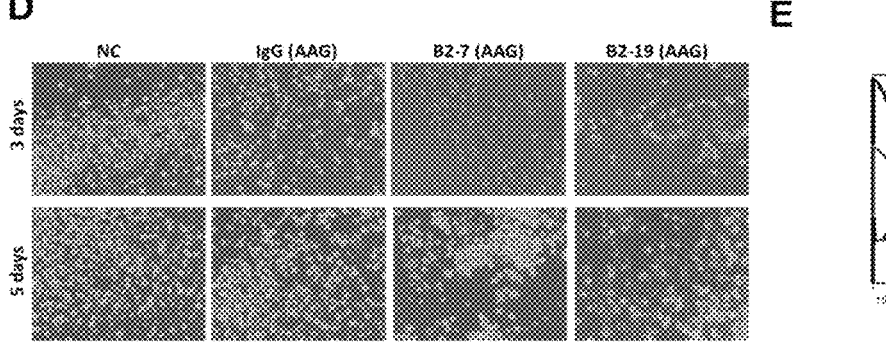
E
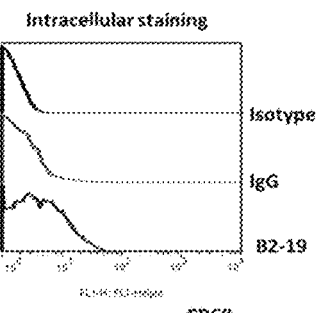
FIGS. 10D-E

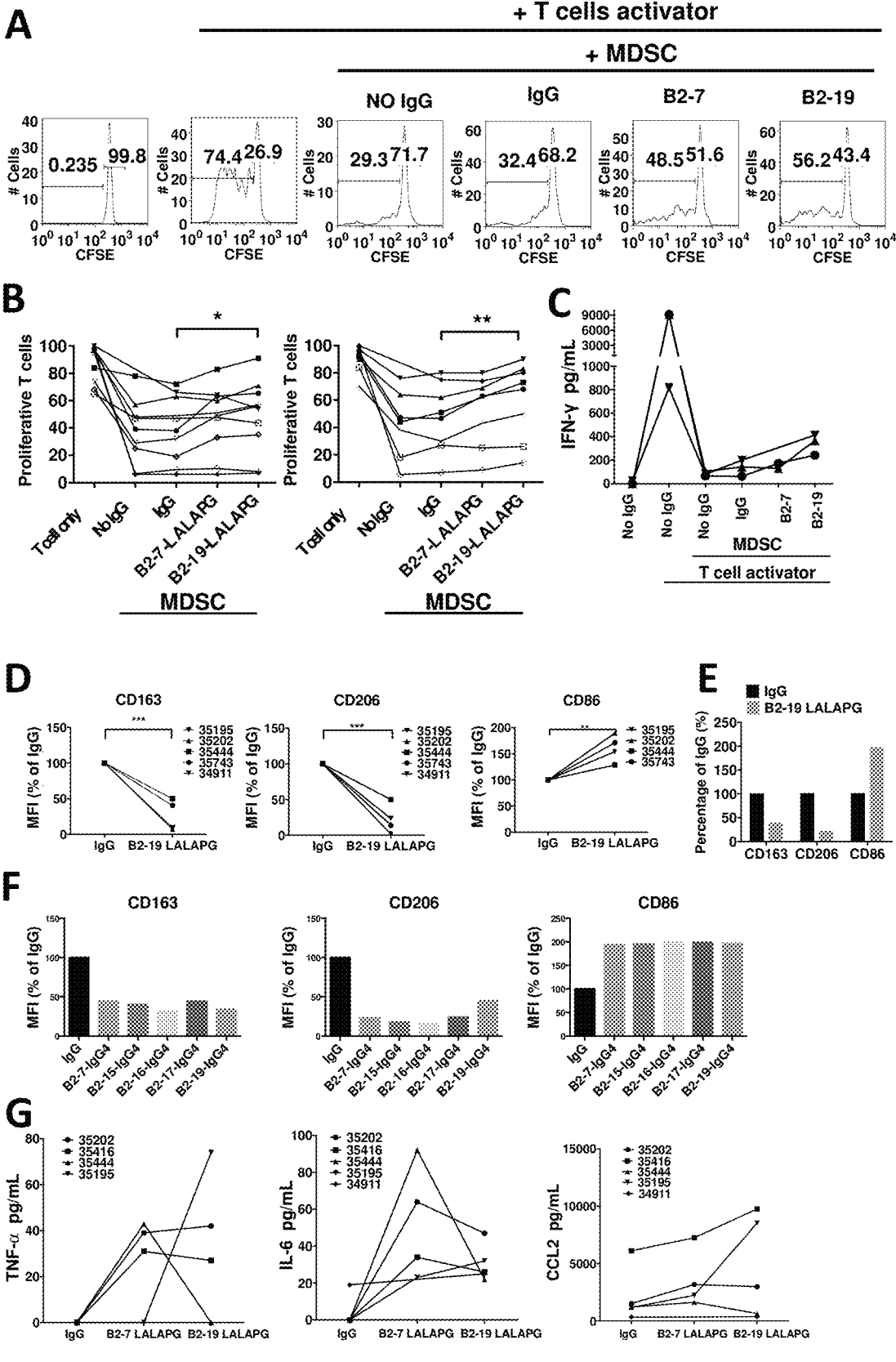
FIGS. 11A-G

A  Phylogenic tree of VH

B2-H17 0.23
B2-H11 0.22455
B2-H19 0.13415
B2-H7 0.13698
B2-H30 0.13
B2-H24 0.06734
B2-H25 0.07673
B2-H10 0.09674
B2-H12 0.15457
B2-H4 0.1249
B2-H16 0.05353
B2-H14 0.03105
B2-H8 0.02777
B2-H13 0.02245
B2-H27 0.02797
B2-H1 0.04707
B2-H23 0.11919
B2-H15 0.10437
B2-H18 0.06512
B2-H3 0.09367
B2-H2 0.07624
B2-H9 0.01859
B2-H22 0.03187
B2-H26 0.02848

Phylogenic tree of VL

B2-L7 0.02933
B2-L25 0.03549
B2-L16 0.27323
B2-L18 0.13273
B2-L2 0.05215
B2-L30 0.06436
B2-L22 0.06272
B2-L23 0.08016
B2-L26 0.06835
B2-L9 0.1067
B2-L14 0.06623
B2-L13 0.04193
B2-L1 0.02101
B2-L8 0.00602
B2-L27 0.00565
B2-L19 0.09582
B2-L15 0.05064
B2-L17 0.05845
B2-L3 0.10327
B2-L4 0.08331
B2-L11 0.10269
B2-L24 0.03368
B2-L10 0.04397
B2-L12 0.03785

B

Phage ELISA

A

B

| Antibody | EC50 (nM) | Antibody | EC50 (nM) |
|----------|-----------|----------|-----------|
| B2-1 | 1.196 | B2-15 | 46.49 |
| B2-2 | 1.603 | B2-16 | 9.967 |
| B2-3 | 0.787 | B2-17 | 24.61 |
| B2-4 | 1.756 | B2-18 | 0.3549 |
| B2-7 | 82.94 | B2-19 | 3.823 |
| B2-8 | 0.5573 | B2-22 | 0.3476 |
| B2-9 | 0.608 | B2-23 | 2.442 |
| B2-10 | 0.5749 | B2-24 | 5.06 |
| B2-11 | 3.785 | B2-25 | 1.725 |
| B2-12 | 0.4436 | B2-26 | 1.023 |
| B2-13 | 5.154 | B2-27 | 379.1 |
| B2-14 | 1.968 | B2-30 | 1.188 |

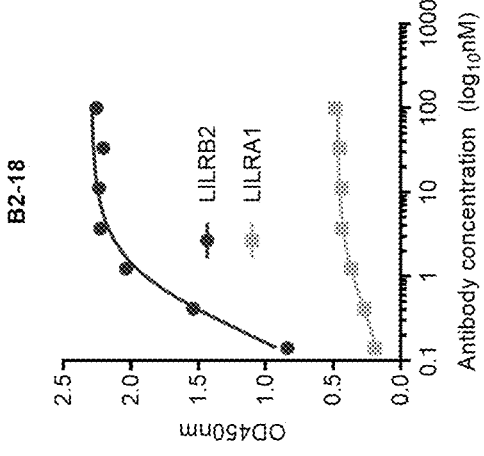
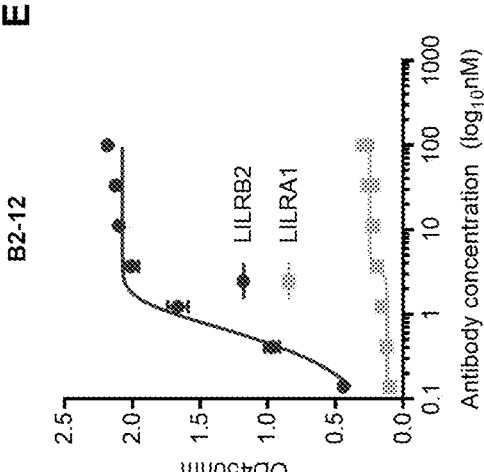
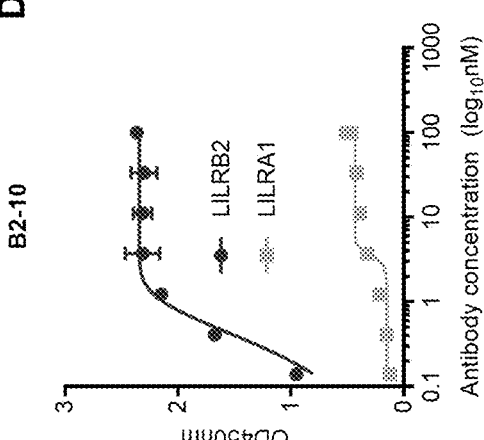
FIGS. 14C-E

Bin 1
Bin 2
Bin 3
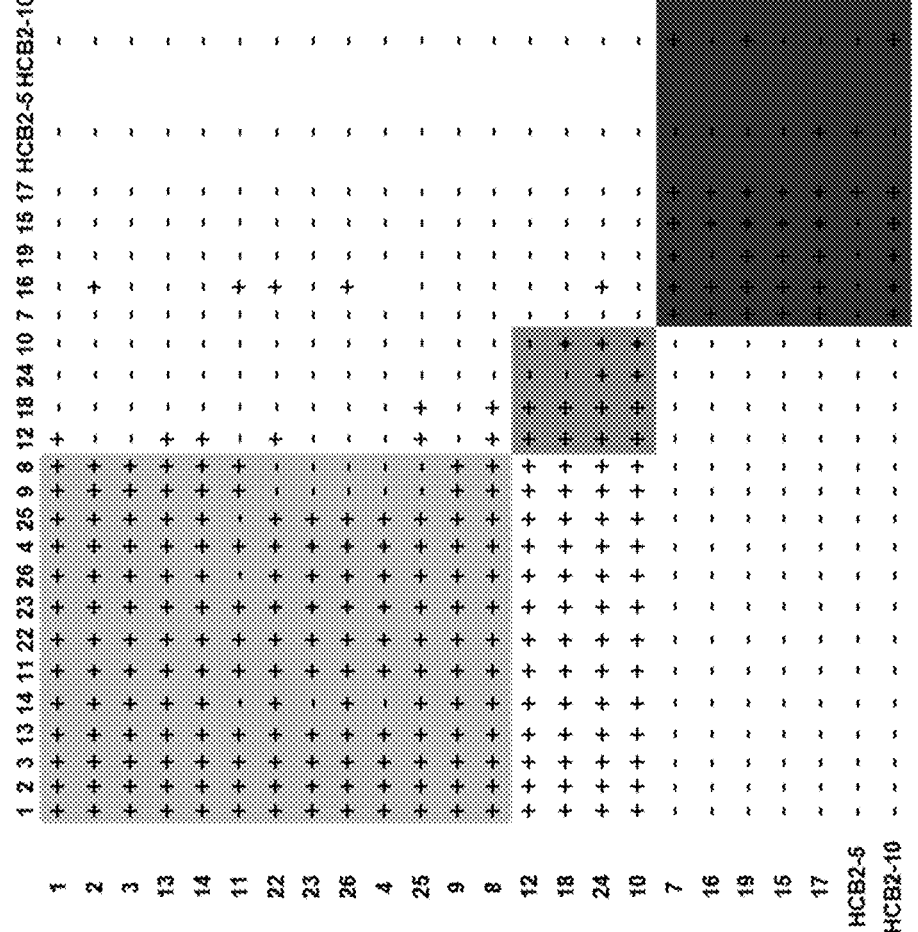
FIG. 15
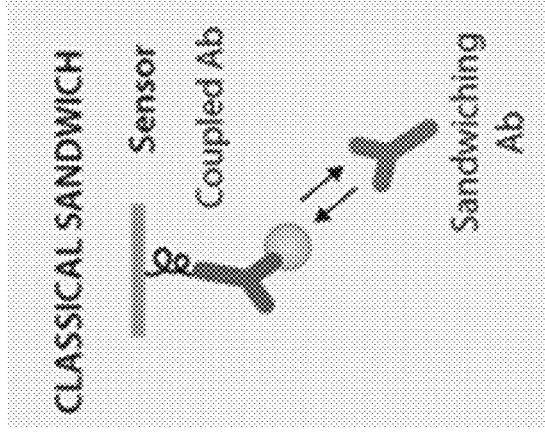

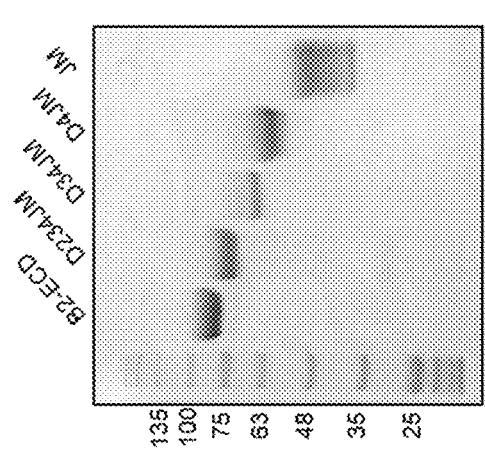
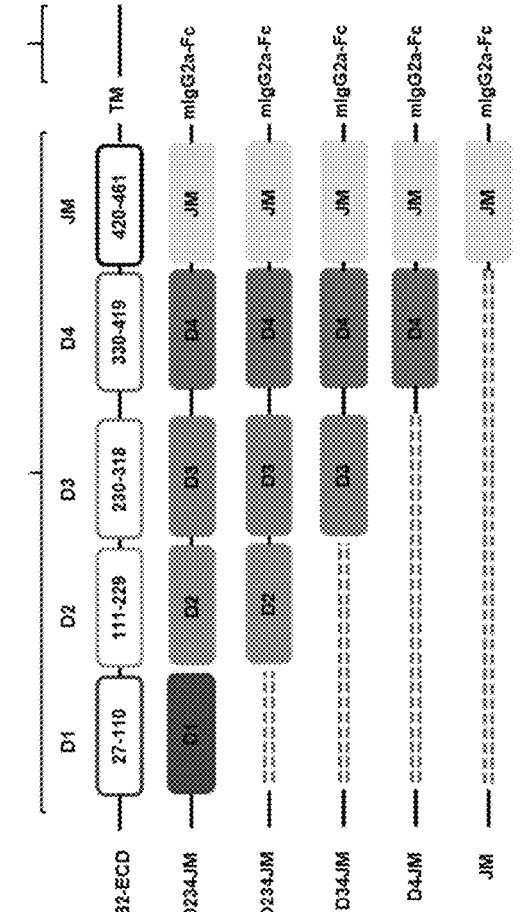
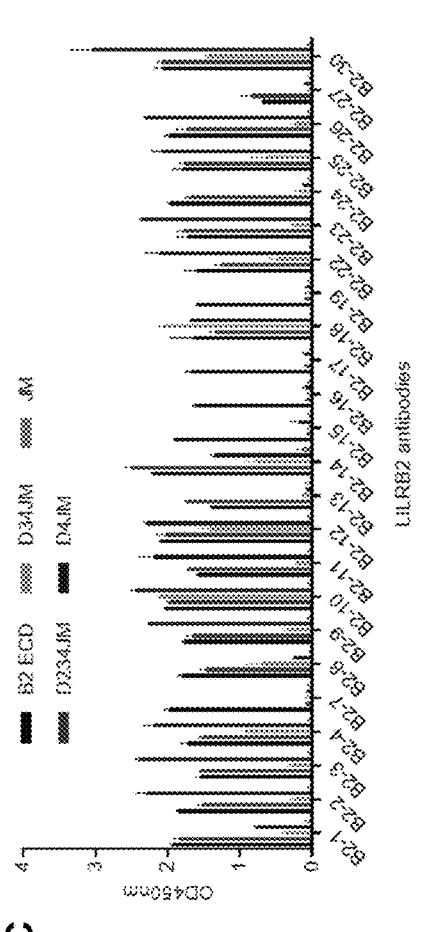
FIGS. 16A-D

A

Alignment of D1 of LILRB1 and LILRB2

B

Alignment of D4 of LILRB1 and LILRB2

C

| D1 mutants | Amino acid | Mutate to |
|---|---|---|
| D1M1 | SLEA | GQET |
| D1M2 | KSAS | KTAL |
| D1M3 | IRPE | IPQE |
| D1M4 | RARWSEL | DTAGRSES |

D

| D4 mutants | Amino acid | Mutate to |
|---|---|---|
| D4M1 | WRQ | QGW |
| D4M2 | IHEYP | TYQSQ |
| D4M3 | LNSD | QSSK |
| D4M4 | SEP | SDP |

FIGS. 17A-D

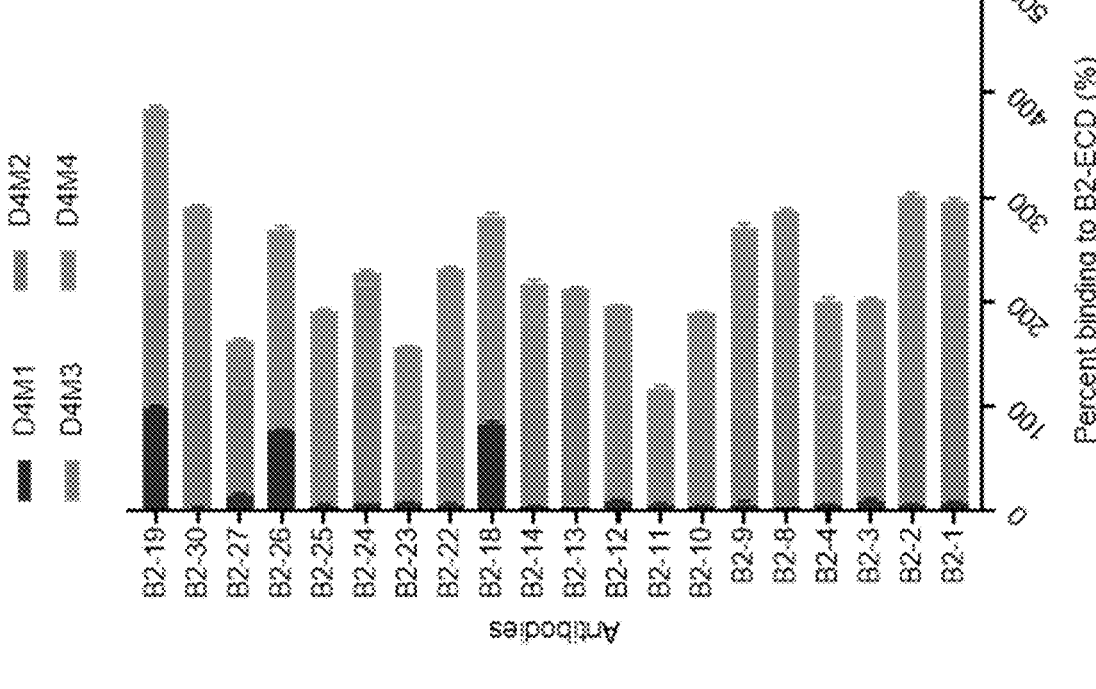
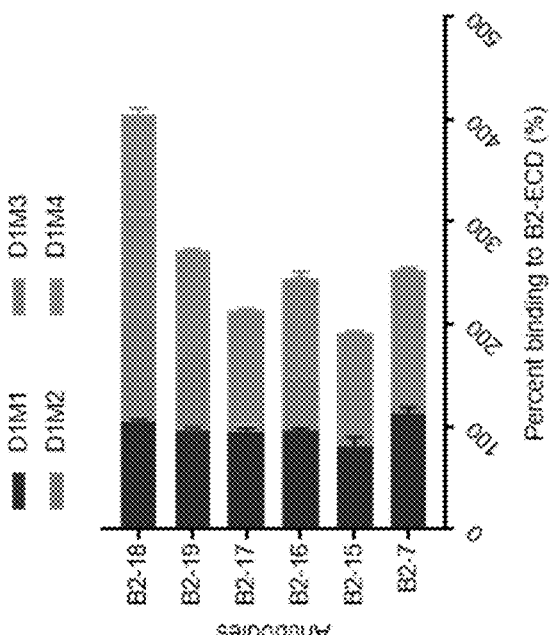
FIGS. 17E-F

| Antibody | KD (nM) | kon(1/Ms) | kdis(1/s) | R² |
|---|---|---|---|---|
| B2-7 | 15.2±0.2 | 2.00E+5 | 3.05E-3 | 0.9803 |
| B2-15 | 18.9±0.4 | 2.99E+5 | 5.65E-3 | 0.9631 |
| B2-16 | 7.45±0.02 | 1.21E+5 | 9.00E-4 | 0.9993 |
| B2-17 | 35.9±0.9 | 3.38E+5 | 1.21E-2 | 0.9675 |
| B2-19 | 1.84±0.01 | 2.50E+5 | 4.60E-4 | 0.9929 |
| HCB2-5 | 10.2±0.08 | 3.17E+5 | 3.24E-3 | 0.8083 |
| HCB2-10 | 8.67±0.41 | 7.03E+5 | 6.10E-3 | 0.9497 |

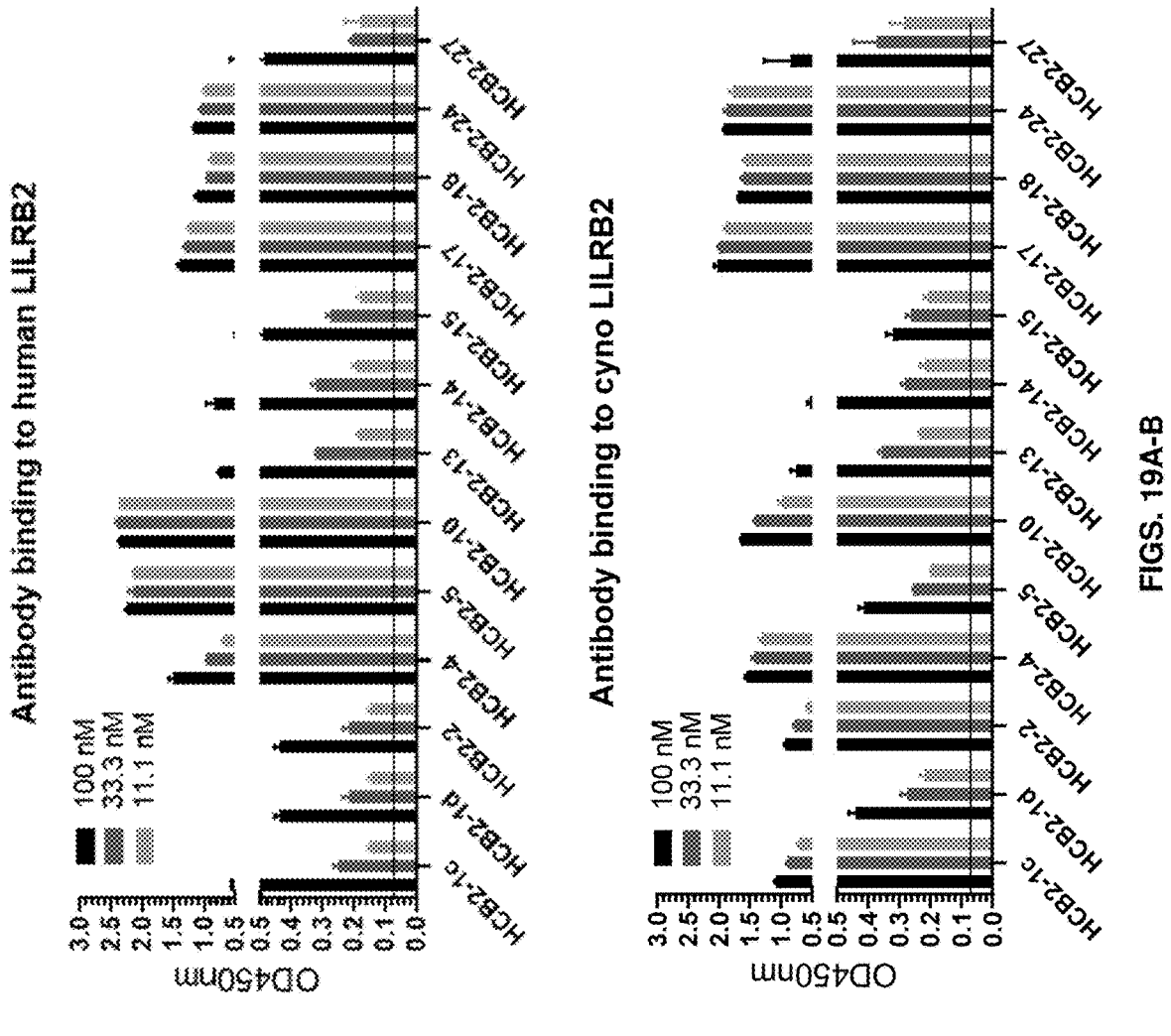
FIGS. 19A-B

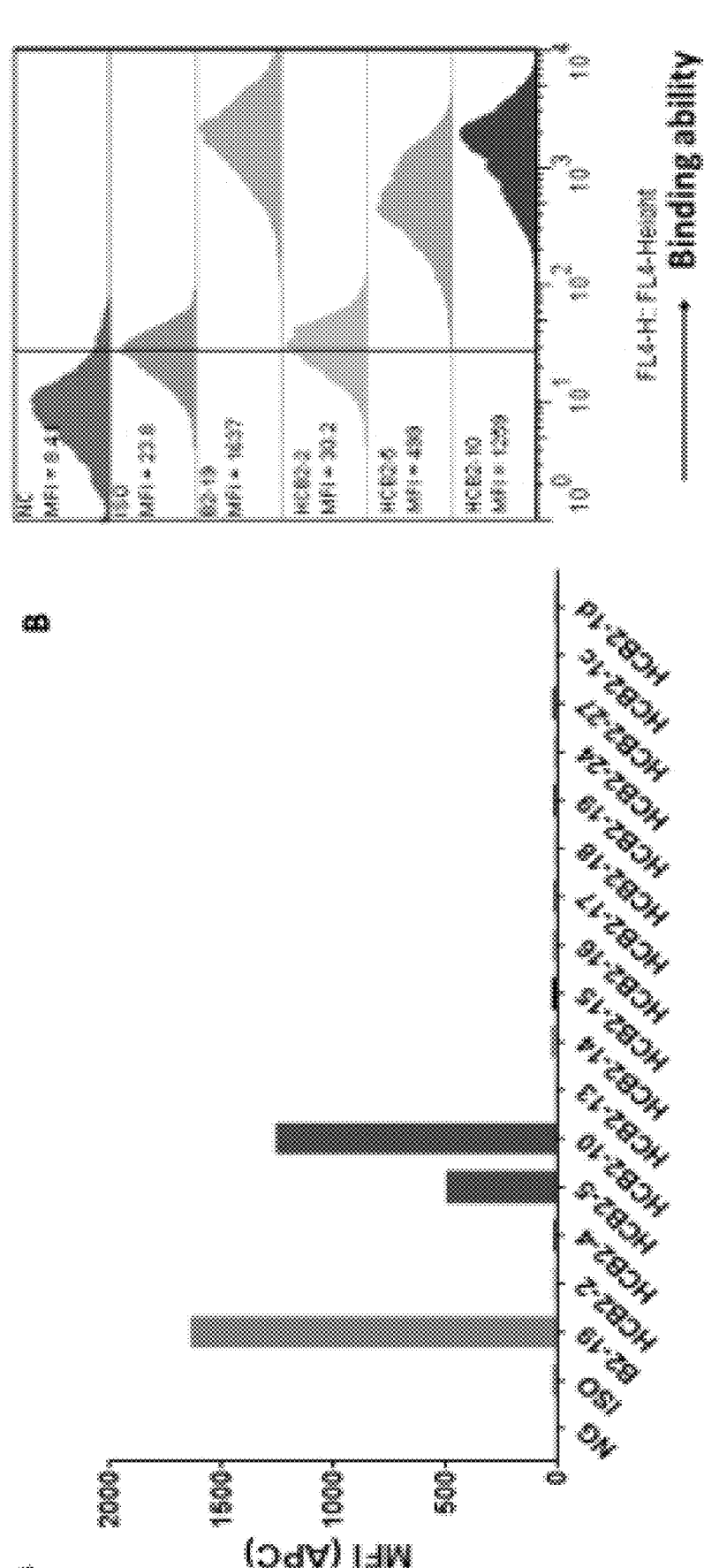
FIGS. 20A-B

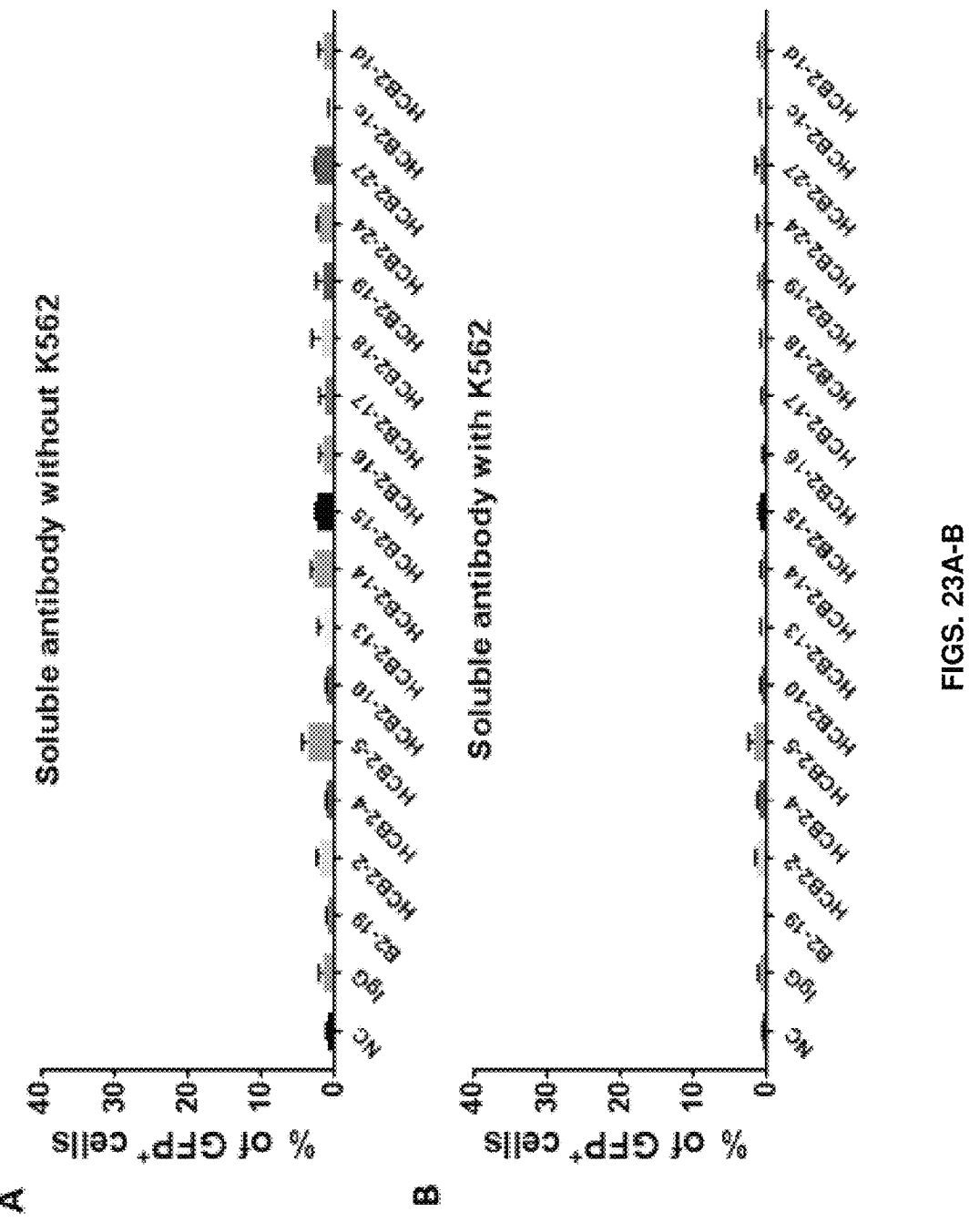
FIGS. 23A-B

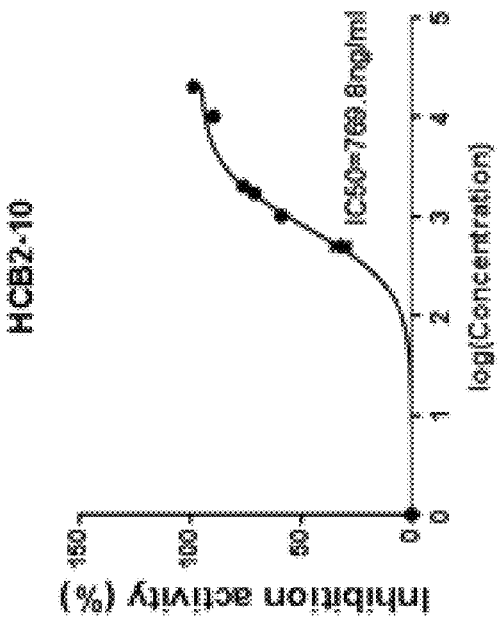
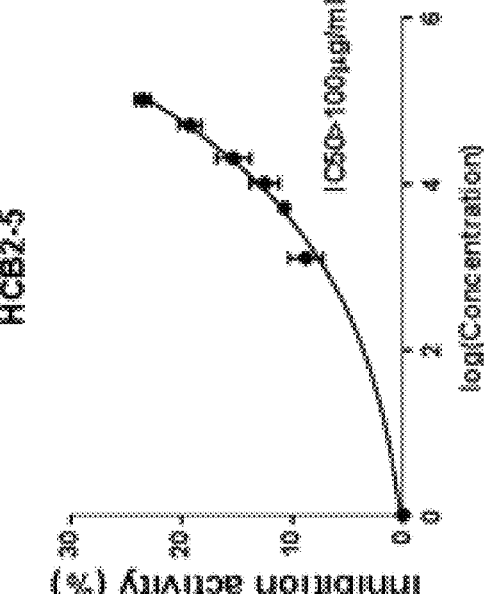
FIG. 26C

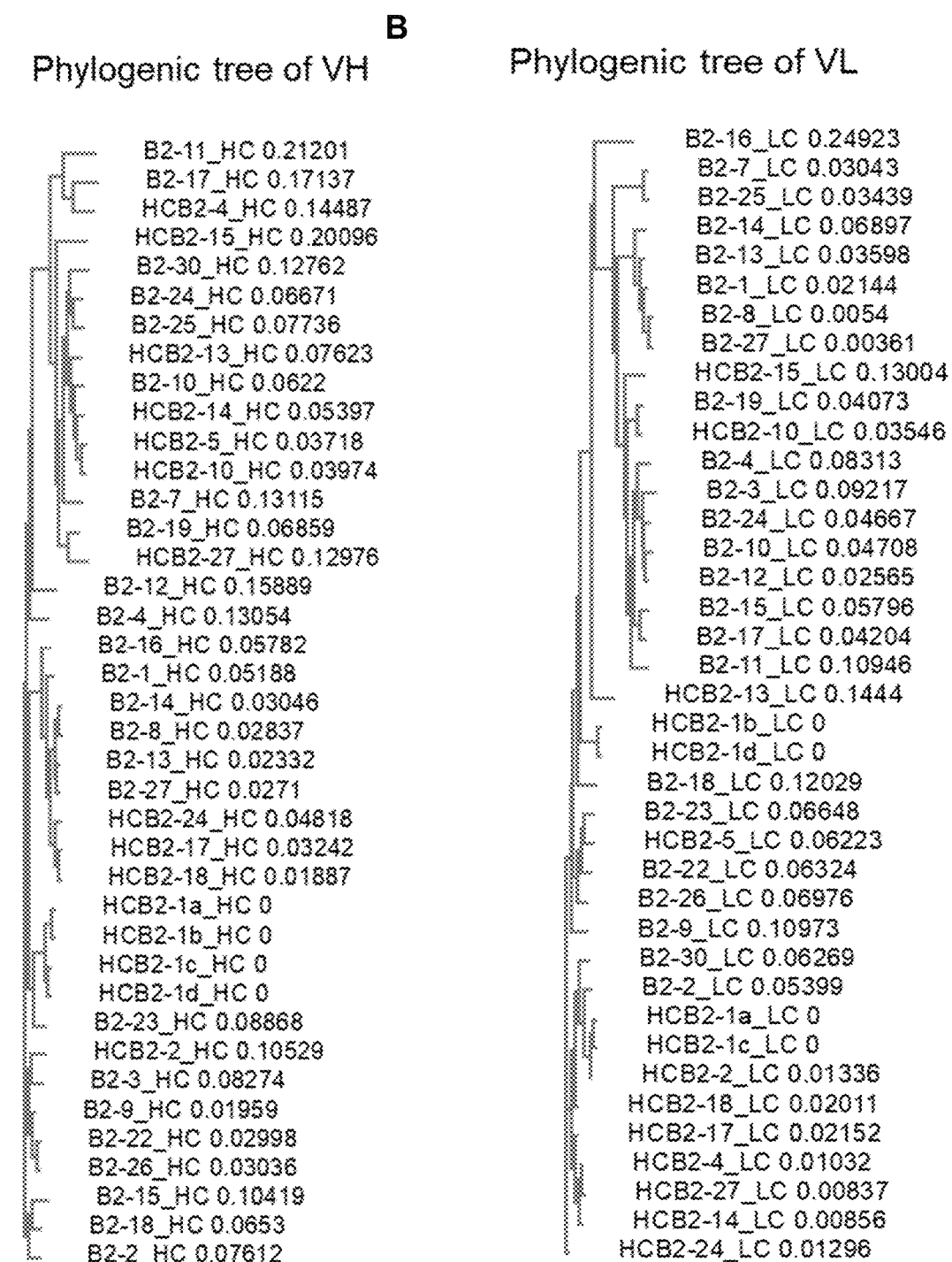
FIG. 28A-B

| | LiLRA1 | LiLRA2 | LiLRA3 | LiLRA4 | LiLRA5 | LiLRA6 | LiLRB1 | LiLRB2 | LiLRB3 | LiLRB4 | LiLRB5 | LAIR1 |
|---|---|---|---|---|---|---|---|---|---|---|---|---|
| Ctrl+ Ab | 533 | 22 | 587 | 44 | 164 | 586 | 7721 | 518 | 8030 | 472 | 1381 | 2555 |
| 2nd Ab | 10 | 9 | 10 | 10 | 11 | 10 | 9 | 10 | 9 | 13 | 11 | 23 |
| B2-7 | 12 | 10 | 10 | 10 | 11 | 11 | 10 | 1155 | 11 | 15 | 11 | 23 |
| B2-15 | 10 | 10 | 10 | 9 | 11 | 10 | 9 | 910 | 9 | 14 | 11 | 22 |
| B2-16 | 12 | 10 | 10 | 10 | 12 | 12 | 10 | 940 | 10 | 14 | 11 | 24 |
| B2-17 | 11 | 10 | 10 | 10 | 10 | 11 | 9 | 1100 | 10 | 13 | 10 | 23 |
| B2-19 | 11 | 10 | 10 | 10 | 11 | 11 | 10 | 1277 | 9 | 14 | 11 | 22 |

| | B2-7 | B2-15 | B2-16 | B2-17 | B2-19 |
|---|---|---|---|---|---|
| EC$_{50}$ (µg/mL) | 0.212 | 0.101 | 0.277 | 0.105 | 0.208 |

| | B2-7 | B2-15 | B2-16 | B2-17 | B2-19 |
|---|---|---|---|---|---|
| EC$_{50}$ (µg/mL) | 0.332 | 0.056 | 0.547 | >10 | 0.219 |

| | B2-7 | B2-15 | B2-16 | B2-17 | B2-19 |
|---|---|---|---|---|---|
| $IC_{50}$ (µg/mL) | 0.507 | 0.160 | 0.915 | 0.209 | 0.583 |

| | B2-7 | B2-15 | B2-16 | B2-17 | B2-19 |
|---|---|---|---|---|---|
| $IC_{50}$ (µg/mL) | 2.660 | 0.482 | 3.190 | 0.657 | 2.116 |

| Dose (mg/kg) | CL obs (mL/day/kg) | t1/2 (days) | Vss, obs (mL/kg) | Cmax (ug/mL) | Cmax_D (ug/mL)/(mg/kg) |
|---|---|---|---|---|---|
| 5 | 5.47 | 8.63 | 64.28 | 123.44 | 24.69 |

SEQUENCE LISTING

```
<160> NUMBER OF SEQ ID NOS: 613

<210> SEQ ID NO 1
<211> LENGTH: 8
<212> TYPE: PRT
<213> ORGANISM: Artificial sequence
<220> FEATURE:
<223> OTHER INFORMATION: Synthetic antibody

<400> SEQUENCE: 1

Gly Gly Thr Phe Ser Ser Tyr Ala
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic antibody

<400> SEQUENCE: 2

Ile Ile Pro Ile Phe Gly Thr Ala
1               5

<210> SEQ ID NO 3
<211> LENGTH: 12
<212> TYPE: PRT
<213> ORGANISM: Artificial sequence
<220> FEATURE:
<223> OTHER INFORMATION: Synthetic antibody

<400> SEQUENCE: 3

Ala Arg Gly Asn Gln Gly Asp Thr Ala Phe Asp Ile
1               5                   10

<210> SEQ ID NO 4
<211> LENGTH: 9
<212> TYPE: PRT
<213> ORGANISM: Artificial sequence
<220> FEATURE:
<223> OTHER INFORMATION: Synthetic antibody

<400> SEQUENCE: 4

Ser Ser Asp Val Gly Gly Tyr Asn Tyr
1               5

<210> SEQ ID NO 5
<211> LENGTH: 3
<212> TYPE: PRT
<213> ORGANISM: Artificial sequence
<220> FEATURE:
<223> OTHER INFORMATION: Synthetic antibody

<400> SEQUENCE: 5

Asp Val Ser
1
```

```
<210> SEQ ID NO 6
<211> LENGTH: 11
<212> TYPE: PRT
<213> ORGANISM: Artificial sequence
<220> FEATURE:
<223> OTHER INFORMATION: Synthetic antibody

<400> SEQUENCE: 6

Ser Ser Tyr Thr Ser Ser Ser Thr Pro Tyr Val
1               5                   10

<210> SEQ ID NO 7
<211> LENGTH: 8
<212> TYPE: PRT
<213> ORGANISM: Artificial sequence
<220> FEATURE:
<223> OTHER INFORMATION: Synthetic antibody

<400> SEQUENCE: 7

Gly Tyr Thr Phe Ser Asp Tyr Gly
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic antibody

<400> SEQUENCE: 8

Ile Ser Gly Tyr Asn Gly Asn Thr
1               5

<210> SEQ ID NO 9
<211> LENGTH: 12
<212> TYPE: PRT
<213> ORGANISM: Artificial sequence
<220> FEATURE:
<223> OTHER INFORMATION: Synthetic antibody

<400> SEQUENCE: 9

Ala Arg Leu Leu Leu Gly Tyr Tyr Gly Met Asp Val
1               5                   10

<210> SEQ ID NO 10
<211> LENGTH: 6
<212> TYPE: PRT
<213> ORGANISM: Artificial sequence
<220> FEATURE:
<223> OTHER INFORMATION: Synthetic antibody

<400> SEQUENCE: 10

Gln Ser Ile Gly Asn Tyr
1               5

<210> SEQ ID NO 11
<211> LENGTH: 3
<212> TYPE: PRT
<213> ORGANISM: Artificial sequence
<220> FEATURE:
<223> OTHER INFORMATION: Synthetic antibody

<400> SEQUENCE: 11

Ala Ala Ser
1

<210> SEQ ID NO 12
```

```
<211> LENGTH: 10
<212> TYPE: PRT
<213> ORGANISM: Artificial sequence
<220> FEATURE:
<223> OTHER INFORMATION: Synthetic antibody

<400> SEQUENCE: 12

Gln Gln Ser Phe Ser Ile Pro Pro Ile Thr
1               5                   10

<210> SEQ ID NO 13
<211> LENGTH: 8
<212> TYPE: PRT
<213> ORGANISM: Artificial sequence
<220> FEATURE:
<223> OTHER INFORMATION: Synthetic antibody

<400> SEQUENCE: 13

Gly Tyr Thr Phe Ser Ser Tyr Gly
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic antibody

<400> SEQUENCE: 14

Ile Ser Gly Asn Thr Gly Asn Thr
1               5

<210> SEQ ID NO 15
<211> LENGTH: 14
<212> TYPE: PRT
<213> ORGANISM: Artificial sequence
<220> FEATURE:
<223> OTHER INFORMATION: Synthetic antibody

<400> SEQUENCE: 15

Ala Arg Asp Arg Gly Ile Ala Ala Gly Arg Ala Phe Asp Ile
1               5                   10

<210> SEQ ID NO 16
<211> LENGTH: 8
<212> TYPE: PRT
<213> ORGANISM: Artificial sequence
<220> FEATURE:
<223> OTHER INFORMATION: Synthetic antibody

<400> SEQUENCE: 16

Ser Ser Asn Ile Gly Thr Asn Pro
1               5

<210> SEQ ID NO 17
<211> LENGTH: 3
<212> TYPE: PRT
<213> ORGANISM: Artificial sequence
<220> FEATURE:
<223> OTHER INFORMATION: Synthetic antibody

<400> SEQUENCE: 17

Asn Asn Asn
1

<210> SEQ ID NO 18
<211> LENGTH: 11
```

```
<212> TYPE: PRT
<213> ORGANISM: Artificial sequence
<220> FEATURE:
<223> OTHER INFORMATION: Synthetic antibody

<400> SEQUENCE: 18

Ser Ser Trp Asp Asp Ser Leu Ser Ala Trp Val
1               5                   10

<210> SEQ ID NO 19
<211> LENGTH: 8
<212> TYPE: PRT
<213> ORGANISM: Artificial sequence
<220> FEATURE:
<223> OTHER INFORMATION: Synthetic antibody

<400> SEQUENCE: 19

Gly Tyr Pro Phe Thr Ser Asn Gly
1               5

<210> SEQ ID NO 20
<211> LENGTH: 8
<212> TYPE: PRT
<213> ORGANISM: Artificial sequence
<220> FEATURE:
<223> OTHER INFORMATION: Synthetic antibody

<400> SEQUENCE: 20

Ile Ser Thr Asn Ser Gly Asn Thr
1               5

<210> SEQ ID NO 21
<211> LENGTH: 10
<212> TYPE: PRT
<213> ORGANISM: Artificial sequence
<220> FEATURE:
<223> OTHER INFORMATION: Synthetic antibody

<400> SEQUENCE: 21

Ala Arg Asp Val Gln Tyr Arg Met Asp Val
1               5                   10

<210> SEQ ID NO 22
<211> LENGTH: 8
<212> TYPE: PRT
<213> ORGANISM: Artificial sequence
<220> FEATURE:
<223> OTHER INFORMATION: Synthetic antibody

<400> SEQUENCE: 22

Arg Ser Asn Ile Gly Ser Asn Pro
1               5

<210> SEQ ID NO 23
<211> LENGTH: 3
<212> TYPE: PRT
<213> ORGANISM: Artificial sequence
<220> FEATURE:
<223> OTHER INFORMATION: Synthetic antibody

<400> SEQUENCE: 23

Ser Asn Asn
1

<210> SEQ ID NO 24
<211> LENGTH: 10
<212> TYPE: PRT
```

```
<213> ORGANISM: Artificial sequence
<220> FEATURE:
<223> OTHER INFORMATION: Synthetic antibody

<400> SEQUENCE: 24

Ala Ala Trp Asp Asp Asn Val His Gly Val
1               5                   10

<210> SEQ ID NO 25
<211> LENGTH: 8
<212> TYPE: PRT
<213> ORGANISM: Artificial sequence
<220> FEATURE:
<223> OTHER INFORMATION: Synthetic antibody

<400> SEQUENCE: 25

Gly Phe Thr Ile Ser Ser Tyr Gly
1               5

<210> SEQ ID NO 26
<211> LENGTH: 8
<212> TYPE: PRT
<213> ORGANISM: Artificial sequence
<220> FEATURE:
<223> OTHER INFORMATION: Synthetic antibody

<400> SEQUENCE: 26

Ile Ser Tyr Asp Gly Ser Asn Lys
1               5

<210> SEQ ID NO 27
<211> LENGTH: 22
<212> TYPE: PRT
<213> ORGANISM: Artificial sequence
<220> FEATURE:
<223> OTHER INFORMATION: Synthetic antibody

<400> SEQUENCE: 27

Ala Lys Asp Leu Leu Leu Arg Tyr Phe Asp Trp Ser Pro Lys Tyr Tyr
1               5                   10                  15

Tyr Asn Gly Met Asp Val
            20

<210> SEQ ID NO 28
<211> LENGTH: 6
<212> TYPE: PRT
<213> ORGANISM: Artificial sequence
<220> FEATURE:
<223> OTHER INFORMATION: Synthetic antibody

<400> SEQUENCE: 28

Asn Ile Gly Ser Lys Ser
1               5

<210> SEQ ID NO 29
<211> LENGTH: 3
<212> TYPE: PRT
<213> ORGANISM: Artificial sequence
<220> FEATURE:
<223> OTHER INFORMATION: Synthetic antibody

<400> SEQUENCE: 29

Asp Asp Ser
1

<210> SEQ ID NO 30
```

```
<211> LENGTH: 12
<212> TYPE: PRT
<213> ORGANISM: Artificial sequence
<220> FEATURE:
<223> OTHER INFORMATION: Synthetic antibody

<400> SEQUENCE: 30

Gln Val Trp Asp Ser Ser Ser Asp His Pro Gly Val
1               5                   10

<210> SEQ ID NO 31
<211> LENGTH: 8
<212> TYPE: PRT
<213> ORGANISM: Artificial sequence
<220> FEATURE:
<223> OTHER INFORMATION: Synthetic antibody

<400> SEQUENCE: 31

Gly Gly Thr Phe Ser Ser Tyr Ala
1               5

<210> SEQ ID NO 32
<211> LENGTH: 8
<212> TYPE: PRT
<213> ORGANISM: Artificial sequence
<220> FEATURE:
<223> OTHER INFORMATION: Synthetic antibody

<400> SEQUENCE: 32

Ile Ile Pro Ile Phe Gly Thr Ala
1               5

<210> SEQ ID NO 33
<211> LENGTH: 12
<212> TYPE: PRT
<213> ORGANISM: Artificial sequence
<220> FEATURE:
<223> OTHER INFORMATION: Synthetic antibody

<400> SEQUENCE: 33

Ala Arg Val Ala Val Ala Asp Thr Phe Phe Asp Tyr
1               5                   10

<210> SEQ ID NO 34
<211> LENGTH: 9
<212> TYPE: PRT
<213> ORGANISM: Artificial sequence
<220> FEATURE:
<223> OTHER INFORMATION: Synthetic antibody

<400> SEQUENCE: 34

Ser Ser Asp Val Gly Gly Tyr Asn Tyr
1               5

<210> SEQ ID NO 35
<211> LENGTH: 3
<212> TYPE: PRT
<213> ORGANISM: Artificial sequence
<220> FEATURE:
<223> OTHER INFORMATION: Synthetic antibody

<400> SEQUENCE: 35

Asp Val Ser
1

<210> SEQ ID NO 36
<211> LENGTH: 11
```

```
<212> TYPE: PRT
<213> ORGANISM: Artificial sequence
<220> FEATURE:
<223> OTHER INFORMATION: Synthetic antibody

<400> SEQUENCE: 36

Ser Ser Tyr Thr Ser Ser Ser Thr Pro Tyr Val
1               5                   10

<210> SEQ ID NO 37
<211> LENGTH: 8
<212> TYPE: PRT
<213> ORGANISM: Artificial sequence
<220> FEATURE:
<223> OTHER INFORMATION: Synthetic antibody

<400> SEQUENCE: 37

Gly Tyr Thr Phe Thr Ser Tyr Gly
1               5

<210> SEQ ID NO 38
<211> LENGTH: 8
<212> TYPE: PRT
<213> ORGANISM: Artificial sequence
<220> FEATURE:
<223> OTHER INFORMATION: Synthetic antibody

<400> SEQUENCE: 38

Ile Ser Ala Tyr Asn Gly Asn Thr
1               5

<210> SEQ ID NO 39
<211> LENGTH: 9
<212> TYPE: PRT
<213> ORGANISM: Artificial sequence
<220> FEATURE:
<223> OTHER INFORMATION: Synthetic antibody

<400> SEQUENCE: 39

Ala Arg Asp Gly Tyr Gly Met Asp Val
1               5

<210> SEQ ID NO 40
<211> LENGTH: 6
<212> TYPE: PRT
<213> ORGANISM: Artificial sequence
<220> FEATURE:
<223> OTHER INFORMATION: Synthetic antibody

<400> SEQUENCE: 40

His Thr Val Asn Ser Tyr
1               5

<210> SEQ ID NO 41
<211> LENGTH: 3
<212> TYPE: PRT
<213> ORGANISM: Artificial sequence
<220> FEATURE:
<223> OTHER INFORMATION: Synthetic antibody

<400> SEQUENCE: 41

Ala Ala Ser
1

<210> SEQ ID NO 42
<211> LENGTH: 9
<212> TYPE: PRT
```

<213> ORGANISM: Artificial sequence
<220> FEATURE:
<223> OTHER INFORMATION: Synthetic antibody

<400> SEQUENCE: 42

Gln Gln Ser Tyr Arg Thr Pro Leu Thr
1               5

<210> SEQ ID NO 43
<211> LENGTH: 8
<212> TYPE: PRT
<213> ORGANISM: Artificial sequence
<220> FEATURE:
<223> OTHER INFORMATION: Synthetic antibody

<400> SEQUENCE: 43

Gly Phe Thr Phe Ser Ser Tyr Ala
1               5

<210> SEQ ID NO 44
<211> LENGTH: 8
<212> TYPE: PRT
<213> ORGANISM: Artificial sequence
<220> FEATURE:
<223> OTHER INFORMATION: Synthetic antibody

<400> SEQUENCE: 44

Ile Asn Asp Ser Gly Gly Ser Thr
1               5

<210> SEQ ID NO 45
<211> LENGTH: 15
<212> TYPE: PRT
<213> ORGANISM: Artificial sequence
<220> FEATURE:
<223> OTHER INFORMATION: Synthetic antibody

<400> SEQUENCE: 45

Ala Lys Asp His Ile Thr Ile Phe Gly Val Ala Pro Phe Asp Tyr
1               5                   10                  15

<210> SEQ ID NO 46
<211> LENGTH: 8
<212> TYPE: PRT
<213> ORGANISM: Artificial sequence
<220> FEATURE:
<223> OTHER INFORMATION: Synthetic antibody

<400> SEQUENCE: 46

Ser Ser Asn Ile Gly Gly Asn Pro
1               5

<210> SEQ ID NO 47
<211> LENGTH: 3
<212> TYPE: PRT
<213> ORGANISM: Artificial sequence
<220> FEATURE:
<223> OTHER INFORMATION: Synthetic antibody

<400> SEQUENCE: 47

Tyr Asn Asp
1

<210> SEQ ID NO 48
<211> LENGTH: 11
<212> TYPE: PRT
<213> ORGANISM: Artificial sequence
<220> FEATURE:
<223> OTHER INFORMATION: Synthetic antibody

<400> SEQUENCE: 48

Ala Thr Trp Asp Asp Ser Leu Asn Gly Trp Val
1               5                   10

<210> SEQ ID NO 49
<211> LENGTH: 10
<212> TYPE: PRT
<213> ORGANISM: Artificial sequence
<220> FEATURE:
<223> OTHER INFORMATION: Synthetic antibody

<400> SEQUENCE: 49

Gly Asp Ser Val Ser Ser Asn Ser Ala Ala
1               5                   10

<210> SEQ ID NO 50
<211> LENGTH: 9
<212> TYPE: PRT
<213> ORGANISM: Artificial sequence
<220> FEATURE:
<223> OTHER INFORMATION: Synthetic antibody

<400> SEQUENCE: 50

Thr Tyr Tyr Arg Ser Lys Trp Tyr Asn
1               5

<210> SEQ ID NO 51
<211> LENGTH: 14
<212> TYPE: PRT
<213> ORGANISM: Artificial sequence
<220> FEATURE:
<223> OTHER INFORMATION: Synthetic antibody

<400> SEQUENCE: 51

Ala Arg Gln Asp Glu Ser Ala Ala Asp Asp Ala Phe Asp Ile
1               5                   10

<210> SEQ ID NO 52
<211> LENGTH: 8
<212> TYPE: PRT
<213> ORGANISM: Artificial sequence
<220> FEATURE:
<223> OTHER INFORMATION: Synthetic antibody

<400> SEQUENCE: 52

Lys Ser Asn Val Gly Asn Asn Phe
1               5

<210> SEQ ID NO 53
<211> LENGTH: 3
<212> TYPE: PRT
<213> ORGANISM: Artificial sequence
<220> FEATURE:
<223> OTHER INFORMATION: Synthetic antibody

<400> SEQUENCE: 53

Ser Asn Leu
1

<210> SEQ ID NO 54
<211> LENGTH: 11
<212> TYPE: PRT
<213> ORGANISM: Artificial sequence
<220> FEATURE:

<223> OTHER INFORMATION: Synthetic antibody

<400> SEQUENCE: 54

Ala Ala Trp Asp Asp Ser Leu Pro Gly Trp Val
1               5                   10

<210> SEQ ID NO 55
<211> LENGTH: 8
<212> TYPE: PRT
<213> ORGANISM: Artificial sequence
<220> FEATURE:
<223> OTHER INFORMATION: Synthetic antibody

<400> SEQUENCE: 55

Gly Tyr Thr Phe Pro Asp Asn Gly
1               5

<210> SEQ ID NO 56
<211> LENGTH: 8
<212> TYPE: PRT
<213> ORGANISM: Artificial sequence
<220> FEATURE:
<223> OTHER INFORMATION: Synthetic antibody

<400> SEQUENCE: 56

Ile Asn Val Asp Thr Gly Tyr Thr
1               5

<210> SEQ ID NO 57
<211> LENGTH: 10
<212> TYPE: PRT
<213> ORGANISM: Artificial sequence
<220> FEATURE:
<223> OTHER INFORMATION: Synthetic antibody

<400> SEQUENCE: 57

Ala Arg Glu Ile Glu Gly Val Trp Thr Ala
1               5                   10

<210> SEQ ID NO 58
<211> LENGTH: 8
<212> TYPE: PRT
<213> ORGANISM: Artificial sequence
<220> FEATURE:
<223> OTHER INFORMATION: Synthetic antibody

<400> SEQUENCE: 58

Ser Ser Asn Ile Gly Ser Asn Pro
1               5

<210> SEQ ID NO 59
<211> LENGTH: 3
<212> TYPE: PRT
<213> ORGANISM: Artificial sequence
<220> FEATURE:
<223> OTHER INFORMATION: Synthetic antibody

<400> SEQUENCE: 59

Asn Asn Asn
1

<210> SEQ ID NO 60
<211> LENGTH: 11
<212> TYPE: PRT
<213> ORGANISM: Artificial sequence
<220> FEATURE:
<223> OTHER INFORMATION: Synthetic antibody

<400> SEQUENCE: 60

Ala Ala Trp Asp Asp Ser Leu Asn Gly Trp Val
1               5                   10

<210> SEQ ID NO 61
<211> LENGTH: 8
<212> TYPE: PRT
<213> ORGANISM: Artificial sequence
<220> FEATURE:
<223> OTHER INFORMATION: Synthetic antibody

<400> SEQUENCE: 61

Gly Gly Thr Phe Ser Ser Tyr Ala
1               5

<210> SEQ ID NO 62
<211> LENGTH: 8
<212> TYPE: PRT
<213> ORGANISM: Artificial sequence
<220> FEATURE:
<223> OTHER INFORMATION: Synthetic antibody

<400> SEQUENCE: 62

Ile Ile Pro Ile Phe Gly Thr Ala
1               5

<210> SEQ ID NO 63
<211> LENGTH: 12
<212> TYPE: PRT
<213> ORGANISM: Artificial sequence
<220> FEATURE:
<223> OTHER INFORMATION: Synthetic antibody

<400> SEQUENCE: 63

Ala Arg Ser Asp Tyr Gly Asp Ser Tyr Phe Asp Tyr
1               5                   10

<210> SEQ ID NO 64
<211> LENGTH: 9
<212> TYPE: PRT
<213> ORGANISM: Artificial sequence
<220> FEATURE:
<223> OTHER INFORMATION: Synthetic antibody

<400> SEQUENCE: 64

Ser Ser Asp Val Gly Gly Phe Asn Tyr
1               5

<210> SEQ ID NO 65
<211> LENGTH: 3
<212> TYPE: PRT
<213> ORGANISM: Artificial sequence
<220> FEATURE:
<223> OTHER INFORMATION: Synthetic antibody

<400> SEQUENCE: 65

Asp Val Ser
1

<210> SEQ ID NO 66
<211> LENGTH: 11
<212> TYPE: PRT
<213> ORGANISM: Artificial sequence
<220> FEATURE:
<223> OTHER INFORMATION: Synthetic antibody

```
<400> SEQUENCE: 66

Ser Ser Tyr Thr Ser Ser Thr Ala Pro Tyr Val
1               5                   10

<210> SEQ ID NO 67
<211> LENGTH: 8
<212> TYPE: PRT
<213> ORGANISM: Artificial sequence
<220> FEATURE:
<223> OTHER INFORMATION: Synthetic antibody

<400> SEQUENCE: 67

Gly Gly Thr Phe Ser Ser Tyr Ala
1               5

<210> SEQ ID NO 68
<211> LENGTH: 8
<212> TYPE: PRT
<213> ORGANISM: Artificial sequence
<220> FEATURE:
<223> OTHER INFORMATION: Synthetic antibody

<400> SEQUENCE: 68

Ile Ile Pro Ile Phe Gly Thr Ala
1               5

<210> SEQ ID NO 69
<211> LENGTH: 12
<212> TYPE: PRT
<213> ORGANISM: Artificial sequence
<220> FEATURE:
<223> OTHER INFORMATION: Synthetic antibody

<400> SEQUENCE: 69

Ala Arg Ala Ser Met Val Glu Thr Tyr Phe Asp Tyr
1               5                   10

<210> SEQ ID NO 70
<211> LENGTH: 9
<212> TYPE: PRT
<213> ORGANISM: Artificial sequence
<220> FEATURE:
<223> OTHER INFORMATION: Synthetic antibody

<400> SEQUENCE: 70

Ser Ser Asp Val Gly Gly Tyr Asn Tyr
1               5

<210> SEQ ID NO 71
<211> LENGTH: 3
<212> TYPE: PRT
<213> ORGANISM: Artificial sequence
<220> FEATURE:
<223> OTHER INFORMATION: Synthetic antibody

<400> SEQUENCE: 71

Glu Val Ser
1

<210> SEQ ID NO 72
<211> LENGTH: 11
<212> TYPE: PRT
<213> ORGANISM: Artificial sequence
<220> FEATURE:
<223> OTHER INFORMATION: Synthetic antibody

<400> SEQUENCE: 72
```

-continued

```
Ser Ser Tyr Ala Gly Gly Tyr Thr Pro Tyr Val
1               5                   10

<210> SEQ ID NO 73
<211> LENGTH: 8
<212> TYPE: PRT
<213> ORGANISM: Artificial sequence
<220> FEATURE:
<223> OTHER INFORMATION: Synthetic antibody

<400> SEQUENCE: 73

Gly Tyr Thr Phe Thr Asn Tyr Gly
1               5

<210> SEQ ID NO 74
<211> LENGTH: 8
<212> TYPE: PRT
<213> ORGANISM: Artificial sequence
<220> FEATURE:
<223> OTHER INFORMATION: Synthetic antibody

<400> SEQUENCE: 74

Ile Ser Gly Asp Ala Gly Asp Thr
1               5

<210> SEQ ID NO 75
<211> LENGTH: 21
<212> TYPE: PRT
<213> ORGANISM: Artificial sequence
<220> FEATURE:
<223> OTHER INFORMATION: Synthetic antibody

<400> SEQUENCE: 75

Ala Arg Asp Gly Glu Tyr Ile Pro Met Phe Arg Gly Phe Asp Asn Tyr
1               5                   10                  15

Tyr Gly Leu Asp Val
            20

<210> SEQ ID NO 76
<211> LENGTH: 8
<212> TYPE: PRT
<213> ORGANISM: Artificial sequence
<220> FEATURE:
<223> OTHER INFORMATION: Synthetic antibody

<400> SEQUENCE: 76

Asn Ala Asn Ile Gly Ser Asn Pro
1               5

<210> SEQ ID NO 77
<211> LENGTH: 3
<212> TYPE: PRT
<213> ORGANISM: Artificial sequence
<220> FEATURE:
<223> OTHER INFORMATION: Synthetic antibody

<400> SEQUENCE: 77

Ser Asn Asn
1

<210> SEQ ID NO 78
<211> LENGTH: 11
<212> TYPE: PRT
<213> ORGANISM: Artificial sequence
<220> FEATURE:
<223> OTHER INFORMATION: Synthetic antibody
```

```
<400> SEQUENCE: 78

Glu Gly Trp Asp Asp Ser Leu Asn Gly Tyr Val
1               5                   10

<210> SEQ ID NO 79
<211> LENGTH: 8
<212> TYPE: PRT
<213> ORGANISM: Artificial sequence
<220> FEATURE:
<223> OTHER INFORMATION: Synthetic antibody

<400> SEQUENCE: 79

Gly Gly Thr Phe Ser Ser Tyr Ala
1               5

<210> SEQ ID NO 80
<211> LENGTH: 8
<212> TYPE: PRT
<213> ORGANISM: Artificial sequence
<220> FEATURE:
<223> OTHER INFORMATION: Synthetic antibody

<400> SEQUENCE: 80

Ile Ile Pro Ile Phe Gly Thr Ala
1               5

<210> SEQ ID NO 81
<211> LENGTH: 14
<212> TYPE: PRT
<213> ORGANISM: Artificial sequence
<220> FEATURE:
<223> OTHER INFORMATION: Synthetic antibody

<400> SEQUENCE: 81

Ala Ser Gly Ile Ile Pro Asp Asn Pro Tyr Gly Met Asp Val
1               5                   10

<210> SEQ ID NO 82
<211> LENGTH: 11
<212> TYPE: PRT
<213> ORGANISM: Artificial sequence
<220> FEATURE:
<223> OTHER INFORMATION: Synthetic antibody

<400> SEQUENCE: 82

Gln Ser Leu Val Tyr Ser Asp Gly Asn Thr Tyr
1               5                   10

<210> SEQ ID NO 83
<211> LENGTH: 3
<212> TYPE: PRT
<213> ORGANISM: Artificial sequence
<220> FEATURE:
<223> OTHER INFORMATION: Synthetic antibody

<400> SEQUENCE: 83

Lys Val Ser
1

<210> SEQ ID NO 84
<211> LENGTH: 9
<212> TYPE: PRT
<213> ORGANISM: Artificial sequence
<220> FEATURE:
<223> OTHER INFORMATION: Synthetic antibody
```

```
<400> SEQUENCE: 84

Met Gln Gly Thr His Trp Pro Val Thr
1               5

<210> SEQ ID NO 85
<211> LENGTH: 9
<212> TYPE: PRT
<213> ORGANISM: Artificial sequence
<220> FEATURE:
<223> OTHER INFORMATION: Synthetic antibody

<400> SEQUENCE: 85

Gly Val Ser Thr Ser Ser Thr His Trp
1               5

<210> SEQ ID NO 86
<211> LENGTH: 7
<212> TYPE: PRT
<213> ORGANISM: Artificial sequence
<220> FEATURE:
<223> OTHER INFORMATION: Synthetic antibody

<400> SEQUENCE: 86

Ile Leu His Asn Gly Asn Thr
1               5

<210> SEQ ID NO 87
<211> LENGTH: 15
<212> TYPE: PRT
<213> ORGANISM: Artificial sequence
<220> FEATURE:
<223> OTHER INFORMATION: Synthetic antibody

<400> SEQUENCE: 87

Ala Ser Ala Ser Pro Asn Trp Gly Ala Ser Gly Ala Phe Asp Ala
1               5                   10                  15

<210> SEQ ID NO 88
<211> LENGTH: 8
<212> TYPE: PRT
<213> ORGANISM: Artificial sequence
<220> FEATURE:
<223> OTHER INFORMATION: Synthetic antibody

<400> SEQUENCE: 88

Ser Ser Asn Ile Gly Ser Asn Pro
1               5

<210> SEQ ID NO 89
<211> LENGTH: 3
<212> TYPE: PRT
<213> ORGANISM: Artificial sequence
<220> FEATURE:
<223> OTHER INFORMATION: Synthetic antibody

<400> SEQUENCE: 89

Ser Asp Asn
1

<210> SEQ ID NO 90
<211> LENGTH: 11
<212> TYPE: PRT
<213> ORGANISM: Artificial sequence
<220> FEATURE:
<223> OTHER INFORMATION: Synthetic antibody

<400> SEQUENCE: 90
```

```
Ser Thr Trp Asp Asp Ser Leu Asn Gly Leu Val
1               5                   10

<210> SEQ ID NO 91
<211> LENGTH: 8
<212> TYPE: PRT
<213> ORGANISM: Artificial sequence
<220> FEATURE:
<223> OTHER INFORMATION: Synthetic antibody

<400> SEQUENCE: 91

Gly Tyr Thr Phe Thr Arg Tyr Gly
1               5

<210> SEQ ID NO 92
<211> LENGTH: 8
<212> TYPE: PRT
<213> ORGANISM: Artificial sequence
<220> FEATURE:
<223> OTHER INFORMATION: Synthetic antibody

<400> SEQUENCE: 92

Ile Ser Gly Tyr Asn Gly Asn Thr
1               5

<210> SEQ ID NO 93
<211> LENGTH: 11
<212> TYPE: PRT
<213> ORGANISM: Artificial sequence
<220> FEATURE:
<223> OTHER INFORMATION: Synthetic antibody

<400> SEQUENCE: 93

Ala Arg Asp Arg Gly Ser Gly Tyr Leu Glu Tyr
1               5                   10

<210> SEQ ID NO 94
<211> LENGTH: 6
<212> TYPE: PRT
<213> ORGANISM: Artificial sequence
<220> FEATURE:
<223> OTHER INFORMATION: Synthetic antibody

<400> SEQUENCE: 94

Gln Gly Ile Tyr Ser Ser
1               5

<210> SEQ ID NO 95
<211> LENGTH: 3
<212> TYPE: PRT
<213> ORGANISM: Artificial sequence
<220> FEATURE:
<223> OTHER INFORMATION: Synthetic antibody

<400> SEQUENCE: 95

Gly Thr Ser
1

<210> SEQ ID NO 96
<211> LENGTH: 9
<212> TYPE: PRT
<213> ORGANISM: Artificial sequence
<220> FEATURE:
<223> OTHER INFORMATION: Synthetic antibody

<400> SEQUENCE: 96
```

```
Gln Gln His Tyr Asn Leu Pro Ile Thr
1               5

<210> SEQ ID NO 97
<211> LENGTH: 8
<212> TYPE: PRT
<213> ORGANISM: Artificial sequence
<220> FEATURE:
<223> OTHER INFORMATION: Synthetic antibody

<400> SEQUENCE: 97

Gly Phe Thr Phe Ser Asn Ala Trp
1               5

<210> SEQ ID NO 98
<211> LENGTH: 10
<212> TYPE: PRT
<213> ORGANISM: Artificial sequence
<220> FEATURE:
<223> OTHER INFORMATION: Synthetic antibody

<400> SEQUENCE: 98

Ile Lys Ser Lys Thr Asp Gly Gly Thr Thr
1               5                   10

<210> SEQ ID NO 99
<211> LENGTH: 16
<212> TYPE: PRT
<213> ORGANISM: Artificial sequence
<220> FEATURE:
<223> OTHER INFORMATION: Synthetic antibody

<400> SEQUENCE: 99

Thr Thr Asp Arg Tyr Ser Ser Ser Trp Tyr Ser Pro Ala Phe Asp Ile
1               5                   10                  15

<210> SEQ ID NO 100
<211> LENGTH: 8
<212> TYPE: PRT
<213> ORGANISM: Artificial sequence
<220> FEATURE:
<223> OTHER INFORMATION: Synthetic antibody

<400> SEQUENCE: 100

Ser Ser Asn Ile Gly Asn Asn Val
1               5

<210> SEQ ID NO 101
<211> LENGTH: 3
<212> TYPE: PRT
<213> ORGANISM: Artificial sequence
<220> FEATURE:
<223> OTHER INFORMATION: Synthetic antibody

<400> SEQUENCE: 101

Tyr Asp Asp
1

<210> SEQ ID NO 102
<211> LENGTH: 11
<212> TYPE: PRT
<213> ORGANISM: Artificial sequence
<220> FEATURE:
<223> OTHER INFORMATION: Synthetic antibody

<400> SEQUENCE: 102

Ala Thr Trp Asp Asp Ser Leu Asn Gly Pro Val
```

-continued

```
1               5               10

<210> SEQ ID NO 103
<211> LENGTH: 8
<212> TYPE: PRT
<213> ORGANISM: Artificial sequence
<220> FEATURE:
<223> OTHER INFORMATION: Synthetic antibody

<400> SEQUENCE: 103

Gly Tyr Thr Phe Thr Ser Tyr Gly
1               5

<210> SEQ ID NO 104
<211> LENGTH: 8
<212> TYPE: PRT
<213> ORGANISM: Artificial sequence
<220> FEATURE:
<223> OTHER INFORMATION: Synthetic antibody

<400> SEQUENCE: 104

Ile Ser Ala Tyr Asn Gly Asn Thr
1               5

<210> SEQ ID NO 105
<211> LENGTH: 9
<212> TYPE: PRT
<213> ORGANISM: Artificial sequence
<220> FEATURE:
<223> OTHER INFORMATION: Synthetic antibody

<400> SEQUENCE: 105

Ala Arg Val Gly Ser Tyr Gly Asp Tyr
1               5

<210> SEQ ID NO 106
<211> LENGTH: 6
<212> TYPE: PRT
<213> ORGANISM: Artificial sequence
<220> FEATURE:
<223> OTHER INFORMATION: Synthetic antibody

<400> SEQUENCE: 106

Gln Gly Ile Ser Asn Tyr
1               5

<210> SEQ ID NO 107
<211> LENGTH: 3
<212> TYPE: PRT
<213> ORGANISM: Artificial sequence
<220> FEATURE:
<223> OTHER INFORMATION: Synthetic antibody

<400> SEQUENCE: 107

Ala Ala Ser
1

<210> SEQ ID NO 108
<211> LENGTH: 9
<212> TYPE: PRT
<213> ORGANISM: Artificial sequence
<220> FEATURE:
<223> OTHER INFORMATION: Synthetic antibody

<400> SEQUENCE: 108

Gln Lys Tyr Asn Ser Ala Pro Leu Thr
1               5
```

<210> SEQ ID NO 109
<211> LENGTH: 8
<212> TYPE: PRT
<213> ORGANISM: Artificial sequence
<220> FEATURE:
<223> OTHER INFORMATION: Synthetic antibody

<400> SEQUENCE: 109

Gly Tyr Thr Phe Thr His Ser Tyr
1               5

<210> SEQ ID NO 110
<211> LENGTH: 8
<212> TYPE: PRT
<213> ORGANISM: Artificial sequence
<220> FEATURE:
<223> OTHER INFORMATION: Synthetic antibody

<400> SEQUENCE: 110

Ile Asn Pro Val Gly Gly Ser Thr
1               5

<210> SEQ ID NO 111
<211> LENGTH: 14
<212> TYPE: PRT
<213> ORGANISM: Artificial sequence
<220> FEATURE:
<223> OTHER INFORMATION: Synthetic antibody

<400> SEQUENCE: 111

Ala Arg Ala Gly Gly Asp Gly Tyr Asn Pro Tyr Phe Asp Tyr
1               5                   10

<210> SEQ ID NO 112
<211> LENGTH: 6
<212> TYPE: PRT
<213> ORGANISM: Artificial sequence
<220> FEATURE:
<223> OTHER INFORMATION: Synthetic antibody

<400> SEQUENCE: 112

Gln Ser Ile Ser Ser Trp
1               5

<210> SEQ ID NO 113
<211> LENGTH: 3
<212> TYPE: PRT
<213> ORGANISM: Artificial sequence
<220> FEATURE:
<223> OTHER INFORMATION: Synthetic antibody

<400> SEQUENCE: 113

Lys Ala Ser
1

<210> SEQ ID NO 114
<211> LENGTH: 8
<212> TYPE: PRT
<213> ORGANISM: Artificial sequence
<220> FEATURE:
<223> OTHER INFORMATION: Synthetic antibody

<400> SEQUENCE: 114

Gln Gln Tyr Asn Ser Tyr Leu Thr
1               5

```
<210> SEQ ID NO 115
<211> LENGTH: 8
<212> TYPE: PRT
<213> ORGANISM: Artificial sequence
<220> FEATURE:
<223> OTHER INFORMATION: Synthetic antibody

<400> SEQUENCE: 115

Gly Phe Thr Phe Ser Asp Tyr Tyr
1               5

<210> SEQ ID NO 116
<211> LENGTH: 8
<212> TYPE: PRT
<213> ORGANISM: Artificial sequence
<220> FEATURE:
<223> OTHER INFORMATION: Synthetic antibody

<400> SEQUENCE: 116

Ile Ser Ser Ser Ser Ser Tyr Thr
1               5

<210> SEQ ID NO 117
<211> LENGTH: 11
<212> TYPE: PRT
<213> ORGANISM: Artificial sequence
<220> FEATURE:
<223> OTHER INFORMATION: Synthetic antibody

<400> SEQUENCE: 117

Ala Arg Val Gly Asp Leu Asp Ala Phe Asp Ile
1               5                   10

<210> SEQ ID NO 118
<211> LENGTH: 8
<212> TYPE: PRT
<213> ORGANISM: Artificial sequence
<220> FEATURE:
<223> OTHER INFORMATION: Synthetic antibody

<400> SEQUENCE: 118

Ser Ser Asn Ile Gly Ser Asn Tyr
1               5

<210> SEQ ID NO 119
<211> LENGTH: 3
<212> TYPE: PRT
<213> ORGANISM: Artificial sequence
<220> FEATURE:
<223> OTHER INFORMATION: Synthetic antibody

<400> SEQUENCE: 119

Arg Asn Asn
1

<210> SEQ ID NO 120
<211> LENGTH: 11
<212> TYPE: PRT
<213> ORGANISM: Artificial sequence
<220> FEATURE:
<223> OTHER INFORMATION: Synthetic antibody

<400> SEQUENCE: 120

Ala Ala Trp Asp Asp Ser Leu Ser Gly Trp Val
1               5                   10
```

```
<210> SEQ ID NO 121
<211> LENGTH: 8
<212> TYPE: PRT
<213> ORGANISM: Artificial sequence
<220> FEATURE:
<223> OTHER INFORMATION: Synthetic antibody

<400> SEQUENCE: 121

Gly Phe Thr Phe Ser Asp His Tyr
1               5

<210> SEQ ID NO 122
<211> LENGTH: 8
<212> TYPE: PRT
<213> ORGANISM: Artificial sequence
<220> FEATURE:
<223> OTHER INFORMATION: Synthetic antibody

<400> SEQUENCE: 122

Ile Thr Thr Thr Gly Ser Thr Met
1               5

<210> SEQ ID NO 123
<211> LENGTH: 13
<212> TYPE: PRT
<213> ORGANISM: Artificial sequence
<220> FEATURE:
<223> OTHER INFORMATION: Synthetic antibody

<400> SEQUENCE: 123

Ala Arg Asp Ser Ile His Val Asp Gly Ala Phe Asp Ile
1               5                   10

<210> SEQ ID NO 124
<211> LENGTH: 6
<212> TYPE: PRT
<213> ORGANISM: Artificial sequence
<220> FEATURE:
<223> OTHER INFORMATION: Synthetic antibody

<400> SEQUENCE: 124

Asn Ile Gly Ser Lys Ser
1               5

<210> SEQ ID NO 125
<211> LENGTH: 3
<212> TYPE: PRT
<213> ORGANISM: Artificial sequence
<220> FEATURE:
<223> OTHER INFORMATION: Synthetic antibody

<400> SEQUENCE: 125

Asp Asp Ser
1

<210> SEQ ID NO 126
<211> LENGTH: 11
<212> TYPE: PRT
<213> ORGANISM: Artificial sequence
<220> FEATURE:
<223> OTHER INFORMATION: Synthetic antibody

<400> SEQUENCE: 126

Gln Val Trp Asp Ser Ser Ser Asp His Trp Val
1               5                   10

<210> SEQ ID NO 127
```

-continued

```
<211> LENGTH: 8
<212> TYPE: PRT
<213> ORGANISM: Artificial sequence
<220> FEATURE:
<223> OTHER INFORMATION: Synthetic antibody

<400> SEQUENCE: 127

Gly Tyr Thr Phe Thr Ser Tyr Gly
1               5

<210> SEQ ID NO 128
<211> LENGTH: 8
<212> TYPE: PRT
<213> ORGANISM: Artificial sequence
<220> FEATURE:
<223> OTHER INFORMATION: Synthetic antibody

<400> SEQUENCE: 128

Ile Ser Ala Tyr Asn Gly Asn Thr
1               5

<210> SEQ ID NO 129
<211> LENGTH: 10
<212> TYPE: PRT
<213> ORGANISM: Artificial sequence
<220> FEATURE:
<223> OTHER INFORMATION: Synthetic antibody

<400> SEQUENCE: 129

Ala Arg Asp Arg Gly Gly Trp Phe Asp Pro
1               5                   10

<210> SEQ ID NO 130
<211> LENGTH: 6
<212> TYPE: PRT
<213> ORGANISM: Artificial sequence
<220> FEATURE:
<223> OTHER INFORMATION: Synthetic antibody

<400> SEQUENCE: 130

Gln Ser Ile Ser Asn Phe
1               5

<210> SEQ ID NO 131
<211> LENGTH: 3
<212> TYPE: PRT
<213> ORGANISM: Artificial sequence
<220> FEATURE:
<223> OTHER INFORMATION: Synthetic antibody

<400> SEQUENCE: 131

Gly Ala Ser
1

<210> SEQ ID NO 132
<211> LENGTH: 9
<212> TYPE: PRT
<213> ORGANISM: Artificial sequence
<220> FEATURE:
<223> OTHER INFORMATION: Synthetic antibody

<400> SEQUENCE: 132

Gln Gln Gly Tyr Ser Val Pro Leu Thr
1               5

<210> SEQ ID NO 133
<211> LENGTH: 8
```

-continued

```
<212> TYPE: PRT
<213> ORGANISM: Artificial sequence
<220> FEATURE:
<223> OTHER INFORMATION: Synthetic antibody

<400> SEQUENCE: 133

Gly Gly Thr Phe Ser Ser Tyr Ala
1               5

<210> SEQ ID NO 134
<211> LENGTH: 8
<212> TYPE: PRT
<213> ORGANISM: Artificial sequence
<220> FEATURE:
<223> OTHER INFORMATION: Synthetic antibody

<400> SEQUENCE: 134

Ile Ile Pro Ile Phe Gly Thr Ala
1               5

<210> SEQ ID NO 135
<211> LENGTH: 12
<212> TYPE: PRT
<213> ORGANISM: Artificial sequence
<220> FEATURE:
<223> OTHER INFORMATION: Synthetic antibody

<400> SEQUENCE: 135

Ala Arg Glu Ser Tyr Ser Ser Ser Ser Phe Asp Tyr
1               5                   10

<210> SEQ ID NO 136
<211> LENGTH: 9
<212> TYPE: PRT
<213> ORGANISM: Artificial sequence
<220> FEATURE:
<223> OTHER INFORMATION: Synthetic antibody

<400> SEQUENCE: 136

Ser Ser Asp Val Gly Gly Tyr Asn Tyr
1               5

<210> SEQ ID NO 137
<211> LENGTH: 3
<212> TYPE: PRT
<213> ORGANISM: Artificial sequence
<220> FEATURE:
<223> OTHER INFORMATION: Synthetic antibody

<400> SEQUENCE: 137

Asp Val Ser
1

<210> SEQ ID NO 138
<211> LENGTH: 11
<212> TYPE: PRT
<213> ORGANISM: Artificial sequence
<220> FEATURE:
<223> OTHER INFORMATION: Synthetic antibody

<400> SEQUENCE: 138

Ser Ser Tyr Thr Ser Ser Ser Thr Pro Tyr Val
1               5                   10

<210> SEQ ID NO 139
<211> LENGTH: 8
<212> TYPE: PRT
```

-continued

```
<213> ORGANISM: Artificial sequence
<220> FEATURE:
<223> OTHER INFORMATION: Synthetic antibody

<400> SEQUENCE: 139

Gly Phe Thr Phe Ser Ser Tyr Asp
1               5

<210> SEQ ID NO 140
<211> LENGTH: 7
<212> TYPE: PRT
<213> ORGANISM: Artificial sequence
<220> FEATURE:
<223> OTHER INFORMATION: Synthetic antibody

<400> SEQUENCE: 140

Ile Gly Thr Ala Gly Asp Thr
1               5

<210> SEQ ID NO 141
<211> LENGTH: 18
<212> TYPE: PRT
<213> ORGANISM: Artificial sequence
<220> FEATURE:
<223> OTHER INFORMATION: Synthetic antibody

<400> SEQUENCE: 141

Ala Arg Ala Lys Glu Tyr Cys Ser Gly Gly Ser Cys Gln Asp Ala Phe
1               5                   10                  15

Asp Ile

<210> SEQ ID NO 142
<211> LENGTH: 6
<212> TYPE: PRT
<213> ORGANISM: Artificial sequence
<220> FEATURE:
<223> OTHER INFORMATION: Synthetic antibody

<400> SEQUENCE: 142

Gln Ser Ile Arg Thr Tyr
1               5

<210> SEQ ID NO 143
<211> LENGTH: 3
<212> TYPE: PRT
<213> ORGANISM: Artificial sequence
<220> FEATURE:
<223> OTHER INFORMATION: Synthetic antibody

<400> SEQUENCE: 143

Ala Ala Thr
1

<210> SEQ ID NO 144
<211> LENGTH: 10
<212> TYPE: PRT
<213> ORGANISM: Artificial sequence
<220> FEATURE:
<223> OTHER INFORMATION: Synthetic antibody

<400> SEQUENCE: 144

Gln Gln Ser Tyr Ser Ala Pro Val Phe Thr
1               5                   10

<210> SEQ ID NO 145
<211> LENGTH: 8
```

```
<212> TYPE: PRT
<213> ORGANISM: Artificial sequence
<220> FEATURE:
<223> OTHER INFORMATION: Synthetic antibody

<400> SEQUENCE: 145

Gly Tyr Thr Phe Thr Asp Tyr Tyr
1               5

<210> SEQ ID NO 146
<211> LENGTH: 8
<212> TYPE: PRT
<213> ORGANISM: Artificial sequence
<220> FEATURE:
<223> OTHER INFORMATION: Synthetic antibody

<400> SEQUENCE: 146

Val Asn Ala Asn Gly Gly Asp Thr
1               5

<210> SEQ ID NO 147
<211> LENGTH: 16
<212> TYPE: PRT
<213> ORGANISM: Artificial sequence
<220> FEATURE:
<223> OTHER INFORMATION: Synthetic antibody

<400> SEQUENCE: 147

Ala Arg Asp Trp Tyr Tyr Tyr Ser Ser Gly Ser Phe Pro Phe Asp Tyr
1               5                   10                  15

<210> SEQ ID NO 148
<211> LENGTH: 6
<212> TYPE: PRT
<213> ORGANISM: Artificial sequence
<220> FEATURE:
<223> OTHER INFORMATION: Synthetic antibody

<400> SEQUENCE: 148

Gln Ser Ile Ser Ser Phe
1               5

<210> SEQ ID NO 149
<211> LENGTH: 3
<212> TYPE: PRT
<213> ORGANISM: Artificial sequence
<220> FEATURE:
<223> OTHER INFORMATION: Synthetic antibody

<400> SEQUENCE: 149

Gly Ala Ser
1

<210> SEQ ID NO 150
<211> LENGTH: 9
<212> TYPE: PRT
<213> ORGANISM: Artificial sequence
<220> FEATURE:
<223> OTHER INFORMATION: Synthetic antibody

<400> SEQUENCE: 150

Gln Gln Ser Tyr Ser Ile Pro Ile Thr
1               5

<210> SEQ ID NO 151
<211> LENGTH: 8
<212> TYPE: PRT
```

```
<213> ORGANISM: Artificial sequence
<220> FEATURE:
<223> OTHER INFORMATION: Synthetic antibody

<400> SEQUENCE: 151

Gly Tyr Thr Phe Thr Asp Tyr Tyr
1               5

<210> SEQ ID NO 152
<211> LENGTH: 8
<212> TYPE: PRT
<213> ORGANISM: Artificial sequence
<220> FEATURE:
<223> OTHER INFORMATION: Synthetic antibody

<400> SEQUENCE: 152

Val Asn Ala Asn Gly Gly Asp Thr
1               5

<210> SEQ ID NO 153
<211> LENGTH: 16
<212> TYPE: PRT
<213> ORGANISM: Artificial sequence
<220> FEATURE:
<223> OTHER INFORMATION: Synthetic antibody

<400> SEQUENCE: 153

Ala Arg Asp Trp Tyr Tyr Tyr Ser Ser Gly Ser Phe Pro Phe Asp Tyr
1               5                   10                  15

<210> SEQ ID NO 154
<211> LENGTH: 6
<212> TYPE: PRT
<213> ORGANISM: Artificial sequence
<220> FEATURE:
<223> OTHER INFORMATION: Synthetic antibody

<400> SEQUENCE: 154

Gln Asp Val Ser Ile Ala
1               5

<210> SEQ ID NO 155
<211> LENGTH: 3
<212> TYPE: PRT
<213> ORGANISM: Artificial sequence
<220> FEATURE:
<223> OTHER INFORMATION: Synthetic antibody

<400> SEQUENCE: 155

Ser Ala Ser
1

<210> SEQ ID NO 156
<211> LENGTH: 9
<212> TYPE: PRT
<213> ORGANISM: Artificial sequence
<220> FEATURE:
<223> OTHER INFORMATION: Synthetic antibody

<400> SEQUENCE: 156

Gln Gln His Tyr Ile Thr Pro Leu Thr
1               5

<210> SEQ ID NO 157
<211> LENGTH: 8
<212> TYPE: PRT
<213> ORGANISM: Artificial sequence
```

<220> FEATURE:
<223> OTHER INFORMATION: Synthetic antibody

<400> SEQUENCE: 157

Gly Tyr Ile Phe Asn Thr Tyr Gly
1               5

<210> SEQ ID NO 158
<211> LENGTH: 8
<212> TYPE: PRT
<213> ORGANISM: Artificial sequence
<220> FEATURE:
<223> OTHER INFORMATION: Synthetic antibody

<400> SEQUENCE: 158

Thr Asn Val Tyr Asn Ser Asn Thr
1               5

<210> SEQ ID NO 159
<211> LENGTH: 11
<212> TYPE: PRT
<213> ORGANISM: Artificial sequence
<220> FEATURE:
<223> OTHER INFORMATION: Synthetic antibody

<400> SEQUENCE: 159

Ala Arg Asp Pro Gly Ser Ala Ile Phe Asp Met
1               5                   10

<210> SEQ ID NO 160
<211> LENGTH: 6
<212> TYPE: PRT
<213> ORGANISM: Artificial sequence
<220> FEATURE:
<223> OTHER INFORMATION: Synthetic antibody

<400> SEQUENCE: 160

Gln Ser Ile Ser Ser Phe
1               5

<210> SEQ ID NO 161
<211> LENGTH: 3
<212> TYPE: PRT
<213> ORGANISM: Artificial sequence
<220> FEATURE:
<223> OTHER INFORMATION: Synthetic antibody

<400> SEQUENCE: 161

Gly Ala Ser
1

<210> SEQ ID NO 162
<211> LENGTH: 9
<212> TYPE: PRT
<213> ORGANISM: Artificial sequence
<220> FEATURE:
<223> OTHER INFORMATION: Synthetic antibody

<400> SEQUENCE: 162

Gln Gln Ser Tyr Ser Ile Pro Ile Thr
1               5

<210> SEQ ID NO 163
<211> LENGTH: 8
<212> TYPE: PRT
<213> ORGANISM: Artificial sequence
<220> FEATURE:

-continued

```
<223> OTHER INFORMATION: Synthetic antibody

<400> SEQUENCE: 163

Gly Asp Ala Ile Lys Asp Lys Tyr
1               5

<210> SEQ ID NO 164
<211> LENGTH: 7
<212> TYPE: PRT
<213> ORGANISM: Artificial sequence
<220> FEATURE:
<223> OTHER INFORMATION: Synthetic antibody

<400> SEQUENCE: 164

Ile Ser Asn Ser Gly Ser Thr
1               5

<210> SEQ ID NO 165
<211> LENGTH: 11
<212> TYPE: PRT
<213> ORGANISM: Artificial sequence
<220> FEATURE:
<223> OTHER INFORMATION: Synthetic antibody

<400> SEQUENCE: 165

Ala Arg Gly Ser Gly Tyr Thr Ala Phe Asp Ile
1               5                   10

<210> SEQ ID NO 166
<211> LENGTH: 6
<212> TYPE: PRT
<213> ORGANISM: Artificial sequence
<220> FEATURE:
<223> OTHER INFORMATION: Synthetic antibody

<400> SEQUENCE: 166

Gln Ser Ile Ser Ser Tyr
1               5

<210> SEQ ID NO 167
<211> LENGTH: 3
<212> TYPE: PRT
<213> ORGANISM: Artificial sequence
<220> FEATURE:
<223> OTHER INFORMATION: Synthetic antibody

<400> SEQUENCE: 167

Ala Ala Ser
1

<210> SEQ ID NO 168
<211> LENGTH: 9
<212> TYPE: PRT
<213> ORGANISM: Artificial sequence
<220> FEATURE:
<223> OTHER INFORMATION: Synthetic antibody

<400> SEQUENCE: 168

Gln Gln Ser Tyr Ser Thr Pro Pro Thr
1               5

<210> SEQ ID NO 169
<211> LENGTH: 8
<212> TYPE: PRT
<213> ORGANISM: Artificial sequence
<220> FEATURE:
<223> OTHER INFORMATION: Synthetic antibody
```

<400> SEQUENCE: 169

Gly Phe Thr Phe Ser Ser Tyr Ala
1               5

<210> SEQ ID NO 170
<211> LENGTH: 8
<212> TYPE: PRT
<213> ORGANISM: Artificial sequence
<220> FEATURE:
<223> OTHER INFORMATION: Synthetic antibody

<400> SEQUENCE: 170

Ile Ser Gly Ser Gly Gly Ser Thr
1               5

<210> SEQ ID NO 171
<211> LENGTH: 14
<212> TYPE: PRT
<213> ORGANISM: Artificial sequence
<220> FEATURE:
<223> OTHER INFORMATION: Synthetic antibody

<400> SEQUENCE: 171

Ala Lys Asp Val Asp Pro Tyr Ser Ser Gly Tyr Phe Asp Tyr
1               5                   10

<210> SEQ ID NO 172
<211> LENGTH: 6
<212> TYPE: PRT
<213> ORGANISM: Artificial sequence
<220> FEATURE:
<223> OTHER INFORMATION: Synthetic antibody

<400> SEQUENCE: 172

Gln Gly Ile Gly Ser Trp
1               5

<210> SEQ ID NO 173
<211> LENGTH: 3
<212> TYPE: PRT
<213> ORGANISM: Artificial sequence
<220> FEATURE:
<223> OTHER INFORMATION: Synthetic antibody

<400> SEQUENCE: 173

Val Ala Ser
1

<210> SEQ ID NO 174
<211> LENGTH: 9
<212> TYPE: PRT
<213> ORGANISM: Artificial sequence
<220> FEATURE:
<223> OTHER INFORMATION: Synthetic antibody

<400> SEQUENCE: 174

Gln Gln Ala Asn Ser Phe Pro Leu Thr
1               5

<210> SEQ ID NO 175
<211> LENGTH: 8
<212> TYPE: PRT
<213> ORGANISM: Artificial sequence
<220> FEATURE:
<223> OTHER INFORMATION: Synthetic antibody

```
<400> SEQUENCE: 175

Gly Phe Thr Phe Ser Asn Tyr Ala
1               5

<210> SEQ ID NO 176
<211> LENGTH: 8
<212> TYPE: PRT
<213> ORGANISM: Artificial sequence
<220> FEATURE:
<223> OTHER INFORMATION: Synthetic antibody

<400> SEQUENCE: 176

Ile Ser Gly Ser Ser Ile Ser Thr
1               5

<210> SEQ ID NO 177
<211> LENGTH: 10
<212> TYPE: PRT
<213> ORGANISM: Artificial sequence
<220> FEATURE:
<223> OTHER INFORMATION: Synthetic antibody

<400> SEQUENCE: 177

Ala Ser Ser Gly Phe Gly Ser Phe Asp Tyr
1               5                   10

<210> SEQ ID NO 178
<211> LENGTH: 8
<212> TYPE: PRT
<213> ORGANISM: Artificial sequence
<220> FEATURE:
<223> OTHER INFORMATION: Synthetic antibody

<400> SEQUENCE: 178

Ser Ser Asn Ile Gly Asp Asn Ser
1               5

<210> SEQ ID NO 179
<211> LENGTH: 3
<212> TYPE: PRT
<213> ORGANISM: Artificial sequence
<220> FEATURE:
<223> OTHER INFORMATION: Synthetic antibody

<400> SEQUENCE: 179

Leu Asp Asp
1

<210> SEQ ID NO 180
<211> LENGTH: 11
<212> TYPE: PRT
<213> ORGANISM: Artificial sequence
<220> FEATURE:
<223> OTHER INFORMATION: Synthetic antibody

<400> SEQUENCE: 180

Ala Thr Trp Asp Asp Ser Leu Asn Gly Val Val
1               5                   10

<210> SEQ ID NO 181
<211> LENGTH: 8
<212> TYPE: PRT
<213> ORGANISM: Artificial sequence
<220> FEATURE:
<223> OTHER INFORMATION: Synthetic antibody

<400> SEQUENCE: 181
```

Gly Phe Thr Leu Ser Ser Tyr Ala
1               5

<210> SEQ ID NO 182
<211> LENGTH: 7
<212> TYPE: PRT
<213> ORGANISM: Artificial sequence
<220> FEATURE:
<223> OTHER INFORMATION: Synthetic antibody

<400> SEQUENCE: 182

Ile Asn Ser Gly Gly Ser Thr
1               5

<210> SEQ ID NO 183
<211> LENGTH: 12
<212> TYPE: PRT
<213> ORGANISM: Artificial sequence
<220> FEATURE:
<223> OTHER INFORMATION: Synthetic antibody

<400> SEQUENCE: 183

Ala Lys Ala Lys Ser Tyr Ser Ser Asp Leu Asp His
1               5                   10

<210> SEQ ID NO 184
<211> LENGTH: 12
<212> TYPE: PRT
<213> ORGANISM: Artificial sequence
<220> FEATURE:
<223> OTHER INFORMATION: Synthetic antibody

<400> SEQUENCE: 184

Gln Ser Leu Leu Asn Ser Gly Asn Gln Lys Thr Tyr
1               5                   10

<210> SEQ ID NO 185
<211> LENGTH: 3
<212> TYPE: PRT
<213> ORGANISM: Artificial sequence
<220> FEATURE:
<223> OTHER INFORMATION: Synthetic antibody

<400> SEQUENCE: 185

Gly Ala Ser
1

<210> SEQ ID NO 186
<211> LENGTH: 9
<212> TYPE: PRT
<213> ORGANISM: Artificial sequence
<220> FEATURE:
<223> OTHER INFORMATION: Synthetic antibody

<400> SEQUENCE: 186

Gln Asn Asp His Ser Tyr Pro Phe Thr
1               5

<210> SEQ ID NO 187
<211> LENGTH: 8
<212> TYPE: PRT
<213> ORGANISM: Artificial sequence
<220> FEATURE:
<223> OTHER INFORMATION: Synthetic antibody

<400> SEQUENCE: 187

```
Gly Phe Thr Phe Ser Ser Tyr Ala
1               5

<210> SEQ ID NO 188
<211> LENGTH: 8
<212> TYPE: PRT
<213> ORGANISM: Artificial sequence
<220> FEATURE:
<223> OTHER INFORMATION: Synthetic antibody

<400> SEQUENCE: 188

Ile Ser Gly Ser Gly Gly Ser Thr
1               5

<210> SEQ ID NO 189
<211> LENGTH: 16
<212> TYPE: PRT
<213> ORGANISM: Artificial sequence
<220> FEATURE:
<223> OTHER INFORMATION: Synthetic antibody

<400> SEQUENCE: 189

Ala Lys Asp Leu Leu Gly Asp Ser Gly Ser Tyr Pro Ala Phe Asp Ile
1               5                   10                  15

<210> SEQ ID NO 190
<211> LENGTH: 6
<212> TYPE: PRT
<213> ORGANISM: Artificial sequence
<220> FEATURE:
<223> OTHER INFORMATION: Synthetic antibody

<400> SEQUENCE: 190

Gln Ser Ile Ser Ser Tyr
1               5

<210> SEQ ID NO 191
<211> LENGTH: 3
<212> TYPE: PRT
<213> ORGANISM: Artificial sequence
<220> FEATURE:
<223> OTHER INFORMATION: Synthetic antibody

<400> SEQUENCE: 191

Ala Ala Ser
1

<210> SEQ ID NO 192
<211> LENGTH: 9
<212> TYPE: PRT
<213> ORGANISM: Artificial sequence
<220> FEATURE:
<223> OTHER INFORMATION: Synthetic antibody

<400> SEQUENCE: 192

Gln Gln Ser Tyr Ser Thr Pro Tyr Thr
1               5

<210> SEQ ID NO 193
<211> LENGTH: 8
<212> TYPE: PRT
<213> ORGANISM: Artificial sequence
<220> FEATURE:
<223> OTHER INFORMATION: Synthetic antibody

<400> SEQUENCE: 193

Gly Phe Pro Phe Ala Asp Tyr Ala
```

-continued

```
1               5

<210> SEQ ID NO 194
<211> LENGTH: 10
<212> TYPE: PRT
<213> ORGANISM: Artificial sequence
<220> FEATURE:
<223> OTHER INFORMATION: Synthetic antibody

<400> SEQUENCE: 194

Ile Lys Ser Lys Thr Arg Asp Gly Thr Thr
1               5                   10

<210> SEQ ID NO 195
<211> LENGTH: 8
<212> TYPE: PRT
<213> ORGANISM: Artificial sequence
<220> FEATURE:
<223> OTHER INFORMATION: Synthetic antibody

<400> SEQUENCE: 195

Ala Leu Gly Gly Ala Ala Ala Leu
1               5

<210> SEQ ID NO 196
<211> LENGTH: 9
<212> TYPE: PRT
<213> ORGANISM: Artificial sequence
<220> FEATURE:
<223> OTHER INFORMATION: Synthetic antibody

<400> SEQUENCE: 196

Ser Ser Asn Ile Gly Ala Gly Tyr Gly
1               5

<210> SEQ ID NO 197
<211> LENGTH: 3
<212> TYPE: PRT
<213> ORGANISM: Artificial sequence
<220> FEATURE:
<223> OTHER INFORMATION: Synthetic antibody

<400> SEQUENCE: 197

Gly Asp Asn
1

<210> SEQ ID NO 198
<211> LENGTH: 11
<212> TYPE: PRT
<213> ORGANISM: Artificial sequence
<220> FEATURE:
<223> OTHER INFORMATION: Synthetic antibody

<400> SEQUENCE: 198

Gln Ser Tyr Asp Ser Ser Leu Gly Val Gly Val
1               5                   10

<210> SEQ ID NO 199
<211> LENGTH: 8
<212> TYPE: PRT
<213> ORGANISM: Artificial sequence
<220> FEATURE:
<223> OTHER INFORMATION: Synthetic antibody

<400> SEQUENCE: 199

Gly Gly Thr Phe Ser Ser Tyr Ala
1               5
```

```
<210> SEQ ID NO 200
<211> LENGTH: 8
<212> TYPE: PRT
<213> ORGANISM: Artificial sequence
<220> FEATURE:
<223> OTHER INFORMATION: Synthetic antibody

<400> SEQUENCE: 200

Ile Ile Pro Ile Phe Gly Thr Ala
1               5

<210> SEQ ID NO 201
<211> LENGTH: 13
<212> TYPE: PRT
<213> ORGANISM: Artificial sequence
<220> FEATURE:
<223> OTHER INFORMATION: Synthetic antibody

<400> SEQUENCE: 201

Ala Ile Ser Ser Gly Tyr Tyr Tyr Asn Pro Phe Asp Tyr
1               5                   10

<210> SEQ ID NO 202
<211> LENGTH: 6
<212> TYPE: PRT
<213> ORGANISM: Artificial sequence
<220> FEATURE:
<223> OTHER INFORMATION: Synthetic antibody

<400> SEQUENCE: 202

Gln Ser Ile Ser Ser Tyr
1               5

<210> SEQ ID NO 203
<211> LENGTH: 3
<212> TYPE: PRT
<213> ORGANISM: Artificial sequence
<220> FEATURE:
<223> OTHER INFORMATION: Synthetic antibody

<400> SEQUENCE: 203

Ala Ala Ser
1

<210> SEQ ID NO 204
<211> LENGTH: 9
<212> TYPE: PRT
<213> ORGANISM: Artificial sequence
<220> FEATURE:
<223> OTHER INFORMATION: Synthetic antibody

<400> SEQUENCE: 204

Gln Gln Ser Tyr Ser Thr Pro Leu Thr
1               5

<210> SEQ ID NO 205
<211> LENGTH: 8
<212> TYPE: PRT
<213> ORGANISM: Artificial sequence
<220> FEATURE:
<223> OTHER INFORMATION: Synthetic antibody

<400> SEQUENCE: 205

Gly Gly Thr Phe Ser Ser Tyr Ala
1               5
```

<210> SEQ ID NO 206
<211> LENGTH: 8
<212> TYPE: PRT
<213> ORGANISM: Artificial sequence
<220> FEATURE:
<223> OTHER INFORMATION: Synthetic antibody

<400> SEQUENCE: 206

Ile Ile Pro Ile Phe Gly Thr Ala
1               5

<210> SEQ ID NO 207
<211> LENGTH: 10
<212> TYPE: PRT
<213> ORGANISM: Artificial sequence
<220> FEATURE:
<223> OTHER INFORMATION: Synthetic antibody

<400> SEQUENCE: 207

Ala Arg Gly Gly Tyr Gln Pro Leu Asp Tyr
1               5                   10

<210> SEQ ID NO 208
<211> LENGTH: 6
<212> TYPE: PRT
<213> ORGANISM: Artificial sequence
<220> FEATURE:
<223> OTHER INFORMATION: Synthetic antibody

<400> SEQUENCE: 208

Gln Ser Ile Ser Ser Tyr
1               5

<210> SEQ ID NO 209
<211> LENGTH: 3
<212> TYPE: PRT
<213> ORGANISM: Artificial sequence
<220> FEATURE:
<223> OTHER INFORMATION: Synthetic antibody

<400> SEQUENCE: 209

Ala Ala Ser
1

<210> SEQ ID NO 210
<211> LENGTH: 9
<212> TYPE: PRT
<213> ORGANISM: Artificial sequence
<220> FEATURE:
<223> OTHER INFORMATION: Synthetic antibody

<400> SEQUENCE: 210

Gln Gln Ser Tyr Ser Thr Pro Phe Thr
1               5

<210> SEQ ID NO 211
<211> LENGTH: 8
<212> TYPE: PRT
<213> ORGANISM: Artificial sequence
<220> FEATURE:
<223> OTHER INFORMATION: Synthetic antibody

<400> SEQUENCE: 211

Gly Gly Thr Phe Ser Ser Tyr Ala
1               5

<210> SEQ ID NO 212
<211> LENGTH: 8
<212> TYPE: PRT
<213> ORGANISM: Artificial sequence
<220> FEATURE:
<223> OTHER INFORMATION: Synthetic antibody

<400> SEQUENCE: 212

Ile Ile Pro Ile Phe Gly Thr Ala
1               5

<210> SEQ ID NO 213
<211> LENGTH: 14
<212> TYPE: PRT
<213> ORGANISM: Artificial sequence
<220> FEATURE:
<223> OTHER INFORMATION: Synthetic antibody

<400> SEQUENCE: 213

Ala Arg Ala Gly Gly Ile His Tyr Tyr Asp Ser Leu Asp Tyr
1               5                   10

<210> SEQ ID NO 214
<211> LENGTH: 6
<212> TYPE: PRT
<213> ORGANISM: Artificial sequence
<220> FEATURE:
<223> OTHER INFORMATION: Synthetic antibody

<400> SEQUENCE: 214

Gln Ser Ile Ser Ser Tyr
1               5

<210> SEQ ID NO 215
<211> LENGTH: 3
<212> TYPE: PRT
<213> ORGANISM: Artificial sequence
<220> FEATURE:
<223> OTHER INFORMATION: Synthetic antibody

<400> SEQUENCE: 215

Ala Ala Ser
1

<210> SEQ ID NO 216
<211> LENGTH: 9
<212> TYPE: PRT
<213> ORGANISM: Artificial sequence
<220> FEATURE:
<223> OTHER INFORMATION: Synthetic antibody

<400> SEQUENCE: 216

Gln Gln Ser Tyr Ser Thr Pro Leu Thr
1               5

<210> SEQ ID NO 217
<211> LENGTH: 8
<212> TYPE: PRT
<213> ORGANISM: Artificial sequence
<220> FEATURE:
<223> OTHER INFORMATION: Synthetic antibody

<400> SEQUENCE: 217

Gly Phe Thr Phe Ala Asn Ala Trp
1               5

<210> SEQ ID NO 218

```
<211> LENGTH: 10
<212> TYPE: PRT
<213> ORGANISM: Artificial sequence
<220> FEATURE:
<223> OTHER INFORMATION: Synthetic antibody

<400> SEQUENCE: 218

Ile Lys Pro Ser Ser Ser Gly Gly Arg Thr
1               5                   10

<210> SEQ ID NO 219
<211> LENGTH: 13
<212> TYPE: PRT
<213> ORGANISM: Artificial sequence
<220> FEATURE:
<223> OTHER INFORMATION: Synthetic antibody

<400> SEQUENCE: 219

Cys Val Thr Gly Arg Arg Val Ala Lys Thr Phe Asp Phe
1               5                   10

<210> SEQ ID NO 220
<211> LENGTH: 6
<212> TYPE: PRT
<213> ORGANISM: Artificial sequence
<220> FEATURE:
<223> OTHER INFORMATION: Synthetic antibody

<400> SEQUENCE: 220

Gln Ser Ile Ser Ser Tyr
1               5

<210> SEQ ID NO 221
<211> LENGTH: 3
<212> TYPE: PRT
<213> ORGANISM: Artificial sequence
<220> FEATURE:
<223> OTHER INFORMATION: Synthetic antibody

<400> SEQUENCE: 221

Ala Ala Ser
1

<210> SEQ ID NO 222
<211> LENGTH: 9
<212> TYPE: PRT
<213> ORGANISM: Artificial sequence
<220> FEATURE:
<223> OTHER INFORMATION: Synthetic antibody

<400> SEQUENCE: 222

Gln Gln Ser Tyr Ser Thr Pro Arg Thr
1               5

<210> SEQ ID NO 223
<211> LENGTH: 24
<212> TYPE: DNA
<213> ORGANISM: Artificial sequence
<220> FEATURE:
<223> OTHER INFORMATION: Synthetic antibody

<400> SEQUENCE: 223
ggaggcacct tcagcagcta tgct                                            24

<210> SEQ ID NO 224
<211> LENGTH: 24
<212> TYPE: DNA
```

-continued

<213> ORGANISM: Artificial sequence
<220> FEATURE:
<223> OTHER INFORMATION: Synthetic antibody

<400> SEQUENCE: 224
atcatcccta tctttggtac agca                                                         24

<210> SEQ ID NO 225
<211> LENGTH: 36
<212> TYPE: DNA
<213> ORGANISM: Artificial sequence
<220> FEATURE:
<223> OTHER INFORMATION: Synthetic antibody

<400> SEQUENCE: 225
gcgaggggga atcagggga tacggctttt gatatc                                             36

<210> SEQ ID NO 226
<211> LENGTH: 27
<212> TYPE: DNA
<213> ORGANISM: Artificial sequence
<220> FEATURE:
<223> OTHER INFORMATION: Synthetic antibody

<400> SEQUENCE: 226
agcagtgacg ttggtggtta taactat                                                      27

<210> SEQ ID NO 227
<211> LENGTH: 9
<212> TYPE: DNA
<213> ORGANISM: Artificial sequence
<220> FEATURE:
<223> OTHER INFORMATION: Synthetic antibody

<400> SEQUENCE: 227 gatgtcagt                                                                          9

<210> SEQ ID NO 228
<211> LENGTH: 33
<212> TYPE: DNA
<213> ORGANISM: Artificial sequence
<220> FEATURE:
<223> OTHER INFORMATION: Synthetic antibody

<400> SEQUENCE: 228
agctcatata caagcagcag cactccttat gtc                                               33

<210> SEQ ID NO 229
<211> LENGTH: 24
<212> TYPE: DNA
<213> ORGANISM: Artificial sequence
<220> FEATURE:
<223> OTHER INFORMATION: Synthetic antibody

<400> SEQUENCE: 229
ggttacacct ttagcgacta tggt                                                         24

<210> SEQ ID NO 230
<211> LENGTH: 24
<212> TYPE: DNA
<213> ORGANISM: Artificial sequence
<220> FEATURE:
<223> OTHER INFORMATION: Synthetic antibody

<400> SEQUENCE: 230
atcagtggtt acaatggtaa caca                                                         24

-continued

```
<210> SEQ ID NO 231
<211> LENGTH: 36
<212> TYPE: DNA
<213> ORGANISM: Artificial sequence
<220> FEATURE:
<223> OTHER INFORMATION: Synthetic antibody

<400> SEQUENCE: 231
gcgagattgc tgctgggtta ctacggtatg gacgtc                                36

<210> SEQ ID NO 232
<211> LENGTH: 18
<212> TYPE: DNA
<213> ORGANISM: Artificial sequence
<220> FEATURE:
<223> OTHER INFORMATION: Synthetic antibody

<400> SEQUENCE: 232
cagagcattg gcaactat                                                    18

<210> SEQ ID NO 233
<211> LENGTH: 9
<212> TYPE: DNA
<213> ORGANISM: Artificial sequence
<220> FEATURE:
<223> OTHER INFORMATION: Synthetic antibody

<400> SEQUENCE: 233 gctgcatcc                                                              9

<210> SEQ ID NO 234
<211> LENGTH: 30
<212> TYPE: DNA
<213> ORGANISM: Artificial sequence
<220> FEATURE:
<223> OTHER INFORMATION: Synthetic antibody

<400> SEQUENCE: 234
caacagagtt tcagtatccc cccgataact                                       30

<210> SEQ ID NO 235
<211> LENGTH: 24
<212> TYPE: DNA
<213> ORGANISM: Artificial sequence
<220> FEATURE:
<223> OTHER INFORMATION: Synthetic antibody

<400> SEQUENCE: 235
ggttacacgt ttagcagcta tggt                                             24

<210> SEQ ID NO 236
<211> LENGTH: 24
<212> TYPE: DNA
<213> ORGANISM: Artificial sequence
<220> FEATURE:
<223> OTHER INFORMATION: Synthetic antibody

<400> SEQUENCE: 236
atcagtggta acactggtaa caca                                             24

<210> SEQ ID NO 237
<211> LENGTH: 42
<212> TYPE: DNA
<213> ORGANISM: Artificial sequence
<220> FEATURE:
```

-continued

<223> OTHER INFORMATION: Synthetic antibody

<400> SEQUENCE: 237
gcgagagatc gtggtatagc ggcaggccgt gcttttgata tc                     42

<210> SEQ ID NO 238
<211> LENGTH: 24
<212> TYPE: DNA
<213> ORGANISM: Artificial sequence
<220> FEATURE:
<223> OTHER INFORMATION: Synthetic antibody

<400> SEQUENCE: 238
agctccaaca tcggaactaa tcct                                         24

<210> SEQ ID NO 239
<211> LENGTH: 9
<212> TYPE: DNA
<213> ORGANISM: Artificial sequence
<220> FEATURE:
<223> OTHER INFORMATION: Synthetic antibody

<400> SEQUENCE: 239 aataataat                                                          9

<210> SEQ ID NO 240
<211> LENGTH: 33
<212> TYPE: DNA
<213> ORGANISM: Artificial sequence
<220> FEATURE:
<223> OTHER INFORMATION: Synthetic antibody

<400> SEQUENCE: 240
tcgtcatggg acgacagcct gagtgcgtgg gtg                               33

<210> SEQ ID NO 241
<211> LENGTH: 24
<212> TYPE: DNA
<213> ORGANISM: Artificial sequence
<220> FEATURE:
<223> OTHER INFORMATION: Synthetic antibody

<400> SEQUENCE: 241
ggttacccct ttaccagcaa tggt                                         24

<210> SEQ ID NO 242
<211> LENGTH: 24
<212> TYPE: DNA
<213> ORGANISM: Artificial sequence
<220> FEATURE:
<223> OTHER INFORMATION: Synthetic antibody

<400> SEQUENCE: 242
atcagcacta acagcggaaa caca                                         24

<210> SEQ ID NO 243
<211> LENGTH: 30
<212> TYPE: DNA
<213> ORGANISM: Artificial sequence
<220> FEATURE:
<223> OTHER INFORMATION: Synthetic antibody

<400> SEQUENCE: 243
gcgagagatg ttcaatatcg tatggacgtc                                   30

-continued

<210> SEQ ID NO 244
<211> LENGTH: 24
<212> TYPE: DNA
<213> ORGANISM: Artificial sequence
<220> FEATURE:
<223> OTHER INFORMATION: Synthetic antibody

<400> SEQUENCE: 244
aggtccaaca tcggaagtaa tcct                                              24

<210> SEQ ID NO 245
<211> LENGTH: 9
<212> TYPE: DNA
<213> ORGANISM: Artificial sequence
<220> FEATURE:
<223> OTHER INFORMATION: Synthetic antibody

<400> SEQUENCE: 245 agtaataat                                                              9

<210> SEQ ID NO 246
<211> LENGTH: 30
<212> TYPE: DNA
<213> ORGANISM: Artificial sequence
<220> FEATURE:
<223> OTHER INFORMATION: Synthetic antibody

<400> SEQUENCE: 246
gcagcgtggg atgacaacgt gcacggagtt                                        30

<210> SEQ ID NO 247
<211> LENGTH: 24
<212> TYPE: DNA
<213> ORGANISM: Artificial sequence
<220> FEATURE:
<223> OTHER INFORMATION: Synthetic antibody

<400> SEQUENCE: 247
ggattcacca tcagcagtta tggc                                              24

<210> SEQ ID NO 248
<211> LENGTH: 24
<212> TYPE: DNA
<213> ORGANISM: Artificial sequence
<220> FEATURE:
<223> OTHER INFORMATION: Synthetic antibody

<400> SEQUENCE: 248
atatcatatg atggaagtaa taaa                                              24

<210> SEQ ID NO 249
<211> LENGTH: 66
<212> TYPE: DNA
<213> ORGANISM: Artificial sequence
<220> FEATURE:
<223> OTHER INFORMATION: Synthetic antibody

<400> SEQUENCE: 249
gcgaaagatc tcttattacg atattttgac tggagcccca aatactacta caacggtatg        60
gacgtc                                                                 66

<210> SEQ ID NO 250
<211> LENGTH: 18
<212> TYPE: DNA
<213> ORGANISM: Artificial sequence
<220> FEATURE:

-continued

<223> OTHER INFORMATION: Synthetic antibody

<400> SEQUENCE: 250
aacattggaa gtaaaagt                                                        18

<210> SEQ ID NO 251
<211> LENGTH: 9
<212> TYPE: DNA
<213> ORGANISM: Artificial sequence
<220> FEATURE:
<223> OTHER INFORMATION: Synthetic antibody

<400> SEQUENCE: 251 gatgatagc                                                                  9

<210> SEQ ID NO 252
<211> LENGTH: 36
<212> TYPE: DNA
<213> ORGANISM: Artificial sequence
<220> FEATURE:
<223> OTHER INFORMATION: Synthetic antibody

<400> SEQUENCE: 252
caggtgtggg atagtagtag tgatcatccg ggggtc                                    36

<210> SEQ ID NO 253
<211> LENGTH: 24
<212> TYPE: DNA
<213> ORGANISM: Artificial sequence
<220> FEATURE:
<223> OTHER INFORMATION: Synthetic antibody

<400> SEQUENCE: 253
ggaggcacct tcagcagcta tgct                                                 24

<210> SEQ ID NO 254
<211> LENGTH: 24
<212> TYPE: DNA
<213> ORGANISM: Artificial sequence
<220> FEATURE:
<223> OTHER INFORMATION: Synthetic antibody

<400> SEQUENCE: 254
atcatcccta tctttggtac agca                                                 24

<210> SEQ ID NO 255
<211> LENGTH: 36
<212> TYPE: DNA
<213> ORGANISM: Artificial sequence
<220> FEATURE:
<223> OTHER INFORMATION: Synthetic antibody

<400> SEQUENCE: 255
gcgagagtgg cagtggctga caccttcttt gactac                                    36

<210> SEQ ID NO 256
<211> LENGTH: 27
<212> TYPE: DNA
<213> ORGANISM: Artificial sequence
<220> FEATURE:
<223> OTHER INFORMATION: Synthetic antibody

<400> SEQUENCE: 256
agcagtgacg ttggtggtta taactat                                             27

-continued

```
<210> SEQ ID NO 257
<211> LENGTH: 9
<212> TYPE: DNA
<213> ORGANISM: Artificial sequence
<220> FEATURE:
<223> OTHER INFORMATION: Synthetic antibody

<400> SEQUENCE: 257 gatgtcagt                                                                9

<210> SEQ ID NO 258
<211> LENGTH: 33
<212> TYPE: DNA
<213> ORGANISM: Artificial sequence
<220> FEATURE:
<223> OTHER INFORMATION: Synthetic antibody

<400> SEQUENCE: 258
agctcatata caagcagcag caccccttat gtc                                     33

<210> SEQ ID NO 259
<211> LENGTH: 24
<212> TYPE: DNA
<213> ORGANISM: Artificial sequence
<220> FEATURE:
<223> OTHER INFORMATION: Synthetic antibody

<400> SEQUENCE: 259
ggttacacct ttaccagcta tggt                                               24

<210> SEQ ID NO 260
<211> LENGTH: 24
<212> TYPE: DNA
<213> ORGANISM: Artificial sequence
<220> FEATURE:
<223> OTHER INFORMATION: Synthetic antibody

<400> SEQUENCE: 260
atcagcgctt acaatggtaa caca                                               24

<210> SEQ ID NO 261
<211> LENGTH: 27
<212> TYPE: DNA
<213> ORGANISM: Artificial sequence
<220> FEATURE:
<223> OTHER INFORMATION: Synthetic antibody

<400> SEQUENCE: 261
gcgagagacg gctacggtat ggacgtc                                            27

<210> SEQ ID NO 262
<211> LENGTH: 18
<212> TYPE: DNA
<213> ORGANISM: Artificial sequence
<220> FEATURE:
<223> OTHER INFORMATION: Synthetic antibody

<400> SEQUENCE: 262
cacaccgtta acagctat                                                      18

<210> SEQ ID NO 263
<211> LENGTH: 9
<212> TYPE: DNA
<213> ORGANISM: Artificial sequence
<220> FEATURE:
<223> OTHER INFORMATION: Synthetic antibody
```

-continued

```
<400> SEQUENCE: 263 gctgcatcc                                                                      9

<210> SEQ ID NO 264
<211> LENGTH: 27
<212> TYPE: DNA
<213> ORGANISM: Artificial sequence
<220> FEATURE:
<223> OTHER INFORMATION: Synthetic antibody

<400> SEQUENCE: 264
caacagagtt acagaacccc tctcact                                                  27

<210> SEQ ID NO 265
<211> LENGTH: 24
<212> TYPE: DNA
<213> ORGANISM: Artificial sequence
<220> FEATURE:
<223> OTHER INFORMATION: Synthetic antibody

<400> SEQUENCE: 265
ggattcacct ttagcagcta tgcc                                                     24

<210> SEQ ID NO 266
<211> LENGTH: 24
<212> TYPE: DNA
<213> ORGANISM: Artificial sequence
<220> FEATURE:
<223> OTHER INFORMATION: Synthetic antibody

<400> SEQUENCE: 266
attaatgata gtggtggtag caca                                                     24

<210> SEQ ID NO 267
<211> LENGTH: 45
<212> TYPE: DNA
<213> ORGANISM: Artificial sequence
<220> FEATURE:
<223> OTHER INFORMATION: Synthetic antibody

<400> SEQUENCE: 267
gcgaaagatc atattacgat ttttggagtg gccccgtttg actac                             45

<210> SEQ ID NO 268
<211> LENGTH: 24
<212> TYPE: DNA
<213> ORGANISM: Artificial sequence
<220> FEATURE:
<223> OTHER INFORMATION: Synthetic antibody

<400> SEQUENCE: 268
agctccaaca tcggaggtaa tcct                                                     24

<210> SEQ ID NO 269
<211> LENGTH: 9
<212> TYPE: DNA
<213> ORGANISM: Artificial sequence
<220> FEATURE:
<223> OTHER INFORMATION: Synthetic antibody

<400> SEQUENCE: 269 tataatgat                                                                      9

<210> SEQ ID NO 270
<211> LENGTH: 33
```

```
<212> TYPE: DNA
<213> ORGANISM: Artificial sequence
<220> FEATURE:
<223> OTHER INFORMATION: Synthetic antibody

<400> SEQUENCE: 270
gcaacatggg atgacagcct gaatggttgg gtg                                   33

<210> SEQ ID NO 271
<211> LENGTH: 30
<212> TYPE: DNA
<213> ORGANISM: Artificial sequence
<220> FEATURE:
<223> OTHER INFORMATION: Synthetic antibody

<400> SEQUENCE: 271
ggggacagtg tctctagcaa cagtgctgct                                       30

<210> SEQ ID NO 272
<211> LENGTH: 27
<212> TYPE: DNA
<213> ORGANISM: Artificial sequence
<220> FEATURE:
<223> OTHER INFORMATION: Synthetic antibody

<400> SEQUENCE: 272
acatactaca ggtccaagtg gtataat                                          27

<210> SEQ ID NO 273
<211> LENGTH: 42
<212> TYPE: DNA
<213> ORGANISM: Artificial sequence
<220> FEATURE:
<223> OTHER INFORMATION: Synthetic antibody

<400> SEQUENCE: 273
gcaagacaag atgaatcggc agccgatgat gcttttgata tc                         42

<210> SEQ ID NO 274
<211> LENGTH: 24
<212> TYPE: DNA
<213> ORGANISM: Artificial sequence
<220> FEATURE:
<223> OTHER INFORMATION: Synthetic antibody

<400> SEQUENCE: 274
aagtccaacg tcggaaataa tttt                                             24

<210> SEQ ID NO 275
<211> LENGTH: 9
<212> TYPE: DNA
<213> ORGANISM: Artificial sequence
<220> FEATURE:
<223> OTHER INFORMATION: Synthetic antibody

<400> SEQUENCE: 275 agcaatctt                                                              9

<210> SEQ ID NO 276
<211> LENGTH: 33
<212> TYPE: DNA
<213> ORGANISM: Artificial sequence
<220> FEATURE:
<223> OTHER INFORMATION: Synthetic antibody

<400> SEQUENCE: 276
```

-continued gcagcatggg atgacagcct gcccggttgg gtg                                    33

<210> SEQ ID NO 277
<211> LENGTH: 24
<212> TYPE: DNA
<213> ORGANISM: Artificial sequence
<220> FEATURE:
<223> OTHER INFORMATION: Synthetic antibody

<400> SEQUENCE: 277
ggttacacgt ttcccgacaa cggt                                             24

<210> SEQ ID NO 278
<211> LENGTH: 24
<212> TYPE: DNA
<213> ORGANISM: Artificial sequence
<220> FEATURE:
<223> OTHER INFORMATION: Synthetic antibody

<400> SEQUENCE: 278
atcaacgttg acactggata cacc                                             24

<210> SEQ ID NO 279
<211> LENGTH: 30
<212> TYPE: DNA
<213> ORGANISM: Artificial sequence
<220> FEATURE:
<223> OTHER INFORMATION: Synthetic antibody

<400> SEQUENCE: 279
gcgagagaaa tcgagggagt gtggacagct                                       30

<210> SEQ ID NO 280
<211> LENGTH: 24
<212> TYPE: DNA
<213> ORGANISM: Artificial sequence
<220> FEATURE:
<223> OTHER INFORMATION: Synthetic antibody

<400> SEQUENCE: 280
agctccaaca tcggaagtaa tcct                                             24

<210> SEQ ID NO 281
<211> LENGTH: 9
<212> TYPE: DNA
<213> ORGANISM: Artificial sequence
<220> FEATURE:
<223> OTHER INFORMATION: Synthetic antibody

<400> SEQUENCE: 281 aataataat                                                              9

<210> SEQ ID NO 282
<211> LENGTH: 33
<212> TYPE: DNA
<213> ORGANISM: Artificial sequence
<220> FEATURE:
<223> OTHER INFORMATION: Synthetic antibody

<400> SEQUENCE: 282
gcggcatggg atgacagcct gaatggttgg gtg                                    33

<210> SEQ ID NO 283
<211> LENGTH: 24
<212> TYPE: DNA
<213> ORGANISM: Artificial sequence -continued
<220> FEATURE:
<223> OTHER INFORMATION: Synthetic antibody

<400> SEQUENCE: 283
ggaggcacct tcagcagcta tgct                                               24

<210> SEQ ID NO 284
<211> LENGTH: 24
<212> TYPE: DNA
<213> ORGANISM: Artificial sequence
<220> FEATURE:
<223> OTHER INFORMATION: Synthetic antibody

<400> SEQUENCE: 284
atcatcccta tctttggtac agca                                               24

<210> SEQ ID NO 285
<211> LENGTH: 36
<212> TYPE: DNA
<213> ORGANISM: Artificial sequence
<220> FEATURE:
<223> OTHER INFORMATION: Synthetic antibody

<400> SEQUENCE: 285
gcgaggtcgg actacggtga ctcctacttt gactac                                 36

<210> SEQ ID NO 286
<211> LENGTH: 27
<212> TYPE: DNA
<213> ORGANISM: Artificial sequence
<220> FEATURE:
<223> OTHER INFORMATION: Synthetic antibody

<400> SEQUENCE: 286
agcagtgacg ttggtggttt taactat                                           27

<210> SEQ ID NO 287
<211> LENGTH: 9
<212> TYPE: DNA
<213> ORGANISM: Artificial sequence
<220> FEATURE:
<223> OTHER INFORMATION: Synthetic antibody

<400> SEQUENCE: 287 gatgtcagt                                                                9

<210> SEQ ID NO 288
<211> LENGTH: 33
<212> TYPE: DNA
<213> ORGANISM: Artificial sequence
<220> FEATURE:
<223> OTHER INFORMATION: Synthetic antibody

<400> SEQUENCE: 288
agctcatata caagcagcac cgctccttat gtc                                     33

<210> SEQ ID NO 289
<211> LENGTH: 24
<212> TYPE: DNA
<213> ORGANISM: Artificial sequence
<220> FEATURE:
<223> OTHER INFORMATION: Synthetic antibody

<400> SEQUENCE: 289
ggaggcacct tcagcagcta tgct                                               24

<210> SEQ ID NO 290
<211> LENGTH: 24
<212> TYPE: DNA
<213> ORGANISM: Artificial sequence
<220> FEATURE:
<223> OTHER INFORMATION: Synthetic antibody

<400> SEQUENCE: 290
atcatcccta tctttggtac agca                                                 24

<210> SEQ ID NO 291
<211> LENGTH: 36
<212> TYPE: DNA
<213> ORGANISM: Artificial sequence
<220> FEATURE:
<223> OTHER INFORMATION: Synthetic antibody

<400> SEQUENCE: 291
gcgagagcct ctatggtcga gacttacttt gactac                                    36

<210> SEQ ID NO 292
<211> LENGTH: 27
<212> TYPE: DNA
<213> ORGANISM: Artificial sequence
<220> FEATURE:
<223> OTHER INFORMATION: Synthetic antibody

<400> SEQUENCE: 292
agcagtgatg ttggtggtta taactat                                              27

<210> SEQ ID NO 293
<211> LENGTH: 9
<212> TYPE: DNA
<213> ORGANISM: Artificial sequence
<220> FEATURE:
<223> OTHER INFORMATION: Synthetic antibody

<400> SEQUENCE: 293 gaggtcagt                                                                  9

<210> SEQ ID NO 294
<211> LENGTH: 33
<212> TYPE: DNA
<213> ORGANISM: Artificial sequence
<220> FEATURE:
<223> OTHER INFORMATION: Synthetic antibody

<400> SEQUENCE: 294
tcctcatatg caggcgggta caccccctat gtc                                       33

<210> SEQ ID NO 295
<211> LENGTH: 24
<212> TYPE: DNA
<213> ORGANISM: Artificial sequence
<220> FEATURE:
<223> OTHER INFORMATION: Synthetic antibody

<400> SEQUENCE: 295
ggttacacct ttaccaacta tggt                                                 24

<210> SEQ ID NO 296
<211> LENGTH: 24
<212> TYPE: DNA
<213> ORGANISM: Artificial sequence
<220> FEATURE:
<223> OTHER INFORMATION: Synthetic antibody

<400> SEQUENCE: 296
atcagcggtg acgctggtga caca                                                      24

<210> SEQ ID NO 297
<211> LENGTH: 63
<212> TYPE: DNA
<213> ORGANISM: Artificial sequence
<220> FEATURE:
<223> OTHER INFORMATION: Synthetic antibody

<400> SEQUENCE: 297
gcgagagatg gggaatatat tcctatgttt cggggatttg acaactacta cggtctggac     60
gtc                                                                         63

<210> SEQ ID NO 298
<211> LENGTH: 24
<212> TYPE: DNA
<213> ORGANISM: Artificial sequence
<220> FEATURE:
<223> OTHER INFORMATION: Synthetic antibody

<400> SEQUENCE: 298
aacgccaaca tcggaagtaa tcct                                                       24

<210> SEQ ID NO 299
<211> LENGTH: 9
<212> TYPE: DNA
<213> ORGANISM: Artificial sequence
<220> FEATURE:
<223> OTHER INFORMATION: Synthetic antibody

<400> SEQUENCE: 299 agtaataat                                                                         9

<210> SEQ ID NO 300
<211> LENGTH: 33
<212> TYPE: DNA
<213> ORGANISM: Artificial sequence
<220> FEATURE:
<223> OTHER INFORMATION: Synthetic antibody

<400> SEQUENCE: 300
gaaggatggg atgacagcct gaatggctat gtc                                             33

<210> SEQ ID NO 301
<211> LENGTH: 24
<212> TYPE: DNA
<213> ORGANISM: Artificial sequence
<220> FEATURE:
<223> OTHER INFORMATION: Synthetic antibody

<400> SEQUENCE: 301
ggaggcacct tcagcagcta tgct                                                       24

<210> SEQ ID NO 302
<211> LENGTH: 24
<212> TYPE: DNA
<213> ORGANISM: Artificial sequence
<220> FEATURE:
<223> OTHER INFORMATION: Synthetic antibody

<400> SEQUENCE: 302
atcatcccta tctttggtac agca                                                       24

-continued

```
<210> SEQ ID NO 303
<211> LENGTH: 42
<212> TYPE: DNA
<213> ORGANISM: Artificial sequence
<220> FEATURE:
<223> OTHER INFORMATION: Synthetic antibody

<400> SEQUENCE: 303
gcgagcggga ttatacctga taatccctac ggtatggacg tc                    42

<210> SEQ ID NO 304
<211> LENGTH: 33
<212> TYPE: DNA
<213> ORGANISM: Artificial sequence
<220> FEATURE:
<223> OTHER INFORMATION: Synthetic antibody

<400> SEQUENCE: 304
caaagcctcg tatacagtga tggaaacacc tac                              33

<210> SEQ ID NO 305
<211> LENGTH: 9
<212> TYPE: DNA
<213> ORGANISM: Artificial sequence
<220> FEATURE:
<223> OTHER INFORMATION: Synthetic antibody

<400> SEQUENCE: 305 aaggtttct                                                          9

<210> SEQ ID NO 306
<211> LENGTH: 27
<212> TYPE: DNA
<213> ORGANISM: Artificial sequence
<220> FEATURE:
<223> OTHER INFORMATION: Synthetic antibody

<400> SEQUENCE: 306
atgcaaggta cacactggcc ggtcacc                                     27

<210> SEQ ID NO 307
<211> LENGTH: 27
<212> TYPE: DNA
<213> ORGANISM: Artificial sequence
<220> FEATURE:
<223> OTHER INFORMATION: Synthetic antibody

<400> SEQUENCE: 307
ggtgtctcca ccagcagtac tcattgg                                     27

<210> SEQ ID NO 308
<211> LENGTH: 21
<212> TYPE: DNA
<213> ORGANISM: Artificial sequence
<220> FEATURE:
<223> OTHER INFORMATION: Synthetic antibody

<400> SEQUENCE: 308
atccttcata atggaaacac c                                           21

<210> SEQ ID NO 309
<211> LENGTH: 45
<212> TYPE: DNA
<213> ORGANISM: Artificial sequence
<220> FEATURE:
<223> OTHER INFORMATION: Synthetic antibody
```

<400> SEQUENCE: 309
gcgtcagcgt cgcctaactg gggagctagc ggggcttttg atgcc                    45

<210> SEQ ID NO 310
<211> LENGTH: 24
<212> TYPE: DNA
<213> ORGANISM: Artificial sequence
<220> FEATURE:
<223> OTHER INFORMATION: Synthetic antibody

<400> SEQUENCE: 310
agctccaaca tcggaagtaa tcct                                          24

<210> SEQ ID NO 311
<211> LENGTH: 9
<212> TYPE: DNA
<213> ORGANISM: Artificial sequence
<220> FEATURE:
<223> OTHER INFORMATION: Synthetic antibody

<400> SEQUENCE: 311 agtgataat                                                            9

<210> SEQ ID NO 312
<211> LENGTH: 33
<212> TYPE: DNA
<213> ORGANISM: Artificial sequence
<220> FEATURE:
<223> OTHER INFORMATION: Synthetic antibody

<400> SEQUENCE: 312
tcaacatggg atgacagcct gaatggtctt gtc                                33

<210> SEQ ID NO 313
<211> LENGTH: 24
<212> TYPE: DNA
<213> ORGANISM: Artificial sequence
<220> FEATURE:
<223> OTHER INFORMATION: Synthetic antibody

<400> SEQUENCE: 313
ggttacacct ttaccaggta tggt                                          24

<210> SEQ ID NO 314
<211> LENGTH: 24
<212> TYPE: DNA
<213> ORGANISM: Artificial sequence
<220> FEATURE:
<223> OTHER INFORMATION: Synthetic antibody

<400> SEQUENCE: 314
atcagcggtt acaatggtaa taca                                          24

<210> SEQ ID NO 315
<211> LENGTH: 33
<212> TYPE: DNA
<213> ORGANISM: Artificial sequence
<220> FEATURE:
<223> OTHER INFORMATION: Synthetic antibody

<400> SEQUENCE: 315
gcgagagatc ggggtagtgg ttatcttgaa tac                                33

<210> SEQ ID NO 316

-continued

```
<211> LENGTH: 18
<212> TYPE: DNA
<213> ORGANISM: Artificial sequence
<220> FEATURE:
<223> OTHER INFORMATION: Synthetic antibody

<400> SEQUENCE: 316
cagggcattt acagttct                                              18

<210> SEQ ID NO 317
<211> LENGTH: 9
<212> TYPE: DNA
<213> ORGANISM: Artificial sequence
<220> FEATURE:
<223> OTHER INFORMATION: Synthetic antibody

<400> SEQUENCE: 317 ggtacgtcg                                                         9

<210> SEQ ID NO 318
<211> LENGTH: 27
<212> TYPE: DNA
<213> ORGANISM: Artificial sequence
<220> FEATURE:
<223> OTHER INFORMATION: Synthetic antibody

<400> SEQUENCE: 318
caacaacatt acaatctacc catcacc                                    27

<210> SEQ ID NO 319
<211> LENGTH: 24
<212> TYPE: DNA
<213> ORGANISM: Artificial sequence
<220> FEATURE:
<223> OTHER INFORMATION: Synthetic antibody

<400> SEQUENCE: 319
ggattcactt tcagtaacgc ctgg                                       24

<210> SEQ ID NO 320
<211> LENGTH: 30
<212> TYPE: DNA
<213> ORGANISM: Artificial sequence
<220> FEATURE:
<223> OTHER INFORMATION: Synthetic antibody

<400> SEQUENCE: 320
attaaaagca aaactgatgg tgggacaaca                                 30

<210> SEQ ID NO 321
<211> LENGTH: 48
<212> TYPE: DNA
<213> ORGANISM: Artificial sequence
<220> FEATURE:
<223> OTHER INFORMATION: Synthetic antibody

<400> SEQUENCE: 321
accacagatc gatatagcag cagctggtac tcccctgctt ttgatatc             48

<210> SEQ ID NO 322
<211> LENGTH: 24
<212> TYPE: DNA
<213> ORGANISM: Artificial sequence
<220> FEATURE:
<223> OTHER INFORMATION: Synthetic antibody

<400> SEQUENCE: 322
```

-continued agctccaaca tcggaaataa tgtt                                           24

<210> SEQ ID NO 323
<211> LENGTH: 9
<212> TYPE: DNA
<213> ORGANISM: Artificial sequence
<220> FEATURE:
<223> OTHER INFORMATION: Synthetic antibody

<400> SEQUENCE: 323 tatgatgat                                                            9

<210> SEQ ID NO 324
<211> LENGTH: 33
<212> TYPE: DNA
<213> ORGANISM: Artificial sequence
<220> FEATURE:
<223> OTHER INFORMATION: Synthetic antibody

<400> SEQUENCE: 324
gcaacatggg atgacagcct gaatggccct gta                                 33

<210> SEQ ID NO 325
<211> LENGTH: 24
<212> TYPE: DNA
<213> ORGANISM: Artificial sequence
<220> FEATURE:
<223> OTHER INFORMATION: Synthetic antibody

<400> SEQUENCE: 325
ggttacacct ttaccagcta tggt                                           24

<210> SEQ ID NO 326
<211> LENGTH: 24
<212> TYPE: DNA
<213> ORGANISM: Artificial sequence
<220> FEATURE:
<223> OTHER INFORMATION: Synthetic antibody

<400> SEQUENCE: 326
atcagcgctt acaatggtaa caca                                           24

<210> SEQ ID NO 327
<211> LENGTH: 27
<212> TYPE: DNA
<213> ORGANISM: Artificial sequence
<220> FEATURE:
<223> OTHER INFORMATION: Synthetic antibody

<400> SEQUENCE: 327
gcgagagtgg gcagctatgg tgactac                                        27

<210> SEQ ID NO 328
<211> LENGTH: 18
<212> TYPE: DNA
<213> ORGANISM: Artificial sequence
<220> FEATURE:
<223> OTHER INFORMATION: Synthetic antibody

<400> SEQUENCE: 328
cagggcatta gcaattat                                                  18

<210> SEQ ID NO 329
<211> LENGTH: 9
<212> TYPE: DNA

```
<213> ORGANISM: Artificial sequence
<220> FEATURE:
<223> OTHER INFORMATION: Synthetic antibody

<400> SEQUENCE: 329 gctgcatcc                                                                                    9

<210> SEQ ID NO 330
<211> LENGTH: 27
<212> TYPE: DNA
<213> ORGANISM: Artificial sequence
<220> FEATURE:
<223> OTHER INFORMATION: Synthetic antibody

<400> SEQUENCE: 330
caaaagtata acagtgcccc gctcact                                                                 27

<210> SEQ ID NO 331
<211> LENGTH: 24
<212> TYPE: DNA
<213> ORGANISM: Artificial sequence
<220> FEATURE:
<223> OTHER INFORMATION: Synthetic antibody

<400> SEQUENCE: 331
gggtacacct tcacccactc ctat                                                                    24

<210> SEQ ID NO 332
<211> LENGTH: 24
<212> TYPE: DNA
<213> ORGANISM: Artificial sequence
<220> FEATURE:
<223> OTHER INFORMATION: Synthetic antibody

<400> SEQUENCE: 332
atcaaccctg ttggtggtag caca                                                                    24

<210> SEQ ID NO 333
<211> LENGTH: 42
<212> TYPE: DNA
<213> ORGANISM: Artificial sequence
<220> FEATURE:
<223> OTHER INFORMATION: Synthetic antibody

<400> SEQUENCE: 333
gctagagcgg ggggagatgg ctacaatcct tactttgact ac                                                42

<210> SEQ ID NO 334
<211> LENGTH: 18
<212> TYPE: DNA
<213> ORGANISM: Artificial sequence
<220> FEATURE:
<223> OTHER INFORMATION: Synthetic antibody

<400> SEQUENCE: 334
cagagtatta gtagctgg                                                                           18

<210> SEQ ID NO 335
<211> LENGTH: 9
<212> TYPE: DNA
<213> ORGANISM: Artificial sequence
<220> FEATURE:
<223> OTHER INFORMATION: Synthetic antibody

<400> SEQUENCE: 335 aaggcgtct                                                                                     9
```

-continued

```
<210> SEQ ID NO 336
<211> LENGTH: 24
<212> TYPE: DNA
<213> ORGANISM: Artificial sequence
<220> FEATURE:
<223> OTHER INFORMATION: Synthetic antibody

<400> SEQUENCE: 336
caacagtata atagttatct cact                                          24

<210> SEQ ID NO 337
<211> LENGTH: 24
<212> TYPE: DNA
<213> ORGANISM: Artificial sequence
<220> FEATURE:
<223> OTHER INFORMATION: Synthetic antibody

<400> SEQUENCE: 337
ggattcacct tcagtgacta ctac                                          24

<210> SEQ ID NO 338
<211> LENGTH: 24
<212> TYPE: DNA
<213> ORGANISM: Artificial sequence
<220> FEATURE:
<223> OTHER INFORMATION: Synthetic antibody

<400> SEQUENCE: 338
attagtagta gtagtagtta caca                                          24

<210> SEQ ID NO 339
<211> LENGTH: 33
<212> TYPE: DNA
<213> ORGANISM: Artificial sequence
<220> FEATURE:
<223> OTHER INFORMATION: Synthetic antibody

<400> SEQUENCE: 339
gcgagagtcg gagatcttga tgcttttgat atc                                33

<210> SEQ ID NO 340
<211> LENGTH: 24
<212> TYPE: DNA
<213> ORGANISM: Artificial sequence
<220> FEATURE:
<223> OTHER INFORMATION: Synthetic antibody

<400> SEQUENCE: 340
agctccaaca tcggaagtaa ttat                                          24

<210> SEQ ID NO 341
<211> LENGTH: 9
<212> TYPE: DNA
<213> ORGANISM: Artificial sequence
<220> FEATURE:
<223> OTHER INFORMATION: Synthetic antibody

<400> SEQUENCE: 341 aggaataat                                                            9

<210> SEQ ID NO 342
<211> LENGTH: 33
<212> TYPE: DNA
<213> ORGANISM: Artificial sequence
<220> FEATURE:
```

-continued

<223> OTHER INFORMATION: Synthetic antibody

<400> SEQUENCE: 342
gcagcatggg atgacagcct gagtggttgg gtg                                       33

<210> SEQ ID NO 343
<211> LENGTH: 24
<212> TYPE: DNA
<213> ORGANISM: Artificial sequence
<220> FEATURE:
<223> OTHER INFORMATION: Synthetic antibody

<400> SEQUENCE: 343
ggattcacct tcagtgacca ctac                                                 24

<210> SEQ ID NO 344
<211> LENGTH: 24
<212> TYPE: DNA
<213> ORGANISM: Artificial sequence
<220> FEATURE:
<223> OTHER INFORMATION: Synthetic antibody

<400> SEQUENCE: 344
attactacta ctggtagtac catg                                                 24

<210> SEQ ID NO 345
<211> LENGTH: 39
<212> TYPE: DNA
<213> ORGANISM: Artificial sequence
<220> FEATURE:
<223> OTHER INFORMATION: Synthetic antibody

<400> SEQUENCE: 345
gcgagagatt ccatacatgt ggatggtgct tttgatatt                                 39

<210> SEQ ID NO 346
<211> LENGTH: 18
<212> TYPE: DNA
<213> ORGANISM: Artificial sequence
<220> FEATURE:
<223> OTHER INFORMATION: Synthetic antibody

<400> SEQUENCE: 346
aacattggaa gtaaaagt                                                        18

<210> SEQ ID NO 347
<211> LENGTH: 9
<212> TYPE: DNA
<213> ORGANISM: Artificial sequence
<220> FEATURE:
<223> OTHER INFORMATION: Synthetic antibody

<400> SEQUENCE: 347 gatgatagc                                                                   9

<210> SEQ ID NO 348
<211> LENGTH: 33
<212> TYPE: DNA
<213> ORGANISM: Artificial sequence
<220> FEATURE:
<223> OTHER INFORMATION: Synthetic antibody

<400> SEQUENCE: 348
caggtgtggg atagtagtag tgatcattgg gtg                                       33

-continued

```
<210> SEQ ID NO 349
<211> LENGTH: 24
<212> TYPE: DNA
<213> ORGANISM: Artificial sequence
<220> FEATURE:
<223> OTHER INFORMATION: Synthetic antibody

<400> SEQUENCE: 349
ggttacacct ttaccagcta tggt                                      24

<210> SEQ ID NO 350
<211> LENGTH: 24
<212> TYPE: DNA
<213> ORGANISM: Artificial sequence
<220> FEATURE:
<223> OTHER INFORMATION: Synthetic antibody

<400> SEQUENCE: 350
atcagcgctt acaatggtaa caca                                      24

<210> SEQ ID NO 351
<211> LENGTH: 30
<212> TYPE: DNA
<213> ORGANISM: Artificial sequence
<220> FEATURE:
<223> OTHER INFORMATION: Synthetic antibody

<400> SEQUENCE: 351
gcgagagatc ggggagggtg gttcgacccc                                30

<210> SEQ ID NO 352
<211> LENGTH: 18
<212> TYPE: DNA
<213> ORGANISM: Artificial sequence
<220> FEATURE:
<223> OTHER INFORMATION: Synthetic antibody

<400> SEQUENCE: 352
cagagcataa gcaacttt                                             18

<210> SEQ ID NO 353
<211> LENGTH: 9
<212> TYPE: DNA
<213> ORGANISM: Artificial sequence
<220> FEATURE:
<223> OTHER INFORMATION: Synthetic antibody

<400> SEQUENCE: 353 ggtgcatcc                                                       9

<210> SEQ ID NO 354
<211> LENGTH: 27
<212> TYPE: DNA
<213> ORGANISM: Artificial sequence
<220> FEATURE:
<223> OTHER INFORMATION: Synthetic antibody

<400> SEQUENCE: 354
caacagggtt acagtgtccc actcact                                   27

<210> SEQ ID NO 355
<211> LENGTH: 24
<212> TYPE: DNA
<213> ORGANISM: Artificial sequence
<220> FEATURE:
<223> OTHER INFORMATION: Synthetic antibody
```

-continued

```
<400> SEQUENCE: 355
ggaggcacct tcagcagcta tgct                                        24

<210> SEQ ID NO 356
<211> LENGTH: 24
<212> TYPE: DNA
<213> ORGANISM: Artificial sequence
<220> FEATURE:
<223> OTHER INFORMATION: Synthetic antibody

<400> SEQUENCE: 356
atcatcccta tctttggtac agca                                        24

<210> SEQ ID NO 357
<211> LENGTH: 36
<212> TYPE: DNA
<213> ORGANISM: Artificial sequence
<220> FEATURE:
<223> OTHER INFORMATION: Synthetic antibody

<400> SEQUENCE: 357
gcgagagagt cgtatagcag ctcgtccttt gactac                           36

<210> SEQ ID NO 358
<211> LENGTH: 27
<212> TYPE: DNA
<213> ORGANISM: Artificial sequence
<220> FEATURE:
<223> OTHER INFORMATION: Synthetic antibody

<400> SEQUENCE: 358
agcagtgacg ttggtggtta taactat                                     27

<210> SEQ ID NO 359
<211> LENGTH: 9
<212> TYPE: DNA
<213> ORGANISM: Artificial sequence
<220> FEATURE:
<223> OTHER INFORMATION: Synthetic antibody

<400> SEQUENCE: 359 gatgtcagt                                                          9

<210> SEQ ID NO 360
<211> LENGTH: 33
<212> TYPE: DNA
<213> ORGANISM: Artificial sequence
<220> FEATURE:
<223> OTHER INFORMATION: Synthetic antibody

<400> SEQUENCE: 360
agctcatata caagcagcag cactccctat gtc                              33

<210> SEQ ID NO 361
<211> LENGTH: 24
<212> TYPE: DNA
<213> ORGANISM: Artificial sequence
<220> FEATURE:
<223> OTHER INFORMATION: Synthetic antibody

<400> SEQUENCE: 361
ggattcacct tcagtagcta cgac                                        24

<210> SEQ ID NO 362
<211> LENGTH: 21
```

-continued

```
<212> TYPE: DNA
<213> ORGANISM: Artificial sequence
<220> FEATURE:
<223> OTHER INFORMATION: Synthetic antibody

<400> SEQUENCE: 362
attggtactg ctggtgacac a                                               21

<210> SEQ ID NO 363
<211> LENGTH: 54
<212> TYPE: DNA
<213> ORGANISM: Artificial sequence
<220> FEATURE:
<223> OTHER INFORMATION: Synthetic antibody

<400> SEQUENCE: 363
gcaagggcga aggaatattg tagtggtggt agctgccaag atgcttttga tatc          54

<210> SEQ ID NO 364
<211> LENGTH: 18
<212> TYPE: DNA
<213> ORGANISM: Artificial sequence
<220> FEATURE:
<223> OTHER INFORMATION: Synthetic antibody

<400> SEQUENCE: 364
cagagcatta ggacctac                                                  18

<210> SEQ ID NO 365
<211> LENGTH: 9
<212> TYPE: DNA
<213> ORGANISM: Artificial sequence
<220> FEATURE:
<223> OTHER INFORMATION: Synthetic antibody

<400> SEQUENCE: 365 gctgcaacc                                                             9

<210> SEQ ID NO 366
<211> LENGTH: 30
<212> TYPE: DNA
<213> ORGANISM: Artificial sequence
<220> FEATURE:
<223> OTHER INFORMATION: Synthetic antibody

<400> SEQUENCE: 366
caacagagtt acagtgcccc cgtgttcact                                     30

<210> SEQ ID NO 367
<211> LENGTH: 24
<212> TYPE: DNA
<213> ORGANISM: Artificial sequence
<220> FEATURE:
<223> OTHER INFORMATION: Synthetic antibody

<400> SEQUENCE: 367
gggtacacct tcaccgacta ttat                                           24

<210> SEQ ID NO 368
<211> LENGTH: 24
<212> TYPE: DNA
<213> ORGANISM: Artificial sequence
<220> FEATURE:
<223> OTHER INFORMATION: Synthetic antibody

<400> SEQUENCE: 368
```

```
gtcaacgcta atggtggtga caca                                          24
```

```
<210> SEQ ID NO 369
<211> LENGTH: 48
<212> TYPE: DNA
<213> ORGANISM: Artificial sequence
<220> FEATURE:
<223> OTHER INFORMATION: Synthetic antibody

<400> SEQUENCE: 369
gctagagatt ggtattacta ttcttcgggg agtttccctt ttgactac                48
```

```
<210> SEQ ID NO 370
<211> LENGTH: 18
<212> TYPE: DNA
<213> ORGANISM: Artificial sequence
<220> FEATURE:
<223> OTHER INFORMATION: Synthetic antibody

<400> SEQUENCE: 370
cagagcatta gcagcttt                                                 18
```

```
<210> SEQ ID NO 371
<211> LENGTH: 9
<212> TYPE: DNA
<213> ORGANISM: Artificial sequence
<220> FEATURE:
<223> OTHER INFORMATION: Synthetic antibody

<400> SEQUENCE: 371 ggtgcatcc                                                            9
```

```
<210> SEQ ID NO 372
<211> LENGTH: 27
<212> TYPE: DNA
<213> ORGANISM: Artificial sequence
<220> FEATURE:
<223> OTHER INFORMATION: Synthetic antibody

<400> SEQUENCE: 372
caacagagtt acagtatccc gatcacc                                       27
```

```
<210> SEQ ID NO 373
<211> LENGTH: 24
<212> TYPE: DNA
<213> ORGANISM: Artificial sequence
<220> FEATURE:
<223> OTHER INFORMATION: Synthetic antibody

<400> SEQUENCE: 373
gggtacacct tcaccgacta ttat                                          24
```

```
<210> SEQ ID NO 374
<211> LENGTH: 24
<212> TYPE: DNA
<213> ORGANISM: Artificial sequence
<220> FEATURE:
<223> OTHER INFORMATION: Synthetic antibody

<400> SEQUENCE: 374
gtcaacgcta atggtggtga caca                                          24
```

```
<210> SEQ ID NO 375
<211> LENGTH: 48
<212> TYPE: DNA
<213> ORGANISM: Artificial sequence
```

-continued

```
<220> FEATURE:
<223> OTHER INFORMATION: Synthetic antibody

<400> SEQUENCE: 375
gctagagatt ggtattacta ttcttcgggg agtttccctt ttgactac                48

<210> SEQ ID NO 376
<211> LENGTH: 18
<212> TYPE: DNA
<213> ORGANISM: Artificial sequence
<220> FEATURE:
<223> OTHER INFORMATION: Synthetic antibody

<400> SEQUENCE: 376
caagatgtgt ccatcgcc                                                 18

<210> SEQ ID NO 377
<211> LENGTH: 9
<212> TYPE: DNA
<213> ORGANISM: Artificial sequence
<220> FEATURE:
<223> OTHER INFORMATION: Synthetic antibody

<400> SEQUENCE: 377 tccgccagc                                                            9

<210> SEQ ID NO 378
<211> LENGTH: 27
<212> TYPE: DNA
<213> ORGANISM: Artificial sequence
<220> FEATURE:
<223> OTHER INFORMATION: Synthetic antibody

<400> SEQUENCE: 378
cagcagcact acatcacccc tttaaca                                        27

<210> SEQ ID NO 379
<211> LENGTH: 24
<212> TYPE: DNA
<213> ORGANISM: Artificial sequence
<220> FEATURE:
<223> OTHER INFORMATION: Synthetic antibody

<400> SEQUENCE: 379
ggttacatct tcaacaccta tggt                                           24

<210> SEQ ID NO 380
<211> LENGTH: 24
<212> TYPE: DNA
<213> ORGANISM: Artificial sequence
<220> FEATURE:
<223> OTHER INFORMATION: Synthetic antibody

<400> SEQUENCE: 380
accaacgttt acaatagtaa caca                                           24

<210> SEQ ID NO 381
<211> LENGTH: 33
<212> TYPE: DNA
<213> ORGANISM: Artificial sequence
<220> FEATURE:
<223> OTHER INFORMATION: Synthetic antibody

<400> SEQUENCE: 381
gcgagagacc cgggctcggc tatttttgat atg                                 33
```

<210> SEQ ID NO 382
<211> LENGTH: 18
<212> TYPE: DNA
<213> ORGANISM: Artificial sequence
<220> FEATURE:
<223> OTHER INFORMATION: Synthetic antibody

<400> SEQUENCE: 382
cagagcatta gcagcttt                                                                                18

<210> SEQ ID NO 383
<211> LENGTH: 9
<212> TYPE: DNA
<213> ORGANISM: Artificial sequence
<220> FEATURE:
<223> OTHER INFORMATION: Synthetic antibody

<400> SEQUENCE: 383 ggtgcatcc                                                                                           9

<210> SEQ ID NO 384
<211> LENGTH: 27
<212> TYPE: DNA
<213> ORGANISM: Artificial sequence
<220> FEATURE:
<223> OTHER INFORMATION: Synthetic antibody

<400> SEQUENCE: 384
caacagagtt acagtatccc gatcacc                                                                       27

<210> SEQ ID NO 385
<211> LENGTH: 24
<212> TYPE: DNA
<213> ORGANISM: Artificial sequence
<220> FEATURE:
<223> OTHER INFORMATION: Synthetic antibody

<400> SEQUENCE: 385
ggtgacgcca tcaaagataa gtac                                                                          24

<210> SEQ ID NO 386
<211> LENGTH: 21
<212> TYPE: DNA
<213> ORGANISM: Artificial sequence
<220> FEATURE:
<223> OTHER INFORMATION: Synthetic antibody

<400> SEQUENCE: 386
atctctaaca gtggaagcac c                                                                             21

<210> SEQ ID NO 387
<211> LENGTH: 33
<212> TYPE: DNA
<213> ORGANISM: Artificial sequence
<220> FEATURE:
<223> OTHER INFORMATION: Synthetic antibody

<400> SEQUENCE: 387
gcgagaggca gcggttatac tgcttttgat atc                                                                33

<210> SEQ ID NO 388
<211> LENGTH: 18
<212> TYPE: DNA
<213> ORGANISM: Artificial sequence
<220> FEATURE:
<223> OTHER INFORMATION: Synthetic antibody -continued

```
<400> SEQUENCE: 388
cagagcatta gcagctat                                                     18

<210> SEQ ID NO 389
<211> LENGTH: 9
<212> TYPE: DNA
<213> ORGANISM: Artificial sequence
<220> FEATURE:
<223> OTHER INFORMATION: Synthetic antibody

<400> SEQUENCE: 389 gctgcatcc                                                               9

<210> SEQ ID NO 390
<211> LENGTH: 27
<212> TYPE: DNA
<213> ORGANISM: Artificial sequence
<220> FEATURE:
<223> OTHER INFORMATION: Synthetic antibody

<400> SEQUENCE: 390
caacagagtt acagtacccc gcccact                                           27

<210> SEQ ID NO 391
<211> LENGTH: 24
<212> TYPE: DNA
<213> ORGANISM: Artificial sequence
<220> FEATURE:
<223> OTHER INFORMATION: Synthetic antibody

<400> SEQUENCE: 391
ggattcacct ttagcagcta tgcc                                              24

<210> SEQ ID NO 392
<211> LENGTH: 24
<212> TYPE: DNA
<213> ORGANISM: Artificial sequence
<220> FEATURE:
<223> OTHER INFORMATION: Synthetic antibody

<400> SEQUENCE: 392
attagtggta gtggtggtag caca                                              24

<210> SEQ ID NO 393
<211> LENGTH: 42
<212> TYPE: DNA
<213> ORGANISM: Artificial sequence
<220> FEATURE:
<223> OTHER INFORMATION: Synthetic antibody

<400> SEQUENCE: 393
gcgaaagatg tcgacccta tagtagtggt tattttgact ac                          42

<210> SEQ ID NO 394
<211> LENGTH: 18
<212> TYPE: DNA
<213> ORGANISM: Artificial sequence
<220> FEATURE:
<223> OTHER INFORMATION: Synthetic antibody

<400> SEQUENCE: 394
cagggtattg gcagctgg                                                     18

<210> SEQ ID NO 395
```

-continued

```
<211> LENGTH: 9
<212> TYPE: DNA
<213> ORGANISM: Artificial sequence
<220> FEATURE:
<223> OTHER INFORMATION: Synthetic antibody

<400> SEQUENCE: 395 gttgcatcc                                                                  9

<210> SEQ ID NO 396
<211> LENGTH: 27
<212> TYPE: DNA
<213> ORGANISM: Artificial sequence
<220> FEATURE:
<223> OTHER INFORMATION: Synthetic antibody

<400> SEQUENCE: 396
caacaggcta acagtttccc gctcact                                              27

<210> SEQ ID NO 397
<211> LENGTH: 24
<212> TYPE: DNA
<213> ORGANISM: Artificial sequence
<220> FEATURE:
<223> OTHER INFORMATION: Synthetic antibody

<400> SEQUENCE: 397
ggattcacct ttagcaacta tgcc                                                 24

<210> SEQ ID NO 398
<211> LENGTH: 24
<212> TYPE: DNA
<213> ORGANISM: Artificial sequence
<220> FEATURE:
<223> OTHER INFORMATION: Synthetic antibody

<400> SEQUENCE: 398
attagtggta gtagtattag caca                                                 24

<210> SEQ ID NO 399
<211> LENGTH: 30
<212> TYPE: DNA
<213> ORGANISM: Artificial sequence
<220> FEATURE:
<223> OTHER INFORMATION: Synthetic antibody

<400> SEQUENCE: 399
gcgtcctcgg gtttcgggtc ctttgactac                                           30

<210> SEQ ID NO 400
<211> LENGTH: 24
<212> TYPE: DNA
<213> ORGANISM: Artificial sequence
<220> FEATURE:
<223> OTHER INFORMATION: Synthetic antibody

<400> SEQUENCE: 400
agctccaata tcggagataa ttct                                                 24

<210> SEQ ID NO 401
<211> LENGTH: 9
<212> TYPE: DNA
<213> ORGANISM: Artificial sequence
<220> FEATURE:
<223> OTHER INFORMATION: Synthetic antibody

<400> SEQUENCE: 401
``` cttgatgat                                                                      9

<210> SEQ ID NO 402
<211> LENGTH: 33
<212> TYPE: DNA
<213> ORGANISM: Artificial sequence
<220> FEATURE:
<223> OTHER INFORMATION: Synthetic antibody

<400> SEQUENCE: 402
gcaacatggg atgacagcct gaacggtgtg gtt                                          33

<210> SEQ ID NO 403
<211> LENGTH: 24
<212> TYPE: DNA
<213> ORGANISM: Artificial sequence
<220> FEATURE:
<223> OTHER INFORMATION: Synthetic antibody

<400> SEQUENCE: 403
ggattcacct taagtagcta tgcc                                                    24

<210> SEQ ID NO 404
<211> LENGTH: 21
<212> TYPE: DNA
<213> ORGANISM: Artificial sequence
<220> FEATURE:
<223> OTHER INFORMATION: Synthetic antibody

<400> SEQUENCE: 404
attaatagtg gtggtagcac a                                                       21

<210> SEQ ID NO 405
<211> LENGTH: 36
<212> TYPE: DNA
<213> ORGANISM: Artificial sequence
<220> FEATURE:
<223> OTHER INFORMATION: Synthetic antibody

<400> SEQUENCE: 405
gcgaaagcga agagttatag cagtgacctt gaccac                                       36

<210> SEQ ID NO 406
<211> LENGTH: 36
<212> TYPE: DNA
<213> ORGANISM: Artificial sequence
<220> FEATURE:
<223> OTHER INFORMATION: Synthetic antibody

<400> SEQUENCE: 406
cagagtctgt taaacagtgg aaatcaaaag acctac                                       36

<210> SEQ ID NO 407
<211> LENGTH: 9
<212> TYPE: DNA
<213> ORGANISM: Artificial sequence
<220> FEATURE:
<223> OTHER INFORMATION: Synthetic antibody

<400> SEQUENCE: 407 ggggcatcc                                                                      9

<210> SEQ ID NO 408
<211> LENGTH: 27
<212> TYPE: DNA

-continued

<213> ORGANISM: Artificial sequence
<220> FEATURE:
<223> OTHER INFORMATION: Synthetic antibody

<400> SEQUENCE: 408
cagaatgatc atagttatcc attcacg                                          27

<210> SEQ ID NO 409
<211> LENGTH: 24
<212> TYPE: DNA
<213> ORGANISM: Artificial sequence
<220> FEATURE:
<223> OTHER INFORMATION: Synthetic antibody

<400> SEQUENCE: 409
ggattcacct ttagcagcta tgcc                                             24

<210> SEQ ID NO 410
<211> LENGTH: 24
<212> TYPE: DNA
<213> ORGANISM: Artificial sequence
<220> FEATURE:
<223> OTHER INFORMATION: Synthetic antibody

<400> SEQUENCE: 410
attagtggta gtggtggtag caca                                             24

<210> SEQ ID NO 411
<211> LENGTH: 48
<212> TYPE: DNA
<213> ORGANISM: Artificial sequence
<220> FEATURE:
<223> OTHER INFORMATION: Synthetic antibody

<400> SEQUENCE: 411
gcgaaagatc ttctcgggga tagtgggagc taccctgctt ttgatatc                  48

<210> SEQ ID NO 412
<211> LENGTH: 18
<212> TYPE: DNA
<213> ORGANISM: Artificial sequence
<220> FEATURE:
<223> OTHER INFORMATION: Synthetic antibody

<400> SEQUENCE: 412
cagagcatta gcagctat                                                    18

<210> SEQ ID NO 413
<211> LENGTH: 9
<212> TYPE: DNA
<213> ORGANISM: Artificial sequence
<220> FEATURE:
<223> OTHER INFORMATION: Synthetic antibody

<400> SEQUENCE: 413 gctgcatcc                                                              9

<210> SEQ ID NO 414
<211> LENGTH: 27
<212> TYPE: DNA
<213> ORGANISM: Artificial sequence
<220> FEATURE:
<223> OTHER INFORMATION: Synthetic antibody

<400> SEQUENCE: 414
caacagagtt acagtacccc gtacact                                         27

<210> SEQ ID NO 415
<211> LENGTH: 24
<212> TYPE: DNA
<213> ORGANISM: Artificial sequence
<220> FEATURE:
<223> OTHER INFORMATION: Synthetic antibody

<400> SEQUENCE: 415
ggattcccct ttgcggacta tgct                                              24

<210> SEQ ID NO 416
<211> LENGTH: 30
<212> TYPE: DNA
<213> ORGANISM: Artificial sequence
<220> FEATURE:
<223> OTHER INFORMATION: Synthetic antibody

<400> SEQUENCE: 416
attaaaagca agactagaga tgggacaaca                                        30

<210> SEQ ID NO 417
<211> LENGTH: 24
<212> TYPE: DNA
<213> ORGANISM: Artificial sequence
<220> FEATURE:
<223> OTHER INFORMATION: Synthetic antibody

<400> SEQUENCE: 417
gccctcgggg gagcagcagc tcta                                              24

<210> SEQ ID NO 418
<211> LENGTH: 27
<212> TYPE: DNA
<213> ORGANISM: Artificial sequence
<220> FEATURE:
<223> OTHER INFORMATION: Synthetic antibody

<400> SEQUENCE: 418
agctccaaca tcggggcagg ttatggt                                           27

<210> SEQ ID NO 419
<211> LENGTH: 9
<212> TYPE: DNA
<213> ORGANISM: Artificial sequence
<220> FEATURE:
<223> OTHER INFORMATION: Synthetic antibody

<400> SEQUENCE: 419 ggtgacaac                                                               9

<210> SEQ ID NO 420
<211> LENGTH: 33
<212> TYPE: DNA
<213> ORGANISM: Artificial sequence
<220> FEATURE:
<223> OTHER INFORMATION: Synthetic antibody

<400> SEQUENCE: 420
cagtcctatg acagcagcct gggggttggt gtg                                    33

<210> SEQ ID NO 421
<211> LENGTH: 24
<212> TYPE: DNA
<213> ORGANISM: Artificial sequence
<220> FEATURE:

-continued

<223> OTHER INFORMATION: Synthetic antibody

<400> SEQUENCE: 421
ggaggcacct tcagcagcta tgct                                             24

<210> SEQ ID NO 422
<211> LENGTH: 24
<212> TYPE: DNA
<213> ORGANISM: Artificial sequence
<220> FEATURE:
<223> OTHER INFORMATION: Synthetic antibody

<400> SEQUENCE: 422
atcatcccta tctttggtac agca                                             24

<210> SEQ ID NO 423
<211> LENGTH: 39
<212> TYPE: DNA
<213> ORGANISM: Artificial sequence
<220> FEATURE:
<223> OTHER INFORMATION: Synthetic antibody

<400> SEQUENCE: 423
gcgattagta gtggttatta ttataaccca tttgactac                             39

<210> SEQ ID NO 424
<211> LENGTH: 18
<212> TYPE: DNA
<213> ORGANISM: Artificial sequence
<220> FEATURE:
<223> OTHER INFORMATION: Synthetic antibody

<400> SEQUENCE: 424
cagagcatta gcagctat                                                    18

<210> SEQ ID NO 425
<211> LENGTH: 9
<212> TYPE: DNA
<213> ORGANISM: Artificial sequence
<220> FEATURE:
<223> OTHER INFORMATION: Synthetic antibody

<400> SEQUENCE: 425 gctgcatcc                                                               9

<210> SEQ ID NO 426
<211> LENGTH: 27
<212> TYPE: DNA
<213> ORGANISM: Artificial sequence
<220> FEATURE:
<223> OTHER INFORMATION: Synthetic antibody

<400> SEQUENCE: 426
caacagagtt acagtacccc cctcact                                          27

<210> SEQ ID NO 427
<211> LENGTH: 24
<212> TYPE: DNA
<213> ORGANISM: Artificial sequence
<220> FEATURE:
<223> OTHER INFORMATION: Synthetic antibody

<400> SEQUENCE: 427
ggaggcacct tcagcagcta tgct                                             24

-continued

```
<210> SEQ ID NO 428
<211> LENGTH: 24
<212> TYPE: DNA
<213> ORGANISM: Artificial sequence
<220> FEATURE:
<223> OTHER INFORMATION: Synthetic antibody

<400> SEQUENCE: 428
atcatcccta tctttggtac agca                                                 24

<210> SEQ ID NO 429
<211> LENGTH: 30
<212> TYPE: DNA
<213> ORGANISM: Artificial sequence
<220> FEATURE:
<223> OTHER INFORMATION: Synthetic antibody

<400> SEQUENCE: 429
gcgagagggg gataccagcc actggattac                                           30

<210> SEQ ID NO 430
<211> LENGTH: 18
<212> TYPE: DNA
<213> ORGANISM: Artificial sequence
<220> FEATURE:
<223> OTHER INFORMATION: Synthetic antibody

<400> SEQUENCE: 430
cagagcatta gcagctat                                                        18

<210> SEQ ID NO 431
<211> LENGTH: 9
<212> TYPE: DNA
<213> ORGANISM: Artificial sequence
<220> FEATURE:
<223> OTHER INFORMATION: Synthetic antibody

<400> SEQUENCE: 431 gctgcatcc                                                                   9

<210> SEQ ID NO 432
<211> LENGTH: 27
<212> TYPE: DNA
<213> ORGANISM: Artificial sequence
<220> FEATURE:
<223> OTHER INFORMATION: Synthetic antibody

<400> SEQUENCE: 432
caacagagtt acagtacccc attcact                                              27

<210> SEQ ID NO 433
<211> LENGTH: 24
<212> TYPE: DNA
<213> ORGANISM: Artificial sequence
<220> FEATURE:
<223> OTHER INFORMATION: Synthetic antibody

<400> SEQUENCE: 433
ggaggcacct tcagcagcta tgct                                                 24

<210> SEQ ID NO 434
<211> LENGTH: 24
<212> TYPE: DNA
<213> ORGANISM: Artificial sequence
<220> FEATURE:
<223> OTHER INFORMATION: Synthetic antibody
```

<400> SEQUENCE: 434
atcatcccta tctttggtac agca                                                      24

<210> SEQ ID NO 435
<211> LENGTH: 42
<212> TYPE: DNA
<213> ORGANISM: Artificial sequence
<220> FEATURE:
<223> OTHER INFORMATION: Synthetic antibody

<400> SEQUENCE: 435
gcgagagctg ggggaatcca ttactatgat agtttagact ac                                  42

<210> SEQ ID NO 436
<211> LENGTH: 18
<212> TYPE: DNA
<213> ORGANISM: Artificial sequence
<220> FEATURE:
<223> OTHER INFORMATION: Synthetic antibody

<400> SEQUENCE: 436
cagagcatta gcagctat                                                             18

<210> SEQ ID NO 437
<211> LENGTH: 9
<212> TYPE: DNA
<213> ORGANISM: Artificial sequence
<220> FEATURE:
<223> OTHER INFORMATION: Synthetic antibody

<400> SEQUENCE: 437 gctgcatcc                                                                        9

<210> SEQ ID NO 438
<211> LENGTH: 27
<212> TYPE: DNA
<213> ORGANISM: Artificial sequence
<220> FEATURE:
<223> OTHER INFORMATION: Synthetic antibody

<400> SEQUENCE: 438
caacagagtt acagtacccc tctgacg                                                   27

<210> SEQ ID NO 439
<211> LENGTH: 24
<212> TYPE: DNA
<213> ORGANISM: Artificial sequence
<220> FEATURE:
<223> OTHER INFORMATION: Synthetic antibody

<400> SEQUENCE: 439
ggattcacct tcgcgaatgc ctgg                                                      24

<210> SEQ ID NO 440
<211> LENGTH: 30
<212> TYPE: DNA
<213> ORGANISM: Artificial sequence
<220> FEATURE:
<223> OTHER INFORMATION: Synthetic antibody

<400> SEQUENCE: 440
attaagccca gttctagcgg cgggaggaca                                                30

<210> SEQ ID NO 441
<211> LENGTH: 39

-continued

```
<212> TYPE: DNA
<213> ORGANISM: Artificial sequence
<220> FEATURE:
<223> OTHER INFORMATION: Synthetic antibody

<400> SEQUENCE: 441
tgtgtcacag gaagaagggt cgcgaagact tttgatttc                          39

<210> SEQ ID NO 442
<211> LENGTH: 18
<212> TYPE: DNA
<213> ORGANISM: Artificial sequence
<220> FEATURE:
<223> OTHER INFORMATION: Synthetic antibody

<400> SEQUENCE: 442
cagagcatta gcagctat                                                 18

<210> SEQ ID NO 443
<211> LENGTH: 9
<212> TYPE: DNA
<213> ORGANISM: Artificial sequence
<220> FEATURE:
<223> OTHER INFORMATION: Synthetic antibody

<400> SEQUENCE: 443 gctgcatcc                                                            9

<210> SEQ ID NO 444
<211> LENGTH: 27
<212> TYPE: DNA
<213> ORGANISM: Artificial sequence
<220> FEATURE:
<223> OTHER INFORMATION: Synthetic antibody

<400> SEQUENCE: 444
caacagagtt acagtacccc tcggacg                                       27

<210> SEQ ID NO 445
<211> LENGTH: 357
<212> TYPE: DNA
<213> ORGANISM: Artificial sequence
<220> FEATURE:
<223> OTHER INFORMATION: Synthetic antibody

<400> SEQUENCE: 445
gaggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggaca aatccacgag cacagcctac   240
atggagctga gcagcctgag atctgaggac acggccgtgt attactgtgc gaggggggaat   300 cagggggata cggctttttga tatctggggc caagggacca cggtcatcgt ctcctca      357

<210> SEQ ID NO 446
<211> LENGTH: 357
<212> TYPE: DNA
<213> ORGANISM: Artificial sequence
<220> FEATURE:
<223> OTHER INFORMATION: Synthetic antibody

<400> SEQUENCE: 446
caggtgcagc tggtgcagtc tggagctgag gtgaagaagc ctggggcctc agtgaaggtc    60
```
tcctgcaagg cttctggtta caccttttagc gactatggtt tcagctgggt gcgacaggcc        120
cctggacaag ggcttgagtg gatgggatgg atcagtggtt acaatggtaa cacaaactat        180
gcacagaagt tccagggcag agtcaccatg accatagacg catccacgag cacagcctac        240
atggagctga ggagcctgaa atctgacgac acggccgtgt attactgtgc gagattgctg        300
ctgggttact acggtatgga cgtctggggc caagggacca cggtcaccgt ctcctca          357

<210> SEQ ID NO 447
<211> LENGTH: 363
<212> TYPE: DNA
<213> ORGANISM: Artificial sequence
<220> FEATURE:
<223> OTHER INFORMATION: Synthetic antibody

<400> SEQUENCE: 447
caggtgcagc tggtgcagtc tggagctgag gtgaagaagc ctggggcctc agtgaaggtc         60
tcctgcagga cttctggtta cacgtttagc agctatggta tcagctgggt gcgacaggcc        120
cctggacaag ggcttgagtg gatgggatgg atcagtggta acactggtaa cacaaagtat        180
acaccgaagc tccaaggcag agtcaccatg accacagaca catccacgag cacagcctac        240
atggagctga ggagcctgag atctgacgac acggccgtgt attactgtgc gagagatcgt        300
ggtatagcgg caggccgtgc tttttgatatc tggggccaag ggacaatggt caccgtctct        360
tca                                                                       363

<210> SEQ ID NO 448
<211> LENGTH: 351
<212> TYPE: DNA
<213> ORGANISM: Artificial sequence
<220> FEATURE:
<223> OTHER INFORMATION: Synthetic antibody

<400> SEQUENCE: 448
caggtgcagc tggtgcagtc tggacccacg gtgaggaagc ctggggcctc agtgagggtc         60
tcctgcaagg cttctggtta cccctttacc agcaatggta tgagctgggt gcggcaggcc        120
cctggacaag gacttgagtg gatgggatgg atcagcacta acagcggaaa cacaaactat        180
gcgcagaaat ttcagggcag agtcaccttg accacagaca catcctcgac cactacgtac        240
ctggatctga ggagcctgac atctgacgac acggccatat attactgtgc gagagatgtt        300
caatatcgta tggacgtctg gggccaaggg accacggtca ccgtctcttc a                351

<210> SEQ ID NO 449
<211> LENGTH: 387
<212> TYPE: DNA
<213> ORGANISM: Artificial sequence
<220> FEATURE:
<223> OTHER INFORMATION: Synthetic antibody

<400> SEQUENCE: 449
gaggtgcagc tggtggagtc tgggggaggc gtggtccagc ccgggaggtc cctgagactc         60
tcctgtgcag cctctggatt caccatcagc agttatggca tgcactgggt ccgccaggct        120
ccaggcaagg ggctggagtg ggtggcagtt atatcatatg atggaagtaa taaatactat        180
gcagactccg tgaagggccg attcaccatc tccagagaca attccaagaa cacgctgtat        240
ctgcaaatga acagcctgag agttgaggac acggctgtgt attactgtgc gaaagatctc        300
ttattacgat attttgactg gagccccaaa tactactaca cggtatgga cgtctggggc         360 caagggacaa tggtcaccgt ctcctca                                             387

```
<210> SEQ ID NO 450
<211> LENGTH: 357
<212> TYPE: DNA
<213> ORGANISM: Artificial sequence
<220> FEATURE:
<223> OTHER INFORMATION: Synthetic antibody

<400> SEQUENCE: 450
caggtgcagc tggtgcaatc tgggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagagtggca     300
gtggctgaca ccttctttga ctactggggc cagggaaccc tggtcaccgt ctcctca        357

<210> SEQ ID NO 451
<211> LENGTH: 348
<212> TYPE: DNA
<213> ORGANISM: Artificial sequence
<220> FEATURE:
<223> OTHER INFORMATION: Synthetic antibody

<400> SEQUENCE: 451
caggtgcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagagacggc     300
tacggtatgg acgtctgggg ccaagggacc acggtcaccg tctcctca                 348

<210> SEQ ID NO 452
<211> LENGTH: 366
<212> TYPE: DNA
<213> ORGANISM: Artificial sequence
<220> FEATURE:
<223> OTHER INFORMATION: Synthetic antibody

<400> SEQUENCE: 452
caggtgcagc tggtgcagtc tggggggaggc ttggtccagc ctggggggtc cctgagactc      60
tcctgtgcag cctctggatt cacctttagc agctatgcca tgagctgggt ccgccaggct     120
ccagggaagg ggctggagtg ggtctcaact attaatgata gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaagatcat     300
attacgattt ttggagtggc cccgtttgac tactggggcc tgggaaccct ggtcaccgtc     360
tcctca                                                              366

<210> SEQ ID NO 453
<211> LENGTH: 372
<212> TYPE: DNA
<213> ORGANISM: Artificial sequence
<220> FEATURE:
<223> OTHER INFORMATION: Synthetic antibody

<400> SEQUENCE: 453
```

-continued

```
caggtgcagc tacagcagtc aggtccagga ctggtgaagc cctcgcagac cctctcactc        60
acctgtgcca tctccgggga cagtgtctct agcaacagtg ctgcttggaa ctggatcagg       120
cagtccccat cgagaggcct tgagtggctg ggaaggacat actacaggtc caagtggtat       180
aatgattatg cagtatctgt gaaaagtcga ataaccatca acccagacac atccaagaac       240
cagttctccc tgcagctgaa ctctgtgact cccgaggaca cggctgtgta ttactgtgca       300
agacaagatg aatcggcagc cgatgatgct tttgatatct ggggccaagg aaccctggtc       360
atcgtctcct ca                                                           372

<210> SEQ ID NO 454
<211> LENGTH: 351
<212> TYPE: DNA
<213> ORGANISM: Artificial sequence
<220> FEATURE:
<223> OTHER INFORMATION: Synthetic antibody

<400> SEQUENCE: 454
caggtgcagc tggtgcagtc tggagatgag gtgaagaagg ctggggcctc agtgagggtc        60
tcctgcaagg cttctggtta cacgtttccc gacaacggta tcagttgggt gcgacaggcc       120
cctggacacg ggcttgagtg gatgggttgg atcaacgttg acactggata cacccactat       180
gcacagaggg tccaggacag agtcgtcatg accacagaca cgtccacgaa cacactccac       240
atgacattga ggagcctgac aacggacgac acggccgttt attattgtgc gagagaaatc       300
gagggagtgt ggacagcttg gggccaggga accctggtca tcgtctcctc a               351

<210> SEQ ID NO 455
<211> LENGTH: 357
<212> TYPE: DNA
<213> ORGANISM: Artificial sequence
<220> FEATURE:
<223> OTHER INFORMATION: Synthetic antibody

<400> SEQUENCE: 455
caggtgcagc tggtgcagtc tggggctgag gtgaagaagc ctgggtcctc ggtgaaggtc        60
tcctgcaagg cttctggagg caccttcagc agctatgcta tcagctgggt gcgacaggcc       120
cctggacaag ggcttgagtg gatgggaggg atcatcccta tctttggtac agcaaactac       180
gcacagaagt tccagggcag agtcacgatt accgcggacg aatccacgag cacagcctac       240
atggagctga gcagcctgag atctgaggac acggccgtgt attactgtgc gaggtcggac       300
tacggtgact cctactttga ctactggggc cagggaaccc tggtcagcgt ctcctca         357

<210> SEQ ID NO 456
<211> LENGTH: 357
<212> TYPE: DNA
<213> ORGANISM: Artificial sequence
<220> FEATURE:
<223> OTHER INFORMATION: Synthetic antibody

<400> SEQUENCE: 456
caggtgcagc tggtgcagtc tggggctgag gtgaagaagc ctgggtcctc ggtgaaggtc        60
tcctgcaagg cttctggagg caccttcagc agctatgcta tcagctgggt gcgacaggcc       120
cctggacaag ggcttgagtg gatgggaggg atcatcccta tctttggtac agcaaactac       180
gcacagaagt tccagggcag agtcacgatt accgcggacg aatccacgag cacagcctac       240
atggagctga gcagcctgag atctgaggac acggccgtgt attactgtgc gagagcctct       300
atggtcgaga cttactttga ctactggggc cagggaacca tggtcaccgt ctcttca         357
```

-continued

```
<210> SEQ ID NO 457
<211> LENGTH: 384
<212> TYPE: DNA
<213> ORGANISM: Artificial sequence
<220> FEATURE:
<223> OTHER INFORMATION: Synthetic antibody

<400> SEQUENCE: 457
gaggtgcagc tggtgcagtc tggagctgag gtgaagaagt ctggggcctc agtgaaggtc      60
tcctgcaagt cttctggtta cacctttacc aactatggta tcagttgggt gcgacaagcc     120
ccgggacaag ggcttgagtg gatgggctgg atcagcggtg acgctggtga cacaaaattt     180
gcacagaagt tccagggcag agtcaccatg acgacagaca catccacgac tacaacgtac     240
atggagctga ggagcctgag atctgacgac acggccgtgt attactgtgc gagagatggg     300
gaatatattc ctatgtttcg gggatttgac aactactacg gtctggacgt ctggggccaa     360
gggaccctgg tcagcgtctc ctca                                           384

<210> SEQ ID NO 458
<211> LENGTH: 363
<212> TYPE: DNA
<213> ORGANISM: Artificial sequence
<220> FEATURE:
<223> OTHER INFORMATION: Synthetic antibody

<400> SEQUENCE: 458
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagcgggatt     300
atacctgata tccctacgg tatggacgtc tggggccaag gacaatggt cagcgtctcc      360 tca                                                                  363

<210> SEQ ID NO 459
<211> LENGTH: 366
<212> TYPE: DNA
<213> ORGANISM: Artificial sequence
<220> FEATURE:
<223> OTHER INFORMATION: Synthetic antibody

<400> SEQUENCE: 459
gaggtgcagc tgttggactc gggcccacga ctgttgaagc cttcggagac cctgtccctc      60
acctgcggtg tgtcaggtgt ctccaccagc agtactcatt ggtggagttg ggtccgccag     120
accccaggga aggggctgga gtggattggt gaaatccttc ataatggaaa caccaactcc     180
aatccgtccc tcaagagtcg agtctccatg tcgattgaca gtcgaggaa ccaattctcc      240 ctacaactga gtctatgac cgccgcggac acggccgtct actactgtgc gtcagcgtcg     300
cctaactggg gagctagcgg ggcttttgat gcctgggccc aagggacaat ggtcaccgtc     360
tcctca                                                               366

<210> SEQ ID NO 460
<211> LENGTH: 354
<212> TYPE: DNA
<213> ORGANISM: Artificial sequence
<220> FEATURE:
```

<223> OTHER INFORMATION: Synthetic antibody

<400> SEQUENCE: 460
caggtgcagc tggtgcagtc tggagctgag gtgaagaagc ctggggcctc agtgaaggtc       60
tcctgcaagg cttctggtta cacctttacc aggtatggtt tcagctgggt gcgacaggcc      120
cctggacaag ggcttgagtg gatgggatgg atcagcggtt acaatggtaa tacaaagtat      180
gcacagaagt tccagggcag agtcaccatg actacagaca catctacgag cacagcctac      240
atggagctga ggagcctaac atctaacgac acggccgttt attactgtgc gagagatcgg      300
ggtagtggtt atcttgaata ctggggcccg ggaaccctgg tcaccgtctc ttca           354

<210> SEQ ID NO 461
<211> LENGTH: 375
<212> TYPE: DNA
<213> ORGANISM: Artificial sequence
<220> FEATURE:
<223> OTHER INFORMATION: Synthetic antibody

<400> SEQUENCE: 461
caggtgcagc tggtgcagtc tggggggaggc ttggtaaagc ctggggggtc ccttagactc      60
tcctgtgcag cctctggatt cactttcagt aacgcctgga tgagctgggt ccgccaggct      120
ccagggaagg ggctggagtg ggttggccgt attaaaagca aaactgatgg tgggacaaca      180
gactacgctg cacccgtgaa aggcagattc accatctcaa gagatgattc aaaaaacacg      240
ctgtatctgc aaatgaacag cctgaaaacc gaggacacag ccgtgtatta ctgtaccaca      300
gatcgatata gcagcagctg gtactcccct gcttttgata tctggggcca agggacaacg      360
gtcagcgtct cctca                                                       375

<210> SEQ ID NO 462
<211> LENGTH: 348
<212> TYPE: DNA
<213> ORGANISM: Artificial sequence
<220> FEATURE:
<223> OTHER INFORMATION: Synthetic antibody

<400> SEQUENCE: 462
caggtgcagc tggtgcagtc tggagctgag gtgaagaagc ctggggcctc agtgaaggtc       60
tcctgcaagg cttctggtta cacctttacc agctatggta tcagctgggt gcgacaggcc      120
cctggacaag ggcttgagtg gatgggatgg atcagcgctt acaatggtaa cacaaactat      180
gcacagaagc tccagggcag agtcaccatg accacagaca catccacgag cacagcctac      240
atggagctga ggagcctgag atctgacgac acggccgtgt attactgtgc gagagtgggc      300
agctatggtg actactgggg ccagggaacc ctggtcaccg tctcctca                  348

<210> SEQ ID NO 463
<211> LENGTH: 363
<212> TYPE: DNA
<213> ORGANISM: Artificial sequence
<220> FEATURE:
<223> OTHER INFORMATION: Synthetic antibody

<400> SEQUENCE: 463
caggtgcagc tggtgcagtc tgggggctgag gtgaagaagc ctggggcctc agtgaaggtt       60
tcctgcaagg catctgggta caccttcacc cactcctata tacactgggt gcgccaggcc      120
cctggacaag ggcttgagtg gatgggagta atcaaccctg ttggtggtag cacaacctac      180
gcacagaggt tccagggcag agtcaccatg accagggaca cgtccacgag cacagtctac      240

```
atggagctga gcagcctgag atctgaggac acggccgtgt attactgtgc tagagcgggg    300
ggagatggct acaatcctta ctttgactac tggggccagg gaaccctggt caccgtctcc    360
tca                                                                   363
```

```
<210> SEQ ID NO 464
<211> LENGTH: 354
<212> TYPE: DNA
<213> ORGANISM: Artificial sequence
<220> FEATURE:
<223> OTHER INFORMATION: Synthetic antibody

<400> SEQUENCE: 464
caggtgcagc tggtggagtc tgggggaggc ttggtcaagc ctggagggtc cctgagactc     60
tcctgtgcag cctctggatt caccttcagt gactactaca tgagctggat ccgccaggct    120
ccagggaagg ggctggagtg ggtttcatac attagtagta gtagtagtta cacaaactac    180
gcagactctg tgaagggccg attcaccatc tccagagaca cgccaagaa ctcactgtat     240 ctgcaaatga acagcctgag agccgaggac acggccgtgt attactgtgc gagagtcgga    300
gatcttgatg cttttgatat ctggggccaa gggacaatgg tcaccgtctc ttca          354
```

```
<210> SEQ ID NO 465
<211> LENGTH: 360
<212> TYPE: DNA
<213> ORGANISM: Artificial sequence
<220> FEATURE:
<223> OTHER INFORMATION: Synthetic antibody

<400> SEQUENCE: 465
caggtgcagc tggtggagtc tgggggaggc ttggtcaagc ctggagggtc cctgagactc     60
tcctgtgcag cctctggatt caccttcagt gaccactaca tgagctggat ccgccaggct    120
ccaggaaagg ggctggagtg ggtttcatac attactacta ctggtagtac catgtcctac    180
gcagactctg tgaagggccg cttcaccatt tccagggaca actccaagaa ctcactgcat    240
ctgcaattga gcagcctgag agccgaggac acggccgtat attactgtgc gagagattcc    300
atacatgtgg atggtgcttt tgatatttgg ggccaaggga caatggtcac cgtctcctca    360
```

```
<210> SEQ ID NO 466
<211> LENGTH: 351
<212> TYPE: DNA
<213> ORGANISM: Artificial sequence
<220> FEATURE:
<223> OTHER INFORMATION: Synthetic antibody

<400> SEQUENCE: 466
caggtgcagc tggtgcagtc tggagctgag gtgaagaagc ctgggggcctc agtgaaggtc    60 tcctgcaagg cttctggtta cacctttacc agctatggta tcagctgggt gcgacaggcc    120
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagagatcgg    300
ggagggtggt cgacccctg gggccaggga accctggtca tcgtctcctc a              351
```

```
<210> SEQ ID NO 467
<211> LENGTH: 357
<212> TYPE: DNA
<213> ORGANISM: Artificial sequence
<220> FEATURE:
```

-continued

<223> OTHER INFORMATION: Synthetic antibody

<400> SEQUENCE: 467

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagagagtcg     300
tatagcagct cgtcctttga ctactggggc cagggaacca cggtcagcgt ctcctca        357
```

```
<210> SEQ ID NO 468
<211> LENGTH: 372
<212> TYPE: DNA
<213> ORGANISM: Artificial sequence
<220> FEATURE:
<223> OTHER INFORMATION: Synthetic antibody
```

<400> SEQUENCE: 468

```
caggtgcagc tggtggagtc tggggggaggc ttggtacagc ctgggggggtc cctgagactc      60 tcctgtgcag cctctggatt caccttcagt agctacgaca tgcactgggt ccgccaagct     120
acaggaaaag gtctggagtg ggtctcagct attggtactg ctggtgacac atactatcca     180
ggctccgtga agggccgatt caccatctcc agagaaaatg ccaagaactc cttgtatctt     240
caaatgaaca gcctgagagc cggggacacg gctgtgtatt actgtgcaag ggcgaaggaa     300
tattgtagtg gtggtagctg ccaagatgct tttgatatct ggggccaagg gacaatggtc     360
agcgtctcct ca                                                         372
```

```
<210> SEQ ID NO 469
<211> LENGTH: 369
<212> TYPE: DNA
<213> ORGANISM: Artificial sequence
<220> FEATURE:
<223> OTHER INFORMATION: Synthetic antibody
```

<400> SEQUENCE: 469

```
gaagtgcagc tggtgcagtc tggggctgag gtgaagaagc ctggggcctc agtgaaggtt      60
gcctgcaagg catctgggta caccttcacc gactattata tacactgggt gcgacaggcc     120
cctggacaag ggcttgagtg gatgggaata gtcaacgcta atggtggtga cacaaactac     180
gcacaacagt tccagggcag agtcaccatg accaggggaca cgtccacgag cacagtctat     240
ttggagttga ccagcctgag atctgacgac acggccgtat attactgtgc tagagattgg     300
tattactatt cttcggggag tttccctttt gactactggg gccagggaac cctggtcagc     360
gtctcctca                                                              369
```

```
<210> SEQ ID NO 470
<211> LENGTH: 369
<212> TYPE: DNA
<213> ORGANISM: Artificial sequence
<220> FEATURE:
<223> OTHER INFORMATION: Synthetic antibody
```

<400> SEQUENCE: 470

```
gaagtgcagc tggtgcagtc tggggctgag gtgaagaagc ctggggcctc agtgaaggtt      60
gcctgcaagg catctgggta caccttcacc gactattata tacactgggt gcgacaggcc     120
cctggacaag ggcttgagtg gatgggaata gtcaacgcta atggtggtga cacaaactac     180
```

-continued

```
gcacaacagt tccagggcag agtcaccatg accagggaca cgtccacgag cacagtctat    240
ttggagttga ccagcctgag atctgacgac acggccgtat attactgtgc tagagattgg    300
tattactatt cttcggggag tttcccttt gactactggg gccagggaac cctggtcagc      360
gtctcctca                                                             369

<210> SEQ ID NO 471
<211> LENGTH: 354
<212> TYPE: DNA
<213> ORGANISM: Artificial sequence
<220> FEATURE:
<223> OTHER INFORMATION: Synthetic antibody

<400> SEQUENCE: 471
caggtgcagc tggtgcagtc tggagctgag gtgaagaagc ctgggggcctc agtgaaggtc    60 tcctgcaagg cttctggtta catcttcaac acctatggta tcagttgggt gcgacaggcc    120
cctggacaag gacttgagtg gatgggatgg accaacgttt acaatagtaa cacagacagt    180
ggacacaagt tccagggcag agtcaccatg accacagaca catccacgga cacagcctac    240
atggaactga ggagcctgag atctgacgac acggccgtgt attactgtgc gagagacccg    300
ggctcggcta tttttgatat gtggggccaa gggacaatgg tcaccgtctc ctca           354

<210> SEQ ID NO 472
<211> LENGTH: 351
<212> TYPE: DNA
<213> ORGANISM: Artificial sequence
<220> FEATURE:
<223> OTHER INFORMATION: Synthetic antibody

<400> SEQUENCE: 472
caggtggagc tgcaggagtc gggcccagga ctggtgaagc cttcggagac cctgtccctc     60
acttgcactg tctctggtga cgccatcaaa gataagtact ggagttgggt ccggcagccc    120
ccagggaagg gactggagtg gattggctac atctctaaca gtggaagcac caactacaac    180 ccctcccta agagtcgagt cagtctatca gtagacacgt ccaagaatca gttctccctg      240
aagcagacct ctgtgaccgc tgcggacacg gccacatatt actgtgcgag aggcagcggt    300
tatactgctt ttgatatctg gggccaaggg acaatggtca ccgtctcctc a              351

<210> SEQ ID NO 473
<211> LENGTH: 363
<212> TYPE: DNA
<213> ORGANISM: Artificial sequence
<220> FEATURE:
<223> OTHER INFORMATION: Synthetic antibody

<400> SEQUENCE: 473
caggtgcagc tggtggagtc tggggggaggc ttggtacagc ctgggggtc cctgagactc     60 tcctgtgcag cctctggatt caccttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaagatgtc    300
gacccctata gtagtggtta ttttgactac tggggccagg gaaccctggt catcgtctcc    360
tca                                                                   363

<210> SEQ ID NO 474
```

```
<211> LENGTH: 351
<212> TYPE: DNA
<213> ORGANISM: Artificial sequence
<220> FEATURE:
<223> OTHER INFORMATION: Synthetic antibody

<400> SEQUENCE: 474
caggtgcagc tggtggagtc tggggggaggc ttggtacagc ctgggggggtc cctgagactc        60 tcctgtgcag cctctggatt caccttttagc aactatgcca tgagctgggt ccgccaggct       120
ccagggaagg ggctggagtg ggtctcagcc attagtggta gtagtattag cacatactac       180
gcagactccg tgaagggccg gttcaccatc tccagagaca attccaagaa cacgcttttat      240 ctgcaaatga acagcctgag agccgaggac acggccgtat attactgtgc gtcctcgggt       300
ttcgggtcct ttgactactg gggccagggc accctggtca ccgtctcttc a                351

<210> SEQ ID NO 475
<211> LENGTH: 354
<212> TYPE: DNA
<213> ORGANISM: Artificial sequence
<220> FEATURE:
<223> OTHER INFORMATION: Synthetic antibody

<400> SEQUENCE: 475
caggtgcagc tggtggagtc tggggggaggc ttggtacagc ctgggggggtc cctgagactc        60 tcctgtgcag cctctggatt caccttaagt agctatgcca tgagctgggt ccgccaggct       120
ccaggggagg ggctggagtg ggtctcaagt attaatagtg gtggtagcac atactacgca       180
ggctccgtga ggggccggtt caccatctcc agagacaatt ccaagaacac gttgtatctg       240
caaatgaaca gcctgagagc cgaggacacg gccgtatatt actgtgcgaa agcgaagagt       300
tatagcagtg accttgacca ctggggccag ggaaccacgg tcaccgtctc ttca             354

<210> SEQ ID NO 476
<211> LENGTH: 369
<212> TYPE: DNA
<213> ORGANISM: Artificial sequence
<220> FEATURE:
<223> OTHER INFORMATION: Synthetic antibody

<400> SEQUENCE: 476
caggtgcaga tggtggagtc tggggggaggc ttggtacagc ctgggggggtc cctgagactc        60 tcctgtgcag cctctggatt caccttttagc agctatgcca tgagctgggt ccgccaggct       120
ccagggaagg ggctggagtg ggtctcagct attagtggta gtggtggtag cacatactac       180
gcagactccg tgaagggccg gttcaccatc tccagagaca attccaagaa cacgctgtat       240
ctgcaaatga acagcctgag agccgaggac acggccgtat attactgtgc gaaagatctt       300
ctcggggata gtgggagcta ccctgctttt gatatctggg gccaagggac aatggtcacc       360
gtctcttca                                                                 369

<210> SEQ ID NO 477
<211> LENGTH: 351
<212> TYPE: DNA
<213> ORGANISM: Artificial sequence
<220> FEATURE:
<223> OTHER INFORMATION: Synthetic antibody

<400> SEQUENCE: 477
caggtgcaga tggtggagtc tggggggagac ttggtacagc caggggcaatc cctgagactc        60 tcctgtgtaa cttctggatt cccctttgcg gactatgcta tgagctggtt ccgccaggct       120
```

```
ccagggcagc ggccggagtg gataggttac attaaaagca agactagaga tgggacaaca    180
aaatacgccg agtctctgcg aggcagattc accatctcaa gagatgattc caaaagcatc    240
gcctatctac aaatgaacaa cttaaaaagg gaagacacag ccgtctatta ctgtgccctc    300
gggggagcag cagctctatg gggcccggga accctggtca gcgtctcctc a    351

<210> SEQ ID NO 478
<211> LENGTH: 360
<212> TYPE: DNA
<213> ORGANISM: Artificial sequence
<220> FEATURE:
<223> OTHER INFORMATION: Synthetic antibody

<400> SEQUENCE: 478
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gattagtagt    300
ggttattatt ataacccatt tgactactgg ggccagggaa ccctggtcac cgtctcctca    360

<210> SEQ ID NO 479
<211> LENGTH: 351
<212> TYPE: DNA
<213> ORGANISM: Artificial sequence
<220> FEATURE:
<223> OTHER INFORMATION: Synthetic antibody

<400> SEQUENCE: 479
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaggggga    300
taccagccac tggattactg gggccaggga accctggtca tcgtctcctc a    351

<210> SEQ ID NO 480
<211> LENGTH: 363
<212> TYPE: DNA
<213> ORGANISM: Artificial sequence
<220> FEATURE:
<223> OTHER INFORMATION: Synthetic antibody

<400> SEQUENCE: 480
caaatgcagc tggagcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggaca aatccacgag cacagcctac    240
atggagctga gcagcctgag atctgaggac acggccgtgt attactgtgc gagagctggg    300
ggaatccatt actatgatag tttagactac tggggccagg gaaccctggt caccgtctcc    360
tca                                                                   363

<210> SEQ ID NO 481
```

```
<211> LENGTH: 366
<212> TYPE: DNA
<213> ORGANISM: Artificial sequence
<220> FEATURE:
<223> OTHER INFORMATION: Synthetic antibody

<400> SEQUENCE: 481
caggtgcagc tggtggagtc tggggggaggc ttggtaaagc cggggggggtc tctaagactc      60 tcctgtgcag cctctggatt caccttcgcg aatgcctgga tgggctgggt tcgccaggct     120
ccagggaagg ggctgcagtg ggtatcccat attaagccca gttctagcgg cgggaggaca     180
acagactacg atgcacccgt gaaaggccga ttcaccatct caagagatga ttcaaacgac     240
acggtgtatc tgcaaatgaa cagcctcaag accgaagaca caggcgtcta ttactgtgtc     300
acaggaagaa gggtcgcgaa gactttgat ttctggggcc aggggacaac ggtcagcgtc     360
tcctca                                                             366

<210> SEQ ID NO 482
<211> LENGTH: 119
<212> TYPE: PRT
<213> ORGANISM: Artificial sequence
<220> FEATURE:
<223> OTHER INFORMATION: Synthetic antibody

<400> SEQUENCE: 482

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Gln Gly Asp Thr Ala Phe Asp Ile Trp Gly Gln Gly
            100                 105                 110

Thr Thr Val Ile Val Ser Ser
        115

<210> SEQ ID NO 483
<211> LENGTH: 119
<212> TYPE: PRT
<213> ORGANISM: Artificial sequence
<220> FEATURE:
<223> OTHER INFORMATION: Synthetic antibody

<400> SEQUENCE: 483

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Gly Phe Ser Trp Val Arg Gln Ala Pro Gly Gln Gly Leu Glu Trp Met
        35                  40                  45

Gly Trp Ile Ser Gly Tyr Asn Gly Asn Thr Asn Tyr Ala Gln Lys Phe
    50                  55                  60

Gln Gly Arg Val Thr Met Thr Ile Asp Ala Ser Thr Ser Thr Ala Tyr
```

-continued

```
65                70                75                80
Met Glu Leu Arg Ser Leu Lys Ser Asp Asp Thr Ala Val Tyr Tyr Cys
                 85                90                95
Ala Arg Leu Leu Leu Gly Tyr Tyr Gly Met Asp Val Trp Gly Gln Gly
                 100               105               110
Thr Thr Val Thr Val Ser Ser
                 115

<210> SEQ ID NO 484
<211> LENGTH: 121
<212> TYPE: PRT
<213> ORGANISM: Artificial sequence
<220> FEATURE:
<223> OTHER INFORMATION: Synthetic antibody

<400> SEQUENCE: 484

Gln Val Gln Leu Val Gln Ser Gly Ala Glu Val Lys Lys Pro Gly Ala
1                5                 10                15
Ser Val Lys Val Ser Cys Arg Thr Ser Gly Tyr Thr Phe Ser Ser Tyr
                 20                25                30
Gly Ile Ser Trp Val Arg Gln Ala Pro Gly Gln Gly Leu Glu Trp Met
           35                40                45
Gly Trp Ile Ser Gly Asn Thr Gly Asn Thr Lys Tyr Thr Pro Lys Leu
      50                55                60
Gln Gly Arg Val Thr Met Thr Thr Asp Thr Ser Thr Ser Thr Ala Tyr
65                70                75                80
Met Glu Leu Arg Ser Leu Arg Ser Asp Asp Thr Ala Val Tyr Tyr Cys
                 85                90                95
Ala Arg Asp Arg Gly Ile Ala Ala Gly Arg Ala Phe Asp Ile Trp Gly
                 100               105               110
Gln Gly Thr Met Val Thr Val Ser Ser
           115               120

<210> SEQ ID NO 485
<211> LENGTH: 117
<212> TYPE: PRT
<213> ORGANISM: Artificial sequence
<220> FEATURE:
<223> OTHER INFORMATION: Synthetic antibody

<400> SEQUENCE: 485

Gln Val Gln Leu Val Gln Ser Gly Pro Thr Val Arg Lys Pro Gly Ala
1                5                 10                15
Ser Val Arg Val Ser Cys Lys Ala Ser Gly Tyr Pro Phe Thr Ser Asn
                 20                25                30
Gly Met Ser Trp Val Arg Gln Ala Pro Gly Gln Gly Leu Glu Trp Met
           35                40                45
Gly Trp Ile Ser Thr Asn Ser Gly Asn Thr Asn Tyr Ala Gln Lys Phe
      50                55                60
Gln Gly Arg Val Thr Leu Thr Thr Asp Thr Ser Ser Thr Thr Thr Tyr
65                70                75                80
Leu Asp Leu Arg Ser Leu Thr Ser Asp Asp Thr Ala Ile Tyr Tyr Cys
                 85                90                95
Ala Arg Asp Val Gln Tyr Arg Met Asp Val Trp Gly Gln Gly Thr Thr
           100               105               110
Val Thr Val Ser Ser
           115
```

<210> SEQ ID NO 486
<211> LENGTH: 129
<212> TYPE: PRT
<213> ORGANISM: Artificial sequence
<220> FEATURE:
<223> OTHER INFORMATION: Synthetic antibody

<400> SEQUENCE: 486

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Ile Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Leu Leu Leu Arg Tyr Phe Asp Trp Ser Pro Lys Tyr Tyr
                100                 105                 110

Tyr Asn Gly Met Asp Val Trp Gly Gln Gly Thr Met Val Thr Val Ser
            115                 120                 125

Ser
```

<210> SEQ ID NO 487
<211> LENGTH: 119
<212> TYPE: PRT
<213> ORGANISM: Artificial sequence
<220> FEATURE:
<223> OTHER INFORMATION: Synthetic antibody

<400> SEQUENCE: 487

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ala Val Ala Asp Thr Phe Phe Asp Tyr Trp Gly Gln Gly
                100                 105                 110

Thr Leu Val Thr Val Ser Ser
            115
```

<210> SEQ ID NO 488
<211> LENGTH: 116
<212> TYPE: PRT
<213> ORGANISM: Artificial sequence
<220> FEATURE:
<223> OTHER INFORMATION: Synthetic antibody

<400> SEQUENCE: 488

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Tyr Gly Met Asp Val Trp Gly Gln Gly Thr Thr Val
            100                 105                 110

Thr Val Ser Ser
        115
```

```
<210> SEQ ID NO 489
<211> LENGTH: 122
<212> TYPE: PRT
<213> ORGANISM: Artificial sequence
<220> FEATURE:
<223> OTHER INFORMATION: Synthetic antibody

<400> SEQUENCE: 489
```

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Asn Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp His Ile Thr Ile Phe Gly Val Ala Pro Phe Asp Tyr Trp
            100                 105                 110

Gly Leu Gly Thr Leu Val Thr Val Ser Ser
        115                 120
```

```
<210> SEQ ID NO 490
<211> LENGTH: 124
<212> TYPE: PRT
<213> ORGANISM: Artificial sequence
<220> FEATURE:
<223> OTHER INFORMATION: Synthetic antibody

<400> SEQUENCE: 490
```

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
```

-continued

```
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Asp Glu Ser Ala Ala Asp Asp Ala Phe Asp
            100                 105                 110

Ile Trp Gly Gln Gly Thr Leu Val Ile Val Ser Ser
        115                 120

<210> SEQ ID NO 491
<211> LENGTH: 117
<212> TYPE: PRT
<213> ORGANISM: Artificial sequence
<220> FEATURE:
<223> OTHER INFORMATION: Synthetic antibody

<400> SEQUENCE: 491

Gln Val Gln Leu Val Gln Ser Gly Asp Glu Val Lys Lys Ala Gly Ala
1                   5                   10                  15

Ser Val Arg Val Ser Cys Lys Ala Ser Gly Tyr Thr Phe Pro Asp Asn
                20                  25                  30

Gly Ile Ser Trp Val Arg Gln Ala Pro Gly His Gly Leu Glu Trp Met
            35                  40                  45

Gly Trp Ile Asn Val Asp Thr Gly Tyr Thr His Tyr Ala Gln Arg Val
        50                  55                  60

Gln Asp Arg Val Val Met Thr Thr Asp Thr Ser Thr Asn Thr Leu His
65                  70                  75                  80

Met Thr Leu Arg Ser Leu Thr Thr Asp Asp Thr Ala Val Tyr Tyr Cys
                85                  90                  95

Ala Arg Glu Ile Glu Gly Val Trp Thr Ala Trp Gly Gln Gly Thr Leu
            100                 105                 110

Val Ile Val Ser Ser
        115

<210> SEQ ID NO 492
<211> LENGTH: 119
<212> TYPE: PRT
<213> ORGANISM: Artificial sequence
<220> FEATURE:
<223> OTHER INFORMATION: Synthetic antibody

<400> SEQUENCE: 492

Gln Val Gln Leu Val Gln Ser Gly Ala Glu Val Lys Lys Pro Gly Ser
1                   5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Tyr Gly Asp Ser Tyr Phe Asp Tyr Trp Gly Gln Gly
            100                 105                 110
```

Thr Leu Val Ser Val Ser Ser
      115

<210> SEQ ID NO 493
<211> LENGTH: 119
<212> TYPE: PRT
<213> ORGANISM: Artificial sequence
<220> FEATURE:
<223> OTHER INFORMATION: Synthetic antibody

<400> SEQUENCE: 493

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Met Val Glu Thr Tyr Phe Asp Tyr Trp Gly Gln Gly
            100                 105                 110

Thr Met Val Thr Val Ser Ser
      115

<210> SEQ ID NO 494
<211> LENGTH: 128
<212> TYPE: PRT
<213> ORGANISM: Artificial sequence
<220> FEATURE:
<223> OTHER INFORMATION: Synthetic antibody

<400> SEQUENCE: 494

Glu Val Gln Leu Val Gln Ser Gly Ala Glu Val Lys Lys Ser Gly Ala
1               5                   10                  15

Ser Val Lys Val Ser Cys Lys Ser Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Gly Asp Ala Gly Asp Thr Lys Phe Ala Gln Lys Phe
    50                  55                  60

Gln Gly Arg Val Thr Met Thr Thr Asp Thr Ser Thr Thr Thr Thr Tyr
65                  70                  75                  80

Met Glu Leu Arg Ser Leu Arg Ser Asp Asp Thr Ala Val Tyr Tyr Cys
                85                  90                  95

Ala Arg Asp Gly Glu Tyr Ile Pro Met Phe Arg Gly Phe Asp Asn Tyr
            100                 105                 110

Tyr Gly Leu Asp Val Trp Gly Gln Gly Thr Leu Val Ser Val Ser Ser
        115                 120                 125

<210> SEQ ID NO 495
<211> LENGTH: 121
<212> TYPE: PRT
<213> ORGANISM: Artificial sequence
<220> FEATURE:
<223> OTHER INFORMATION: Synthetic antibody

<400> SEQUENCE: 495

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Ile Ile Pro Asp Asn Pro Tyr Gly Met Asp Val Trp Gly
            100                 105                 110

Gln Gly Thr Met Val Ser Val Ser Ser
        115                 120
```

<210> SEQ ID NO 496
<211> LENGTH: 122
<212> TYPE: PRT
<213> ORGANISM: Artificial sequence
<220> FEATURE:
<223> OTHER INFORMATION: Synthetic antibody

<400> SEQUENCE: 496

```
Glu Val Gln Leu Leu Asp Ser Gly Pro Arg Leu Leu Lys Pro Ser Glu
1               5                   10                  15

Thr Leu Ser Leu Thr Cys Gly Val Ser Gly Val Ser Thr Ser Ser Thr
            20                  25                  30

His Trp Trp Ser Trp Val Arg Gln Thr Pro Gly Lys Gly Leu Glu Trp
        35                  40                  45

Ile Gly Glu Ile Leu His Asn Gly Asn Thr Asn Ser Asn Pro Ser Leu
    50                  55                  60

Lys Ser Arg Val Ser Met Ser Ile Asp Lys Ser Arg Asn Gln Phe Ser
65                  70                  75                  80

Leu Gln Leu Lys Ser Met Thr Ala Ala Asp Thr Ala Val Tyr Tyr Cys
                85                  90                  95

Ala Ser Ala Ser Pro Asn Trp Gly Ala Ser Gly Ala Phe Asp Ala Trp
            100                 105                 110

Ala Gln Gly Thr Met Val Thr Val Ser Ser
        115                 120
```

<210> SEQ ID NO 497
<211> LENGTH: 118
<212> TYPE: PRT
<213> ORGANISM: Artificial sequence
<220> FEATURE:
<223> OTHER INFORMATION: Synthetic antibody

<400> SEQUENCE: 497

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Phe Ser Trp Val Arg Gln Ala Pro Gly Gln Gly Leu Glu Trp Met
        35                  40                  45
```

Gly Trp Ile Ser Gly Tyr Asn Gly Asn Thr Lys Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Thr Ser Asn Asp Thr Ala Val Tyr Tyr Cys
                85                  90                  95

Ala Arg Asp Arg Gly Ser Gly Tyr Leu Glu Tyr Trp Gly Pro Gly Thr
            100                 105                 110

Leu Val Thr Val Ser Ser
        115

<210> SEQ ID NO 498
<211> LENGTH: 125
<212> TYPE: PRT
<213> ORGANISM: Artificial sequence
<220> FEATURE:
<223> OTHER INFORMATION: Synthetic antibody

<400> SEQUENCE: 498

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Arg Tyr Ser Ser Ser Trp Tyr Ser Pro Ala Phe
            100                 105                 110

Asp Ile Trp Gly Gln Gly Thr Thr Val Ser Val Ser Ser
        115                 120                 125

<210> SEQ ID NO 499
<211> LENGTH: 116
<212> TYPE: PRT
<213> ORGANISM: Artificial sequence
<220> FEATURE:
<223> OTHER INFORMATION: Synthetic antibody

<400> SEQUENCE: 499

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Gly Ser Tyr Gly Asp Tyr Trp Gly Gln Gly Thr Leu Val
            100                 105                 110

Thr Val Ser Ser
        115

<210> SEQ ID NO 500
<211> LENGTH: 121
<212> TYPE: PRT
<213> ORGANISM: Artificial sequence
<220> FEATURE:
<223> OTHER INFORMATION: Synthetic antibody

<400> SEQUENCE: 500

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Ser
            20                  25                  30

Tyr Ile His Trp Val Arg Gln Ala Pro Gly Gln Gly Leu Glu Trp Met
        35                  40                  45

Gly Val Ile Asn Pro Val Gly Gly Ser Thr Thr Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Gly Gly Asp Gly Tyr Asn Pro Tyr Phe Asp Tyr Trp Gly
        100                 105                 110

Gln Gly Thr Leu Val Thr Val Ser Ser
        115                 120

<210> SEQ ID NO 501
<211> LENGTH: 118
<212> TYPE: PRT
<213> ORGANISM: Artificial sequence
<220> FEATURE:
<223> OTHER INFORMATION: Synthetic antibody

<400> SEQUENCE: 501

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Asp Leu Asp Ala Phe Asp Ile Trp Gly Gln Gly Thr
        100                 105                 110

Met Val Thr Val Ser Ser
        115

<210> SEQ ID NO 502
<211> LENGTH: 120
<212> TYPE: PRT
<213> ORGANISM: Artificial sequence
<220> FEATURE:
<223> OTHER INFORMATION: Synthetic antibody

<400> SEQUENCE: 502

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Met Ser Trp Ile Arg Gln Ala Pro Gly Lys Gly Leu Glu Trp Val
        35                  40                  45

Ser Tyr Ile Thr Thr Thr Gly Ser Thr Met Ser Tyr Ala Asp Ser Val
    50                  55                  60

Lys Gly Arg Phe Thr Ile Ser Arg Asp Asn Ser Lys Asn Ser Leu His
65                  70                  75                  80

Leu Gln Leu Ser Ser Leu Arg Ala Glu Asp Thr Ala Val Tyr Tyr Cys
                85                  90                  95

Ala Arg Asp Ser Ile His Val Asp Gly Ala Phe Asp Ile Trp Gly Gln
            100                 105                 110

Gly Thr Met Val Thr Val Ser Ser
        115                 120
```

<210> SEQ ID NO 503
<211> LENGTH: 117
<212> TYPE: PRT
<213> ORGANISM: Artificial sequence
<220> FEATURE:
<223> OTHER INFORMATION: Synthetic antibody

<400> SEQUENCE: 503

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Gly Trp Phe Asp Pro Trp Gly Gln Gly Thr Leu
            100                 105                 110

Val Ile Val Ser Ser
        115
```

<210> SEQ ID NO 504
<211> LENGTH: 119
<212> TYPE: PRT
<213> ORGANISM: Artificial sequence
<220> FEATURE:
<223> OTHER INFORMATION: Synthetic antibody

<400> SEQUENCE: 504

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Tyr Ser Ser Ser Ser Phe Asp Tyr Trp Gly Gln Gly
                100                 105                 110

Thr Thr Val Ser Val Ser Ser
        115

<210> SEQ ID NO 505
<211> LENGTH: 124
<212> TYPE: PRT
<213> ORGANISM: Artificial sequence
<220> FEATURE:
<223> OTHER INFORMATION: Synthetic antibody

<400> SEQUENCE: 505

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Ala Lys Glu Tyr Cys Ser Gly Gly Ser Cys Gln Asp Ala Phe Asp
                100                 105                 110

Ile Trp Gly Gln Gly Thr Met Val Ser Val Ser Ser
        115                 120

<210> SEQ ID NO 506
<211> LENGTH: 123
<212> TYPE: PRT
<213> ORGANISM: Artificial sequence
<220> FEATURE:
<223> OTHER INFORMATION: Synthetic antibody

<400> SEQUENCE: 506

Glu Val Gln Leu Val Gln Ser Gly Ala Glu Val Lys Lys Pro Gly Ala
1               5                   10                  15

Ser Val Lys Val Ala Cys Lys Ala Ser Gly Tyr Thr Phe Thr Asp Tyr
                20                  25                  30

Tyr Ile His Trp Val Arg Gln Ala Pro Gly Gln Gly Leu Glu Trp Met
        35                  40                  45

Gly Ile Val Asn Ala Asn Gly Gly Asp Thr Asn Tyr Ala Gln Gln Phe
    50                  55                  60

Gln Gly Arg Val Thr Met Thr Arg Asp Thr Ser Thr Ser Thr Val Tyr
65                  70                  75                  80

Leu Glu Leu Thr Ser Leu Arg Ser Asp Asp Thr Ala Val Tyr Tyr Cys
                85                  90                  95

Ala Arg Asp Trp Tyr Tyr Tyr Ser Ser Gly Ser Phe Pro Phe Asp Tyr
```

-continued

```
                100                 105                 110

Trp Gly Gln Gly Thr Leu Val Ser Val Ser Ser
        115                 120

<210> SEQ ID NO 507
<211> LENGTH: 123
<212> TYPE: PRT
<213> ORGANISM: Artificial sequence
<220> FEATURE:
<223> OTHER INFORMATION: Synthetic antibody

<400> SEQUENCE: 507

Glu Val Gln Leu Val Gln Ser Gly Ala Glu Val Lys Lys Pro Gly Ala
1               5                   10                  15

Ser Val Lys Val Ala Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Ile Val Asn Ala Asn Gly Gly Asp Thr Asn Tyr Ala Gln Gln Phe
    50                  55                  60

Gln Gly Arg Val Thr Met Thr Arg Asp Thr Ser Thr Ser Thr Val Tyr
65                  70                  75                  80

Leu Glu Leu Thr Ser Leu Arg Ser Asp Asp Thr Ala Val Tyr Tyr Cys
            85                  90                  95

Ala Arg Asp Trp Tyr Tyr Tyr Ser Ser Gly Ser Phe Pro Phe Asp Tyr
            100                 105                 110

Trp Gly Gln Gly Thr Leu Val Ser Val Ser Ser
        115                 120

<210> SEQ ID NO 508
<211> LENGTH: 118
<212> TYPE: PRT
<213> ORGANISM: Artificial sequence
<220> FEATURE:
<223> OTHER INFORMATION: Synthetic antibody

<400> SEQUENCE: 508

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Asn Thr Tyr
            20                  25                  30

Gly Ile Ser Trp Val Arg Gln Ala Pro Gly Gln Gly Leu Glu Trp Met
        35                  40                  45

Gly Trp Thr Asn Val Tyr Asn Ser Asn Thr Asp Ser Gly His Lys Phe
    50                  55                  60

Gln Gly Arg Val Thr Met Thr Thr Asp Thr Ser Thr Asp Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Pro Gly Ser Ala Ile Phe Asp Met Trp Gly Gln Gly Thr
            100                 105                 110

Met Val Thr Val Ser Ser
        115

<210> SEQ ID NO 509
<211> LENGTH: 117
<212> TYPE: PRT
<213> ORGANISM: Artificial sequence
<220> FEATURE:
```

<223> OTHER INFORMATION: Synthetic antibody

<400> SEQUENCE: 509

```
Gln Val Glu Leu Gln Glu Ser Gly Pro Gly Leu Val Lys Pro Ser Glu
1               5                   10                  15

Thr Leu Ser Leu Thr Cys Thr Val Ser Gly Asp Ala Ile Lys Asp Lys
            20                  25                  30

Tyr Trp Ser Trp Val Arg Gln Pro Pro Gly Lys Gly Leu Glu Trp Ile
        35                  40                  45

Gly Tyr Ile Ser Asn Ser Gly Ser Thr Asn Tyr Asn Pro Ser Leu Lys
    50                  55                  60

Ser Arg Val Ser Leu Ser Val Asp Thr Ser Lys Asn Gln Phe Ser Leu
65                  70                  75                  80

Lys Gln Thr Ser Val Thr Ala Ala Asp Thr Ala Thr Tyr Tyr Cys Ala
                85                  90                  95

Arg Gly Ser Gly Tyr Thr Ala Phe Asp Ile Trp Gly Gln Gly Thr Met
            100                 105                 110

Val Thr Val Ser Ser
        115
```

<210> SEQ ID NO 510
<211> LENGTH: 121
<212> TYPE: PRT
<213> ORGANISM: Artificial sequence
<220> FEATURE:
<223> OTHER INFORMATION: Synthetic antibody

<400> SEQUENCE: 510

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Asp Pro Tyr Ser Ser Gly Tyr Phe Asp Tyr Trp Gly
            100                 105                 110

Gln Gly Thr Leu Val Ile Val Ser Ser
        115                 120
```

<210> SEQ ID NO 511
<211> LENGTH: 117
<212> TYPE: PRT
<213> ORGANISM: Artificial sequence
<220> FEATURE:
<223> OTHER INFORMATION: Synthetic antibody

<400> SEQUENCE: 511

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
```

-continued

```
      35                    40                    45
Ser Ala Ile Ser Gly Ser Ser Ile Ser Thr Tyr Tyr Ala Asp Ser Val
      50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Tyr Cys
                  85                    90                    95

Ala Ser Ser Gly Phe Gly Ser Phe Asp Tyr Trp Gly Gln Gly Thr Leu
                  100                   105                   110

Val Thr Val Ser Ser
         115
```

<210> SEQ ID NO 512
<211> LENGTH: 118
<212> TYPE: PRT
<213> ORGANISM: Artificial sequence
<220> FEATURE:
<223> OTHER INFORMATION: Synthetic antibody

<400> SEQUENCE: 512

```
Gln Val Gln Leu Val Glu Ser Gly Gly Gly Leu Val Gln Pro Gly Gly
1                     5                     10                    15

Ser Leu Arg Leu Ser Cys Ala Ala Ser Gly Phe Thr Leu Ser Ser Tyr
                  20                    25                    30

Ala Met Ser Trp Val Arg Gln Ala Pro Gly Glu Gly Leu Glu Trp Val
                  35                    40                    45

Ser Ser Ile Asn Ser Gly Gly Ser Thr Tyr Tyr Ala Gly Ser Val Arg
      50                    55                    60

Gly Arg Phe Thr Ile Ser Arg Asp Asn Ser Lys Asn Thr Leu Tyr Leu
65                    70                    75                    80

Gln Met Asn Ser Leu Arg Ala Glu Asp Thr Ala Val Tyr Tyr Cys Ala
                  85                    90                    95

Lys Ala Lys Ser Tyr Ser Ser Asp Leu Asp His Trp Gly Gln Gly Thr
                  100                   105                   110

Thr Val Thr Val Ser Ser
         115
```

<210> SEQ ID NO 513
<211> LENGTH: 123
<212> TYPE: PRT
<213> ORGANISM: Artificial sequence
<220> FEATURE:
<223> OTHER INFORMATION: Synthetic antibody

<400> SEQUENCE: 513

```
Gln Val Gln Met Val Glu Ser Gly Gly Gly Leu Val Gln Pro Gly Gly
1                     5                     10                    15

Ser Leu Arg Leu Ser Cys Ala Ala Ser Gly Phe Thr Phe Ser Ser Tyr
                  20                    25                    30

Ala Met Ser Trp Val Arg Gln Ala Pro Gly Lys Gly Leu Glu Trp Val
                  35                    40                    45

Ser Ala Ile Ser Gly Ser Gly Gly Ser Thr Tyr Tyr Ala Asp Ser Val
      50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Tyr Cys
                  85                    90                    95
```

-continued

Ala Lys Asp Leu Leu Gly Asp Ser Gly Ser Tyr Pro Ala Phe Asp Ile
            100                 105                 110

Trp Gly Gln Gly Thr Met Val Thr Val Ser Ser
        115                 120

<210> SEQ ID NO 514
<211> LENGTH: 117
<212> TYPE: PRT
<213> ORGANISM: Artificial sequence
<220> FEATURE:
<223> OTHER INFORMATION: Synthetic antibody

<400> SEQUENCE: 514

Gln Val Gln Met Val Glu Ser Gly Gly Asp Leu Val Gln Pro Gly Gln
1                   5                   10                  15

Ser Leu Arg Leu Ser Cys Val Thr Ser Gly Phe Pro Phe Ala Asp Tyr
            20                  25                  30

Ala Met Ser Trp Phe Arg Gln Ala Pro Gly Gln Arg Pro Glu Trp Ile
        35                  40                  45

Gly Tyr Ile Lys Ser Lys Thr Arg Asp Gly Thr Thr Lys Tyr Ala Glu
    50                  55                  60

Ser Leu Arg Gly Arg Phe Thr Ile Ser Arg Asp Asp Ser Lys Ser Ile
65                  70                  75                  80

Ala Tyr Leu Gln Met Asn Asn Leu Lys Arg Glu Asp Thr Ala Val Tyr
                85                  90                  95

Tyr Cys Ala Leu Gly Gly Ala Ala Ala Leu Trp Gly Pro Gly Thr Leu
            100                 105                 110

Val Ser Val Ser Ser
        115

<210> SEQ ID NO 515
<211> LENGTH: 120
<212> TYPE: PRT
<213> ORGANISM: Artificial sequence
<220> FEATURE:
<223> OTHER INFORMATION: Synthetic antibody

<400> SEQUENCE: 515

Gln Val Gln Leu Val Gln Ser Gly Ala Glu Val Lys Lys Pro Gly Ser
1                   5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Ser Ser Gly Tyr Tyr Tyr Asn Pro Phe Asp Tyr Trp Gly Gln
            100                 105                 110

Gly Thr Leu Val Thr Val Ser Ser
        115                 120

<210> SEQ ID NO 516
<211> LENGTH: 117
<212> TYPE: PRT
<213> ORGANISM: Artificial sequence -continued

```
<220> FEATURE:
<223> OTHER INFORMATION: Synthetic antibody

<400> SEQUENCE: 516

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gln Pro Leu Asp Tyr Trp Gly Gln Gly Thr Leu
            100                 105                 110

Val Ile Val Ser Ser
        115

<210> SEQ ID NO 517
<211> LENGTH: 121
<212> TYPE: PRT
<213> ORGANISM: Artificial sequence
<220> FEATURE:
<223> OTHER INFORMATION: Synthetic antibody

<400> SEQUENCE: 517

Gln Met Gln Leu Glu Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Gly Ile His Tyr Tyr Asp Ser Leu Asp Tyr Trp Gly
            100                 105                 110

Gln Gly Thr Leu Val Thr Val Ser Ser
        115                 120

<210> SEQ ID NO 518
<211> LENGTH: 122
<212> TYPE: PRT
<213> ORGANISM: Artificial sequence
<220> FEATURE:
<223> OTHER INFORMATION: Synthetic antibody

<400> SEQUENCE: 518

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ala Asn Ala
            20                  25                  30
```

```
Trp Met Gly Trp Val Arg Gln Ala Pro Gly Lys Gly Leu Gln Trp Val
    35                  40                  45
Ser His Ile Lys Pro Ser Ser Ser Gly Gly Arg Thr Thr Asp Tyr Asp
    50                  55                  60
Ala Pro Val Lys Gly Arg Phe Thr Ile Ser Arg Asp Asp Ser Asn Asp
65                  70                  75                  80
Thr Val Tyr Leu Gln Met Asn Ser Leu Lys Thr Glu Asp Thr Gly Val
                85                  90                  95
Tyr Tyr Cys Val Thr Gly Arg Arg Val Ala Lys Thr Phe Asp Phe Trp
            100                 105                 110
Gly Gln Gly Thr Thr Val Ser Val Ser Ser
        115                 120
```

<210> SEQ ID NO 519
<211> LENGTH: 333
<212> TYPE: DNA
<213> ORGANISM: Artificial sequence
<220> FEATURE:
<223> OTHER INFORMATION: Synthetic antibody

<400> SEQUENCE: 519

```
cagtctgccc tgaatcagcc tgcctccgtg tctgggtctc ctggacagtc gatcaccatc      60
tcctgcactg gaaccagcag tgacgttggt ggttataact atgtctcctg gtaccaacaa     120
cacccaggca aagcccccaa actcatgatt tatgatgtca gtaatcggcc ctcagggggtt    180 tctaatcgct tctctggctc caagtctggc aacacggcct ccctgaccat ctctgggctc     240
caggctgagg acgaggctga ttattactgc agctcatata caagcagcag cactccttat     300
gtcttcggaa ctgggaccaa ggtcaccgtc cta                                  333
```

<210> SEQ ID NO 520
<211> LENGTH: 324
<212> TYPE: DNA
<213> ORGANISM: Artificial sequence
<220> FEATURE:
<223> OTHER INFORMATION: Synthetic antibody

<400> SEQUENCE: 520

```
gacatcgtga tgacccagtc tccatcctcc ctgtctgcat ctgtaggaga cagagtcacc      60
ctcacttgcc gggcaagtca gagcattggc aactatttaa attggtatca acagaaacca     120
gggaaagccc ctaacctcct gatctatgct gcatccagtt tgcaaagtgg ggtcccatca     180
aggttcagtg gcagtggatc tgggacagat ttcactctca ccatcagcag tctgcagcct     240
gaagattttg caacttacta ctgtcaacag agtttcagta tccccccgat aactttcggc     300
caagggacac gactggagat taaa                                            324
```

<210> SEQ ID NO 521
<211> LENGTH: 330
<212> TYPE: DNA
<213> ORGANISM: Artificial sequence
<220> FEATURE:
<223> OTHER INFORMATION: Synthetic antibody

<400> SEQUENCE: 521

```
cagcctgtgc tgactcagcc accctcagcg tctgggaccc ccggccagag ggtcaccatc      60
tcttgttctg gaagcagctc caacatcgga actaatcctg taaactggta ccagcaagtc     120
ccaggaacgg cccccaaact cctcatctat aataataatc agtggccctc aggggtccct     180
gaccgattct ctggctccaa gtctgccacc tcagcctccc tggccatcta tgggctccag     240
```

```
tctggggatg aggctcatta ttactgttcg tcatgggacg acagcctgag tgcgtgggtg     300
ttcggcggag ggaccaaggt caccgtccta                                      330

<210> SEQ ID NO 522
<211> LENGTH: 327
<212> TYPE: DNA
<213> ORGANISM: Artificial sequence
<220> FEATURE:
<223> OTHER INFORMATION: Synthetic antibody

<400> SEQUENCE: 522
cagtctgtgc tgactcagcc accctcagcg tctgggaccc ccgggcagag ggtcaccatc      60
tcttgttctg gaagcaggtc caacatcgga agtaatcctg taaactggta tcagcacctc     120
ccaggaacgg cccccaaact cctcgtctat agtaataatc ggcggccctc aggggtccct     180
gaccgattct ctggctccaa gtctggcacc tcagcctccc tgtccatcag tgggctccag     240
tctgaggatg aaggtgttta ttactgtgca gcgtgggatg acaacgtgca cggagttttc     300
ggcggaggga ccaaggtcac cgtccta                                        327

<210> SEQ ID NO 523
<211> LENGTH: 327
<212> TYPE: DNA
<213> ORGANISM: Artificial sequence
<220> FEATURE:
<223> OTHER INFORMATION: Synthetic antibody

<400> SEQUENCE: 523
cagtctgtgc tgactcagcc accctcggtg tcagtggccc caggaaagac ggccaggatt      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgatcatcc gggggtcttc     300
ggaactggga ccaaggtcac cgtccta                                        327

<210> SEQ ID NO 524
<211> LENGTH: 333
<212> TYPE: DNA
<213> ORGANISM: Artificial sequence
<220> FEATURE:
<223> OTHER INFORMATION: Synthetic antibody

<400> SEQUENCE: 524
cagcctgtgc tgactcagcc tgcctccgtg tctgggtctc ctggacagtc gatcaccatc      60
tcctgcactg gaaccagcag tgacgttggt ggttataact atgtctcctg gtaccaacaa     120
cacccaggca aagccccaa actcatgatt tatgatgtca gtaatcggcc ctcagggagtt       180 tctaatcgct tctctggctc caagtctggc aacacggcct ccctgaccat ctctgggctc     240
caggctgagg acgaggctga ttattactgc agctcatata caagcagcag cacccttat     300 gtcttcggaa ctgggaccaa ggtcaccgtc cta                                 333

<210> SEQ ID NO 525
<211> LENGTH: 306
<212> TYPE: DNA
<213> ORGANISM: Artificial sequence
<220> FEATURE:
<223> OTHER INFORMATION: Synthetic antibody
```

```
<400> SEQUENCE: 525
cagtctccat cctccctgtc tgcatctgta ggcgacagag tcaccatcac ttgccggaca      60
agtcacaccg ttaacagcta tctaaattgg tatcaacaag aaccagggaa agcccctaaa     120
ctcctgatct atgctgcatc caatttgcaa agtggggtcc cgtcaaggtt cagtggcagt     180
ggatctggga cagatttctc tctcaccatc cacaatctgc aacctgaaga ttttgcaact     240
tactactgtc aacagagtta cagaacccct ctcacttttg gccaggggac caaagtggat     300
atcaaa                                                                306

<210> SEQ ID NO 526
<211> LENGTH: 330
<212> TYPE: DNA
<213> ORGANISM: Artificial sequence
<220> FEATURE:
<223> OTHER INFORMATION: Synthetic antibody

<400> SEQUENCE: 526
cagtctgtgc tgactcagcc accctcagcg tctggaaccc ccgggcagag ggtcaccatc      60
tcttgttctg gaagcagctc caacatcgga ggtaatcctg taaactggta ccagcacctc     120
ccaggaacgg cccccaagct cctcatctat tataatgatc agcggccttc aggggtccct     180
gaccgattct ctggctccaa gtctggcacc tcagcctccc tggccatcag tggactccag     240
tctgaggatg agactgatta ttactgtgca acatgggatg acagcctgaa tggttgggtg     300
tttggcggag ggaccagct gaccgtccta                                       330

<210> SEQ ID NO 527
<211> LENGTH: 330
<212> TYPE: DNA
<213> ORGANISM: Artificial sequence
<220> FEATURE:
<223> OTHER INFORMATION: Synthetic antibody

<400> SEQUENCE: 527
cagtctgtgc tgactcagcc accctcagcg tctggcaccc ccgggcagag ggtcaccatc      60
tcttgttctg gaagcaagtc caacgtcgga aataatttttg tacattggta ccagcaactc     120
ccagggacgg cccccaaact cctcctctat agcaatcttg agcggtcctc aggggtccct     180
gagcgattct ctggctccaa gtctggcacc tcagcctacc tggccatcag tgggctccgg     240
tccgacgatg aggctgatta ttactgtgca gcatgggatg acagcctgcc cggttgggtg     300
ttcggcggag ggaccaagct gaccgtccta                                      330

<210> SEQ ID NO 528
<211> LENGTH: 330
<212> TYPE: DNA
<213> ORGANISM: Artificial sequence
<220> FEATURE:
<223> OTHER INFORMATION: Synthetic antibody

<400> SEQUENCE: 528
cagcctgtgc tgactcagcc accctcagcg tctgggaccc ccgggcagag ggtcaccatc      60
tcttgttctg gaagcagctc caacatcgga agtaatcctc taaactggta ccagcaactc     120
ccaggaacgg cccccaaact cctcatctat aataataatc agcggccctc aggggtccct     180
gaccgattct ctggctccaa gtctggcacc tcagcctccc tggccatcag tggactccag     240
tctgaggatg aggctgatta ttactgtgcg gcatgggatg acagcctgaa tggttgggtg     300
ttcggcggag ggaccagct gaccgtccta                                       330
```

<210> SEQ ID NO 529
<211> LENGTH: 333
<212> TYPE: DNA
<213> ORGANISM: Artificial sequence
<220> FEATURE:
<223> OTHER INFORMATION: Synthetic antibody

<400> SEQUENCE: 529
caggctgtgg tgactcagcc tgcctccgtg tctgggtctc ctggacagtc ggtcagcatc      60
tcctgcactg gaaccagcag tgacgttggt ggtttttaact atgtctcctg gtatcaacaa    120
cacccaggca agcccccaa actcatgatt tatgatgtca gtaatcggcc ctcagggggtt     180 tctaatcgct ctctggctc caagtctggc aacacggcct ccctgaccat ctctgggctc      240
caggctgagg acgaggctga ttattactgc agctcatata caagcagcac cgctccttat    300
gtcttcggaa ctgggaccaa ggtcaccgtc cta                                  333

<210> SEQ ID NO 530
<211> LENGTH: 333
<212> TYPE: DNA
<213> ORGANISM: Artificial sequence
<220> FEATURE:
<223> OTHER INFORMATION: Synthetic antibody

<400> SEQUENCE: 530
cagtctgtgc tgactcagcc tcgctcagtg tccgggtctc ctggacagtc agtcaccatc      60
tcctgcactg gaaccagcag tgatgttggt ggttataact atgtctcctg gtaccaacaa    120
cacccaggca agcccccaa actcatgatt tctgaggtca gtaagcggcc ctcaggggtc     180
cctgatcgct ctctggctc caagtctggc aacacggcct ccctgaccgt ctctgggctc      240
caggctgagg atgaggctga ttattactgc tcctcatatg caggcgggta caccccctat    300
gtcttcggaa ctgggaccaa ggtcaccgtc cta                                  333

<210> SEQ ID NO 531
<211> LENGTH: 330
<212> TYPE: DNA
<213> ORGANISM: Artificial sequence
<220> FEATURE:
<223> OTHER INFORMATION: Synthetic antibody

<400> SEQUENCE: 531
cagtctgtgc tgactcagcc accctcagcg tctgcgaccc ccgggcagag ggtcaccatc      60
tcttgttctg gaagaaacgc caacatcgga agtaatcctg taaactggta ccagcagctc    120
ccagggacgg cccccagact cgtcatgtat agtaataatc agcggccctc aggggtccct     180
gaccgattct ctggctccaa gtctggcacc tcagcctccc tggccatcag tgggctccag    240
tctgaggacg aggctgatta ttactgtgaa ggatgggatg acagcctgaa tggctatgtc    300
ttcggaactg ggaccaaggt caccgtccta                                      330

<210> SEQ ID NO 532
<211> LENGTH: 336
<212> TYPE: DNA
<213> ORGANISM: Artificial sequence
<220> FEATURE:
<223> OTHER INFORMATION: Synthetic antibody

<400> SEQUENCE: 532
gatattgtga tgactcagtc tccactctcc ctgcccgtca cccttggaca gccggcctcc      60

```
atctcctgca cgtctagtca aagcctcgta tacagtgatg gaaacaccta cttgaattgg      120
tttcaccaga ggccaggcca gtctccaagg cgcctatttt ataaggtttc taaccgggcc      180
tctggggtcc cagacagatt cagcggcagt gggtcaggca ctgatttcac actgaaaatc      240 agcaggtgg aggctgagga tcttgggggtt tattactgca tgcaaggtac acactggccg      300
gtcaccttcg gccaagggac acgactggag attaaa      336
```

```
<210> SEQ ID NO 533
<211> LENGTH: 330
<212> TYPE: DNA
<213> ORGANISM: Artificial sequence
<220> FEATURE:
<223> OTHER INFORMATION: Synthetic antibody

<400> SEQUENCE: 533
cagtctgtgc tgactcagcc accctcagcg tctgcgaccc ccgggcagag ggtcaccatc      60
tcttgttctg gaagcagctc caacatcgga agtaatcctg taaactggta tcagcaggtc      120
ccaggaatgg cccccgaact cgtcatgtat agtgataatc agcggccctc aggggtcc ct      180 gaccgattct ctggctccaa ctctggcacc tcagcctccc tggccatcag tggcctccag      240
tctgaggatg aggctgatta ttactgttca acatgggatg acagcctgaa tggtcttgtc      300
ttcggaactg ggaccaaggt caccgtccta      330
```

```
<210> SEQ ID NO 534
<211> LENGTH: 321
<212> TYPE: DNA
<213> ORGANISM: Artificial sequence
<220> FEATURE:
<223> OTHER INFORMATION: Synthetic antibody

<400> SEQUENCE: 534
gacgtccaga tgacccagtc tccatcctcc ctgtctgcat ctgtaggaga gagagtcacc      60
ctcacttgcc gggcgagtca gggcatttac agttctttag cctggtatca gcaaaaacca      120
ggtaaagccc ctaaactcct actatatggt acgtcgcaat tggaacgtgg ggtcccatcc      180
agattcagtg gcagtggatc tgggacggat tacactctca ccatcagcag cctgcagcct      240
gaagattctg caacttatta ttgtcaacaa cattacaatc tacccatcac cttcggccaa      300
gggacacgac tggagattaa a      321
```

```
<210> SEQ ID NO 535
<211> LENGTH: 330
<212> TYPE: DNA
<213> ORGANISM: Artificial sequence
<220> FEATURE:
<223> OTHER INFORMATION: Synthetic antibody

<400> SEQUENCE: 535
cagcctgtgc tgactcagcc accctcagtg tctgaagccc ccaggcagag ggtcaccatc      60
tcctgttctg gaagcagctc caacatcgga aataatgttg taaactggta ccagcagctc      120
ccaggaaagg ctcccaaact cctcatctat tatgatgatc tgctgccctc aggggtctct      180
gaccgattct ctggctccaa gtctggcacc tcagcctccc tggccatcag tgggctccag      240
tctgaggatg aggctgatta ttactgtgca acatgggatg acagcctgaa tggccctgta      300
ttcggcggag ggaccaagct gaccgtccta      330
```

```
<210> SEQ ID NO 536
<211> LENGTH: 306
```

```
<212> TYPE: DNA
<213> ORGANISM: Artificial sequence
<220> FEATURE:
<223> OTHER INFORMATION: Synthetic antibody

<400> SEQUENCE: 536
cagtctccat cctccctgtc tgcatctgta ggagacagag tcaccatcac ttgccgggcg       60
agtcagggca ttagcaatta tttagcctgg tatcagcaga aaccagggaa agttcctaag      120
ctcctgatct atgctgcatc cactttgcaa tcaggggtcc catctcggtt cagtggcagt      180
ggatctggga cagatttcac tctcaccatc agcagcctgc agcctgaaga tgttgcaact      240
tattactgtc aaaagtataa cagtgccccg ctcactttcg gcggagggac caagctggag      300
atcaaa                                                                 306

<210> SEQ ID NO 537
<211> LENGTH: 303
<212> TYPE: DNA
<213> ORGANISM: Artificial sequence
<220> FEATURE:
<223> OTHER INFORMATION: Synthetic antibody

<400> SEQUENCE: 537
cagtctcctt ccaccctgtc tgcatctgta ggagacagag tcaccatcac ttgccgggcc       60
agtcagagta ttagtagctg gttggcctgg tatcagcaga aaccagggaa agcccctaag      120
ctcctgatct ataaggcgtc tagtttagaa agtggggtcc catcaaggtt cagcggcagt      180
ggatctggga cagaattcac tctcaccatc agcagcctgc agcctgatga ttttgcaact      240
tattactgcc aacagtataa tagttatctc actttcggcg gagggaccaa agtggatatc      300
aaa                                                                    303

<210> SEQ ID NO 538
<211> LENGTH: 330
<212> TYPE: DNA
<213> ORGANISM: Artificial sequence
<220> FEATURE:
<223> OTHER INFORMATION: Synthetic antibody

<400> SEQUENCE: 538
cagtctgtgc tgactcagcc accctcagcg tctgggaccc ccgggcagag ggtcaccatc       60
tcttgttctg gaagcagctc caacatcgga agtaattatg tatactggta ccagcagctc      120
ccaggaacgg cccccaaact cctcatctat aggaataatc agcggccctc aggggtccct      180
gaccgattct ctggctccaa gtctggcacc tcagcctccc tggccatcag tgggctccgg      240
tccgaggatg aggctgatta ttactgtgca gcatgggatg acagcctgag tggttgggtg      300
ttcggcggag ggaccaaggt caccgtccta                                       330

<210> SEQ ID NO 539
<211> LENGTH: 324
<212> TYPE: DNA
<213> ORGANISM: Artificial sequence
<220> FEATURE:
<223> OTHER INFORMATION: Synthetic antibody

<400> SEQUENCE: 539
tcctatgagc tgactcagcc accctcggtg tcagtggccc caggacagac ggccaggatt       60
acctgtgggg gaaacaacat tggaagtaaa agtgtgcact ggtaccagca gaagccaggc      120
caggcccctg tgctggtcgt ctatgatgat agcgaccggc cctcagggat ccctgagcga      180
```

```
ttctctggct ccaactctgg gaacacggcc accctgacca tcagcagggt cgaagccggg      240
gatgaggccg actattactg tcaggtgtgg gatagtagta gtgatcattg ggtgttcggc      300
ggagggacca agctgaccgt ccta                                            324

<210> SEQ ID NO 540
<211> LENGTH: 306
<212> TYPE: DNA
<213> ORGANISM: Artificial sequence
<220> FEATURE:
<223> OTHER INFORMATION: Synthetic antibody

<400> SEQUENCE: 540
cagtctccat cctccctgtc tgcatctgta ggagacagag tcaccatcac ttgccgggca       60
agtcagagca taagcaactt tgtaaattgg tatcagcaga aaccagggga agtccctaag      120
ctcctgatct acggtgcatc cagtttgcag agtggggtcc catcaaggtt cagtggcagt      180
ggatctggga cggatttcac tctcaccatc agcagtctgc aacctgaaga ttttgcgact      240
tactactgtc aacagggtta cagtgtccca ctcactttcg gcggagggac tacagtggat      300
atcaaa                                                                306

<210> SEQ ID NO 541
<211> LENGTH: 333
<212> TYPE: DNA
<213> ORGANISM: Artificial sequence
<220> FEATURE:
<223> OTHER INFORMATION: Synthetic antibody

<400> SEQUENCE: 541
cagcctgtgc tgactcagcc tgcctccgtg tctgggtctc ctggacagtc gatcaccatc       60
tcctgcactg gaaccagcag tgacgttggt ggttataact atgtctcctg gtaccaacaa      120
cacccaggca aagccccaa actcatgatt tatgatgtca gtaatcggcc ctcgggggtt       180
tctaatcgct tctctggctc caagtctggc aactcggcct ccctgaccat ctctgggctc      240
caggctgagg acgaggctga ttattactgc agctcatata caagcagcag cactccctat      300
gtcttcggaa ctgggaccaa ggtcaccgtc cta                                  333

<210> SEQ ID NO 542
<211> LENGTH: 309
<212> TYPE: DNA
<213> ORGANISM: Artificial sequence
<220> FEATURE:
<223> OTHER INFORMATION: Synthetic antibody

<400> SEQUENCE: 542
cagtctccat cctccttgtc tgcatctgta ggagacagag tcaccatcac ttgccgggca       60
agtcagagca ttaggaccta cttaaattgg tatcagcaga aaccaggcaa agaccctgaa      120
ctcctgatct atgctgcaac cagtttgcaa agtggggtcc catcaaggtt cactggcagc      180
ggatctggga cagacttcac tctcaccatc agcagtctgc agcctgaaga ttttgcaact      240
tattactgtc aacagagtta cagtgccccc gtgttcactt ttggccaggg gaccaagctg      300
gagatcaaa                                                             309

<210> SEQ ID NO 543
<211> LENGTH: 321
<212> TYPE: DNA
<213> ORGANISM: Artificial sequence
<220> FEATURE:
<223> OTHER INFORMATION: Synthetic antibody
```

-continued

<400> SEQUENCE: 543
gccatccaga tgacccagtc tccatcctcc ctgtctgcat ctgtaggaga cagagtctcc    60
atcacttgcc gggcaagtca gagcattagc agctttttaa attggtatca gcagagacca   120
gggaaagccc ctgagctcct gatctatggt gcatccagct tgcaaagtgg ggtcccatca   180
aggttcagtg gcagtggatc tgggacagat ttcactctca ccatcagtag tctgcaacct   240
gaagattttg caacttacta ctgtcaacag agttacagta tcccgatcac cttcggccaa   300
gggacacagc tggagatcaa a                                             321

<210> SEQ ID NO 544
<211> LENGTH: 321
<212> TYPE: DNA
<213> ORGANISM: Artificial sequence
<220> FEATURE:
<223> OTHER INFORMATION: Synthetic antibody

<400> SEQUENCE: 544
gacgtccaga tgacccagtc cccttcctct ttatccgcta gcgtgggcga tcgtgtgtcc    60
atcacttgta aggcctccca agatgtgtcc atcgccgtgg cttggtacca gcagaagccc   120
ggcaaggccc ccaagctgct gatctactcc gccagctatc gttacaccgg cgtgcccgat   180
cgtttctccg gctccggatc cggcaccgac ttcactttaa ccatctcctc tttacagccc   240
gaggacttcg ccgtctacta ctgccagcag cactacatca cccctttaac attcggcgcc   300
ggcaccaagc tggagatcaa a                                             321

<210> SEQ ID NO 545
<211> LENGTH: 321
<212> TYPE: DNA
<213> ORGANISM: Artificial sequence
<220> FEATURE:
<223> OTHER INFORMATION: Synthetic antibody

<400> SEQUENCE: 545
gacgtccaga tgacccagtc tccatcctcc ctgtctgcat ctgtaggaga cagagtctcc    60
atcacttgcc gggcaagtca gagcattagc agctttttaa attggtatca gcagagacca   120
gggaaagccc ctgagctcct gatctatggt gcatccagct tgcaaagtgg ggtcccatca   180
aggttcagtg gcagtggatc tgggacagat ttcactctca ccatcagtag tctgcaacct   240
gaagattttg caacttacta ctgtcaacag agttacagta tcccgatcac cttcggccaa   300
gggacacgac tggagatcaa a                                             321

<210> SEQ ID NO 546
<211> LENGTH: 321
<212> TYPE: DNA
<213> ORGANISM: Artificial sequence
<220> FEATURE:
<223> OTHER INFORMATION: Synthetic antibody

<400> SEQUENCE: 546
aacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgccac tttcggcgga   300 gggactacag tggagatcaa a                                              321

<210> SEQ ID NO 547
<211> LENGTH: 321
<212> TYPE: DNA
<213> ORGANISM: Artificial sequence
<220> FEATURE:
<223> OTHER INFORMATION: Synthetic antibody

<400> SEQUENCE: 547
gccatccaga tgacccagtc tccatcttcc gtgtctgcat ctgtaggaga cagagtcacc      60
atcacttgtc gggcgagtca gggtattggc agctggttag cctggtatca gcagaaacca     120
gggaaagccc ctaagctcct gatctctgtt gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt ccccgctcac ttttggcgga     300
gggactacag tggagatcaa a                                              321

<210> SEQ ID NO 548
<211> LENGTH: 315
<212> TYPE: DNA
<213> ORGANISM: Artificial sequence
<220> FEATURE:
<223> OTHER INFORMATION: Synthetic antibody

<400> SEQUENCE: 548
cagccaccct cggtgtctgc agccccagg cagagggtca ccatctcctg ttctggaagc       60
agctccaata tcggagataa ttctgttaac tggtaccagc agctcccagg aaaggctccc     120
aaactcctca tttatcttga tgatctcctg ccctcagggg tctctggccg attctctggc     180
tccaagtctg gcacctcagc ctccctggtc atcagtggcc tccagtctga ggatgaggct     240
gattattact gtgcaacatg ggatgacagc ctgaacggtg tggtttttcgg cggagggacc     300 aaggtcaccg tccta                                                     315

<210> SEQ ID NO 549
<211> LENGTH: 339
<212> TYPE: DNA
<213> ORGANISM: Artificial sequence
<220> FEATURE:
<223> OTHER INFORMATION: Synthetic antibody

<400> SEQUENCE: 549
gatgttgtga tgacgcagtc tccatcctcc ctgagtgtgt cagcaggaga gaaggtcact       60
atgagctgca agtccagtca gagtctgtta aacagtggaa atcaaaagac ctacttggcc     120
tggtaccagc agaaaccagg gcagcctcct aaactgttga tctacggggc atccactagg     180
gaatctgggg tccctgatcg cttcacaggc agtggatctg gaaccgattt cactcttacc     240
atcagcagtg tgcaggctga agacctggca gtttattact gtcagaatga tcatagttat     300
ccattcacgt tcggctcggg gacaaaggtg gaaatcaaa                           339

<210> SEQ ID NO 550
<211> LENGTH: 321
<212> TYPE: DNA
<213> ORGANISM: Artificial sequence
<220> FEATURE:
<223> OTHER INFORMATION: Synthetic antibody

<400> SEQUENCE: 550
aacatccaga tgacccagtc tccatcctcc ctgtctgcat ctgtaggaga cagagtcacc      60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta ccccgtacac ttttggccag      300
gggaccaagc tggagatcaa a      321

<210> SEQ ID NO 551
<211> LENGTH: 319
<212> TYPE: DNA
<213> ORGANISM: Artificial sequence
<220> FEATURE:
<223> OTHER INFORMATION: Synthetic antibody

<400> SEQUENCE: 551
cagccgccct cggtgtctgg ggccccaggg cagagggtca ccatctcctg cgctgggagc      60
agctccaaca tcggggcagg ttatggtgtg cactggtatc aacaccttcc aggaacagcc      120
cccaaactcc tcatctatgg tgacaacaat cggccctcag gggtccctta ccgattctct      180
gggtccaagt ctggcacctc agcctccctg gccatcactg gactccaggc tgaggatgag      240
gctgattatt tctgccagtc ctatgacagc agcctggggg ttggtgtgtt cggcggaggg      300
accaaggtca ccgtcctac      319

<210> SEQ ID NO 552
<211> LENGTH: 321
<212> TYPE: DNA
<213> ORGANISM: Artificial sequence
<220> FEATURE:
<223> OTHER INFORMATION: Synthetic antibody

<400> SEQUENCE: 552
gccatccagt tgacccagtc tccatcctcc ctgtctgcat ctgtaggaga cagagtcacc      60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta ccccccctcac tttcggcgga      300 gggaccaagc tggagatcaa a      321

<210> SEQ ID NO 553
<211> LENGTH: 321
<212> TYPE: DNA
<213> ORGANISM: Artificial sequence
<220> FEATURE:
<223> OTHER INFORMATION: Synthetic antibody

<400> SEQUENCE: 553
gacatcgtga tgacccagtc tccatcctcc ctgtctgcat ctgtaggaga cagagtcacc      60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta ccccattcac tttcggccct      300
gggaccaagc tggagatcaa a      321

<210> SEQ ID NO 554

<211> LENGTH: 321
<212> TYPE: DNA
<213> ORGANISM: Artificial sequence
<220> FEATURE:
<223> OTHER INFORMATION: Synthetic antibody

<400> SEQUENCE: 554
gacgtccaga tgacccagtc tccatcctcc ctgtctgcat ctgtaggaga cagagtcacc         60
atcacttgcc gggcaagtca gagcattagc agctatttaa attggtatca gcagaaacca        120
gggaaagccc ctaagctcct gatctatgct gcatccagtt tgcaaagtgg ggtcccatca        180
aggttcagtg gcagtggatc tgggacagat ttcactctca ccatcagcag tctgcaacct        240
gaagattttg caacttacta ctgtcaacag agttacagta cccctctgac gttcggccaa        300
gggaccaagc tggagatcaa a                                                   321

<210> SEQ ID NO 555
<211> LENGTH: 321
<212> TYPE: DNA
<213> ORGANISM: Artificial sequence
<220> FEATURE:
<223> OTHER INFORMATION: Synthetic antibody

<400> SEQUENCE: 555
aacatccaga tgacccagtc tccatcctcc ctgtctgcat ctgtaggaga cagagtcacc         60
atcacttgcc gggcaagtca gagcattagc agctatttaa attggtatca gcagaaacca        120
gggaaagccc ctaagctcct gatctatgct gcatccagtt tgcaaagtgg ggtcccatca        180
aggttcagtg gcagtggatc tgggacagat ttcactctca ccatcagcag tctgcaacct        240
gaagattttg caacttacta ctgtcaacag agttacagta cccctcggac gttcggccaa        300
gggactacgg tggaaatcaa a                                                   321

<210> SEQ ID NO 556
<211> LENGTH: 111
<212> TYPE: PRT
<213> ORGANISM: Artificial sequence
<220> FEATURE:
<223> OTHER INFORMATION: Synthetic antibody

<400> SEQUENCE: 556

Gln Ser Ala Leu Asn Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Pro Tyr Val Phe Gly Thr Gly Thr Lys Val Thr Val Leu
            100                 105                 110

<210> SEQ ID NO 557
<211> LENGTH: 108
<212> TYPE: PRT
<213> ORGANISM: Artificial sequence
<220> FEATURE:

-continued

<223> OTHER INFORMATION: Synthetic antibody

<400> SEQUENCE: 557

Asp Ile Val Met Thr Gln Ser Pro Ser Ser Leu Ser Ala Ser Val Gly
1               5                   10                  15

Asp Arg Val Thr Leu Thr Cys Arg Ala Ser Gln Ser Ile Gly Asn Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Ile Pro Pro
                85                  90                  95

Ile Thr Phe Gly Gln Gly Thr Arg Leu Glu Ile Lys
                100                 105

<210> SEQ ID NO 558
<211> LENGTH: 110
<212> TYPE: PRT
<213> ORGANISM: Artificial sequence
<220> FEATURE:
<223> OTHER INFORMATION: Synthetic antibody

<400> SEQUENCE: 558

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Asn
            20                  25                  30

Pro Val Asn Trp Tyr Gln Gln Val Pro Gly Thr Gly Pro Lys Leu Leu
        35                  40                  45

Ile Tyr Asn Asn Asn Gln Trp Pro Ser Gly Val Pro Asp Arg Phe Ser
    50                  55                  60

Gly Ser Lys Ser Ala Thr Ser Ala Ser Leu Ala Ile Tyr Gly Leu Gln
65                  70                  75                  80

Ser Gly Asp Glu Ala His Tyr Tyr Cys Ser Ser Trp Asp Asp Ser Leu
                85                  90                  95

Ser Ala Trp Val Phe Gly Gly Gly Thr Lys Val Thr Val Leu
                100                 105                 110

<210> SEQ ID NO 559
<211> LENGTH: 109
<212> TYPE: PRT
<213> ORGANISM: Artificial sequence
<220> FEATURE:
<223> OTHER INFORMATION: Synthetic antibody

<400> SEQUENCE: 559

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser Asn
            20                  25                  30

Pro Val Asn Trp Tyr Gln His Leu Pro Gly Thr Ala Pro Lys Leu Leu
        35                  40                  45

Val Tyr Ser Asn Asn Arg Arg Pro Ser Gly Val Pro Asp Arg Phe Ser
    50                  55                  60

Gly Ser Lys Ser Gly Thr Ser Ala Ser Leu Ser Ile Ser Gly Leu Gln

-continued

```
65              70              75              80

Ser Glu Asp Glu Gly Val Tyr Tyr Cys Ala Ala Trp Asp Asp Asn Val
                85              90              95

His Gly Val Phe Gly Gly Gly Thr Lys Val Thr Val Leu
            100             105
```

<210> SEQ ID NO 560
<211> LENGTH: 109
<212> TYPE: PRT
<213> ORGANISM: Artificial sequence
<220> FEATURE:
<223> OTHER INFORMATION: Synthetic antibody

<400> SEQUENCE: 560

```
Gln Ser Val Leu Thr Gln Pro Pro Ser Val Ser Val Ala Pro Gly Lys
1               5               10              15

Thr Ala Arg Ile Thr Cys Gly Gly Asn Asn Ile Gly Ser Lys Ser Val
                20              25              30

His Trp Tyr Gln Gln Lys Pro Gly Gln Ala Pro Val Leu Val Val Tyr
            35              40              45

Asp Asp Ser Asp Arg Pro Ser Gly Ile Pro Glu Arg Phe Ser Gly Ser
            50              55              60

Asn Ser Gly Asn Thr Ala Thr Leu Thr Ile Ser Arg Val Glu Ala Gly
65              70              75              80

Asp Glu Ala Asp Tyr Tyr Cys Gln Val Trp Asp Ser Ser Ser Asp His
                85              90              95

Pro Gly Val Phe Gly Thr Gly Thr Lys Val Thr Val Leu
            100             105
```

<210> SEQ ID NO 561
<211> LENGTH: 111
<212> TYPE: PRT
<213> ORGANISM: Artificial sequence
<220> FEATURE:
<223> OTHER INFORMATION: Synthetic antibody

<400> SEQUENCE: 561

```
Gln Pro Val Leu Thr Gln Pro Ala Ser Val Ser Gly Ser Pro Gly Gln
1               5               10              15

Ser Ile Thr Ile Ser Cys Thr Gly Thr Ser Ser Asp Val Gly Gly Tyr
                20              25              30

Asn Tyr Val Ser Trp Tyr Gln Gln His Pro Gly Lys Ala Pro Lys Leu
            35              40              45

Met Ile Tyr Asp Val Ser Asn Arg Pro Ser Gly Val Ser Asn Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Asp Tyr Tyr Cys Ser Ser Tyr Thr Ser Ser
                85              90              95

Ser Thr Pro Tyr Val Phe Gly Thr Gly Thr Lys Val Thr Val Leu
            100             105             110
```

<210> SEQ ID NO 562
<211> LENGTH: 102
<212> TYPE: PRT
<213> ORGANISM: Artificial sequence
<220> FEATURE:
<223> OTHER INFORMATION: Synthetic antibody

<400> SEQUENCE: 562

```
Gln Ser Pro Ser Ser Leu Ser Ala Ser Val Gly Asp Arg Val Thr Ile
1               5                   10                  15

Thr Cys Arg Thr Ser His Thr Val Asn Ser Tyr Leu Asn Trp Tyr Gln
            20                  25                  30

Gln Glu Pro Gly Lys Ala Pro Lys Leu Leu Ile Tyr Ala Ala Ser Asn
        35                  40                  45

Leu Gln Ser Gly Val Pro Ser Arg Phe Ser Gly Ser Gly Ser Gly Thr
    50                  55                  60

Asp Phe Ser Leu Thr Ile His Asn Leu Gln Pro Glu Asp Phe Ala Thr
65                  70                  75                  80

Tyr Tyr Cys Gln Gln Ser Tyr Arg Thr Pro Leu Thr Phe Gly Gln Gly
            85                  90                  95

Thr Lys Val Asp Ile Lys
            100
```

<210> SEQ ID NO 563
<211> LENGTH: 110
<212> TYPE: PRT
<213> ORGANISM: Artificial sequence
<220> FEATURE:
<223> OTHER INFORMATION: Synthetic antibody

<400> SEQUENCE: 563

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Gly Asn
            20                  25                  30

Pro Val Asn Trp Tyr Gln His Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Thr Asp Tyr Tyr Cys Ala Thr Trp Asp Asp Ser Leu
            85                  90                  95

Asn Gly Trp Val Phe Gly Gly Gly Thr Gln Leu Thr Val Leu
            100                 105                 110
```

<210> SEQ ID NO 564
<211> LENGTH: 110
<212> TYPE: PRT
<213> ORGANISM: Artificial sequence
<220> FEATURE:
<223> OTHER INFORMATION: Synthetic antibody

<400> SEQUENCE: 564

```
Gln Ser Val Leu Thr Gln Pro Pro Ser Ala Ser Gly Thr Pro Gly Gln
1               5                   10                  15

Arg Val Thr Ile Ser Cys Ser Gly Ser Lys Ser Asn Val Gly Asn Asn
            20                  25                  30

Phe Val His Trp Tyr Gln Gln Leu Pro Gly Thr Ala Pro Lys Leu Leu
        35                  40                  45

Leu Tyr Ser Asn Leu Glu Arg Ser Ser Gly Val Pro Glu Arg Phe Ser
    50                  55                  60

Gly Ser Lys Ser Gly Thr Ser Ala Tyr Leu Ala Ile Ser Gly Leu Arg
65                  70                  75                  80

Ser Asp Asp Glu Ala Asp Tyr Tyr Cys Ala Ala Trp Asp Asp Ser Leu
```

-continued

```
                  85                    90                    95

Pro Gly Trp Val Phe Gly Gly Gly Thr Lys Leu Thr Val Leu
            100                   105                   110

<210> SEQ ID NO 565
<211> LENGTH: 110
<212> TYPE: PRT
<213> ORGANISM: Artificial sequence
<220> FEATURE:
<223> OTHER INFORMATION: Synthetic antibody

<400> SEQUENCE: 565

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Leu Asn Trp Tyr Gln Gln Leu Pro Gly Thr Ala Pro Lys Leu Leu
        35                  40                  45

Ile Tyr Asn Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Gln Leu Thr Val Leu
            100                   105                   110

<210> SEQ ID NO 566
<211> LENGTH: 111
<212> TYPE: PRT
<213> ORGANISM: Artificial sequence
<220> FEATURE:
<223> OTHER INFORMATION: Synthetic antibody

<400> SEQUENCE: 566

Gln Ala Val Val Thr Gln Pro Ala Ser Val Ser Gly Ser Pro Gly Gln
1               5                   10                  15

Ser Val Ser Ile Ser Cys Thr Gly Thr Ser Ser Asp Val Gly Gly Phe
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Thr Ala Pro Tyr Val Phe Gly Thr Gly Thr Lys Val Thr Val Leu
            100                   105                   110

<210> SEQ ID NO 567
<211> LENGTH: 111
<212> TYPE: PRT
<213> ORGANISM: Artificial sequence
<220> FEATURE:
<223> OTHER INFORMATION: Synthetic antibody

<400> SEQUENCE: 567

Gln Ser Val Leu Thr Gln Pro Arg Ser Val Ser Gly Ser Pro Gly Gln
1               5                   10                  15
```

-continued

```
Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Ser Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Gly
                85                  90                  95

Tyr Thr Pro Tyr Val Phe Gly Thr Gly Thr Lys Val Thr Val Leu
            100                 105                 110

<210> SEQ ID NO 568
<211> LENGTH: 110
<212> TYPE: PRT
<213> ORGANISM: Artificial sequence
<220> FEATURE:
<223> OTHER INFORMATION: Synthetic antibody

<400> SEQUENCE: 568

Gln Ser Val Leu Thr Gln Pro Pro Ser Ala Ser Ala Thr Pro Gly Gln
1               5                   10                  15

Arg Val Thr Ile Ser Cys Ser Gly Arg Asn Ala Asn Ile Gly Ser Asn
            20                  25                  30

Pro Val Asn Trp Tyr Gln Gln Leu Pro Gly Thr Ala Pro Arg Leu Val
            35                  40                  45

Met Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Glu Gly Trp Asp Asp Ser Leu
                85                  90                  95

Asn Gly Tyr Val Phe Gly Thr Gly Thr Lys Val Thr Val Leu
            100                 105                 110

<210> SEQ ID NO 569
<211> LENGTH: 112
<212> TYPE: PRT
<213> ORGANISM: Artificial sequence
<220> FEATURE:
<223> OTHER INFORMATION: Synthetic antibody

<400> SEQUENCE: 569

Asp Ile Val Met Thr Gln Ser Pro Leu Ser Leu Pro Val Thr Leu Gly
1               5                   10                  15

Gln Pro Ala Ser Ile Ser Cys Thr Ser Ser Gln Ser Leu Val Tyr Ser
            20                  25                  30

Asp Gly Asn Thr Tyr Leu Asn Trp Phe His Gln Arg Pro Gly Gln Ser
            35                  40                  45

Pro Arg Arg Leu Phe Tyr Lys Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Met Gln Gly
                85                  90                  95

Thr His Trp Pro Val Thr Phe Gly Gln Gly Thr Arg Leu Glu Ile Lys
```

-continued

```
            100             105             110
```

<210> SEQ ID NO 570
<211> LENGTH: 110
<212> TYPE: PRT
<213> ORGANISM: Artificial sequence
<220> FEATURE:
<223> OTHER INFORMATION: Synthetic antibody

<400> SEQUENCE: 570

```
Gln Ser Val Leu Thr Gln Pro Pro Ser Ala Ser Ala Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Val Pro Gly Met Ala Pro Glu Leu Val
        35                  40                  45

Met Tyr Ser Asp Asn Gln Arg Pro Ser Gly Val Pro Asp Arg Phe Ser
    50                  55                  60

Gly Ser Asn Ser Gly Thr Ser Ala Ser Leu Ala Ile Ser Gly Leu Gln
65                  70                  75                  80

Ser Glu Asp Glu Ala Asp Tyr Tyr Cys Ser Thr Trp Asp Asp Ser Leu
                85                  90                  95

Asn Gly Leu Val Phe Gly Thr Gly Thr Lys Val Thr Val Leu
            100                 105                 110
```

<210> SEQ ID NO 571
<211> LENGTH: 107
<212> TYPE: PRT
<213> ORGANISM: Artificial sequence
<220> FEATURE:
<223> OTHER INFORMATION: Synthetic antibody

<400> SEQUENCE: 571

```
Asp Val Gln Met Thr Gln Ser Pro Ser Ser Leu Ser Ala Ser Val Gly
1               5                   10                  15

Glu Arg Val Thr Leu Thr Cys Arg Ala Ser Gln Gly Ile Tyr Ser Ser
            20                  25                  30

Leu Ala Trp Tyr Gln Gln Lys Pro Gly Lys Ala Pro Lys Leu Leu Leu
        35                  40                  45

Tyr Gly Thr Ser Gln Leu Glu Arg Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ser Ala Thr Tyr Tyr Cys Gln Gln His Tyr Asn Leu Pro Ile
                85                  90                  95

Thr Phe Gly Gln Gly Thr Arg Leu Glu Ile Lys
            100                 105
```

<210> SEQ ID NO 572
<211> LENGTH: 110
<212> TYPE: PRT
<213> ORGANISM: Artificial sequence
<220> FEATURE:
<223> OTHER INFORMATION: Synthetic antibody

<400> SEQUENCE: 572

```
Gln Pro Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30
```

```
Val Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Pro Val Phe Gly Gly Gly Thr Lys Leu Thr Val Leu
                100                 105                 110
```

<210> SEQ ID NO 573
<211> LENGTH: 102
<212> TYPE: PRT
<213> ORGANISM: Artificial sequence
<220> FEATURE:
<223> OTHER INFORMATION: Synthetic antibody

<400> SEQUENCE: 573

```
Gln Ser Pro Ser Ser Leu Ser Ala Ser Val Gly Asp Arg Val Thr Ile
1               5                   10                  15

Thr Cys Arg Ala Ser Gln Gly Ile Ser Asn Tyr Leu Ala Trp Tyr Gln
            20                  25                  30

Gln Lys Pro Gly Lys Val Pro Lys Leu Leu Ile Tyr Ala Ala Ser Thr
        35                  40                  45

Leu Gln Ser Gly Val Pro Ser Arg Phe Ser Gly Ser Gly Ser Gly Thr
    50                  55                  60

Asp Phe Thr Leu Thr Ile Ser Ser Leu Gln Pro Glu Asp Val Ala Thr
65                  70                  75                  80

Tyr Tyr Cys Gln Lys Tyr Asn Ser Ala Pro Leu Thr Phe Gly Gly Gly
                85                  90                  95

Thr Lys Leu Glu Ile Lys
            100
```

<210> SEQ ID NO 574
<211> LENGTH: 101
<212> TYPE: PRT
<213> ORGANISM: Artificial sequence
<220> FEATURE:
<223> OTHER INFORMATION: Synthetic antibody

<400> SEQUENCE: 574

```
Gln Ser Pro Ser Thr Leu Ser Ala Ser Val Gly Asp Arg Val Thr Ile
1               5                   10                  15

Thr Cys Arg Ala Ser Gln Ser Ile Ser Ser Trp Leu Ala Trp Tyr Gln
            20                  25                  30

Gln Lys Pro Gly Lys Ala Pro Lys Leu Leu Ile Tyr Lys Ala Ser Ser
        35                  40                  45

Leu Glu Ser Gly Val Pro Ser Arg Phe Ser Gly Ser Gly Ser Gly Thr
    50                  55                  60

Glu Phe Thr Leu Thr Ile Ser Ser Leu Gln Pro Asp Asp Phe Ala Thr
65                  70                  75                  80

Tyr Tyr Cys Gln Gln Tyr Asn Ser Tyr Leu Thr Phe Gly Gly Gly Thr
                85                  90                  95

Lys Val Asp Ile Lys
            100
```

<210> SEQ ID NO 575
<211> LENGTH: 110
<212> TYPE: PRT
<213> ORGANISM: Artificial sequence
<220> FEATURE:
<223> OTHER INFORMATION: Synthetic antibody

<400> SEQUENCE: 575

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Val Thr Val Leu
            100                 105                 110

<210> SEQ ID NO 576
<211> LENGTH: 108
<212> TYPE: PRT
<213> ORGANISM: Artificial sequence
<220> FEATURE:
<223> OTHER INFORMATION: Synthetic antibody

<400> SEQUENCE: 576

Ser Tyr Glu Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105

<210> SEQ ID NO 577
<211> LENGTH: 102
<212> TYPE: PRT
<213> ORGANISM: Artificial sequence
<220> FEATURE:
<223> OTHER INFORMATION: Synthetic antibody

<400> SEQUENCE: 577

Gln Ser Pro Ser Ser Leu Ser Ala Ser Val Gly Asp Arg Val Thr Ile
1               5                   10                  15

Thr Cys Arg Ala Ser Gln Ser Ile Ser Asn Phe Val Asn Trp Tyr Gln
            20                  25                  30

Gln Lys Pro Gly Glu Val Pro Lys Leu Leu Ile Tyr Gly Ala Ser Ser
        35                  40                  45

```
Leu Gln Ser Gly Val Pro Ser Arg Phe Ser Gly Ser Gly Ser Gly Thr
    50                  55                  60

Asp Phe Thr Leu Thr Ile Ser Ser Leu Gln Pro Glu Asp Phe Ala Thr
65                  70                  75                  80

Tyr Tyr Cys Gln Gln Gly Tyr Ser Val Pro Leu Thr Phe Gly Gly Gly
                85                  90                  95

Thr Thr Val Asp Ile Lys
            100

<210> SEQ ID NO 578
<211> LENGTH: 111
<212> TYPE: PRT
<213> ORGANISM: Artificial sequence
<220> FEATURE:
<223> OTHER INFORMATION: Synthetic antibody

<400> SEQUENCE: 578

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60

Ser Gly Ser Lys Ser Gly Asn Ser Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Pro Tyr Val Phe Gly Thr Gly Thr Lys Val Thr Val Leu
            100                 105                 110

<210> SEQ ID NO 579
<211> LENGTH: 103
<212> TYPE: PRT
<213> ORGANISM: Artificial sequence
<220> FEATURE:
<223> OTHER INFORMATION: Synthetic antibody

<400> SEQUENCE: 579

Gln Ser Pro Ser Ser Leu Ser Ala Ser Val Gly Asp Arg Val Thr Ile
1               5                   10                  15

Thr Cys Arg Ala Ser Gln Ser Ile Arg Thr Tyr Leu Asn Trp Tyr Gln
                20                  25                  30

Gln Lys Pro Gly Lys Asp Pro Glu Leu Leu Ile Tyr Ala Ala Thr Ser
            35                  40                  45

Leu Gln Ser Gly Val Pro Ser Arg Phe Thr Gly Ser Gly Ser Gly Thr
    50                  55                  60

Asp Phe Thr Leu Thr Ile Ser Ser Leu Gln Pro Glu Asp Phe Ala Thr
65                  70                  75                  80

Tyr Tyr Cys Gln Gln Ser Tyr Ser Ala Pro Val Phe Thr Phe Gly Gln
                85                  90                  95

Gly Thr Lys Leu Glu Ile Lys
            100

<210> SEQ ID NO 580
<211> LENGTH: 107
<212> TYPE: PRT
```

<213> ORGANISM: Artificial sequence
<220> FEATURE:
<223> OTHER INFORMATION: Synthetic antibody

<400> SEQUENCE: 580

Ala Ile Gln Met Thr Gln Ser Pro Ser Ser Leu Ser Ala Ser Val Gly
1               5                   10                  15

Asp Arg Val Ser Ile Thr Cys Arg Ala Ser Gln Ser Ile Ser Ser Phe
            20                  25                  30

Leu Asn Trp Tyr Gln Gln Arg Pro Gly Lys Ala Pro Glu Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Ile
                85                  90                  95

Thr Phe Gly Gln Gly Thr Gln Leu Glu Ile Lys
            100                 105

<210> SEQ ID NO 581
<211> LENGTH: 107
<212> TYPE: PRT
<213> ORGANISM: Artificial sequence
<220> FEATURE:
<223> OTHER INFORMATION: Synthetic antibody

<400> SEQUENCE: 581

Asp Val Gln Met Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Leu Glu Ile Lys
            100                 105

<210> SEQ ID NO 582
<211> LENGTH: 107
<212> TYPE: PRT
<213> ORGANISM: Artificial sequence
<220> FEATURE:
<223> OTHER INFORMATION: Synthetic antibody

<400> SEQUENCE: 582

Asp Val Gln Met Thr Gln Ser Pro Ser Ser Leu Ser Ala Ser Val Gly
1               5                   10                  15

Asp Arg Val Ser Ile Thr Cys Arg Ala Ser Gln Ser Ile Ser Ser Phe
            20                  25                  30

Leu Asn Trp Tyr Gln Gln Arg Pro Gly Lys Ala Pro Glu Leu Leu Ile
        35                  40                  45

Tyr Gly Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Ile
                85                  90                  95

Thr Phe Gly Gln Gly Thr Arg Leu Glu Ile Lys
            100                 105

<210> SEQ ID NO 583
<211> LENGTH: 107
<212> TYPE: PRT
<213> ORGANISM: Artificial sequence
<220> FEATURE:
<223> OTHER INFORMATION: Synthetic antibody

<400> SEQUENCE: 583

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gly Gly Thr Thr Val Glu Ile Lys
            100                 105

<210> SEQ ID NO 584
<211> LENGTH: 107
<212> TYPE: PRT
<213> ORGANISM: Artificial sequence
<220> FEATURE:
<223> OTHER INFORMATION: Synthetic antibody

<400> SEQUENCE: 584

Ala Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Gly Ser Trp
                20                  25                  30

Leu Ala Trp Tyr Gln Gln Lys Pro Gly Lys Ala Pro Lys Leu Leu Ile
            35                  40                  45

Ser Val Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Thr Val Glu Ile Lys
            100                 105

<210> SEQ ID NO 585
<211> LENGTH: 105
<212> TYPE: PRT
<213> ORGANISM: Artificial sequence
<220> FEATURE:
<223> OTHER INFORMATION: Synthetic antibody
```

<400> SEQUENCE: 585

Gln Pro Pro Ser Val Ser Ala Ala Pro Arg Gln Arg Val Thr Ile Ser
1               5                   10                  15

Cys Ser Gly Ser Ser Ser Asn Ile Gly Asp Asn Ser Val Asn Trp Tyr
            20                  25                  30

Gln Gln Leu Pro Gly Lys Ala Pro Lys Leu Leu Ile Tyr Leu Asp Asp
        35                  40                  45

Leu Leu Pro Ser Gly Val Ser Gly Arg Phe Ser Gly Ser Lys Ser Gly
        50                  55                  60

Thr Ser Ala Ser Leu Val Ile Ser Gly Leu Gln Ser Glu Asp Glu Ala
65                  70                  75                  80

Asp Tyr Tyr Cys Ala Thr Trp Asp Asp Ser Leu Asn Gly Val Val Phe
                85                  90                  95

Gly Gly Gly Thr Lys Val Thr Val Leu
            100                 105

<210> SEQ ID NO 586
<211> LENGTH: 118
<212> TYPE: PRT
<213> ORGANISM: Artificial sequence
<220> FEATURE:
<223> OTHER INFORMATION: Synthetic antibody

<400> SEQUENCE: 586

Asp Val Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Thr Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Phe Thr Phe Gly Ser Gly Thr Lys Val Glu Ile
            100                 105                 110

Lys Arg Thr Val Ala Ala
        115

<210> SEQ ID NO 587
<211> LENGTH: 107
<212> TYPE: PRT
<213> ORGANISM: Artificial sequence
<220> FEATURE:
<223> OTHER INFORMATION: Synthetic antibody

<400> SEQUENCE: 587

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

-continued

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 588
<211> LENGTH: 106
<212> TYPE: PRT
<213> ORGANISM: Artificial sequence
<220> FEATURE:
<223> OTHER INFORMATION: Synthetic antibody

<400> SEQUENCE: 588

Gln Pro Pro Ser Val Ser Gly Ala Pro Gly Gln Arg Val Thr Ile Ser
1                   5                   10                  15

Cys Ala Gly Ser Ser Ser Asn Ile Gly Ala Gly Tyr Gly Val His Trp
                20                  25                  30

Tyr Gln His Leu Pro Gly Thr Ala Pro Lys Leu Leu Ile Tyr Gly Asp
        35                  40                  45

Asn Asn Arg Pro Ser Gly Val Pro Tyr Arg Phe Ser Gly Ser Lys Ser
    50                  55                  60

Gly Thr Ser Ala Ser Leu Ala Ile Thr Gly Leu Gln Ala Glu Asp Glu
65                  70                  75                  80

Ala Asp Tyr Phe Cys Gln Ser Tyr Asp Ser Ser Leu Gly Val Gly Val
                85                  90                  95

Phe Gly Gly Gly Thr Lys Val Thr Val Leu
            100                 105

<210> SEQ ID NO 589
<211> LENGTH: 107
<212> TYPE: PRT
<213> ORGANISM: Artificial sequence
<220> FEATURE:
<223> OTHER INFORMATION: Synthetic antibody

<400> SEQUENCE: 589

Ala Ile Gln Leu Thr Gln Ser Pro Ser Ser Leu Ser Ala Ser Val Gly
1                   5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys
            100                 105

<210> SEQ ID NO 590
<211> LENGTH: 107
<212> TYPE: PRT
<213> ORGANISM: Artificial sequence
<220> FEATURE:
<223> OTHER INFORMATION: Synthetic antibody

<400> SEQUENCE: 590

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Leu Glu Ile Lys
            100                 105

<210> SEQ ID NO 591
<211> LENGTH: 107
<212> TYPE: PRT
<213> ORGANISM: Artificial sequence
<220> FEATURE:
<223> OTHER INFORMATION: Synthetic antibody

<400> SEQUENCE: 591

Asp Val Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Leu Glu Ile Lys
            100                 105

<210> SEQ ID NO 592
<211> LENGTH: 107
<212> TYPE: PRT
<213> ORGANISM: Artificial sequence
<220> FEATURE:
<223> OTHER INFORMATION: Synthetic antibody

<400> SEQUENCE: 592

Asn Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

-continued

```
Glu Asp Phe Ala Thr Tyr Tyr Cys Gln Gln Ser Tyr Ser Thr Pro Arg
            85                  90                  95

Thr Phe Gly Gln Gly Thr Thr Val Glu Ile Lys
            100                 105

<210> SEQ ID NO 593
<211> LENGTH: 89
<212> TYPE: PRT
<213> ORGANISM: Artificial sequence
<220> FEATURE:
<223> OTHER INFORMATION: Synthetic antibody

<400> SEQUENCE: 593

Pro Lys Pro Thr Leu Trp Ala Glu Pro Gly Ser Val Ile Thr Gln Gly
1               5                   10                  15

Ser Pro Val Thr Leu Arg Cys Gln Gly Gly Gln Glu Thr Gln Glu Tyr
            20                  25                  30

Arg Leu Tyr Arg Glu Lys Lys Thr Ala Leu Trp Ile Thr Arg Ile Pro
        35                  40                  45

Gln Glu Leu Val Lys Lys Gly Gln Phe Pro Ile Pro Ser Ile Thr Trp
    50                  55                  60

Glu His Ala Gly Arg Tyr Arg Cys Tyr Tyr Gly Ser Lys Thr Ala Gly
65                  70                  75                  80

Arg Ser Glu Ser Ser Asp Pro Leu Glu
                85

<210> SEQ ID NO 594
<211> LENGTH: 84
<212> TYPE: PRT
<213> ORGANISM: Artificial sequence
<220> FEATURE:
<223> OTHER INFORMATION: Synthetic antibody

<400> SEQUENCE: 594

Pro Lys Pro Thr Leu Trp Ala Glu Pro Asp Ser Val Ile Thr Gln Gly
1               5                   10                  15

Ser Pro Val Thr Leu Ser Cys Gln Gly Ser Leu Glu Ala Gln Glu Tyr
            20                  25                  30

Arg Leu Tyr Arg Glu Lys Lys Ser Ala Ser Trp Ile Thr Arg Ile Arg
        35                  40                  45

Pro Glu Leu Val Lys Asn Gly Gln Phe His Ile Pro Ser Ile Thr Trp
    50                  55                  60

Glu His Thr Gly Arg Tyr Gly Cys Gln Tyr Tyr Ser Arg Ala Arg Trp
65                  70                  75                  80

Ser Glu Leu Ser

<210> SEQ ID NO 595
<211> LENGTH: 63
<212> TYPE: PRT
<213> ORGANISM: Artificial sequence
<220> FEATURE:
<223> OTHER INFORMATION: Synthetic antibody

<400> SEQUENCE: 595

Pro Lys Pro Thr Leu Trp Ala Glu Pro Ser Val Ile Thr Gln Gly Ser
1               5                   10                  15

Pro Val Thr Leu Cys Gln Gly Glu Gln Glu Tyr Arg Leu Tyr Arg Glu
            20                  25                  30

Lys Lys Ser Ala Trp Ile Thr Arg Ile Glu Leu Val Lys Gly Gln Phe
```

-continued

```
         35                    40                    45

Ile Pro Ser Ile Thr Trp Glu His Gly Arg Tyr Cys Tyr Ser Ser
    50                    55                    60
```

<210> SEQ ID NO 596
<211> LENGTH: 155
<212> TYPE: PRT
<213> ORGANISM: Artificial sequence
<220> FEATURE:
<223> OTHER INFORMATION: Synthetic antibody

<400> SEQUENCE: 596

```
Trp Ser Ala Pro Ser Asp Pro Leu Asp Ile Leu Ile Ala Gly Gln Phe
1               5                   10                  15

Tyr Asp Arg Val Ser Leu Ser Val Gln Pro Gly Pro Thr Cys Ala Ser
            20                  25                  30

Gly Glu Asn Val Thr Leu Leu Cys Gln Ser Gln Gly Trp Met Gln Thr
        35                  40                  45

Phe Leu Leu Thr Lys Glu Gly Ala Ala Asp Asp Pro Trp Arg Leu Arg
    50                  55                  60

Ser Thr Tyr Gln Ser Gln Lys Tyr Gln Ala Glu Phe Pro Met Gly Pro
65                  70                  75                  80

Val Thr Ser Ala His Ala Gly Thr Tyr Arg Cys Tyr Gly Ser Gln Ser
            85                  90                  95

Ser Lys Pro Tyr Leu Leu Thr His Pro Ser Asp Pro Leu Glu Leu Val
            100                 105                 110

Val Ser Gly Pro Ser Gly Gly Pro Ser Ser Pro Thr Thr Gly Pro Thr
            115                 120                 125

Ser Thr Ser Gly Pro Glu Asp Gln Pro Leu Thr Pro Thr Gly Ser Asp
    130                 135                 140

Pro Gln Ser Gly Leu Gly Arg His Leu Gly Val
145                 150                 155
```

<210> SEQ ID NO 597
<211> LENGTH: 157
<212> TYPE: PRT
<213> ORGANISM: Artificial sequence
<220> FEATURE:
<223> OTHER INFORMATION: Synthetic antibody

<400> SEQUENCE: 597

```
Cys Ser Ala Pro Ser Asp Pro Leu Asp Ile Leu Ile Thr Gly Gln Ile
1               5                   10                  15

Arg Gly Thr Pro Phe Ile Ser Val Gln Pro Gly Pro Thr Val Ala Ser
            20                  25                  30

Gly Glu Asn Val Thr Leu Leu Cys Gln Ser Trp Arg Gln Phe His Thr
        35                  40                  45

Phe Leu Leu Thr Lys Ala Gly Ala Ala Asp Ala Pro Leu Arg Leu Arg
    50                  55                  60

Ser Ile His Glu Tyr Pro Lys Tyr Gln Ala Glu Phe Pro Met Ser Pro
65                  70                  75                  80

Val Thr Ser Ala His Ala Gly Thr Tyr Arg Cys Tyr Gly Ser Leu Asn
            85                  90                  95

Ser Asp Pro Tyr Leu Leu Ser Thr His Pro Ser Glu Pro Leu Glu Leu
            100                 105                 110

Val Val Ser Gly Pro Ser Met Gly Ser Ser Pro Pro Pro Thr Gly Pro
            115                 120                 125
```

-continued

```
Ile Ser Thr Pro Ala Gly Pro Glu Asp Gln Pro Leu Thr Pro Thr Gly
    130                 135                 140

Ser Asp Pro Gln Ser Gly Leu Gly Arg His Leu Gly Val
145                 150                 155

<210> SEQ ID NO 598
<211> LENGTH: 4
<212> TYPE: PRT
<213> ORGANISM: Artificial sequence
<220> FEATURE:
<223> OTHER INFORMATION: Synthetic antibody

<400> SEQUENCE: 598

Ser Leu Glu Ala
1

<210> SEQ ID NO 599
<211> LENGTH: 4
<212> TYPE: PRT
<213> ORGANISM: Artificial sequence
<220> FEATURE:
<223> OTHER INFORMATION: Synthetic antibody

<400> SEQUENCE: 599

Gly Gln Glu Thr
1

<210> SEQ ID NO 600
<211> LENGTH: 4
<212> TYPE: PRT
<213> ORGANISM: Artificial sequence
<220> FEATURE:
<223> OTHER INFORMATION: Synthetic antibody

<400> SEQUENCE: 600

Lys Ser Ala Ser
1

<210> SEQ ID NO 601
<211> LENGTH: 4
<212> TYPE: PRT
<213> ORGANISM: Artificial sequence
<220> FEATURE:
<223> OTHER INFORMATION: Synthetic antibody

<400> SEQUENCE: 601

Lys Thr Ala Leu
1

<210> SEQ ID NO 602
<211> LENGTH: 4
<212> TYPE: PRT
<213> ORGANISM: Artificial sequence
<220> FEATURE:
<223> OTHER INFORMATION: Synthetic antibody

<400> SEQUENCE: 602

Ile Arg Pro Glu
1

<210> SEQ ID NO 603
<211> LENGTH: 4
<212> TYPE: PRT
<213> ORGANISM: Artificial sequence
<220> FEATURE:
<223> OTHER INFORMATION: Synthetic antibody
```

```
<400> SEQUENCE: 603

Ile Pro Gln Glu
1

<210> SEQ ID NO 604
<211> LENGTH: 7
<212> TYPE: PRT
<213> ORGANISM: Artificial sequence
<220> FEATURE:
<223> OTHER INFORMATION: Synthetic antibody

<400> SEQUENCE: 604

Arg Ala Arg Trp Ser Glu Leu
1               5

<210> SEQ ID NO 605
<211> LENGTH: 8
<212> TYPE: PRT
<213> ORGANISM: Artificial sequence
<220> FEATURE:
<223> OTHER INFORMATION: Synthetic antibody

<400> SEQUENCE: 605

Asp Thr Ala Gly Arg Ser Glu Ser
1               5

<210> SEQ ID NO 606
<211> LENGTH: 3
<212> TYPE: PRT
<213> ORGANISM: Artificial sequence
<220> FEATURE:
<223> OTHER INFORMATION: Synthetic antibody

<400> SEQUENCE: 606

Trp Arg Gln
1

<210> SEQ ID NO 607
<211> LENGTH: 3
<212> TYPE: PRT
<213> ORGANISM: Artificial sequence
<220> FEATURE:
<223> OTHER INFORMATION: Synthetic antibody

<400> SEQUENCE: 607

Gln Gly Trp
1

<210> SEQ ID NO 608
<211> LENGTH: 5
<212> TYPE: PRT
<213> ORGANISM: Artificial sequence
<220> FEATURE:
<223> OTHER INFORMATION: Synthetic antibody

<400> SEQUENCE: 608

Ile His Glu Tyr Pro
1               5

<210> SEQ ID NO 609
<211> LENGTH: 5
<212> TYPE: PRT
<213> ORGANISM: Artificial sequence
<220> FEATURE:
<223> OTHER INFORMATION: Synthetic antibody

<400> SEQUENCE: 609
```

-continued

```
Thr Tyr Gln Ser Gln
1               5

<210> SEQ ID NO 610
<211> LENGTH: 4
<212> TYPE: PRT
<213> ORGANISM: Artificial sequence
<220> FEATURE:
<223> OTHER INFORMATION: Synthetic antibody

<400> SEQUENCE: 610

Leu Asn Ser Asp
1

<210> SEQ ID NO 611
<211> LENGTH: 4
<212> TYPE: PRT
<213> ORGANISM: Artificial sequence
<220> FEATURE:
<223> OTHER INFORMATION: Synthetic antibody

<400> SEQUENCE: 611

Gln Ser Ser Lys
1

<210> SEQ ID NO 612
<211> LENGTH: 3
<212> TYPE: PRT
<213> ORGANISM: Artificial sequence
<220> FEATURE:
<223> OTHER INFORMATION: Synthetic antibody

<400> SEQUENCE: 612

Ser Glu Pro
1

<210> SEQ ID NO 613
<211> LENGTH: 3
<212> TYPE: PRT
<213> ORGANISM: Artificial sequence
<220> FEATURE:
<223> OTHER INFORMATION: Synthetic antibody

<400> SEQUENCE: 613

Ser Asp Pro
1
```

LILRB2 ANTIBODIES AND USES THEREOF

PRIORITY CLAIM

This application is a national phase application under 35 U.S.C. § 371 of International Application No. PCT/US2021/015362, filed Jan. 28, 2021, which claims benefit of priority to U.S. Provisional Application Ser. No. 62/970,496, filed Feb. 5, 2020, the entire contents of which are hereby incorporated by reference.

SEQUENCE LISTING

The sequence listing that is contained in the file named "UTFHP0359WO_ST25", which is 213 KB (as measured in Microsoft Windows) and was created on Jan. 27, 2021, is filed herewith by electronic submission and is incorporated by reference herein.

BACKGROUND

1. Field

The present disclosure relates generally to the fields of medicine, oncology, immunology and immuno-oncology. More particular, the disclosure relates to antibodies that bind to LILRBs and can treat cancers, including leukemia and solid tumors.

2. Description of Related Art

Current immune checkpoint blockade strategies have been successful in treating certain types of solid cancer. However, most cancer patients do not respond to current checkpoint blockade or they relapse after treatment. Additionally, checkpoint blockade monotherapies have not been successful against most hematologic malignancies including multiple myeloma and leukemia.

It is believed that tumor microenvironment (TME) plays a critical role in regulating immune responses to tumors. Among the complex factors and components that constitute the tumor microenvironment, myeloid derived suppressor cells (MDSC), tumor associated macrophages (TAMs) and extracellular matrix all play critical role in suppressing the immune responses to tumor.

Recently, it has been shown that inhibitory leukocyte immunoglobulin-like receptors (LILRBs) and a related immunoreceptor tyrosine-based inhibitory motif (ITIM)-containing receptor, LAIR1, have tumor-promoting functions in various hematopoietic and solid cancer cells and in the immunosuppressive tumor microenvironment. ITIM-containing receptors are expressed on a wide range of immune cells and transduce signals by recruitment of phosphatases SHP-1, SHP-2, or SHIP, leading to negative regulation of immune cell activation. Similar to CTLA-4 and PD-1, LILRBs are considered immune checkpoint factors.

LILRB2 has been identified as a key regulator of myeloid cell phenotype in vitro and in vivo as its activation by various ligands suppresses the pro-inflammatory activity of myeloid cells. Because myeloid cells with a suppressive/anti-inflammatory phenotype can down-regulate the activation, proliferation and cytotoxic activity of T cells in the solid tumor microenvironment, therapeutic blocking of LILRB2 in myeloid-rich solid tumors has the potential to reactivate or enhance anti-tumor immune responses in patients presenting with disease unresponsive/relapsed to T cell checkpoint inhibitors.

LILRBs may inhibit activities of a number of immune cell types facilitating tumour immune escape. LILRB2 belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on myeloid cells; it binds to multiple types of ligands, including HLA class I molecules, ANGPTLs, myelin inhibitors (including Nogo66, MAG, and OMgp), and β-amyloid, transducing a negative signal that inhibits stimulation of an immune response. It is thought to control inflammatory responses and cytotoxicity to help focus the immune response and limit autoreactivity. Multiple transcript variants encoding different isoforms have been found for this gene.

Conversely, by agonising LILRB family of receptors, we may be able to suppress immune response or inflammations found in autoimmune or inflammatory diseases.

SUMMARY

Thus, in one aspect, the present disclosure provides an isolated monoclonal antibody or an antigen-binding fragment thereof that binds specifically to LILRB2. In certain embodiments, the antibody or antigen-binding fragment, when bound to LILRB2, modulates the activation of LILRB2. In certain embodiments, the antibody or antigen-binding fragment, when bound to LILRB2, activates LILRB2. In certain embodiments, the antibody or antigen-binding fragment, when bound to LILRB2, suppresses activation of LILRB2. In certain embodiments, the antibody or antigen-binding fragment, when bound to LILRB2, specifically blocks binding of MHC and other ligands to LILRB2.

In one aspect, the isolated monoclonal antibody or an antigen-binding fragment thereof comprises a heavy chain (HC) variable region (VH) and a light chain (LC) variable region (VL) comprising the clone-paired CDR sequences as set forth in Table 2; and variants thereof wherein one or more of the LC-CDRs has one, two, or three amino acid substitutions, additions, deletions, or combinations thereof. The isolated monoclonal antibody or an antigen binding fragment thereof of claim 1, wherein the isolated monoclonal antibody is a murine, a rodent, a rabbit, a chimeric, humanized, or human antibody. The isolated monoclonal antibody or an antigen-binding fragment thereof may have VH and VL chains with amino acid sequences at least 90% or 95% identical to the clone-paired sequences of Appendices II and IV, respectively. The isolated monoclonal antibody or an antigen-binding fragment thereof may have VH and VL chains encoded by nucleic acid sequences at least 80% or 90% identical to the clone-paired sequences of Appendices I and III, respectively. The isolated monoclonal antibody or an antigen-binding fragment thereof of may have VH and VL chains with amino acid sequences identical to the clone-paired sequences of Appendices II and IV, respectively. The isolated monoclonal antibody or an antigen binding fragment thereof may have VH and VL chains encoded by nucleic acid sequences identical to the clone-paired sequences of Appendices I and III, respectively.

The variants may be those where one or more of the HC-CDRs or LC-CDRs has one, two, or three amino acid substitutions, additions, deletions, or combinations thereof. In certain embodiments, each CDR is defined in accordance with Kabat definition, the Chothia definition, the combination of Kabat definition and Chothia definition, the AbM definition, or the contact definition of CDR.

In another aspect, the present disclosure provides an isolated monoclonal antibody or an antigen-binding fragment thereof, which competes for the same epitope with an antibody having clone-paired heavy and light chain CDR sequences from Table 2. In certain embodiments, the epitope bound by the antibody or antigen-binding fragment is located within the linker region between the D1 and D2 domain of human LILRB2.

In certain embodiments, the isolated monoclonal antibody described herein is a chimeric, humanized, or human antibody. In certain embodiments, isolated monoclonal antibody described herein is of the IgG1, IgG2, IgG3 or IgG4 type. In certain embodiments, the antigen-binding fragment described herein is a recombinant ScFv (single chain fragment variable) antibody, Fab fragment, F(ab')2 fragment, or Fv fragment.

In another aspect, there is provided a pharmaceutical composition comprising an isolated monoclonal antibody or an antigen-binding fragment thereof as provided herein, and at least one pharmaceutically acceptable carrier.

In another aspect, there is provided an isolated nucleic acid that encodes the isolated monoclonal antibody or an antigen-binding fragment thereof as provided herein.

In another aspect, there is provided a vector comprising the isolated nucleic acid as provided herein.

In another aspect, there is provided a host cell comprising the vector as provided herein. The host cell may be a mammalian cell. The host cell may be a CHO cell.

In another aspect, there is provided a hybridoma encoding or producing the isolated monoclonal antibody as provided herein.

In another aspect, there is provided a process of producing an antibody. The method may comprise culturing the host cell as provided herein under conditions suitable for expressing the antibody and recovering the antibody.

In another aspect, there is provided a chimeric antigen receptor (CAR) protein comprising an antigen-binding fragment as provided herein.

In another aspect, there is provided an isolated nucleic acid that encodes a CAR protein as provided herein.

In another aspect, there is provided an engineered cell comprising the isolated nucleic acid as provided herein. In certain embodiments, the cell is a T cell, NK cell, or myeloid cell.

In another, there is provided a method of treating or ameliorating the effect of a cancer in a subject, the method comprising administering to the subject a therapeutically effective amount of the antibody or an antigen-binding fragment thereof as defined herein.

The method may reduce or eradicate the tumor burden in the subject, may and/or slow tumor growth rate, may reduce the number of tumor cells, may reduce tumor size, may reduce tumor infiltration, may reduce tumor metastasis, may eradicate the tumor in the subject. The cancer may be a solid tumor or hematologic malignancy.

In certain embodiments, the cancer is a solid tumor including adrenal cancer, bile duct carcinoma, bone cancer, brain cancer, breast cancer, cervical cancer, choriocarcinoma, colon cancer, colorectal cancer, esophageal cancer, eye cancer, gastric cancer, glioblastoma, head and neck cancer, kidney cancer, liver cancer, lung cancer, mesothelioma, melanoma, merkel cell cancer, nasopharyngeal carcinoma, neuroblastoma, oral cancer, ovarian cancer, pancreatic cancer, penile cancer, pinealoma, prostate cancer, renal cell cancer, retinoblastoma, sarcoma, skin cancer, testicular cancer, thymic carcinoma, thyroid cancer, uterine cancer, and vaginal cancer.

In some embodiments, the cancer is a metastatic, recurrent or drug-resistant cancer.

In some embodiments, said cancer is hematologic malignancies including acute lymphocytic leukemia (ALL), acute myeloid leukemia (AML), B-cell leukemia, blastic plasmacytoid dendritic cell neoplasm (BPDCN), chronic lymphoblastic leukemia (CLL), chronic myelomonocytic leukemia (CMML), chronic myelocytic leukemia (CML), pre-B acute lymphocytic leukemia (Pre-B ALL), diffuse large B-cell lymphoma (DLBCL), extranodal NK/T-cell lymphoma, hairy cell leukemia, HHV8-associated primary effusion lymphoma, plasmablastic lymphoma, primary CNS lymphoma, primary mediastinal large B-cell lymphoma. T-cell/histiocyte-rich B-cell lymphoma, heavy chain disease, Hodgkin's lymphoma, non-Hodgkin's lymphoma, Waldenstrom's macroglobulinemia, multiple myeloma (MM), myelodysplastic syndromes (MDS), myeloproliferative neoplasms, and polycythemia vera.

The antibody or an antigen-binding fragment thereof may be administered intravenously, intra-arterially, intra-tumorally, or subcutaneously.

In certain embodiments, the method may further comprise administering to the subject one or more drugs selected from the group consisting of administering to the subject one or more drugs selected from the group consisting of a topoisomerase inhibitor, an anthracycline topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection, Vyxeos®, an azacytidine, Vidaza®, a decitabine, an all-trans-retinoic acid (ATRA), an arsenic, an arsenic trioxide, a histamine dihydrochloride, Ceplene®, an interleukin-2, an aldesleukin, Proleukin®, a gemtuzumab ozogamicin, Mylotarg®, an FLT-3 inhibitor, a midostaurin, Rydapt®, a clofarabine, a farnesyl transferase inhibitor, a decitabine, an IDH1 inhibitor, an ivosidenib, Tibsovo®, an IDH2 inhibitor, an enasidenib, Idhifa®, a smoothened (SMO) inhibitor, a glasdegib, an arginase inhibitor, an IDO inhibitor, an epacadostat, a BCL-2 inhibitor, a venetoclax, Venclexta®, a platinum complex derivative, oxaliplatin, a kinase inhibitor, a tyrosine kinase inhibitor, a PI3 kinase inhibitor, a BTK inhibitor, an ibrutinib, IMBRUVICAR, an acalabrutinib, CALQUENCE®, a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, a CD70 antibody, and CLL1 antibody, a CD123 antibody, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor.

The isolated monoclonal antibody or an antigen binding fragment thereof may comprise an antitumor drug linked thereto. The antitumor drug may be linked to said antibody through a photolabile linker. The antitumor drug may be linked to said antibody through an enzymatically-cleaved linker. The antitumor drug may a toxin, a radioisotope, a cytokine, or an enzyme.

In another embodiment, there is provided a method of detecting a cancer cell or cancer stem cell in a sample or subject comprising (a) contacting a subject or a sample from the subject with the antibody or an antigen-binding fragment thereof as defined herein; and (b) detecting binding of said antibody to a cancer cell or cancer stem cell in said subject or sample. The sample may be a body fluid or biopsy, or blood, bone marrow, sputum, tears, saliva, mucous, serum, urine or feces. Detection may comprise immunohistochemistry, flow cytometry, immunoassays (including ELISA, RIA etc.) or Western blot. The method may further comprise performing steps (a) and (b) a second time and determining a change in detection levels as compared to the first time. The isolated monoclonal antibody or an antigen binding fragment thereof may further comprise a label, such as a peptide tag, an enzyme, a magnetic particle, a chromophore, a fluorescent molecule, a chemo-luminescent molecule, or a dye. The isolated monoclonal antibody or an antigen binding fragment thereof may be conjugated to a liposome or nanoparticle.

In still an additional aspect, there is provided a method of treating or ameliorating the effect of an autoimmune disease in a subject, the method comprising administering to the subject a therapeutically effective amount of the antibody or an antigen-binding fragment thereof as defined herein. The antibody or an antigen-binding fragment thereof may be administered intravenously, intra-arterially, intra-tumorally, or subcutaneously. The method may further comprise administering to the subject one or more drugs selected from the group consisting of a steroid or an NSAID. The autoimmune disease may be Guillain-Barre syndrome, Chronic inflammatory demyelinating polyneuropathy, ankylosing spondylitis, psoriatic arthritis, enteropathic arthritis, reactive arthritis, undifferentiated spondyloarthropathy, juvenile spondyloarthropathy, Behcet's disease, enthesitis, ulcerative colitis, Crohn's disease, irritable bowel syndrome, inflammatory bowel disease, fibromyalgia, chronic fatigue syndrome, pain conditions associated with systemic inflammatory disease, systemic lupus erythematosus, Sjogren's syndrome, rheumatoid arthritis, juvenile rheumatoid arthritis, juvenile onset diabetes mellitus (also known as Type I diabetes mellitus), Wegener's granulomatosis, polymyositis, dermatomyositis, inclusion body myositis, multiple endocrine failure, Schmidt's syndrome, autoimmune uveitis, Addison's disease, Grave's Disease, Hashimoto's thyroiditis, autoimmune thyroid disease, pernicious anemia, gastric atrophy, chronic hepatitis, lupoid hepatitis, atherosclerosis, multiple sclerosis, amyotrophic lateral sclerosis, hypoparathyroidism, Dressler's syndrome, myasthenia gravis, Eaton-Lambert syndrome, autoimmune thrombocytopenia, idiopathic thrombocytopenia purpura, hemolytic anemia, pemphigus vulgaris, pemphigus, dermatitis herpetiformis, alopecia, scleroderma, progressive systemic sclerosis, CREST syndrome (calcinosis, Raynaud's phenomenon, esophageal dysmotility, sclerodactyly, and telangtasia), adult onset diabetes mellitus (also known as Type II diabetes mellitus), mixed connective tissue disease, polyarteritis nodosa, systemic necrotizing vasculitis, glomerulonephritis, atopic dermatitis, atopic rhinitis, Goodpasture's syndrome, Chagas' disease, sarcoidosis, rheumatic fever, asthma, anti-phospholipidsyndrome, erythema multiforme, Cushing's syndrome, autoimmune chronic active hepatitis, allergic disease, allergic encephalomyelitis, transfusion reaction, leprosy, malaria, leshmaniasis, trypanosomiasis, Takayasu's arteritis, polymyalgia rheumatica, temporal arteritis, shistosomiasis, giant cell arteritis, eczema, lymphomatoid granulomatosis, Kawasaki's disease, endophthalmitis, psoriasis, erythroblastosis fetalis, eosinophilic faciitis, Shulman's syndrome, Felty's syndrome, Fuch's cyclitis, IgA nephropathy, Henoch-Schonlein purpura, graft versus host disease, transplantation rejection, tularemia, periodic fever syndromes, pyogenic arthritis, Familial Mediterranean Fever, TNF-receptor associated periodic syndrome (TRAPS), Muckle-Wells syndrome, or hyper-IgD syndrome.

Also provided is monoclonal antibody that binds to LILRB2 and (a) does not bind to LILRA or another LILRB; (b) binds to LILRB2 Domain 1 or 4; (c) activates or antagonizes LILRB2; (d) enhances monocyte inflammatory potential: (e) prevents myeloid-derived suppressor cell function; and/or (f) inhibits leukemia cell migration and/or infiltration in vivo.

The use of the word "a" or "an" when used in conjunction with the term "comprising" in the claims and/or the specification may mean "one," but it is also consistent with the meaning of "one or more." "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D. Screening specific monoclonal antibodies for LILRB2. (FIG. 1A) Representative flow cytometric profiles showing that monoclonal antibodies bind to LILRB2 reporter cells. Binding of monoclonal antibodies was screened using flow cytometer on LILRB2 reporter cells. Bound antibodies were detected with Allophycocyanin (APC)-labeled goat anti-human IgG secondary antibody. (FIG. 1B) Quantification of binding ability of monoclonal antibodies to LILRB2 reporter cells. B2-7, B2-15, B2-16, B2-17, B2-19, B2-8, B2-24, B2-25, B2-10, B2-12 and B2-18 highly bind to LILRB2 reporter cells. (FIGS. 1C-D) Quantification of binding ability of monoclonal antibodies B2-7, B2-15, B2-16, B2-17, B2-19, B2-8, B2-24, B2-25, B2-10, B2-12 and B2-18 to LILRAs, LILRBs and LAIR 1 reporter cells.

FIGS. 2A-B. Antibodies B2-8, B2-24, B2-10, B2-10 and B2-15 increase GFP signaling of LILRB2 reporter cells. (FIG. 2A) GFP signaling of LILRB2 reporter cells incubated with soluble antibodies. (FIG. 2B) GFP signaling of LILRB2 reporter cells incubated with soluble antibodies combined with K562.

FIGS. 3A-C. Antibodies B2-7, B-15, B2-16, B2-17 and B2-19 block GFP signaling of LILRB2 reporter cells activated by coated ANGPTL2. (FIG. 3A) Representative flow cytometric profiles showed that coated ANGPTL2 stimulates GFP expression in LILRB2 reporter cells. (FIG. 3B) Representative flow cytometric profiles showed that B2-7, B-15, B2-16, B2-17 and B2-19 effectively block GFP expression in LILRB2 reporter cells activated by coated ANGPTL2. (FIG. 3C) Dose-dependent inhibitory ability of B2-7, B-15, B2-16, B2-17 and B2-19 to GFP expression induced by coated ANGPTL2. Blocking potency ($IC_{50}$) of B2-19, B2-16, B2-7, B2-15 and B2-17 was 48.54 ng/ml, 131.4 ng/ml, 221.1 ng/ml, 341.3 ng/ml and 405.1 ng/ml respectively.

(FIG. 4A) Representative flow cytometric profiles showed that coated SEMA4A stimulates GFP expression in LILRB2 reporter cells. (FIG. 4B) Representative flow cytometric profiles showed that B2-7. B-15. B2-16. B2-17 and B2-19 effectively block GFP expression in LILRB2 reporter cells activated by coated SEMA4A. (FIG. 4C) Dose-dependent inhibition of B2-7. B-15. B2-16, B2-17 and B2-19 to GFP expression induced by coated SEMA4A. Blocking potency ($IC_{50}$) of B2-19. B2-16. B2-7. B2-15 and B2-17 was 167.1 ng/ml. 449 ng/ml. 701 ng/ml. 1001 ng/ml and 1034 ng/ml respectively.

FIGS. 5A-C. Antibodies B2-7, B-15, B2-16, B2-17 and B2-19 block GFP signaling of LILRB2 reporter cells activated by HLA-G overexpressed on K562 cells. (FIG. 5A) Representative flow cytometric profiles showed that HLA-G overexpressed on K562 cells stimulates GFP expression in LILRB2 reporter cells. (FIG. 5B) Representative flow cytometric profiles showed that B2-7. B-15. B2-16. B2-17 and B2-19 effectively block GFP expression in LILRB2 reporter cells activated by HLA-G overexpressed on K562 cells. (FIG. 5C) Quantification of GFP percentage shown in FIG. 5B.

FIGS. 6A-C. The effect of LILRB2 antibodies on LPS response in primary human monocytes. (FIGS. 6A-B) Representative flow cytometric profiles showed that surface CD86 and intracellular TNFα staining of cells gated on CD33+ monocytes. PBMCs were cultured for 48 hours with anti-LILRB2 antibody (10 ng/ml) followed by 6 hours of LPS stimulation (50 ng/ml) in the presence of brefeldin A. (FIG. 6C) Quantification of fold changes was defined by the ratio of mean fluorescence intensity (MFI) of CD86 and TNFα in anti-LILRB2 treated samples relative to their respective MFI in IgG treated samples shown in FIG. 6A-B. MFI values represent cells gated on CD33+ monocytes.

(FIG. 7A) Human LILRB2 expression on mouse C1498 parental cells and human LILRB2 retroviral transduced C1498 cells. (FIG. 7B) LILRB2 promotes the death of leukemia-bearing mice. Kaplan-Meier survival curve of humanized NSG mice which were i.v. injected with LILRB2-overexpressed or control (ctrl) C1498 cells ($1\times10^6$ cells per mouse). (FIG. 7C-D) Representative flow cytometry plots and summary of leukemia cell infiltration in bone marrow (BM), peripheral blood (PB), liver (LV) and spleen (SP) from C57BL/6 which were i.v. injected with LILRB2-overexpressed or ctrl C1498 cells ($1\times10^6$ cells per mouse). (FIG. 7E) Kaplan-Meier survival curve of C57BL/6 mice which were i.v. injected with LILRB2-overexpressed or ctrl C1498 cells ($1\times10^6$ cells per mouse). (FIG. 7F-G) Representative flow cytometry plots and summary of myeloid cell infiltration in peripheral blood (PB), from C57BL/6 which were i.v. injected with LILRB2-overexpressed or ctrl C1498 cells ($1\times10^6$ cells per mouse). (FIG. 7H-I) Representative flow cytometry plots and summary of leukemia cell infiltration in peripheral blood (PB) from C56BL/6 mice with the treatment of LALAPG mutated anti-LILRB2 antibodies or IgG control after leukemia cell transplant. LILRB2-overexpressed C1498 cells ($1\times10^6$ cells per mouse) were injected into C57BL/6 mice followed by treatment with LALAPG Fc mutated anti-LILRB2 antibodies or LALAPG Fc mutated IgG. The percentage of leukemia cell (GFP+) from peripheral blood (PB) was determined by flow cytometry 20 days after transplantation. (FIG. 7J) Summary of myeloid cell infiltration in peripheral blood (PB) from C56BL/6 mice treated at indicated time after leukemia cell transplant with LALAPG mutated anti-LILRB2 antibodies or LALAPG Fc mutated IgG control.

(FIG. 8A) The expression of LILRB2 on PIRB-KO MLL-AF9 leukemia cells transduced with LILRB2 (LILRB2) or Control (Ctrl) leukemia cells. (FIG. 8B-C) Representative flow cytometry plots and summary of leukemia cell infiltration in peripheral blood (PB) from C56BL/6 mice transplanted with PirB-KO MLL-AF9 leukemia cells transduced with LILRB2 (LILRB2) or control PirB-KO MLL-AF9 (Ctrl) leukemia cells. (FIG. 8D) Kaplan-Meier survival curve of leukemia mice which were transplanted with LILRB2-overexpressed or Ctrl PirB-KO MLL-AF9 cells. (FIG. 8E-F) Representative flow cytometry plots and summary of leukemia cell infiltration in peripheral blood (PB) from C56BL/6 mice transplanted with PirB-KO LILRB2 leukemia cells and followed by the treatment of LALAPG mutated anti-LILRB2 antibodies or IgG control.

FIGS. 9A-G. Anti-LILRB2 antibodies inhibit the migration and infiltration of AML cells. (FIG. 9A) LILRB2 expression on THP-1 cells was confirmed using a commercial phycoerythrin (PE)-anti-LILRB2 antibody. (FIG. 9B) Short-term (20 h) infiltration of leukemia cells in NSG mice treated with LALAPG Fc mutated anti-LILRB2 antibodies or LALAPG Fc mutated IgG control after leukemia transplant. THP-1 cells ($1\times10^7$ cells per mouse) were injected into NSG mice followed by treatment with LALAPG mutated IgG control or anti-LILRB2 antibodies immediately. The numbers of leukemia cells (GFP+) from bone marrow (BM), liver (LV) and spleen (SP) were determined by flow cytometry 20 hours after transplantation and normalized to number in peripheral blood (PB). (FIG. 9C) Percentage of leukemia cells (GFP+) in indicated organs such as liver (LV), bone marrow (BM), spleen (SP) and peripheral blood (PB) at day 21 post-transplant in NSG mice treated with LALAPG mutated anti-LILRB2 antibodies or IgG control after THP-1 injection. (FIG. 9D) Body weight for each mouse shown in FIG. 9B was measured at indicated day after THP-1 cells injection. (FIG. 9E) Comparison of the size of livers from NSG mice at 28 days after THP-1 transplant and treated with IgG or anti-LILRB2 antibodies containing the LALAPG Fc mutations. (FIG. 9F) Quantification of liver weight shown in FIG. 9E normalized to respective individual mouse body weight. (FIG. 9G) Survival curve of NSG mice treated with LALAPG Fc mutated IgG control or anti-LILRB2 antibodies after THP-1 transplantation.

FIGS. 10A-E. Antagonistic LILRB2 mAbs inhibit the development of leukemia cells in patient-derived xenograft (PDX) model. (FIG. 10A) LILRB2 expression pattern on primary leukemia cells from AML M5 patients. (FIG. 10B) Analysis of correlation between LILRB2 mRNA levels and the overall survival of patients with AML-M5 (n=132, divided into two groups based on gene expression) in TCGA database (https://xena.ucsc.edu) by Kaplan-Meier long-rank test. (FIG. 10C) Human CD45$^+$CD33$^+$ leukemia cells infiltration in peripheral blood (PB), bone marrow (BM), spleen (SP) and liver (LV) of NSG mice transplanted with primary AML-M5 leukemia samples and treated with anti-LILRB2 antibodies or control IgG. (FIG. 10D) Representative brightfield microcopy image of primary AML-M5 leukemia cell cultured in the present of LALAPG mutated anti-LILRB2 antibodies or IgG control. Anti-LILRB2 treated cells showed more adherent differentiation morphology. (FIG. 10E) Intracellular expression of CD68 on primary AML-M5 leukemia cell cultured in the present of LALAPG mutated anti-LILRB2 antibodies or IgG control.

FIGS. 11A-G. Antagonistic LILRB2 mAbs can prevent the T cell suppressive function of Myeloid-Derived Suppressor Cells (MDSC) in vitro. (FIG. 11A) One representative histogram showed that antagonistic LILRB2 mAbs attenuated the suppressive function of MDSC towards CD8+ T cells. The MDSC were isolated from the PBMC of patients with solid tumor, by depleting HLD-DRbright cells and then enriching the CD14+ cells, using autoMACS. MDSC were cocultured with T cells from the same donor (E: T=1), which was pre-stained with CSFE to monitor the cell proliferation. 10 μg/mL LALAPG mutated IgG, B2-7, or B2-19 was added into the cell culture. The percentage of proliferative T cells, indicated by reduced intensity of CFSE signal, was determined by flow cytometry 5 days after treatments. (FIG. 11B) Quantification of the effects of anti-LILRB2 mAbs on the inhibitory functions of MDSC towards T cells. The percentage of proliferative T cells (left panel: CD8+ T cells, right panel CD4+ T cells), indicated by reduced intensity of CFSE signal, was determined by flow cytometry 5-7 days after treatments. (FIG. 11C) Anti-LILRB2 mAbs attenuated the inhibitory functions of MDSC towards T cells, accessed by measuring the IFN-γ secretion in the supernatants of T cell cultures. (FIG. 11D) Anti-LILRB2 mAbs decreased the expression of M2 macrophage markers, while increased the expression of M1 macrophage markers, on MDSC. The MDSC isolated from peripheral blood of patients with solid tumors were cultured with 10 μg/mL anti-LILRB2 antibodies for 7 days. The expression of CD163, CD206 and CD86 were analyzed by flow cytometry. (FIG. 11E) Anti-LILRB2 mAbs decreased the M2 markers expression, while increased M1 markers expression, on monocyte-derived macrophage from a healthy donor. The monocytes isolated from the peripheral blood of a health donor were cultured and incubated with 10 μg/mL anti-LILRB2 antibodies for 7 days. The expression of CD163, CD206 and CD86 were analyzed by flow cytometry. (FIG. 11F) Anti-LILRB2 mAbs decreased the M2 markers expression, while increased M1 markers expression, on the cell surface of tumor associated macrophage/monocyte in ascites from a patient with ovarian cancer. The CD14+ cells were isolated from the ascites by autoMACS and cultured with anti-LILRB2 mAbs with IgG4 Fc for 7 days. CD163, CD206 and CD86 were analyzed by flow cytometry. (FIG. 11G) Anti-LILRB2 mAbs increased the M1 macrophage cytokines and chemokine secreted from MDSC from 4 to 5 patients with solid tumors.

(FIG. 12A) Phylogenic tree of the heavy chain variable region (VH) and light chain variable region (VL). (FIG. 12B) ELISA binding to LILRB2 of the 24 positive phages.

(FIG. 13A) ELISA binding curves of LILRB2 antibodies. (FIG. 13B) Calculated $EC_{50}$ values of LILRB2 antibodies.

FIGS. 14A-E. Binding specificity of LILRB2 antibodies. (FIGS. 14A-B) ELISA binding of LILRB2 antibodies to antigens of other members in LILR family. (FIGS. 14C-E) Comparison of ELISA binding curves to LILRB2 and LILRA1 of antibody (FIG. 14C) B2-10, (FIG. 14D) B2-12 and (FIG. 14E) B2-18.

FIG. 15. Epitope binning of LILRB2 antibodies. The epitope binning was performed in a sandwich format on Octet RED 96 System. Each antibody was loaded on protein A biosensor as $1^{st}$ antibody. After blocking of biosensor with non-relevant IgG, LILRB2 antigen was then captured and the biosensors were further incubated with the rest of other antibodies ($2^{nd}$ antibodies). "+" indicates the $1^{st}$ antibody blocked the signal of the $2^{nd}$ antibody.

FIGS. 16A-D. Binding domains on LILRB2 by the antibodies. (FIG. 16A) Schematic diagram shown different truncated ECD proteins with Fc fusions. (FIG. 16B) SDS-PAGE of purified fusion proteins. (FIG. 16C) ELISA binding of antibodies to different truncated proteins. (FIG. 16D) Summary of antibody binding domains.

FIGS. 17A-F. Mapping of key residues on D1 and D4. (FIGS. 17A-B) Alignment of the (FIG. 17A (SEQ ID NOS: 593-595)) D1 and the (FIG. 17B (SEQ ID NOS: 596-597)) D4 domain of LILRB2 and LILRB1. The regions that are different between LILRB2 and LILRB1 and are exposed and locate in the loop regions are boxed. (FIGS. 17C-D) the sequences of mutations on the (FIG. 17C (SEQ ID NOS: 598-605)) D1 and the (FIG. 17D (SEQ ID NOS: 606-613)) D4 domain. (FIGS. 17E-F) Binding loss of antibodies to mutants of the (FIG. 17E) D1 and the (FIG. 17F) D4 domain based on ELISA. The percent of binding with each mutant relative to the wildtype B2-ECD were plotted as stack bar graphs.

FIGS. 19A-B. ELISA binding measurement of antibodies to human and non-human primate (cynomolgus monkey, cyno) LIL.RB2 recombinantly produced in HEK293 cells. (FIG. 19A) ELISA binding to human LILRB2. (FIG. 19B) ELISA binding to cyno-LILRB2. The fusion proteins of the extracellular domain (ECD) of human LILRB2 or NHP-LILRB2 with Fc of mouse IgG2a were used to coat ELISA plates and antibodies were titrated in different concentrations as indicated in the graph.

FIGS. 20A-B. Measurements of cell surface LILRB2 binding by monoclonal antibodies by flow cytometry. (FIG. 20A) Quantification of binding ability of monoclonal antibodies to LILRB2 reporter cells. Monoclonal antibodies were screened using flow cytometer on LILRB2 reporter cells labeled with Allophycocyanin (APC) goat anti-human IgG secondary antibody. (FIG. 20B) Representative flow cytometric profiles showing that HCB2-5 and HCB2-10 monoclonal antibodies highly bind to LILRB2 reporter cells and HCB2-2 slightly bind to LILRB2 reporter cells. NC: non-labeled reporter cells. ISO: incubate the reporter cells only (ISO) with secondary Ab (anti-human Fc specific) conjugated with APC. The number indicates mean fluorescence intensity (MFI) of APC or AF647.

FIGS. 23A-B. Determination of soluble antibody engagement of GFP signaling in LILRB2 reporter cells in the present or absence of K562 cells. (FIG. 23A) GFP signaling of LILRB2 reporter cells incubated with soluble antibodies. (FIG. 23B) GFP signaling of LILRB2 reporter cells incubated with soluble antibodies combined with K562.

(FIG. 24A) Representative flow cytometric profiles showing that only positive control mAbs (POS), but not LILRB2 mAbs bind to LILRAs reporter cells (RC). (FIG. 24B) Representative flow cytometric profiles showing that LILRB2 mAbs bind to LILRB2-expressing reporter cells, but not to reporter cells expressing LILRBs and LAIR1. Binding of positive control mAbs (POS) demonstrate expression level of each receptor. Binding of LILRB2 monoclonal antibodies was detected using flow cytometry on LILRAs, LILRBs or LAIR 1-expressing reporter cells using a Allophycocyanin (APC)-labeled goat anti-human IgG Fc specific secondary antibody. Non: nonstained reporter cells. NEG: cells incubated only with secondary Ab. POS: cells incubated with commercial antibody conjugated with APC or AF647 for the respective LIL or LAIR-1 receptors. The number indicates mean fluorescence intensity (MFI) of APC or AF647.

(FIG. 25A) Representative flow cytometric profiles showed that HLA-G overexpressed on K562 cells stimulates GFP induction of LILRB2 reporter cells. (FIG. 25B) Representative flow cytometric profiles showed that HCB2-5 and HCB2-10 effectively block GFP signaling of LILRB2 reporter cells activated by HLA-G overexpressing K562 cells. IgG, isotype control.

FIGS. 26A-C. Blocking activity of LILRB2 antibodies assayed in GFP signaling of LILRB2 reporter cells activated by coated ANGPTL2. (FIG. 26A) Representative flow cytometric profiles showed that HCB2-5 and HCB2-10 effectively block GFP signaling of LILRB2 reporter cells activated by coated ANGPTL2. (FIG. 26B) Quantification of GFP percentage shown in FIG. 26A. (FIG. 26C) Dose-dependent inhibitory ability of HCB2-5 and HCB2-10 to GFP signaling induced by coated ANGPTL2.

(FIG. 27A) Representative flow cytometric profiles showed that HCB2-5 and HCB2-10 effectively block GFP signaling of LILRB2 reporter cells activated by coated SEMA4A. (FIG. 27B) Quantification of GFP percentage shown in FIG. 27A. (FIG. 27C) Dose-dependent inhibitory ability of HCB2-5 and HCB2-10 to GFP signaling induced by coated SEMA4A.

FIGS. 28A-B. Antibody VH and VL phylogenic trees.

LILRB2 antibodies were directly conjugated with AF647. One hundred microliters of whole blood were incubated with antibodies for cell surface markers and LILRB2 antibodies, following protocols available in the literature (Hensley et al., J Vis Exp 2012; 67:4302). Data shown is averaged geometric mean fluorescence intensity±standard error of the mean (s.e.m., N=2 donors) after sample acquisition in flow cytometer (BD FACS Celesta) and subtracted by background fluorescence of stained samples in which LILRB2 antibodies were omitted.

Figure 31:
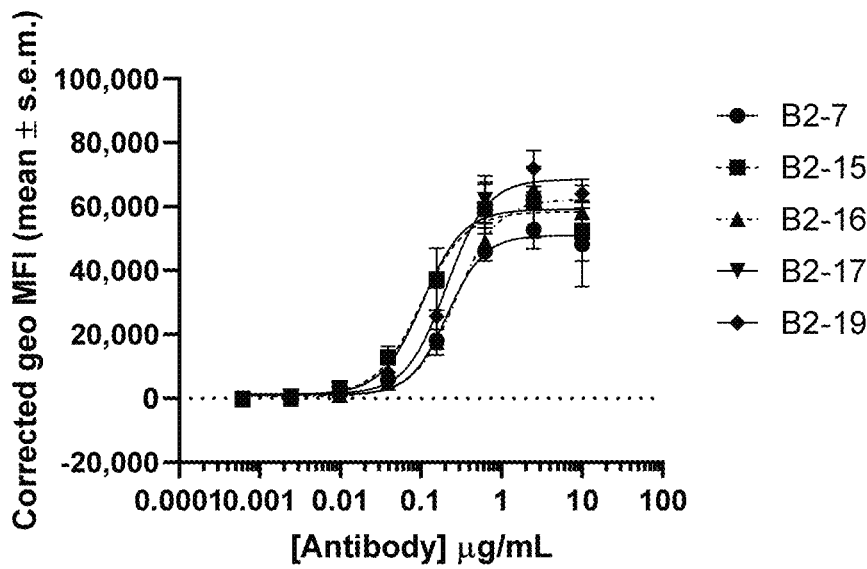

FIG. 31. Binding of LILRB2 antibodies on HEK293 stably expressing full length human LILRB2. Fifty thousand cells were incubated with a dilution series (40-0.0006 µg/mL) of LILRB2 antibodies in a final volume of 100 µL. Bound antibodies were detected with anti-human Fc-specific secondary antibody conjugated to AF647. All incubations were performed for 30 minutes at 4° C. Data shown is averaged geometric mean fluorescence intensity±standard error of the mean (s.e.m.) after sample acquisition (in duplicates) in flow cytometer (BD FACS Celesta) and subtracted by background fluorescence of samples incubated with secondary antibody only.

Figure 32:
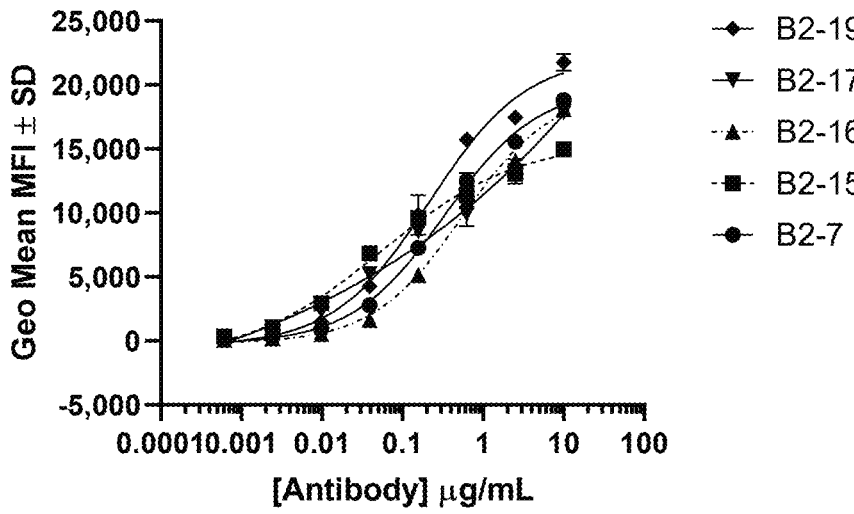

FIG. 32. Binding of LILRB2 antibodies on CD14$^+$CD16$^-$ monocytes isolated from human PBMC from healthy donors. Fifty thousand cells were incubated for 30 minutes at 4° C. with a dilution series (40-0.0006 µg/mL) of LILRB2 antibodies directly conjugated to AF647 in a final volume of 100 µL. Data shown is averaged geometric mean of fluorescence intensity from duplicate samples acquired in a flow cytometer (BD FACS Celesta) from one donor and is representative of 2 experiments with cells isolated from different donors.

Figure 33:
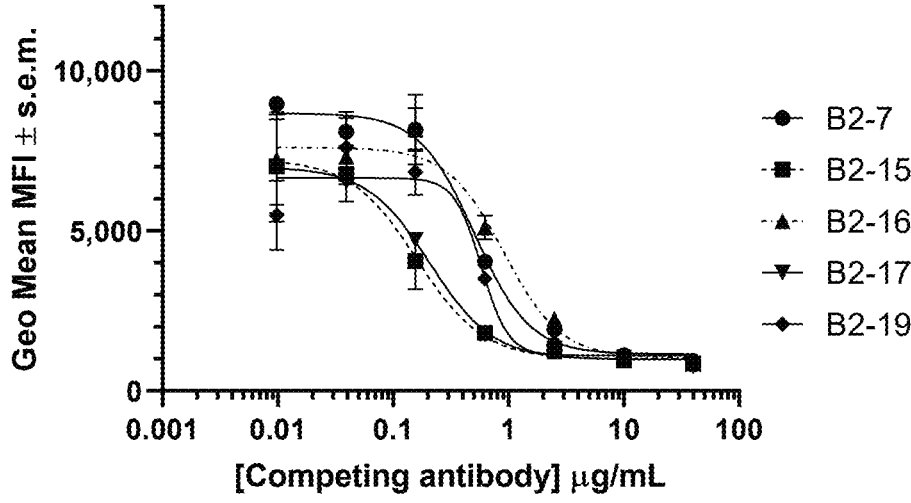

FIG. 33. Inhibition of HLA-G-His (5 µg/mL) binding on HEK293 cells stably expressing full length LILRB2 in the presence of a dilution series (40-0.0098 µg/mL) of competing LILRB2 antibodies. Bound HLA-G was detected by flow cytometry using an anti-His antibody directly conjugated to APC. All incubations were performed for 30 minutes at 4° C. Data shown is averaged geometric mean of fluorescence intensity±standard error of the mean (s.e.m.) from duplicate samples acquired in a flow cytometer (BD FACS Celesta).

Figure 34:
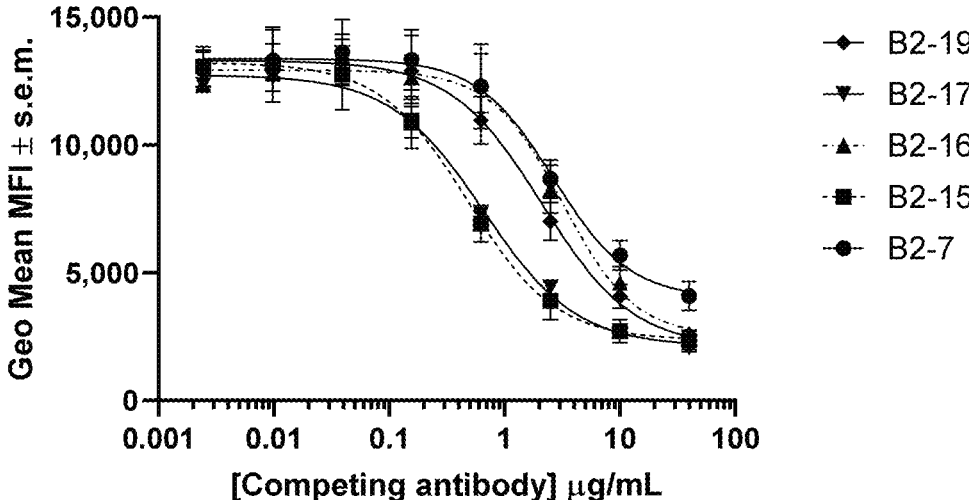

FIG. 34. Inhibition of SEMA4A-hFc-AF647 (5 µg/mL) binding on HEK293_LILRB2 cells in the presence of a dilution series (40-0.0098 µg/mL) of competing LILRB2 antibodies. Incubation was performed for 30 minutes at 4° C. Data shown is averaged geometric mean of fluorescence intensity±standard error of the mean (s.e.m.) from duplicate samples acquired in a flow cytometer (BD FACS Celesta).

Figure 35:
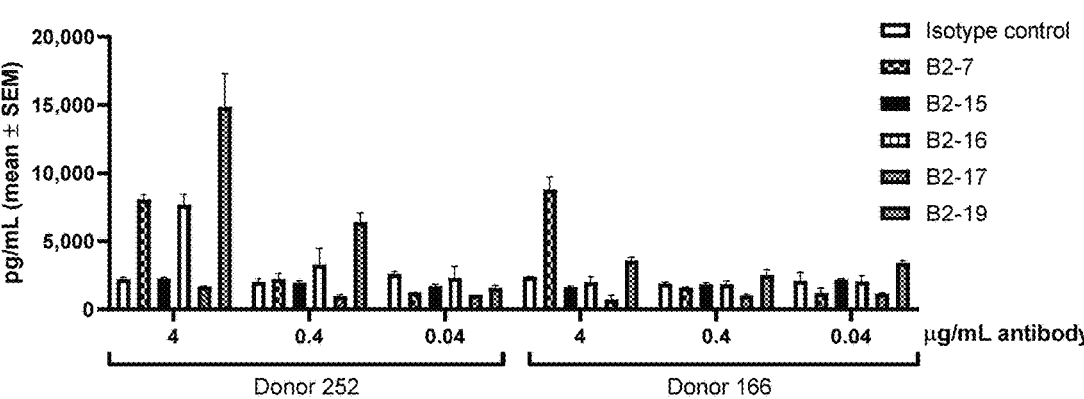

FIG. 35. Effect of LILRB2 blocking antibodies on levels of TNF-α secreted by PBMC stimulated with 50 ng/mL LPS. Data shown is from 2 donors and it is representative from 6 donors (from total of N=6 donors). PBMC isolated from healthy donors were incubated (in duplicates) with LPS (Sigma-Aldrich) and various concentrations of antibodies for 3 days. Cytokines were measured in the culture media supernatant using a Human Cytokine Premixed Magnetic Luminex Performance Assay.

Figure 36:
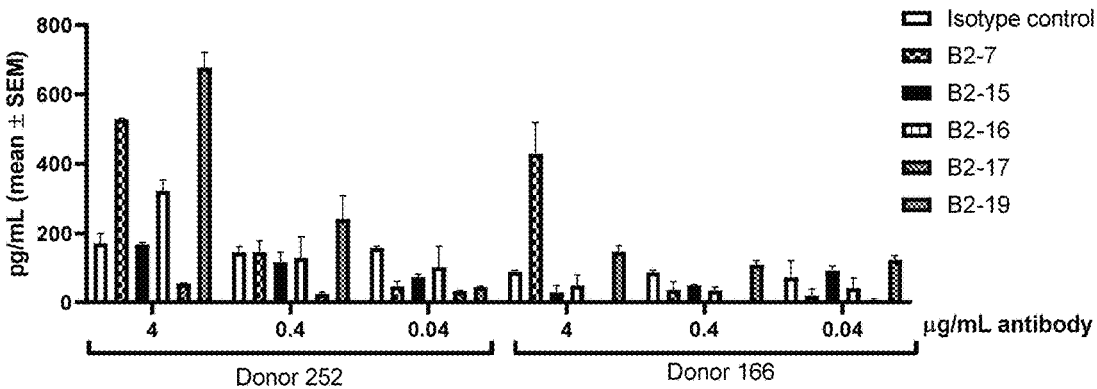

FIG. 36. Effect of LILRB2 blocking antibodies on levels of IFN-γ secreted by PBMC stimulated with 50 ng/mL LPS. Data shown is from 2 donors and it is representative from 5 donors (from total of N=6 donors). PBMC isolated from healthy donors were incubated (in duplicates) with LPS (Sigma-Aldrich) and various concentrations of antibodies for 3 days. Cytokines were measured in the culture media supernatant using a Human Cytokine Premixed Magnetic Luminex Performance Assay.

Figure 37:
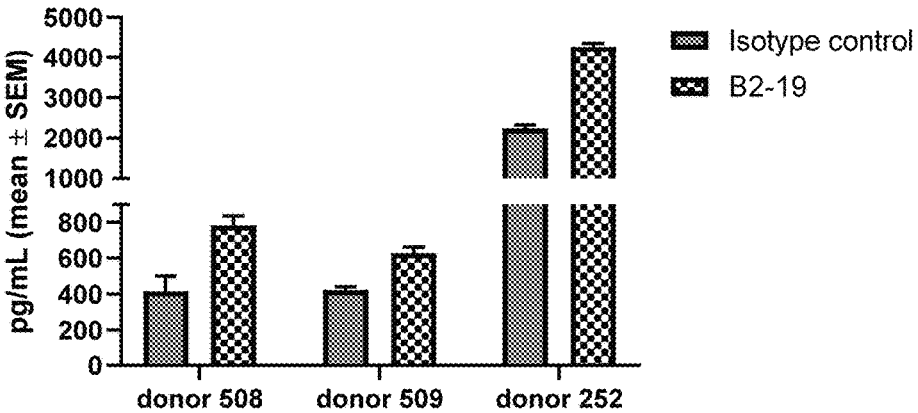

FIG. 37. Effect of LILRB2 blocking antibodies (40 µg/mL) on levels of IL-12p40 secreted by PBMC stimulated with 50 ng/mL LPS (from total of N=3 donors). PBMC isolated from healthy donors were incubated (in duplicates) with LPS (Sigma-Aldrich) and 40 µg/mL of B2-19 antibody for 3 days. IL-12p40 concentration was measured in the culture media supernatant using a human IL-12 ELISA assay (BD Biosciences)

Figure 38:
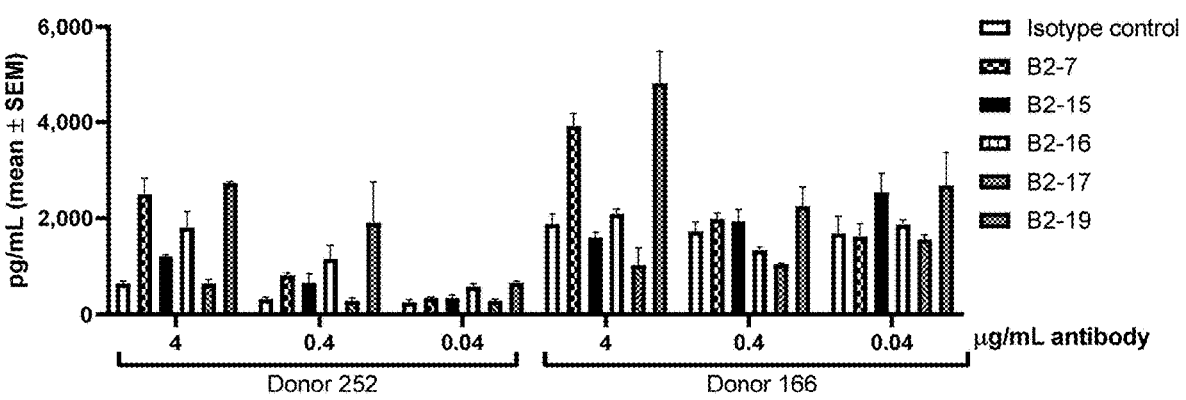

FIG. 38. Effect of LILRB2 blocking antibodies on levels of IFN-γ secreted by PBMC stimulated with 10 ng/mL anti-CD3 activating antibody HIT3a. Data shown is from 2 donors and it is representative from 6 donors (from total of N=6 donors). PBMC isolated from healthy donors were incubated (in duplicates) with HIT3a (Biolegend) and various concentrations of antibodies for 3 days. Cytokines were measured in the culture media supernatant using a Human Cytokine Premixed Magnetic Luminex Performance Assay.

Figure 39:
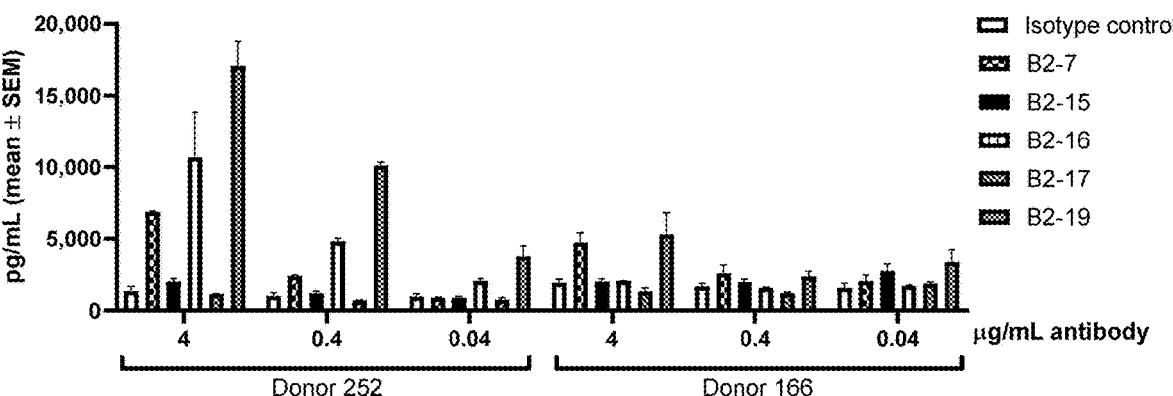

FIG. 39. Effect of LILRB2 blocking antibodies on levels of TNF-α secreted by PBMC stimulated with 10 ng/ml anti-CD3 activating antibody HIT3a. Data shown is from 2 donors and it is representative from 6 donors (from total of N=6 donors). PBMC isolated from healthy donors were incubated (in duplicates) with HIT3a (Biolegend) and various concentrations of antibodies for 3 days. Cytokines were measured in the culture media supernatant using a Human Cytokine Premixed Magnetic Luminex Performance Assay.

Figure 40:
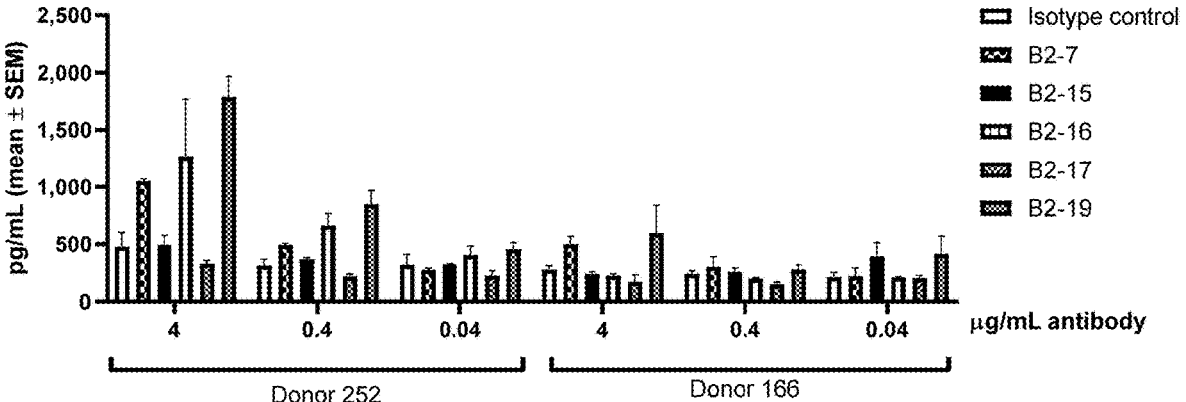

FIG. 40. Effect of LILRB2 blocking antibodies on levels of GM-CSF secreted by PBMC stimulated with 10 ng/mL anti-CD3 activating antibody HIT3a. Data shown is from 2 donors and it is representative from 6 donors (from total of N=6 donors). PBMC isolated from healthy donors were incubated (in duplicates) with HIT3a (Biolegend) and various concentrations of antibodies for 3 days. Cytokines were measured in the culture media supernatant using a Human Cytokine Premixed Magnetic Luminex Performance Assay.

Figure 41:
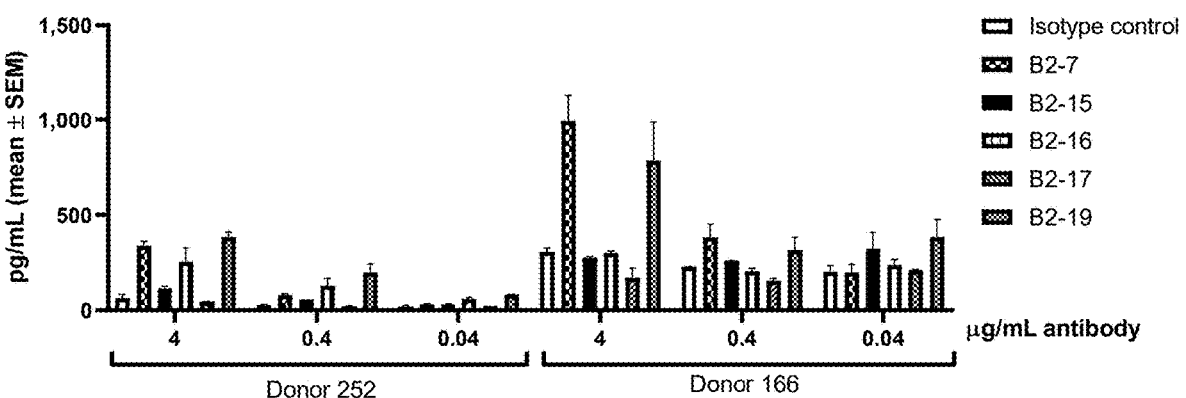

FIG. 41. Effect of LILRB2 blocking antibodies on levels of IL-1a secreted by PBMC stimulated with 10 ng/mL anti-CD3 activating antibody HIT3a. Data shown is from 2 donors and it is representative from 6 donors (from total of N=6 donors). PBMC isolated from healthy donors were incubated (in duplicates) with HIT3a (Biolegend) and various concentrations of antibodies for 3 days. Cytokines were measured in the culture media supernatant using a Human Cytokine Premixed Magnetic Luminex Performance Assay.

Figure 42:
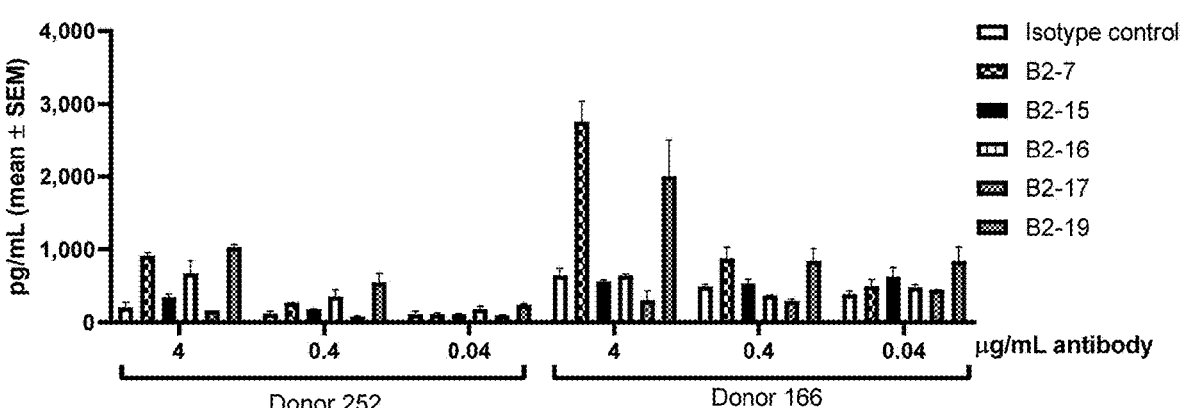

FIG. 42. Effect of LILRB2 blocking antibodies on levels of IL-18 secreted by PBMC stimulated with 10 ng/ml anti-CD3 activating antibody HIT3a. Data shown is from 2 donors and it is representative from 6 donors (from total of N=6 donors). PBMC isolated from healthy donors were incubated (in duplicates) with HIT3a (Biolegend) and various concentrations of antibodies for 3 days. Cytokines were measured in the culture media supernatant using a Human Cytokine Premixed Magnetic Luminex Performance Assay.

Figure 43:
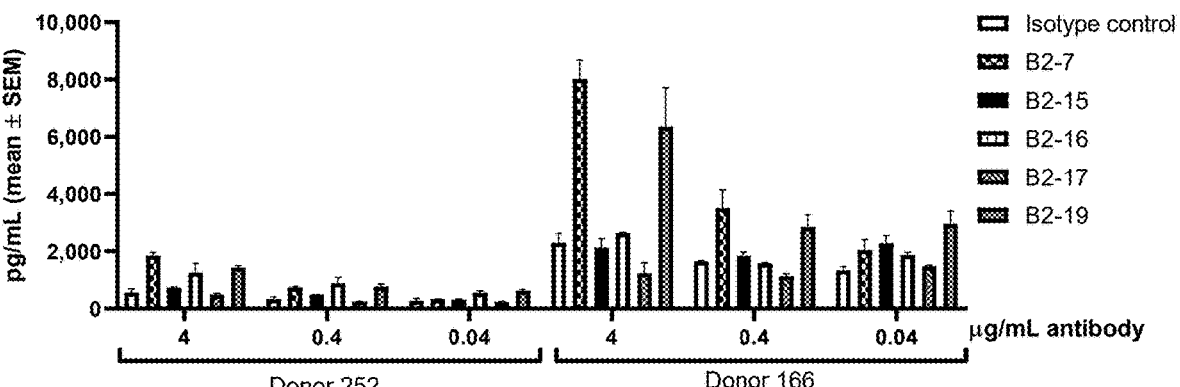

FIG. 43. Effect of LILRB2 blocking antibodies on levels of IL-6 secreted by PBMC stimulated with 10 ng/mL anti-CD3 activating antibody HIT3a. Data shown is from 2 donors and it is representative from 5 donors (from total of N=6 donors). PBMC isolated from healthy donors were incubated (in duplicates) with HIT3a (Biolegend) and various concentrations of antibodies for 3 days. Cytokines were measured in the culture media supernatant using a Human Cytokine Premixed Magnetic Luminex Performance Assay.

Figure 44:
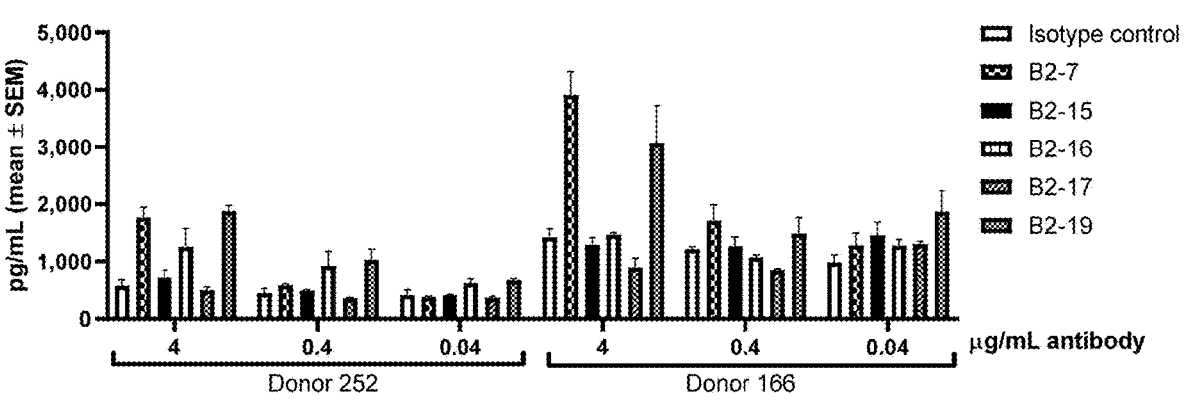

FIG. 44. Effect of LILRB2 blocking antibodies on levels of CXCL2 secreted by PBMC stimulated with 10 ng/mL anti-CD3 activating antibody HIT3a. Data shown is from 2 donors and it is representative from 6 donors (from total of N=6 donors). PBMC isolated from healthy donors were incubated (in duplicates) with HIT3a (Biolegend) and various concentrations of antibodies for 3 days. Cytokines were measured in the culture media supernatant using a Human Cytokine Premixed Magnetic Luminex Performance Assay.

Figure 45:
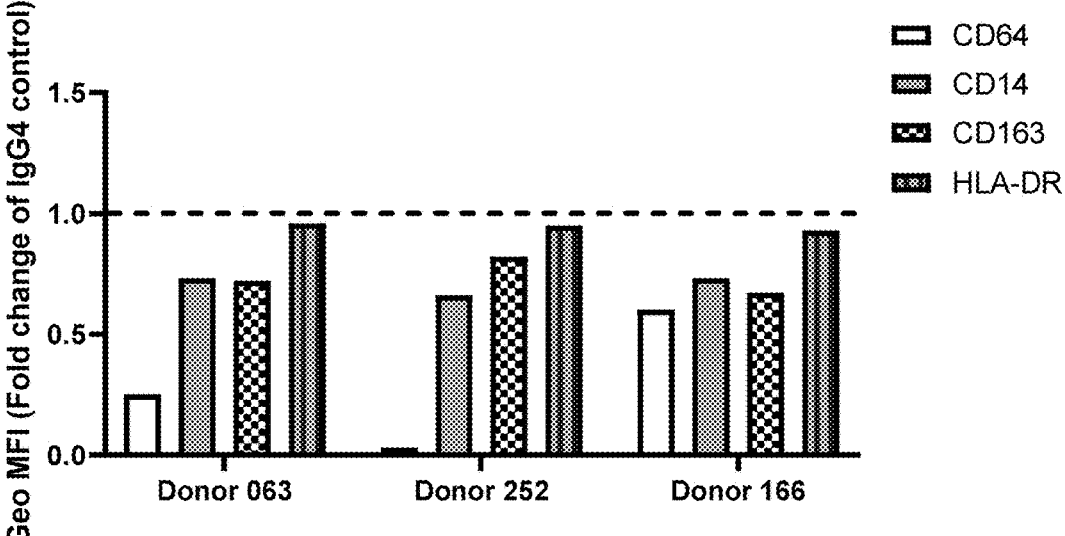

FIG. 45. Effect of 10 µg/mL B2-19 antibody on monocyte-derived macrophage cell surface markers. CD14+ CD16 monocytes isolated from human PBMC from healthy donors were differentiated into macrophages for 6 days in the presence of 100 ng/ml of human CSF-1 followed by 24 hours incubation with 100 ng/ml of human CSF-1, 20 ng/ml human IL-4 and B2-19 antibody or isotype control. Cells were detached and stained for flow cytometric analysis (FACS Celesta) using standard protocols. Data shown is fold change of geometric mean fluorescence intensity (MFI) for cells treated with B2-19 versus cells treated with isotype control.

Figure 46:
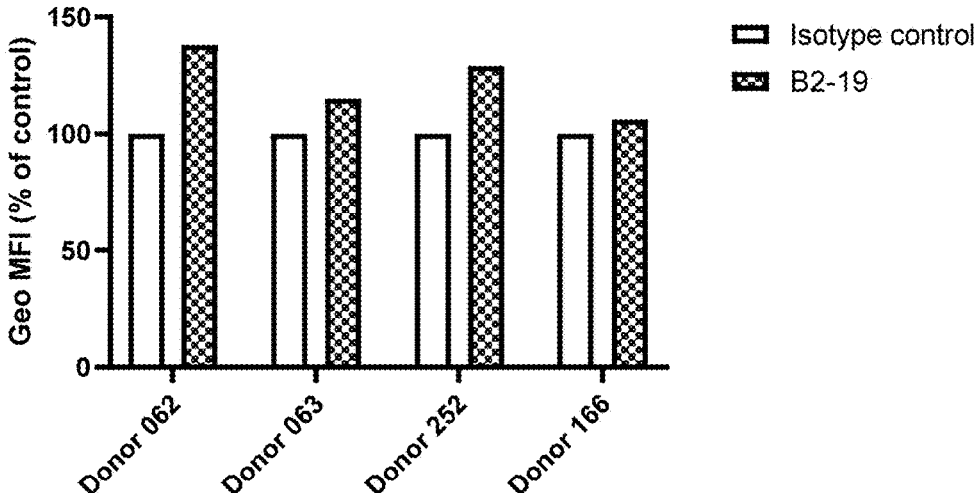

FIG. 46. Effect of 40 µg/mL B2-19 antibody on cell surface expression of CD25 on CD8$^+$ T cells. PBMC isolated from healthy donors were incubated 10 ng/mL with HIT3a (Biolegend) and 40 µg/mL of B2-19 antibody for 3 days. CD8+ T cells were analyzed for cell surface CD25 expression by flow cytometric analysis (FACS Celesta) using standard protocols. Data shown is percent change in geometric mean fluorescence intensity (MFI) for cells treated with B2-19 versus cells treated with isotype control.

Figure 47:
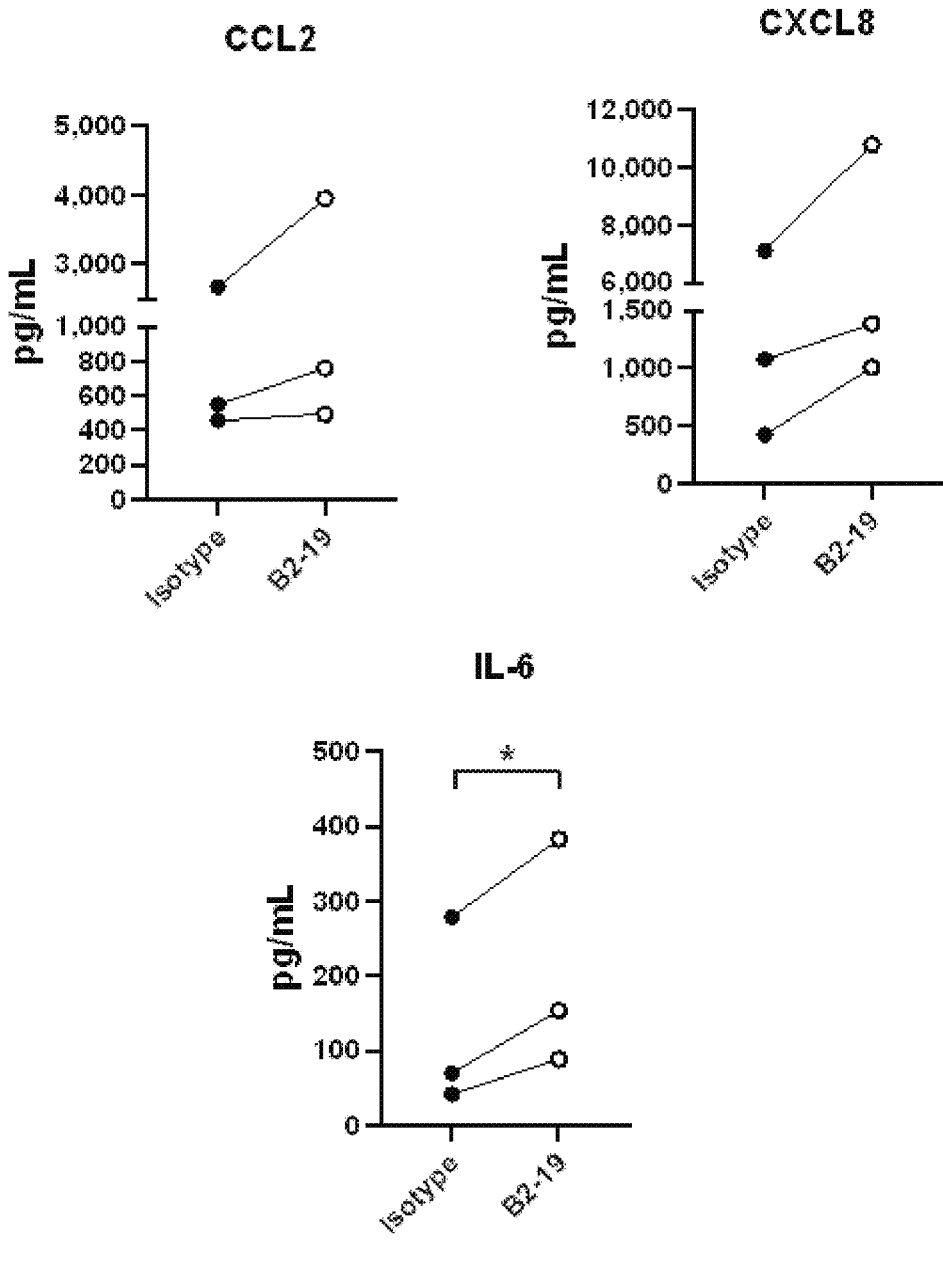

FIG. 47. B2-19 antibody enhances the production of cytokines and chemokines in immature DC treated for 2 days with IL-10 (to induce tolerogenic DC). Each line represents the result from a different donor.

Figure 48:
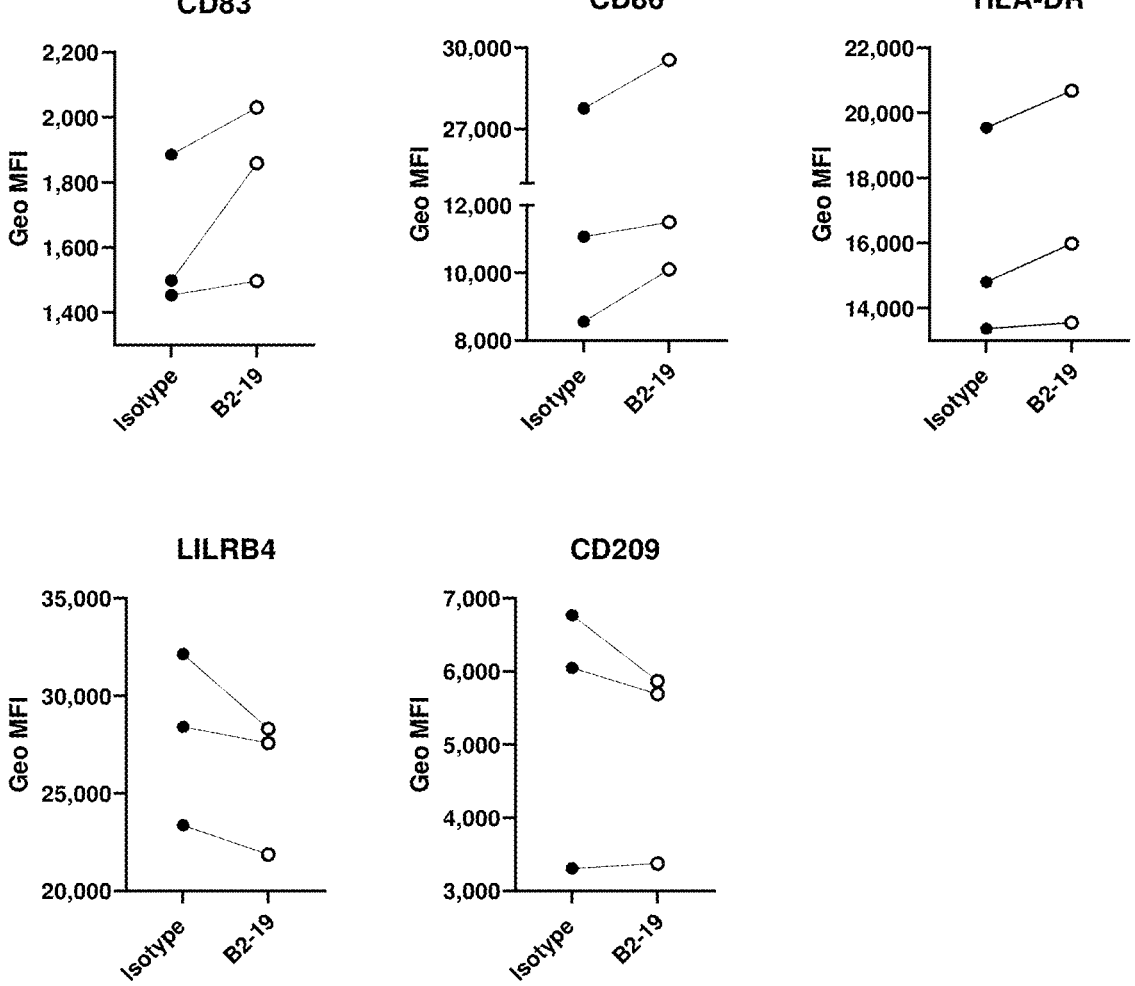

FIG. 48. B2-19 antibody enhanced the pro-inflammatory phenotype of DC treated with LPS, as evidenced by changes in expression of several cell surface markers. Each line represents the result from a different donor.

Figure 49:
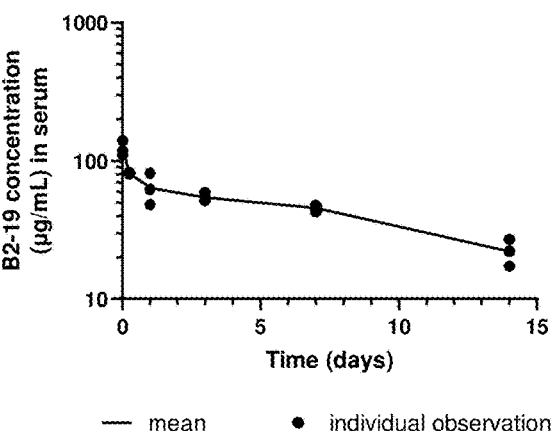

FIG. 49. B2-19 antibody displays the expected pharmacokinetics profile (CL and half-life) of a human IgG4 dosed at 5 mg/kg in C57BL/6J wild-type mice.

Figure 50A:
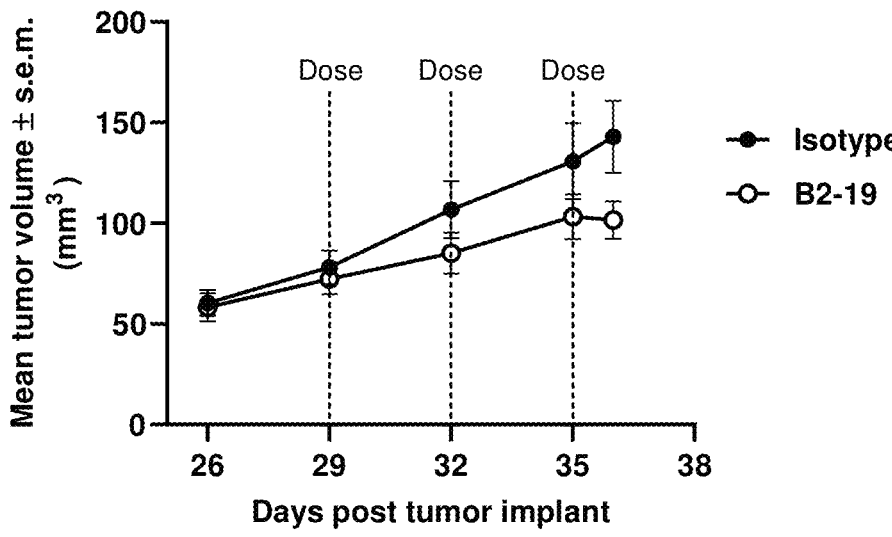
Figure 50B:
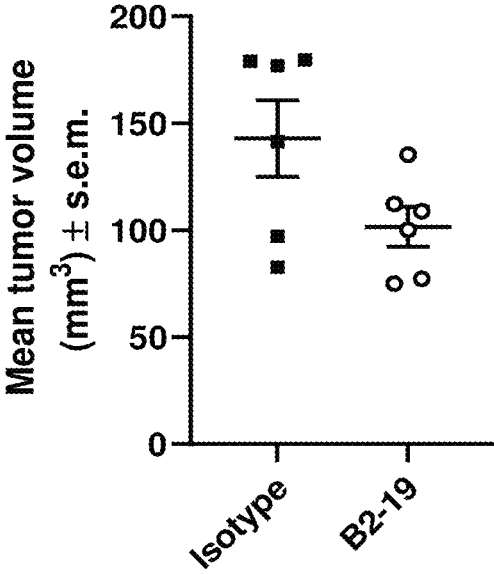

FIGS. 50A-B. (FIG. 50A) B2-19 antibody monotherapy reduces tumor growth rate in humanized NSG-SGM3 mice xenografted with SK-MEL-5 melanoma cell line. (FIG. 50B) B2-19 antibody monotherapy causes tumor growth inhibition in humanized NSG-SGM3 mice xenografted with SK-MEL-5 melanoma cell line.

Figure 51:
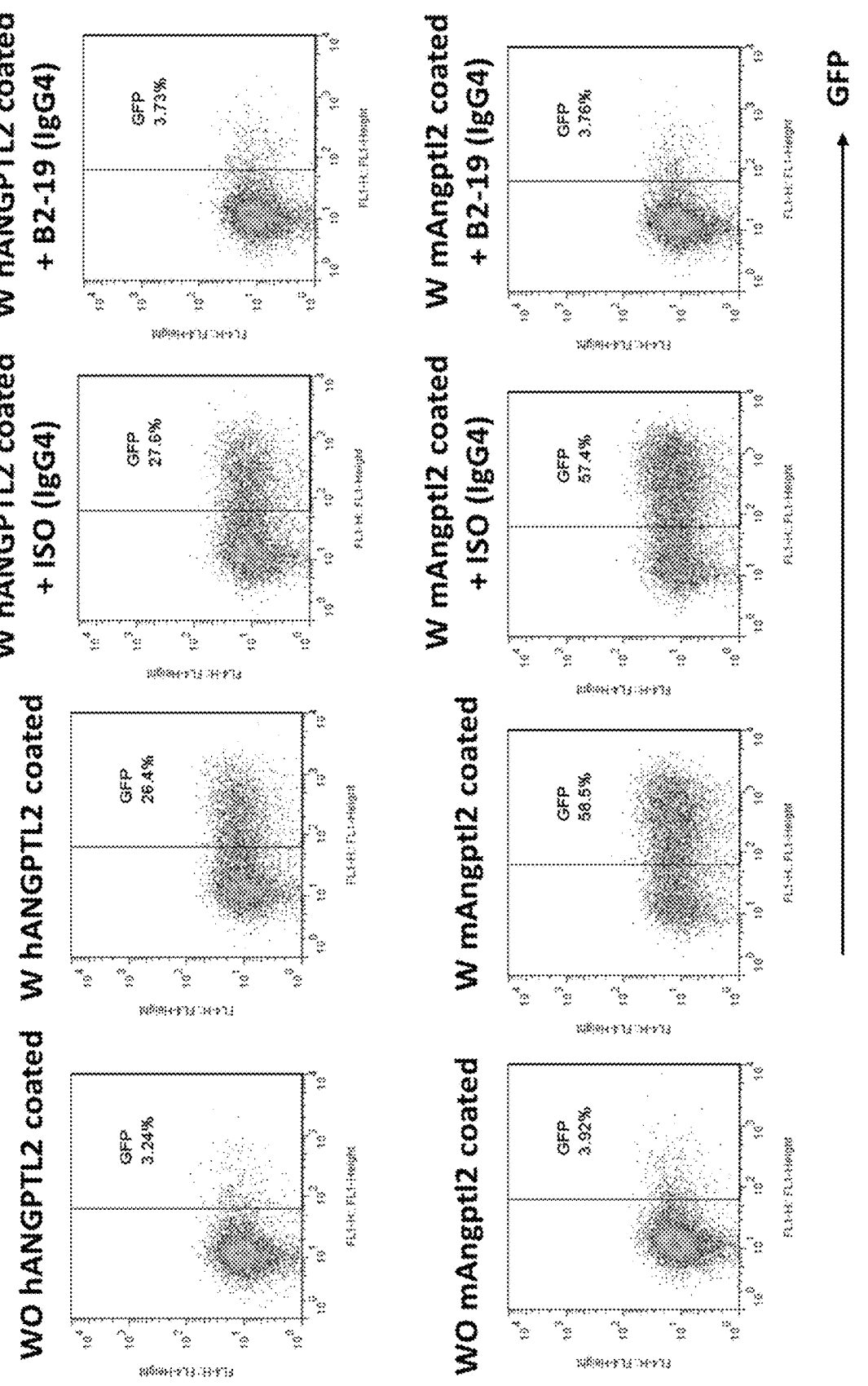

FIG. 51. Representative flow cytometric profiles showed that coated human ANGPTL2 (hANGPLT2) and mouse Angpt12 (mAngpt12) stimulates GFP expression in LILRB2 reporter cells and B2-19 effectively block GFP expression in LILRB2 reporter cells activated by coated hANGPLT2 and mAngpt12.

Figure 52:
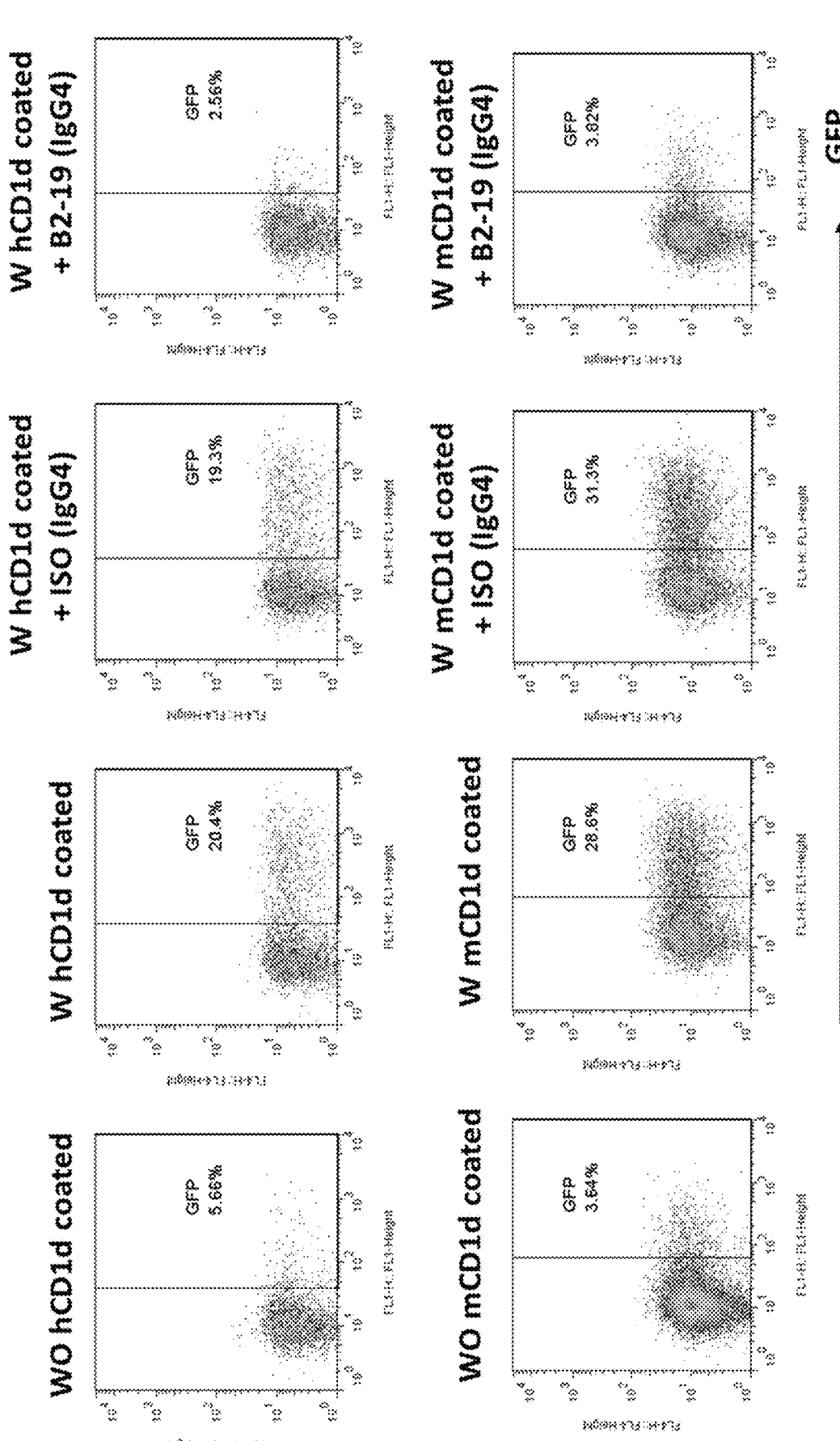

FIG. 52. Representative flow cytometric profiles showed that coated human CD1d (hCD1d) and mouse CD1d (mCD1d) stimulates GFP expression in LILRB2 reporter cells and B2-19 effectively block GFP expression in LILRB2 reporter cells activated by coated hCD1d and mCD1d.

DESCRIPTION OF ILLUSTRATIVE EMBODIMENTS

The inventors determined that LILRB2 plays critical roles in regulation of both innate and adaptive immunity. LILRB2 is expressed on several types of immune cells, such as normal monocytes, dendritic cells, granulocytes and myeloid derived suppressor cells (MDSCs). The inventors have isolated a panel of novel monoclonal antibodies recognizing LILRB2 protein, which can be used for the treatment of cancer and autoimmune diseases. Within this panel of anti-LILRB2 antibodies, there are examples of antagonists and agonists of LILRB2 signalling.

The following description of the disclosure is merely intended to illustrate various embodiments of the disclosure. As such, the specific modifications discussed are not to be construed as limitations on the scope of the disclosure. It will be apparent to one skilled in the art that various equivalents, changes, and modifications may be made without departing from the scope of the disclosure, and it is understood that such equivalent embodiments are to be included herein. All references cited herein, including publications, patents and patent applications are incorporated herein by reference in their entirety.

I. DEFINITION

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987) or Chothia et al., Nature, 342: 878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196:901-17 (1986); Chothia et al., Nature, 342:877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK: Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by itself. Antigens are usually proteins and polysaccharides, less frequently also lipids. Suitable antigens include without limitation parts of bacteria (coats, capsules, cell walls, flagella, fimbrai, and toxins), viruses, and other microorganisms. Antigens also include tumor antigens, e.g., antigens generated by mutations in tumors. As used herein, antigens also include immunogens and haptens.

An "antigen binding protein" ("ABP") as used herein means any protein that binds a specified target antigen. In the instant application, the specified target antigen is the LILRB protein or fragment thereof. "Antigen binding protein" includes but is not limited to antibodies and antigen-binding fragment thereof. Peptibodies are another example of antigen binding proteins.

The term "antigen-binding fragment" as used herein refers to a portion of a protein which is capable of binding specifically to an antigen. In certain embodiment, the antigen-binding fragment is derived from an antibody comprising one or more CDRs, or any other antibody fragment that binds to an antigen but does not comprise an intact native antibody structure. In certain embodiments, the antigen-binding fragment is not derived from an antibody but rather is derived from a receptor. Examples of antigen-binding fragment include, without limitation, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody, a single domain antibody (sdAb), a camelid antibody or a nanobody, a domain antibody, and a bivalent domain antibody. In certain embodiments, an antigen-binding fragment is capable of binding to the same antigen to which the parent antibody binds. In certain embodiments, an antigen-binding fragment may comprise one or more CDRs from a particular human antibody grafted to a framework region from one or more different human antibodies. In certain embodiments, the antigen-binding fragment is derived from a receptor and contains one or more mutations. In certain embodiments, the antigen-binding fragment does not bind to the natural ligand of the receptor from which the antigen-binding fragment is derived.

A "Fab fragment" comprises one light chain and the CH1 and variable regions of one heavy chain. The heavy chain of a Fab molecule cannot form a disulfide bond with another heavy chain molecule.

A "Fab' fragment" comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the CH1 and CH2 domains, such that an interchain disulfide bond is formed between the two heavy chains. A F(ab')$_2$ fragment thus is composed of two Fab' fragments that are held together by a disulfide bond between the two heavy chains.

An "Fc" region comprises two heavy chain fragments comprising the CH1 and CH2 domains of an antibody. The two heavy chain fragments are held together by two or more disulfide bonds and by hydrophobic interactions of the CH3 domains.

The "Fv region" comprises the variable regions from both the heavy and light chains but lacks the constant regions.

"Single-chain antibodies" are Fv molecules in which the heavy and light chain variable regions have been connected by a flexible linker to form a single polypeptide chain, which forms an antigen binding region. Single chain antibodies are discussed in detail in International Patent Application Publication No. WO 88/01649 and U.S. Pat. Nos. 4,946,778 and 5,260,203, the disclosures of which are incorporated by reference.

A "domain antibody" is an immunologically functional immunoglobulin fragment containing only the variable region of a heavy chain or the variable region of a light chain. In some instances, two or more VH regions are covalently joined with a peptide linker to create a bivalent domain antibody. The two VH regions of a bivalent domain antibody can target the same or different antigens.

A "bivalent antigen binding protein" or "bivalent antibody" comprises two antigen binding sites. In some instances, the two binding sites have the same antigen specificities. Bivalent antigen binding proteins and bivalent antibodies can be bispecific, see, infra. A bivalent antibody other than a "multispecific" or "multifunctional" antibody, in certain embodiments, typically is understood to have each of its binding sites identical.

A "multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein antibody and can be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which can reside on the same or different protein targets.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity are described in the following.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the LILRB2 specific antibodies of the present invention are specific to LILRB2. In some embodiments, the antibody that binds to LILRB2 has a dissociation constant (Kd) of $\leq 100$ nM, $\leq 10$ nM, $\leq 1$ nM, $\leq 0.1$ nM, $\leq 0.01$ nM, or $\leq 0.001$ nM (e.g., $10^{-8}$M or less, e.g., from $10^{-8}$M to $10^{-13}$M, e.g., from $10^{-9}$M to $10^{-13}$M). The dissociation constant Kd used herein refers to the ratio of the dissociation rate to the association rate ($k_{off}/k_{on}$), which may be determined by using any conventional method known in the art, including but are not limited to surface plasmon resonance method, microscale thermophoresis method, HPLC-MS method and flow cytometry (such as FACS) method. In certain embodiments, the Kd value can be appropriately determined by using flow cytometry.

The term "compete" when used in the context of antigen binding proteins (e.g., antibody or antigen-binding fragment thereof) that compete for the same epitope means competition between antigen binding proteins as determined by an assay in which the antigen binding protein (e.g., antibody or antigen-binding fragment thereof) being tested prevents or inhibits (e.g., reduces) specific binding of a reference antigen binding protein (e.g., a ligand, or a reference antibody) to a common antigen (e.g., LILRB or a fragment thereof). Numerous types of competitive binding assays can be used to determine if one antigen binding protein competes with another, for example: solid phase direct or indirect radio-immunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "epitope" as used herein refers to the specific group of atoms or amino acids on an antigen to which an antibody binds. The epitope can be either linear epitope or a conformational epitope. A linear epitope is formed by a continuous sequence of amino acids from the antigen and interacts with an antibody based on their primary structure. A conformational epitope, on the other hand, is composed of discontinuous sections of the antigen's amino acid sequence and interacts with the antibody based on the 3D structure of the antigen. In general, an epitope is approximately five or six amino acid in length. Two antibodies may bind the same epitope within an antigen if they exhibit competitive binding for the antigen.

A "cell", as used herein, can be prokaryotic or eukaryotic. A prokaryotic cell includes, for example, bacteria. A eukaryotic cell includes, for example, a fungus, a plant cell, and an animal cell. The types of an animal cell (e.g., a mammalian cell or a human cell) includes, for example, a cell from circulatory/immune system or organ, e.g., a B cell, a T cell (cytotoxic T cell, natural killer T cell, regulatory T cell, T helper cell), a natural killer cell, a granulocyte (e.g., basophil granulocyte, an eosinophil granulocyte, a neutrophil granulocyte and a hypersegmented neutrophil), a monocyte or macrophage, a red blood cell (e.g., reticulocyte), a mast cell, a thrombocyte or megakaryocyte, and a dendritic cell; a cell from an endocrine system or organ, e.g., a thyroid cell (e.g., thyroid epithelial cell, parafollicular cell), a parathyroid cell (e.g., parathyroid chief cell, oxyphil cell), an adrenal cell (e.g., chromaffin cell), and a pineal cell (e.g., pinealocyte); a cell from a nervous system or organ, e.g., a glioblast (e.g., astrocyte and oligodendrocyte), a microglia, a magnocellular neurosecretory cell, a stellate cell, a boettcher cell, and a pituitary cell (e.g., gonadotrope, corticotrope, thyrotrope, somatotrope, and lactotroph); a cell from a respiratory system or organ, e.g., a pneumocyte (a type I pneumocyte and a type II pneumocyte), a clara cell, a goblet cell, and an alveolar macrophage; a cell from circular system or organ (e.g., myocardiocyte and pericyte); a cell from digestive system or organ, e.g., a gastric chief cell, a parietal cell, a goblet cell, a paneth cell, a G cell, a D cell, an ECL cell, an I cell, a K cell, an S cell, an enteroendocrine cell, an enterochromaffin cell, an APUD cell, and a liver cell (e.g., a hepatocyte and Kupffer cell); a cell from integumentary system or organ, e.g., a bone cell (e.g., an osteoblast, an osteocyte, and an osteoclast), a teeth cell (e.g., a cementoblast, and an ameloblast), a cartilage cell (e.g., a chondroblast and a chondrocyte), a skin/hair cell (e.g., a trichocyte, a keratinocyte, and a melanocyte (Nevus cell), a muscle cell (e.g., myocyte), an adipocyte, a fibroblast, and a tendon cell; a cell from urinary system or organ (e.g., a podocyte, a juxtaglomerular cell, an intraglomerular mesangial cell, an extraglomerular mesangial cell, a kidney proximal tubule brush border cell, and a macula densa cell); and a cell from reproductive system or organ (e.g., a spermatozoon, a Sertoli cell, a leydig cell, an ovum, an oocyte). A cell can be normal, healthy cell; or a diseased or unhealthy cell (e.g., a cancer cell). A cell further includes a mammalian zygote or a stem cell which include an embryonic stem cell, a fetal stem cell, an induced pluripotent stem cell, and an adult stem cell. A stem cell is a cell that is capable of undergoing cycles of cell division while maintaining an undifferentiated state and differentiating into specialized cell types. A stem cell can be an omnipotent stem cell, a pluripotent stem cell, a multipotent stem cell, an oligopotent stem cell and a unipotent stem cell, any of which may be induced from a somatic cell. A stem cell may also include a cancer stem cell. A mammalian cell can be a rodent cell, e.g., a mouse, rat, hamster cell. A mammalian cell can be a lagomorpha cell, e.g., a rabbit cell. A mammalian cell can also be a primate cell, e.g., a human cell.

The term "chimeric antigen receptor" or "CAR" as used herein refers to an artificially constructed hybrid protein or polypeptide containing an antigen binding domain of an antibody (e.g., a single chain variable fragment (scFv)) linked to a domain or signaling, e.g., T-cell signaling or T-cell activation domains, that activates an immune cell, e.g., a T cell or a NK cell (see, e.g., Kershaw et al., supra, Eshhar et al., Proc. Natl. Acad. Sci. USA, 90(2): 720-724 (1993), and Sadelain et al., Curr. Opin. Immunol. 21(2): 215-223 (2009)). CARs are capable of redirecting the immune cell specificity and reactivity toward a selected target in a non-MHC-restricted manner, taking advantage of the antigen-binding properties of monoclonal antibodies. The non-MHC-restricted antigen recognition confers immune cells expressing CARs on the ability to recognize an antigen independent of antigen processing, thus bypassing a major mechanism of tumor escape. In addition, when expressed in T-cells, CARs advantageously do not dimerize with endogenous T-cell receptor (TCR) alpha and beta chains.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press: Biocomputing Informatics and Genome Projects, (Smith, D. W., ed.), 1993, New York: Academic Press; Computer Analysis of Sequence Data, Part I. (Griffin, A. M., and Griffin, H. G., eds.), 1994, New Jersey:

Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program can be found in Needleman et al., 1970, J. Mol. Biol. 48:443-453.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

The term "link" as used herein refers to the association via intramolecular interaction, e.g., covalent bonds, metallic bonds, and/or ionic bonding, or inter-molecular interaction, e.g., hydrogen bond or noncovalent bonds.

Leukocyte immunoglobulin-like receptor subfamily B member 2 (LILRB2) is a protein that in humans is encoded by the LILRB2 gene. This gene is a member of the leukocyte immunoglobulin-like receptor (LIR) family, which is found in a gene cluster at chromosomal region 19q13.4. The encoded protein belongs to the subfamily B class of LIR receptors which contain two or four extracellular immunoglobulin domains, a transmembrane domain, and two to four cytoplasmic immunoreceptor tyrosine-based inhibitory motifs (ITIMs). The receptor is expressed on myeloid cells; it binds to multiple types of ligands, including HLA class I molecules, ANGPTLs, myelin inhibitors (including Nogo66, MAG, and OMgp), and β-amyloid, transducing a negative signal that inhibits stimulation of an immune response. It is thought to control inflammatory responses and cytotoxicity to help focus the immune response and limit autoreactivity.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally-occurring amino acid and polymers. The terms "polypeptide" and "protein" specifically encompass LILRB antigen binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a LILRB-binding antibody, useful fragments include but are not limited to a CDR region, a variable domain of a heavy and/or light chain, a portion of an antibody chain or just its variable region including two CDRs, and the like.

The pharmaceutically acceptable carriers useful in this invention are conventional. Remington's Pharmaceutical Sciences, by E. W. Martin, Mack Publishing Co., Easton, PA, 15th Edition (1975), describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "therapeutically effective amount" or "effective dosage" as used herein refers to the dosage or concentration of a drug effective to treat a disease or condition. For example, with regard to the use of the monoclonal antibodies or antigen-binding fragments thereof disclosed herein to treat cancer, a therapeutically effective amount is the dosage or concentration of the monoclonal antibody or antigen-binding fragment thereof capable of reducing the tumor volume, eradicating all or part of a tumor, inhibiting or slowing tumor growth or cancer cell infiltration into other organs, inhibiting growth or proliferation of cells mediating a cancerous condition, inhibiting or slowing tumor cell metastasis, ameliorating any symptom or marker associated with a tumor or cancerous condition, preventing or delaying the development of a tumor or cancerous condition, or some combination thereof.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, a "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

II. LILRB2 RELATED DISEASES

LILRB2 has been identified as a key regulator of myeloid cell phenotype. The activation of LILRB2 suppresses the pro-inflammatory activity of myeloid cells. While myeloid cells with a suppressive/anti-inflammatory phenotype can down-regulate the activation, proliferation and cytotoxic activity of T cells, modulation of LILRB2 has the potential in therapeutic use in conditions and disorders including cancer, autoimmune diseases, and inflammatory diseases.

While hyperproliferative diseases can be associated with any disease which causes a cell to begin to reproduce uncontrollably, the prototypical example is cancer.

Examples of cancer can be generally categorized into solid tumors and hematologic malignancies. Solid tumors include but are not limited to, adrenal cancer, bile duct carcinoma, bone cancer, brain cancer (e.g., astrocytoma, brain stem glioma, craniopharyngioma, ependymoma, hemangioblastoma, medulloblastoma, meningioma, oligodendroglioma, spinal axis tumor), breast cancer (including acoustic neuroma, basal breast carcinoma, ductal carcinoma and lobular breast carcinoma), cervical cancer, choriocarcinoma, colon cancer, colorectal cancer, esophageal cancer, eye cancer, gastric cancer, glioblastoma, head and neck cancer, kidney cancer (including Wilms tumor), liver cancer (including hepatocellular carcinoma (HCC)), lung cancer (including bronchogenic carcinoma, non-small cell lung cancer (squamous/non-squamous), bronchioloalveolar cell lung cancer, papillary adenocarcinomas), mesothelioma, melanoma, merkel cell cancer, nasopharyngeal carcinoma, neuroblastoma, oral cancer, ovarian cancer, pancreatic cancer, penile cancer, pinealoma, prostate cancer, renal cell cancer, retinoblastoma, sarcoma (including chondrosarcoma, Ewing's sarcoma, fibrosarcoma, leiomyosarcoma, liposarcoma, myxosarcoma, osteogenic sarcoma, rhabdomyosarcoma, synovial sarcoma), skin cancer (including basal cell carcinoma, sebaceous gland carcinoma, squamous cell carcinoma), testicular cancer (including seminoma), thymic carcinoma, thyroid cancer (e.g., medullary thyroid carcinoma, papillary thyroid carcinoma), uterine cancer, and vaginal cancer.

Hematologic malignancies include but are not limited to blastic plasmacytoid dendritic cell neoplasm (BPDCN), heavy chain disease, leukemias (including but not limited to acute lymphocytic leukemia (ALL), acute myeloid leukemia (AML) (including but not limited to acute promyelocytic leukemia (APL) or M3 AML, acute myelomonocytic leukemia or M4 AML, acute monocytic leukemia or M5 AML), B-cell leukemia, chronic lymphoblastic leukemia (CLL), chronic myelomonocytic leukemia (CMML), chronic myelocytic leukemia (CML), pre-B acute lymphocytic leukemia (Pre-B ALL), diffuse large B-cell lymphoma (DLBCL), extranodal NK/T-cell lymphoma, hairy cell leukemia, HHV8-associated primary effusion lymphoma, plasmablastic lymphoma, primary CNS lymphoma, primary mediastinal large B-cell lymphoma, T-cell/histiocyte-rich B-cell lymphoma), lymphomas (including but not limited to Hodgkin's lymphoma, non-Hodgkin's lymphoma, Waldenstrom's macroglobulinemia), multiple myeloma (MM), myelodysplastic syndromes (MDS), myeloproliferative neoplasms, and polycythemia vera.

Immunotherapy holds great promise to achieve long-lasting anti-tumor effects. Immune checkpoint PD-1 and CTLA-4 blockade therapies have been successful in treating some types of cancers but not others. These immunotherapies target inhibitory molecules on T cells to reactivate dysfunctional T cells within the tumor microenvironment (TME). Other populations of immune cells, including monocytic cells, are present in the TME in even larger numbers than T cells. In fact, monocyte-derived macrophages are the most abundant immune cell population in tumor tissues. While these innate cells possess the capacity to kill tumor cells and to prime or reactivate T cells, they become dysfunctional in TME and turn into MDSCs and tumor-associated macrophages (TAMs) that support tumor development and suppress immune surveillance and attack. MDSCs, including monocytic MDSCs (M-MDSCs) and polymorphonuclear MDSCs (PMN-MDSCs), represent a heterogeneous population of immature myeloid cells that fail to terminally differentiate. TAMs are a mixed macrophage population in TME. They are anti-inflammatory and correlated with a poor prognosis. Despite their phenotypic plasticity, MDSCs and TAMs are defined by their immunosuppressive function. Removing, reprogramming, or blocking trafficking of these immune-suppressive monocytic cells is becoming an attractive anti-cancer therapeutic strategy.

LILRB2 is expressed on MDSCs and TAMs in TME. Therapeutic blocking of LILRB2 in myeloid-rich solid tumors has the potential to reactivate or enhance anti-tumor immune responses in patients presenting with disease unresponsive/relapsed to T cell checkpoint inhibitors.

LILRB2 expression on myeloid cells may regulate systems involved in autoimmune and inflammatory diseases. Therapeutic activating or agonizing LILRB2 has the potential to treat autoimmune or inflammatory diseases.

Autoimmune or inflammatory diseases include, but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenia purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pemacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma, systemic scleroderma, progressive systemic sclerosis (PSS), systemic sclerosis (SS), Sjogren's syndrome, stiff-man syndrome, systemic lupus erythematosus (SLE), Takayasu arteritis, temporal arteritis/giant cell arteritis, inflammatory bowel disease (IBD), ulcerative colitis, Cohn's disease, intestinal mucosal inflammation, wasting disease associated with colitis, uveitis, vitiligo and Wegener's granulomatosis, Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy, ventilator induced lung injury, viral infections, autoimmune diabetes and the like. Inflammatory disorders include, for example, chronic and acute inflammatory disorders.

III. MONOCLONAL ANTIBODIES AND PRODUCTION THEREOF

The monoclonal antibodies described herein can be prepared using standard methods, followed by screening, characterization and functional assessment. Variable regions can be sequenced and then subcloned into a human expression vector to produce the chimeric antibody genes, which are then expressed and purified. These chimeric antibodies can be tested for antigen binding, signaling blocking, and in xenograft experiments. The monoclonal antibodies described herein can also be prepared using phage display method, in which a large library of phage displayed human scFv is panned against the target protein. The human scFv selected to specifically binding to the target protein can be sequenced and then subcloned into a human expression vector to produce the desired human antibody.

A. General Methods

It will be understood that monoclonal antibodies binding to LILRB2 will have several applications. These include the production of diagnostic kits for use in detecting and diagnosing cancer, as well as for cancer therapies. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The classical methods for generating monoclonal antibodies (MAbs) generally begin along the same lines as those for preparing polyclonal antibodies. The first step for both these methods is immunization of an appropriate host. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986). Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain is also used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately 104 times as many antibodies can be produced and screened in a single round, and that new specificities are generated by H and L chain combination which further increases the chance of finding appropriate antibodies.

Recently, additional methods for generating mAb, such as scFv phage display, have been developed (see CM Hammers and JR Stanley, Antibody phage display: technique and applications, J Invest Dermatol (2014) 134:e17). Generally, a panel of human mAbs that bind to a target protein, e.g., human LILRB2, are generated by panning a large diversity of human scFv phage displayed antibody library.

To generate the human scFv phage displayed antibody library, RNA is extracted from the chosen cell source, e.g., peripheral blood mononuclear cells. The RNA is then reversed-transcribed into cDNA, which is used for PCR of the VH and VL chains of the encoded antibodies. Defined sets of primers specific for the different VH and VL chain region gene families allow the amplification of all transcribed rearranged variable regions within a given immunoglobulin repertoire, reflecting all antibody specificities in a particular individual.

The VH and VL PCR products that represent the antibody repertoire are ligated into a phage display vector that is engineered to express the VH and VL as an scFv fused to the pIII minor capsid protein of a filamentous bacteriophage of *E. coli* that was originally derived from the M13 bacteriophage. This generates a library of phages, each of which expresses on its surface a scFv sequence and harbors the vector with the respective nucleotide sequence within.

The library is then screened for phage binding to a target antigen through its expressed surface scFv by a technique called bio-panning. In short, the target protein is coated on solid phase for incubation with phage libraries. After washing and elution, antigen enriched phages are recovered and used for next rounds of phage panning. After at least three rounds of phage panning, single bacterial colonies are picked for phage ELISA and other functional/genetic analysis.

The positive hits are sequenced for the scFv region and are converted to full human IgG heavy and light chain constructs, which are used to generate the mAb of interest using the methods disclosed supra. For example, the IgG expressing plasmids are cotransfected into Expi293 cells using transfection reagent PEI. After 7 days of expression, supernatants are harvested, and antibodies are purified by affinity chromatography using protein A resin.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

1. Antibodies to LILRB2

Antibodies or antigen-binding fragments thereof according to the present disclosure may be defined, in the first instance, by their binding specificity, which in this case is for LILRB2. Those of skill in the art, by assessing the binding specificity/affinity of a given antibody using techniques well known to those of skill in the art, can determine whether such antibodies fall within the scope of the instant claims.

In one aspect, there are provided antibodies and antigen-binding fragments specifically bind to LILRB2. In some embodiments, when bound to LILRB2, such antibodies modulate the activation of LILRB2. In certain embodiments, the antibody or antigen-binding fragment, when bound to LILRB2, activates LILRB2. In certain embodiments, the antibody or antigen-binding fragment, when bound to LILRB2, suppresses activation of LILRB2. In certain embodiments, the antibody or antigen-binding fragment, when bound to LILRB2, can specifically interfere with, block or reduce the interaction between LILRB2 and its binding partners. In certain embodiments, the antibody or antigen-binding fragment provided herein is capable of inhibiting the immunosuppressive activity of MDSCs and other solid tumor-infiltrating myeloid cells, such as tumor-associated macrophages (TAMs) and tolerogenic dendritic cells (DCs). In certain embodiments, the antibodies or antigen-binding fragments provided herein specifically or selectively bind to human LILRB2.

In some embodiments, the antibodies or antigen-binding fragments bind specifically to human LILRB2 and/or substantially inhibits binding of human LILRB2 to HLA-G, ANGPTLs, SEMA4A by at least about 20%-40%, 40-60%, 60-80%, 80-85%, or more (for example, by an assay as disclosed in the Example). In some embodiments, the antibody or antigen-binding fragment has a Kd of less (binding more tightly) than $10^{-6}$, $10^{-7}$, $10^{-8}$, $10^{-9}$, $10^{-10}$, $10^{-11}$, $10^{-12}$, $10^{-13}$ M. In some embodiments, the antibody or antigen-binding fragment has an $IC_{50}$ for blocking the binding of HLA-G, ANGPTLs, SEMA4A to LILRB2 of less than 10 uM, 10 uM to 1 uM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM. 100 pM to 10 pM, 10 PM to 1 pM.

In some embodiments, the antibodies or antigen-binding fragments provided herein having the clone-paired CDRs illustrated in Table 2.

In certain embodiments, the antibodies may be defined by their variable sequence, which include additional "framework" regions. The antibody is characterized by clone-paired heavy chain and light chain amino acid sequences from Appendices I and III. Furthermore, the antibodies sequences may vary from these sequences, particularly in regions outside the CDRs. For example, the amino acids may vary from those set out above by a given percentage, e.g., 80%, 85%, 90%, 91%, 92%, 93%, 94%, 95%, 96%, 97%, 98% or 99% homology, or the amino acids may vary from those set out above by permitting conservative substitutions (discussed below). Each of the foregoing apply to the amino acid sequences of Appendices I and III. In another embodiment, the antibody derivatives of the present disclosure comprise VL and VH domains having up to 0, 1, 2, 3, 4, 5, 6, 7, 8, 9, 10 or more conservative or non-conservative amino acid substitutions, while still exhibiting the desired binding and functional properties.

While the antibodies of the present disclosure were generated as IgG's, it may be useful to modify the constant regions to alter their function. The constant regions of the antibodies typically mediate the binding of the antibody to host tissues or factors, including various cells of the immune system (e.g., effector cells) and the first component (Clq) of the classical complement system. Thus, the term "antibody" includes intact immunoglobulins of types IgA, IgG. IgE, IgD, IgM (as well as subtypes thereof), wherein the light chains of the immunoglobulin may be of types kappa or lambda. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., $2^{nd}$ ed. Raven Press, N.Y. (1989).

The present disclosure further comprises nucleic acids which hybridize to nucleic acids encoding the antibodies disclosed herein. In general, the nucleic acids hybridize under moderate or high stringency conditions to nucleic acids that encode antibodies disclosed herein and also encode antibodies that maintain the ability to specifically bind to an LILRB2. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook et al., MOLECULAR CLONING: A LABORATORY MANUAL, $3^{rd}$ ed., Cold Spring Harbor Press, Cold Spring Harbor, N.Y. 2001). The conditions of temperature and ionic strength determine the "stringency" of the hybridization. Typical moderate stringency hybridization conditions are 40% formamide, with 5× or 6×SSC and 0.1% SDS at 42° C. High stringency hybridization conditions are 50% formamide, 5× or 6× SSC (0.15M NaCl and 0.015M Na-citrate) at 42° C. or, optionally, at a higher temperature (e.g., 57° C., 59° C., 60° C., 62° C., 63° C., 65° C. or 68° C.). Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook et al., supra). For hybridization with shorter nucleic acids, e.g., oligonucleotides, the position of mismatches becomes more important, and the length of the oligonucleotide determines its specificity (see Sambrook et al., supra).

2. Exemplary Epitopes and Competing Antigen Binding Proteins

In another aspect, the present disclosure provides epitopes to which anti-LILRB2 antibodies bind. In some embodiments, epitopes that are bound by the antibodies described herein are useful. In certain embodiments, an epitope provided herein can be utilized to isolate antibodies or antigen binding proteins that bind to LILRB2. In certain embodiments, an epitope provided herein can be utilized to generate antibodies or antigen binding proteins which bind to LILRB2. In certain embodiments, an epitope or a sequence comprising an epitope provided herein can be utilized as an immunogen to generate antibodies or antigen binding proteins that bind to LILRB2. In certain embodiments, an epitope described herein or a sequence comprising an epitope described herein can be utilized to interfere with biological activity of LILRB2.

In some embodiments, antibodies or antigen-binding fragments thereof that bind to any of the epitopes are particularly useful. In some embodiments, an epitope provided herein, when bound by an antibody, modulates the biological activity of LILRB2. In some embodiments, an epitope provided herein, when bound by an antibody, activates LILRB2. In some embodiments, an epitope provided herein, when bound by an antibody, suppress the activation of LILRB2. In some embodiments, an epitope provided herein, when bound by an antibody, block the interaction between LILRB2 and its binding partners.

In some embodiments, the domain(s)/region(s) containing residues that are in contact with or are buried by an antibody can be identified by mutating specific residues in LILRB2 and determining whether the antibody can bind the mutated LILRB2 protein. By making a number of individual mutations, residues that play a direct role in binding or that are in sufficiently close proximity to the antibody such that a mutation can affect binding between the antibody and antigen can be identified. From knowledge of these amino acids, the domain(s) or region(s) of the antigen that contain residues in contact with the antigen binding protein or covered by the antibody can be elucidated. Such a domain can include the binding epitope of an antigen binding protein.

In another aspect, the present disclosure provides antigen-binding proteins that compete with one of the exemplified antibodies or antigen-binding fragment binding to the epitope described herein for specific binding to LILRB2. Such antigen binding proteins can also bind to the same epitope as one of the herein exemplified antibodies or the antigen-binding fragment, or an overlapping epitope. Antigen-binding proteins that compete with or bind to the same epitope as the exemplified antibodies are expected to show similar functional properties. The exemplified antibodies include those described above, including those with the heavy and light chain variable regions and CDRs included in Table 2, heavy and light chains as shown in Appendices I and III, and heavy and light chain coding regions as shown in Appendices II and IV.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full-length IgG antibodies may be generated by subcloning heavy and light chain Fv DNAs from the cloning vector into an IgG plasmid vector, transfected into 293 Freestyle cells or CHO cells, and antibodies collected a purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

1. Antigen Binding Modifications

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG1 can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombinant expression are addressed elsewhere in this document.

2. Fc Region Modifications

The antibodies disclosed herein can also be engineered to include modifications within the Fc region, typically to alter one or more functional properties of the antibody, such as serum half-life, complement fixation, Fc receptor binding, and/or effector function (e.g., antigen-dependent cellular cytotoxicity). Furthermore, the antibodies disclosed herein can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat. The antibodies disclosed herein also include antibodies with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, enabling less frequent dosing and thus increased convenience and decreased use of material. This mutation has been reported to abolish the heterogeneity of inter-heavy chain disulfide bridges in the hinge region.

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody. In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022. In yet other embodiments, the Fc region is altered by replacing at least one amino acid residue with a different amino acid residue to alter the effector function(s) of the antibodies. For example, one or more amino acids selected from amino acid residues 234, 235, 236, 237, 297, 318, 320 and 322 can be replaced with a different amino acid residue such that the antibody has an altered affinity for an effector ligand but retains the antigen binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acid residues within amino acid positions 231 and 239 are altered to thereby alter the ability of the antibody to fix complement. This approach is described further in PCT Publication WO 94/29351. In yet another example, the Fc region is modified to increase or decrease the ability of the antibodies to mediate antibody dependent cellular cytotoxicity (ADCC) and/or to increase or decrease the affinity of the antibodies for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described. Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antibodies to mediate effector function and/or to increase anti-inflammatory properties by modifying residues 243 and 264. In one embodiment, the Fc region of the antibody is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328.

In one embodiment, the Fc region is modified to abolish the ability of the antibodies to mediate effector function by modifying residues 234, 235 and 329 to alanine or glycine (L234A-L235A-P329G).

In still another embodiment, the antibody comprises a particular glycosylation pattern. For example, an aglycosylated antibody can be made (i.e., the antibody lacks glycosylation). The glycosylation pattern of an antibody may be altered to, for example, increase the affinity or avidity of the antibody for an antigen. Such modifications can be accomplished by, for example, altering one or more of the glycosylation sites within the antibody sequence. For example, one or more amino acid substitutions can be made that result removal of one or more of the variable region framework glycosylation sites to thereby eliminate glycosylation at that site. Such aglycosylation may increase the affinity or avidity of the antibody for antigen. See, e.g., U.S. U.S. Pat. Nos. 5,714,350 and 6,350,861.

An antibody may also be made in which the glycosylation pattern includes hypofucosylated or afucosylated glycans, such as a hypofucosylated antibodies or afucosylated antibodies have reduced amounts of fucosyl residues on the glycan. The antibodies may also include glycans having an increased amount of bisecting GlcNac structures. Such altered glycosylation patterns have been demonstrated to increase the ADCC ability of antibodies. Such modifications can be accomplished by, for example, expressing the antibodies in a host cell in which the glycosylation pathway was been genetically engineered to produce glycoproteins with particular glycosylation patterns. These cells have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 ($\alpha$ (1,6)-fucosyltransferase), such that antibodies expressed in the Ms704, Ms705, and Ms709 cell lines lack fucose on their carbohydrates. The Ms704, Ms705, and Ms709 FUT8-/- cell lines were created by the targeted disruption of the FUT8 gene in CHO/DG44 cells using two replacement vectors (see U.S. Patent Publication No. 20040110704. As another example, EP 1 176 195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1 176 195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn (297)-linked carbohydrates, also resulting in hypofucosylation of antibodies expressed in that host cell. Antibodies with a modified glycosylation profile can also be produced in chicken eggs, as described in PCT Publication WO 06/089231. Alternatively, antibodies with a modified glycosylation profile can be produced in plant cells, such as *Lemna* (U.S. Pat. No. 7,632,983). Methods for production of antibodies in a plant system are disclosed in the U.S. Pat. Nos. 6,998,267 and 7,388,081. PCT Publication WO 99/54342 describes cell lines engineered to express glycoprotein-modifying glycosyl transferases (e.g., $\beta$(1,4)-N-acetylglucosaminyltransferase III (GnTIII)) such that antibodies expressed in the engineered cell lines exhibit increased bisecting GlcNac structures which results in increased ADCC activity of the antibodies.

Alternatively, the fucose residues of the antibodies can be cleaved off using a fucosidase enzyme; e.g., the fucosidase $\alpha$-L-fucosidase removes fucosyl residues from antibodies. Antibodies disclosed herein further include those produced in lower eukaryote host cells, in particular fungal host cells such as yeast and filamentous fungi have been genetically engineered to produce glycoproteins that have mammalian- or human-like glycosylation patterns. A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures.

In addition, since fungi such as yeast or filamentous fungi lack the ability to produce fucosylated glycoproteins, antibodies produced in such cells will lack fucose unless the cells are further modified to include the enzymatic pathway for producing fucosylated glycoproteins (see for example, PCT Publication WO2008112092). In particular embodiments, the antibodies disclosed herein further include those produced in lower eukaryotic host cells and which comprise fucosylated and nonfucosylated hybrid and complex N-glycans, including bisected and multiantennary species, including but not limited to N-glycans such as GlcNAc(1-4)Man3GlcNAc2; Gal(1-4)GlcNAc(1-4)Man3GlcNAc2; NANA(1-4)Gal(1-4)GlcNAc(1-4)Man3GlcNAc2. In particular embodiments, the antibody compositions provided herein may comprise antibodies having at least one hybrid N-glycan selected from the group consisting of GlcNAcMan5GlcNAc2; GalGlcNAcMan5GlcNAc2; and NANAGalGlcNAcMan5GlcNAc2. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the antibody compositions provided herein comprise antibodies having at least one complex N-glycan selected from the group consisting of GlcNAcMan3GlcNAc2; GalGlcNAcMan3GlcNAc2; NANAGalGlcNAcMan3GlcNAc2; GlcNAc2Man3GlcNAc2; GalGlcNAc2Man3GlcNAc2; Gal2GlcNAc2Man3GlcNAc2; NANAGal2GlcNAc2Man3GlcNAc2; and NANA2Gal2GlcNAc2Man3GlcNAc2. In particular aspects, the complex N-glycan is the predominant N-glycan species in the composition. In further aspects, the complex N-glycan is a particular N-glycan species that comprises about 30%, 40%, 50%, 609%, 70%, 80%, 90%, 95%, 97%, 98%, 99%, or 100% of the complex N-glycans in the composition. In particular embodiments, the N-glycan is fusosylated. In general, the fucose is in an $\alpha$1,3-linkage with the GlcNAc at the reducing end of the N-glycan, an $\alpha$1,6-linkage with the GlcNAc at the reducing end of the N-glycan, an $\alpha$1,2-linkage with the Gal at the non-reducing end of the N-glycan, an $\alpha$1,3-linkage with the GlcNac at the non-reducing end of the N-glycan, or an $\alpha$1,4-linkage with a GlcNAc at the non-reducing end of the N-glycan.

Therefore, in particular aspects of the above the glycoprotein compositions, the glycoform is in an $\alpha$1,3-linkage or α1.6-linkage fucose to produce a glycoform selected from the group consisting of Man5GlcNAc2(Fuc), Glc-NAcMan5GlcNAc2(Fuc), Man3GlcNAc2(Fuc), GlcNAc-Man3GlcNAc2(Fuc), GlcNAc2Man3GlcNAc2(Fuc), Gal-GlcNAc2Man3GlcNAc2(Fuc), Gal2GlcNAc2Man3Gl-cNAc2(Fuc), NANAGal2GlcNAc2Man3GlcNAc2(Fuc), and NANA2Gal2GlcNAc2Man3GlcNAc2(Fuc); in an α1,3-linkage or α1,4-linkage fucose to produce a glycoform selected from the group consisting of GlcNAc(Fuc) Man5GlcNAc2, GlcNAc(Fuc) Man3GlcNAc2, GlcNAc2 (Fuc1-2) Man3GlcNAc2, GalGlcNAc2(Fuc1-2) Man-3GlcNAc2, Gal2GlcNAc2(Fuc1-2) Man3GlcNAc2, NAN-AGal2GlcNAc2(Fuc1-2) Man3GlcNAc2, and NANA-2Gal2GlcNAc2(Fuc1-2) Man3GlcNAc2; or in an α1,2-linkage fucose to produce a glycoform selected from the group consisting of Gal(Fuc) GlcNAc2Man3GlcNAc2, Gal2 (Fuc1-2) GlcNAc2Man3GlcNAc2, NANAGal2(Fuc1-2) GlcNAc2Man3GlcNAc2, and NANA2Gal2(Fuc1-2) GlcNAc2Man3GlcNAc2.

In further aspects, the antibodies comprise high mannose N-glycans, including but not limited to, Man8GlcNAc2, Man7GlcNAc2, Man6GlcNAc2, Man5GlcNAc2, Man-4GlcNAc2, or N-glycans that consist of the Man3GlcNAc2 N-glycan structure. In further aspects of the above, the complex N-glycans further include fucosylated and non-fucosylated bisected and multiantennary species. As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein.

D. Single Chain Antibodies

A Single Chain Variable Fragment (scFv) is a fusion of the variable regions of the heavy and light chains of immuno-globulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the VH C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multi-mers in conjunction with the J-chain. Another multimeriza-tion domain is the Gal4 dimerization domain. In other embodiments, the chains may be modified with agents such as biotin/avidin, which permit the combination of two anti-bodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contem-plated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable sta-bility in blood will be employed. Numerous types of disul-fide-bond containing linkers are known that can be success-fully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunc-tional cross-linker containing a disulfide bond that is "ste-rically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Purification

In certain embodiments, the antibodies of the present disclosure may be purified. The term "purified." as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

V. TREATMENT OF CANCER

A. Formulation and Administration

The present disclosure provides pharmaceutical compositions comprising anti-LILRB antibodies and antigens for generating the same. Such compositions comprise a prophylactically or therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc.

Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Antibodies of the present disclosure, as described herein, can be formulated for parenteral administration, e.g., formulated for injection via the intradermal, intravenous, intraarterial, intramuscular, subcutaneous, intra-tumoral or even intraperitoneal routes. The antibodies could alternatively be administered by a topical route directly to the mucosa, for example by nasal drops, inhalation, or by nebulizer. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. Cell Therapies

In another aspect, the present disclosure provides immune cells which express a chimeric antigen receptor (CAR). In some embodiment. The CAR comprises an antigen-binding fragment provided herein. In an embodiment, the CAR protein includes from the N-terminus to the C-terminus: a leader peptide, an anti-LILRB2 heavy chain variable domain, a linker domain, an anti-LILRB2 light chain variable domain, a human IgG1-CH2-CH3 domain, a spacer region, a CD28 transmembrane domain, a 4-1BB intracellular co-stimulatory signaling and a CD3 ζ intracellular T cell signaling domain.

Also provided are methods for immunotherapy comprising administering an effective amount of the immune cells of the present disclosure. In one embodiment, a medical disease or disorder is treated by transfer of an immune cell population that elicits an immune response. In certain embodiments of the present disclosure, cancer or infection is treated by transfer of an immune cell population that elicits an immune response. Provided herein are methods for treating or delaying progression of cancer in an individual comprising administering to the individual an effective amount of an antigen-specific cell therapy.

The immune cells may be T cells (e.g., regulatory T cells, CD4+ T cells, CD8+ T cells, or gamma-delta T cells), NK cells, invariant NK cells, NKT cells, or macrophages. Also provided herein are methods of producing and engineering the immune cells as well as methods of using and administering the cells for adoptive cell therapy, in which case the cells may be autologous or allogeneic. Thus, the immune cells may be used as immunotherapy, such as to target cancer cells.

The immune cells may be isolated from subjects, particularly human subjects. The immune cells can be obtained from healthy human subjects, healthy volunteers, or healthy donors. The immune cells can be obtained from a subject of interest, such as a subject suspected of having a particular disease or condition, a subject suspected of having a predisposition to a particular disease or condition, or a subject who is undergoing therapy for a particular disease or condition. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the immune cells are isolated from blood, such as peripheral blood or cord blood. In some aspects, immune cells isolated from cord blood have enhanced immunomodulation capacity, such as measured by CD4- or CD8-positive T cell suppression. In specific aspects, the immune cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor. The immune cells can be isolated from a pool of subjects and/or donors, such as from pooled cord blood.

When the population of immune cells is obtained from a donor distinct from the subject, the donor is preferably allogeneic, provided that the cells obtained are subject-compatible in that they can be introduced into the subject. Allogeneic donor cells may or may not be human-leukocyte-antigen (HLA)-compatible. To be rendered subject-compatible, allogeneic cells can be treated to reduce immunogenicity.

The immune cells can be genetically engineered to express antigen receptors such as engineered TCRs and/or chimeric antigen receptors (CARs). For example, the host cells (e.g., autologous or allogeneic T-cells) are modified to express a T cell receptor (TCR) having antigenic specificity for a cancer antigen. In particular embodiments, NK cells are engineered to express a TCR. The NK cells may be further engineered to express a CAR. Multiple CARs and/or TCRs, such as to different antigens, may be added to a single cell type, such as T cells or NK cells.

Suitable methods of modification are known in the art. See, for instance, Sambrook et al., supra; and Ausubel et al., CURRENT PROTOCOLS IN MOLECULAR BIOLOGY, Greene Publishing Associates and John Wiley & Sons, NY, 1994. For example, the cells may be transduced to express a T cell receptor (TCR) having antigenic specificity for a cancer antigen using transduction techniques described in Heemskerk et al. (2008) and Johnson et al. (2009).

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

C. Combination Therapies

It may also be desirable to provide combination treatments using antibodies of the present disclosure in conjunction with additional anti-cancer therapies. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the antibody and the other includes the other agent.

Alternatively, the antibody may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several 10 days (2, 3, 4, 5, 6 or 7) to several weeks (1, 2, 3, 4, 5, 6, 7 or 8) lapse between the respective administrations.

It also is conceivable that more than one administration of either the anti-LILRB2 antibody or the other therapy will be desired. Various combinations may be employed, where the antibody is "A," and the other therapy is "B," as exemplified below:

```
A/B/A B/A/B B/B/A A/A/B B/A/A A/B/B B/B/B/A

B/B/A/B A/A/B/B A/B/A/B A/B/B/A B/B/A/A

B/A/B/A B/A/A/B B/B/B/A A/A/A/B B/A/A/A A/B/A/A

A/A/B/A A/B/B/B B/A/B/B B/B/A/B
```

Other combinations are contemplated. To kill cells, inhibit cell growth, inhibit metastasis, inhibit angiogenesis or otherwise reverse or reduce the malignant phenotype of tumor cells, using the methods and compositions of the present invention, one may contact a target cell or site with an antibody and at least one other therapy. These therapies would be provided in a combined amount effective to kill or inhibit proliferation of cancer cells. This process may involve contacting the cells/site/subject with the agents/therapies at the same time.

Particular agents contemplated for combination therapy with antibodies of the present disclosure include chemotherapy and hematopoietic stem cell transplantation. Chemotherapy may include cytarabine (ara-C) and an anthracycline (most often daunorubicin), high-dose cytarabine alone, all-trans-retinoic acid (ATRA) in addition to induction chemotherapy, usually an anthracycline, histamine dihydrochloride (Ceplene) and interleukin 2 (Proleukin) after the completion of consolidation therapy, gemtuzumab ozogamicin (Mylotarg) for patients aged more than 60 years with relapsed AML who are not candidates for high-dose chemotherapy, clofarabine, as well as targeted therapies, such as kinase inhibitors, farnesyl transferase inhibitors, decitabine, and inhibitors of MDR1 (multidrug-resistance protein), or arsenic trioxide or relapsed acute promyelocytic leukemia (APL).

In certain embodiments, the agents for combination therapy are one or more drugs selected from the group consisting of a topoisomerase inhibitor, an anthracycline topoisomerase inhibitor, an anthracycline, a daunorubicin, a nucleoside metabolic inhibitor, a cytarabine, a hypomethylating agent, a low dose cytarabine (LDAC), a combination of daunorubicin and cytarabine, a daunorubicin and cytarabine liposome for injection, Vyxeos®, an azacytidine, Vidaza®, a decitabine, an all-trans-retinoic acid (ATRA), an arsenic, an arsenic trioxide, a histamine dihydrochloride, Ceplene®, an interleukin-2, an aldesleukin, Proleukin®, a gemtuzumab ozogamicin, Mylotarg®, an FLT-3 inhibitor, a midostaurin, Rydapt®, a clofarabine, a farnesyl transferase inhibitor, a decitabine, an IDH1 inhibitor, an ivosidenib, Tibsovo®, an IDH2 inhibitor, an enasidenib, Idhifa®, a smoothened (SMO) inhibitor, a glasdegib, an arginase inhibitor, an IDO inhibitor, an epacadostat, a BCL-2 inhibitor, a venetoclax, Venclexta®, a platinum complex derivative, oxaliplatin, a kinase inhibitor, a tyrosine kinase inhibitor, a PI3 kinase inhibitor, a BTK inhibitor, an ibrutinib, IMBRUVICA®, an acalabrutinib, CALQUENCE®, a zanubrutinib, a PD-1 antibody, a PD-L1 antibody, a CTLA-4 antibody, a LAG3 antibody, an ICOS antibody, a TIGIT antibody, a TIM3 antibody, a CD40 antibody, a 4-1BB antibody, a CD47 antibody, a SIRP1α antibody or fusions protein, a CD70 antibody, and CLL1 antibody, a CD123 antibody, an antagonist of E-selectin, an antibody binding to a tumor antigen, an antibody binding to a T-cell surface marker, an antibody binding to a myeloid cell or NK cell surface marker, an alkylating agent, a nitrosourea agent, an antimetabolite, an antitumor antibiotic, an alkaloid derived from a plant, a hormone therapy medicine, a hormone antagonist, an aromatase inhibitor, and a P-glycoprotein inhibitor.

VI. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, molecules, chemiluminescent molecules, haptens, fluorescent labels, phosphorescent chromophores, photoaffinity molecules, colored particles or ligands, such as biotin.

Antibody-drug conjugates have emerged as a breakthrough approach to the development of cancer therapeutics. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

Antibody conjugates are also preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine[211], [14]carbon, [51]chromium, [36]chlorine, [57]cobalt, [58]cobalt, copper[67], [152]Eu, gallium[67], [3]hydrogen, iodine[123], iodine[125], iodine[131], indium[111], [59]iron, [32]phosphorus, rhenium[186], rhenium[188], [75]selenium, [35]sulphur, technicium[99]) m and/or yttrium[90]. [125]I is often being preferred for use in certain embodiments, and technicium[99m] and/or indium[111] are also often preferred due to their low energy and suitability for long range detection. Radioactively labeled monoclonal antibodies of the present disclosure may be produced according to wellknown methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium[99m] by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as sitedirected photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl) propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

VII. IMMUNODETECTION METHODS

In still further embodiments, the present disclosure concerns immunodetection methods for binding, purifying, removing, quantifying and otherwise generally detecting LILRB-related cancers. While such methods can be applied in a traditional sense, another use will be in quality control and monitoring of vaccine and other virus stocks, where antibodies according to the present disclosure can be used to assess the amount or integrity (i.e., long term stability) of H1 antigens in viruses. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of LILRBs also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing LILRB-related cancers and contacting the sample with a first antibody in accordance with the present disclosure, as the case may be, under conditions effective to allow the formation of immunocomplexes.

These methods include methods for detecting or purifying LILRBs or LILRB-related cancer cells from a sample. The antibody will preferably be linked to a solid support, such as in the form of a column matrix, and the sample suspected of containing the LILRB-related cancer cells will be applied to the immobilized antibody. The unwanted components will be washed from the column, leaving the LILRB-expressing cells immunocomplexed to the immobilized antibody, which is then collected by removing the organism or antigen from the column.

The immunobinding methods also include methods for detecting and quantifying the amount of LILRB-related cancer cells or related components in a sample and the detection and quantification of any immune complexes formed during the binding process. Here, one would obtain a sample suspected of containing LILRB-related cancer cells and contact the sample with an antibody that binds LILRBs or components thereof, followed by detecting and quantifying the amounts of immune complexes formed under the specific conditions. In terms of antigen detection, the biological sample analyzed may be any sample that is suspected of containing LILRB-related cancers, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to LILRBs. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

1. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the LILRB-related cancer cells is added to the wells. After binding and washing to remove non-specifically bound immune complexes, the bound antigen may be detected. Detection may be achieved by the addition of another anti-LILRB antibody that is linked to a detectable label. This type of ELISA is a simple "sandwich ELISA." Detection may also be achieved by the addition of a second anti-LILRB2 antibody, followed by the addition of a third antibody that has binding affinity for the second antibody, with the third antibody being linked to a detectable label.

In another exemplary ELISA, the samples suspected of containing the LILRB2-related cancer cells are immobilized onto the well surface and then contacted with the anti-LILRB2 antibodies of the disclosure. After binding and washing to remove non-specifically bound immune complexes, the bound anti-LILRB2 antibodies are detected. Where the initial anti-LILRB2 antibodies are linked to a detectable label, the immune complexes may be detected directly. Again, the immune complexes may be detected using a second antibody that has binding affinity for the first anti-LILRB2 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

2. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

3. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting: resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

4. Immunodetection Kits

In still further er embodiments, the present disclosure concerns immunodetection kits for use with the immunodetection methods described above. As the antibodies may be used to detect LILRB-related cancer cells, the antibodies may be included in the kit. The immunodetection kits will thus comprise, in suitable container means, a first antibody that binds to an LILRB, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of LILRBs, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

5. Flow Cytometry and FACS

The antibodies of the present disclosure may also be used in flow cytometry or FACS. Flow cytometry is a laser- or impedance-based technology employed in many detection assays, including cell counting, cell sorting, biomarker detection and protein engineering. The technology suspends cells in a stream of fluid and passing them through an electronic detection apparatus, which allows simultaneous multiparametric analysis of the physical and chemical characteristics of up to thousands of particles per second. Flow cytometry is routinely used in the diagnosis disorders, especially blood cancers, but has many other applications in basic research, clinical practice and clinical trials.

Fluorescence-activated cell sorting (FACS) is a specialized type of cytometry. It provides a method for sorting a heterogenous mixture of biological cells into two or more containers, one cell at a time, based on the specific light scattering and fluorescent characteristics of each cell. In general, the technology involves a cell suspension entrained in the center of a narrow, rapidly flowing stream of liquid. The flow is arranged so that there is a large separation between cells relative to their diameter. A vibrating mechanism causes the stream of cells to break into individual droplets. Just before the stream breaks into droplets, the flow passes through a fluorescence measuring station where the fluorescence of each cell is measured. An electrical charging ring is placed just at the point where the stream breaks into droplets. A charge is placed on the ring based immediately prior to fluorescence intensity being measured, and the opposite charge is trapped on the droplet as it breaks form the stream. The charged droplets then fall through an electrostatic deflection system that diverts droplets into containers based upon their charge.

In certain embodiments, to be used in flow cytometry or FACS, the antibodies of the present disclosure are labeled with fluorophores and then allowed to bind to the cells of interest, which are analyzed in a flow cytometer or sorted by a FACS machine.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figures 1, 1A:
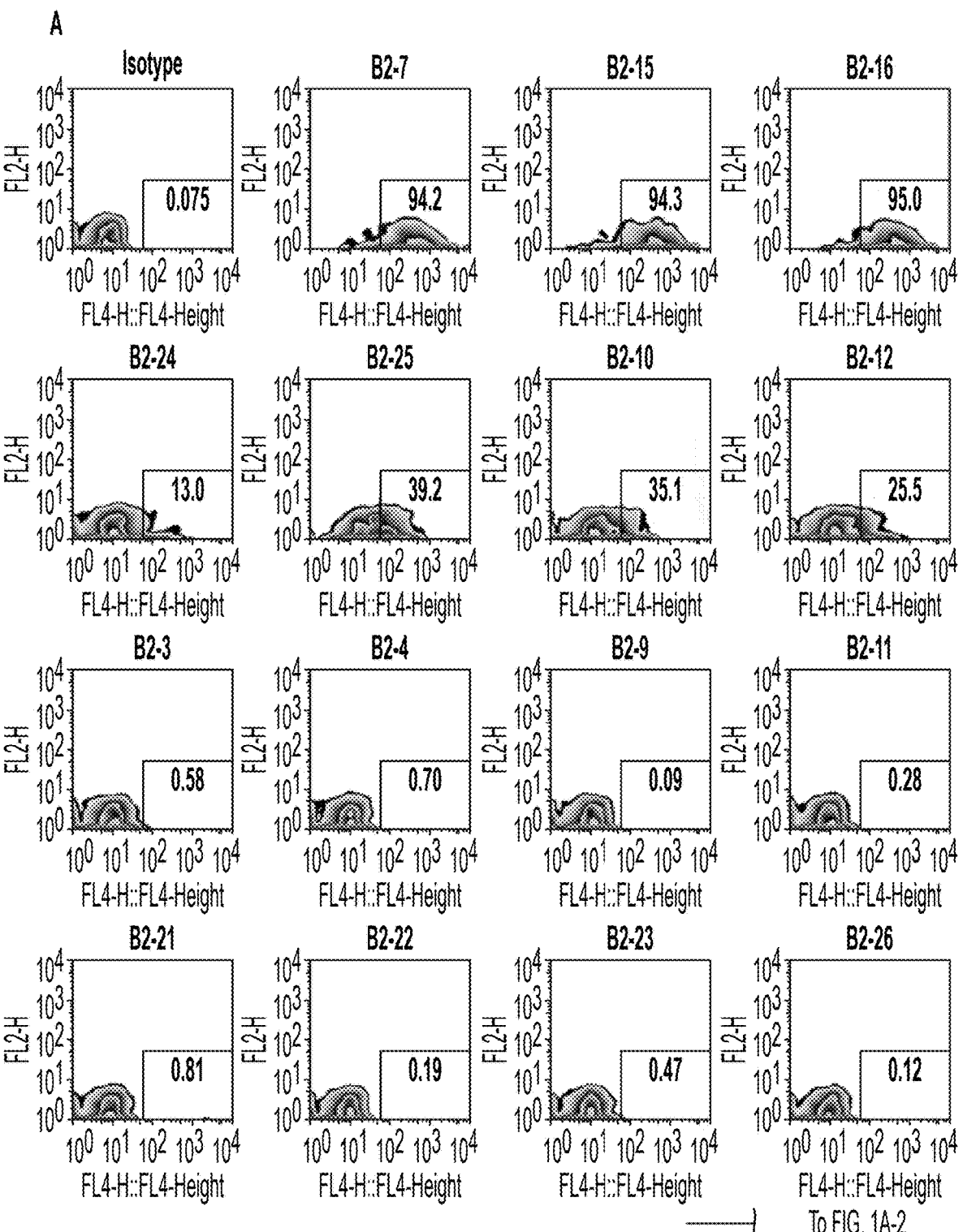
Figures 1, 1A, 2:
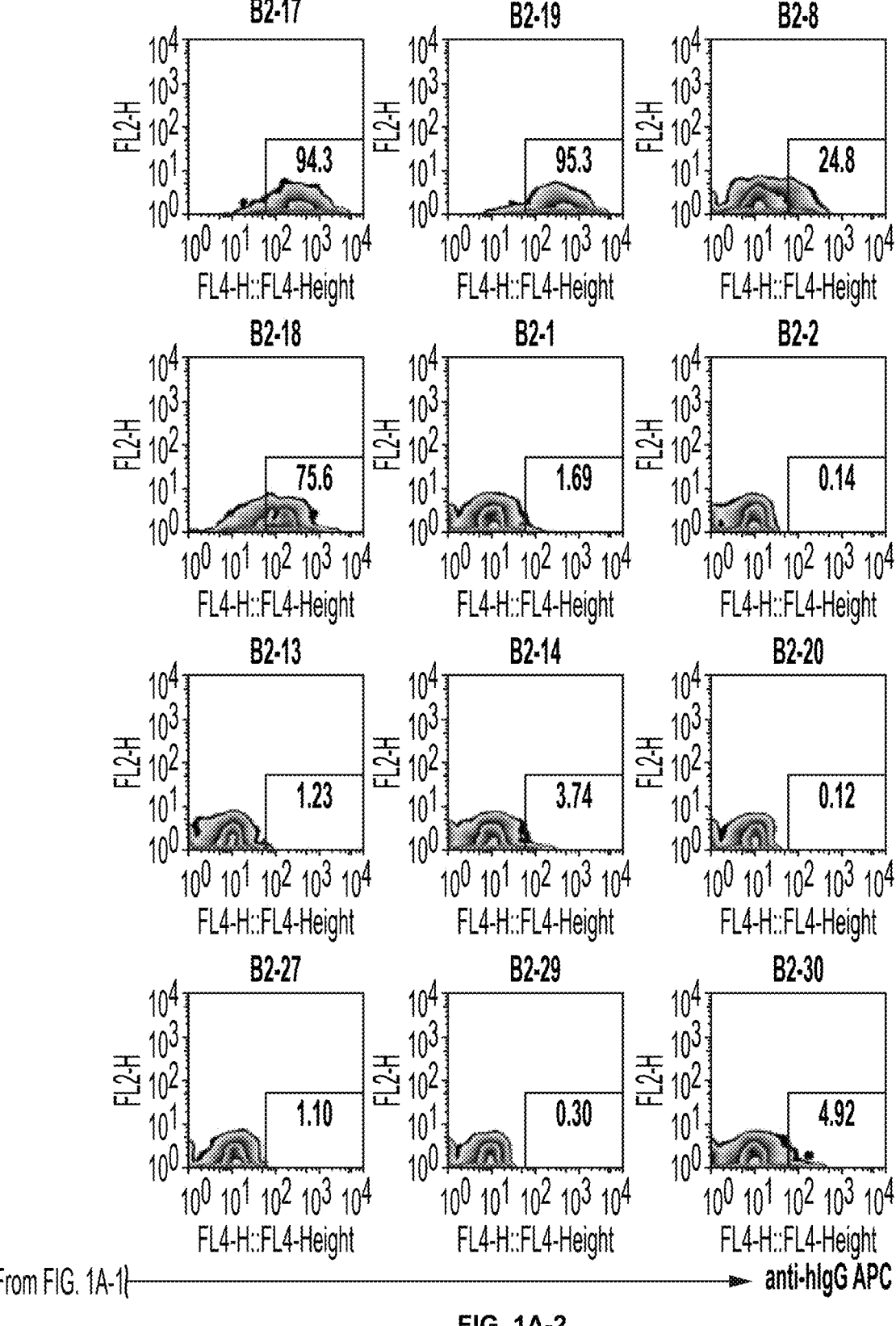
Figure 1B:
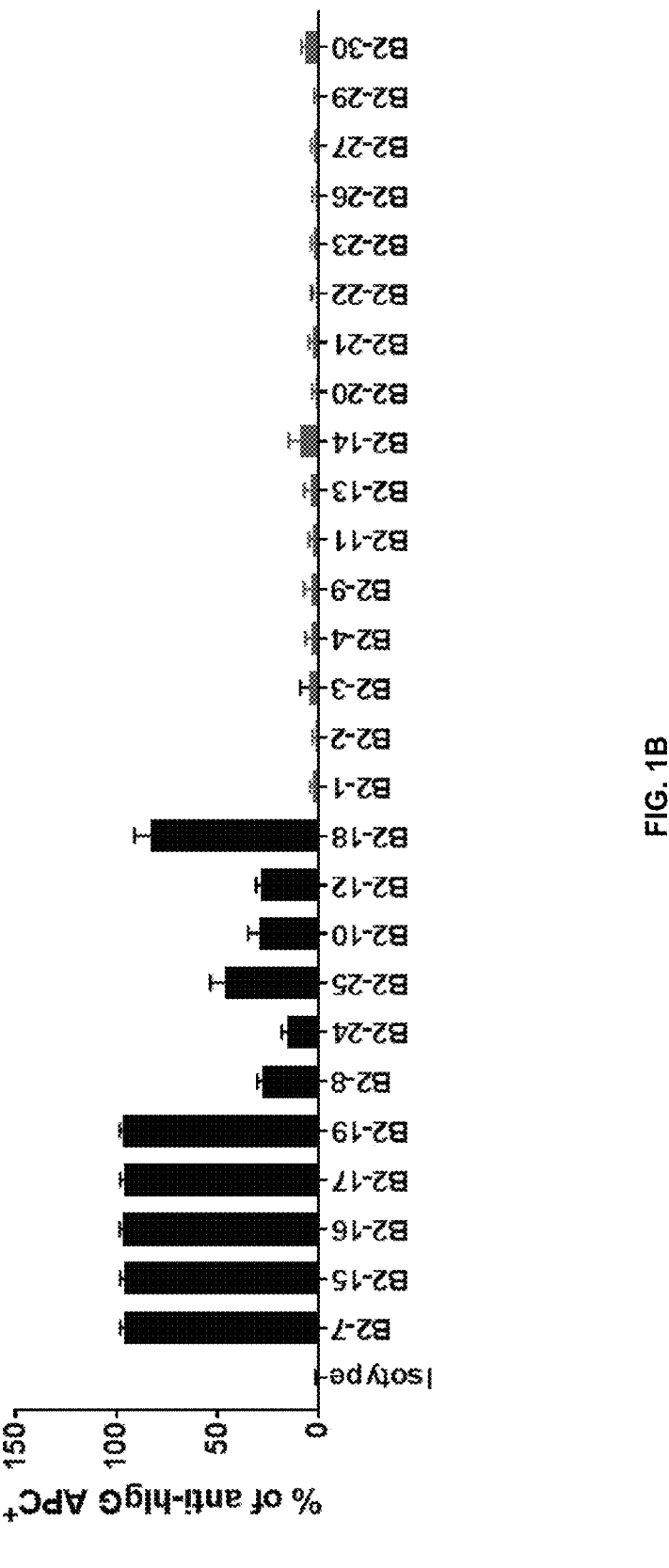
Figure 1C:
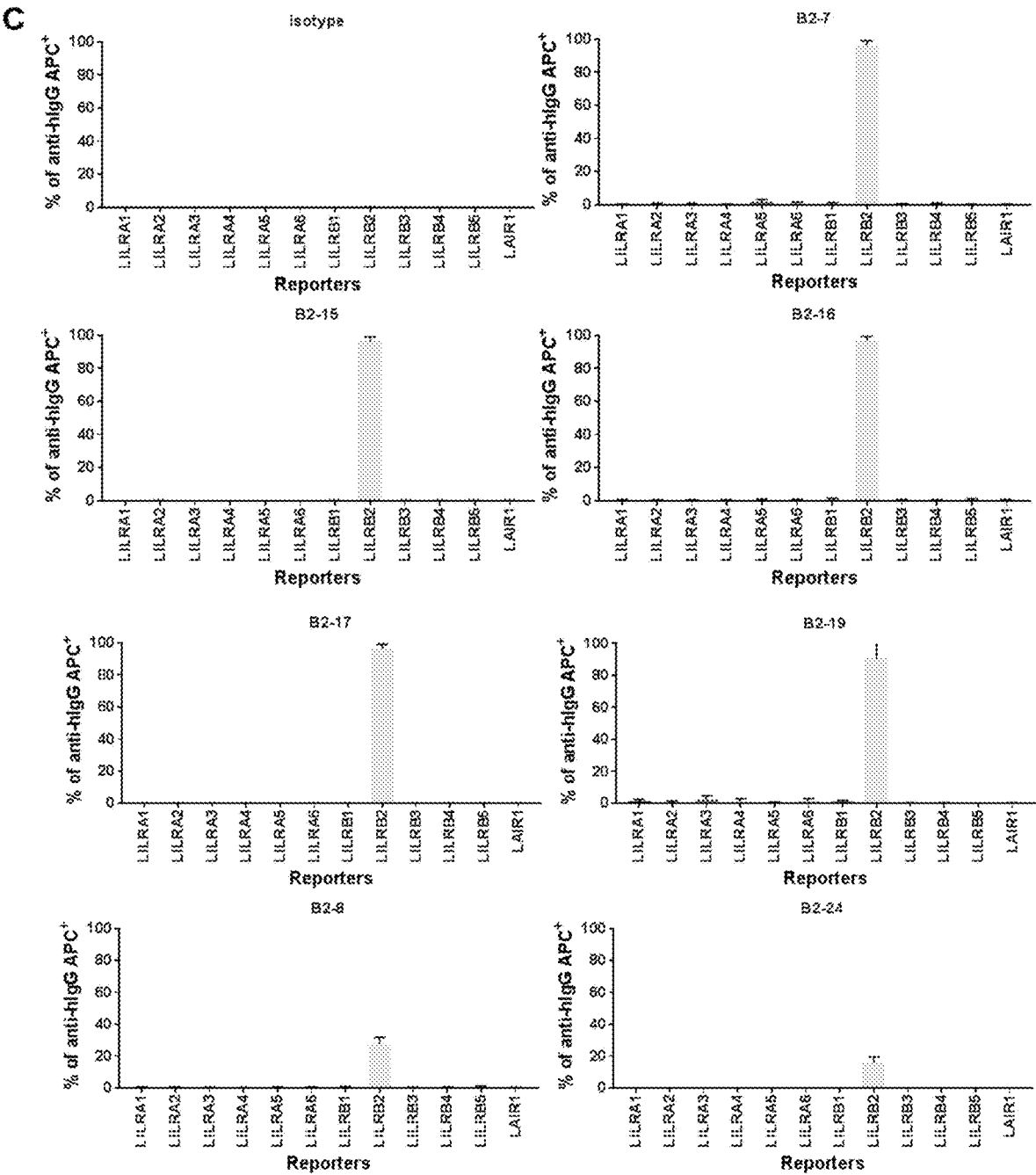
Figure 29:
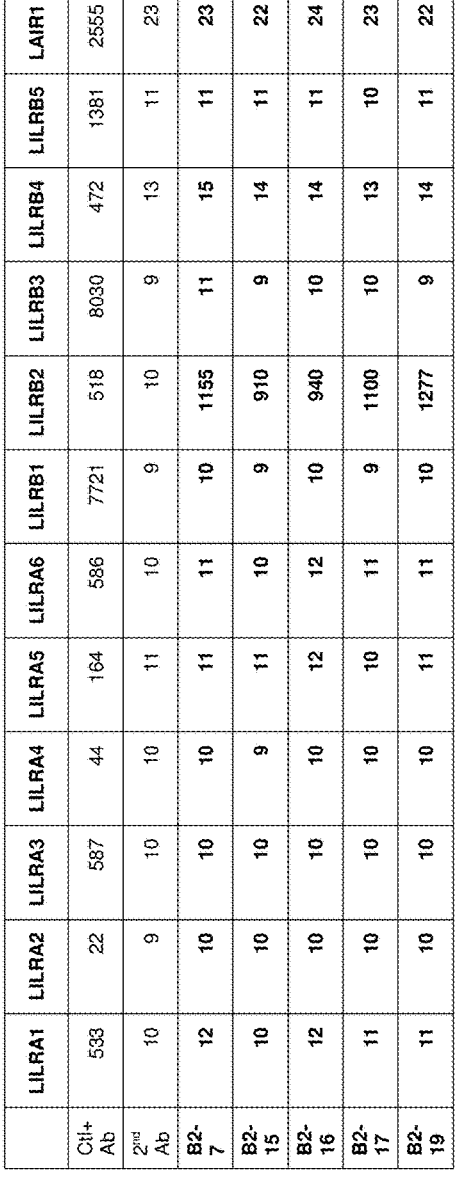
FIG. 29. Binding of LILRB2 antibodies on reporter cell line expressing ectodomain of LILR family proteins on cell surface. Bound antibodies were detected with anti-human Fc-specific secondary antibody (2nd Ab) conjugated to AF647. Expression of each LILR was confirmed using commercially available antibodies directly conjugated with AF647 or APC (Ctl+ Ab). All incubations were performed for 30 minutes at 4° C. Data shown is mean fluorescence intensity after sample acquisition in flow cytometer.
Figure 30:
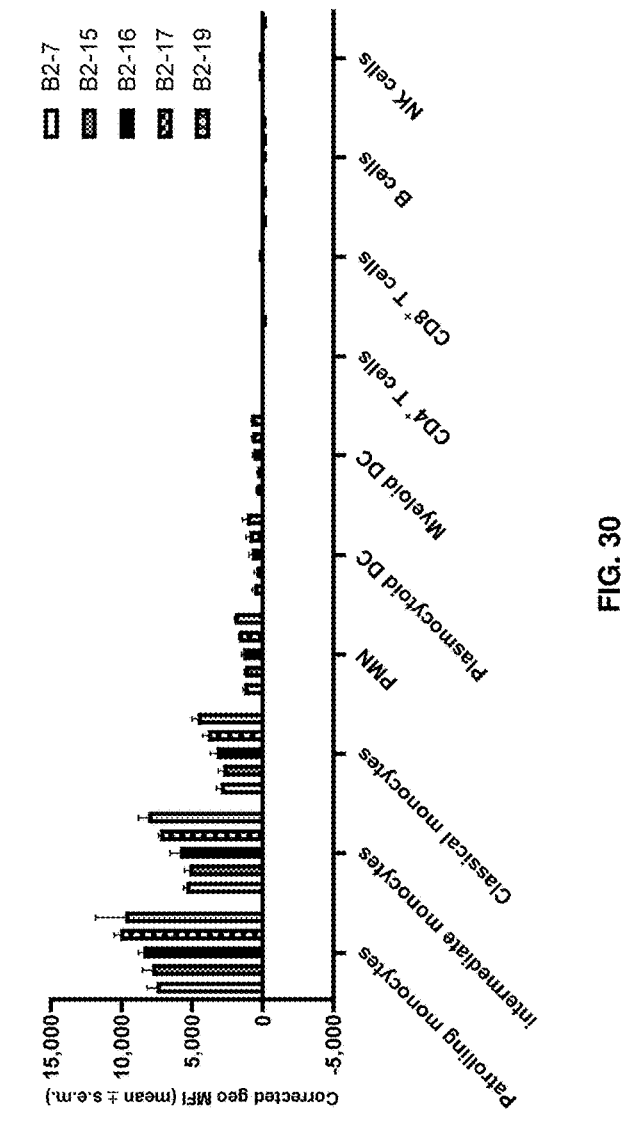
FIG. 30. Binding of LILRB2 antibodies on leukocytes from human whole blood harvested from healthy donors.

Screening specific monoclonal antibodies for LILRB2. The inventors employed a stable reporter cell system to detect the binding ability of selected monoclonal antibodies to LILRB2. In this chimeric receptor reporter system, the extracellular domain (ECD) of LILRB2 is fused with transmembrane/intracellular domains of PILRb that associates with the adaptor protein DAP12 containing an immunoreceptor tyrosine-based activation motif. 27 monoclonal antibodies were screened. The LILRB2 reporter cells were incubated with selected monoclonal antibody, then labeled with (APC) goat anti-human IgG secondary antibody. Flow cytometer analysis demonstrated that more than 95% LILRB2 reporter cells were labeled with clones B2-7, B2-15, B2-16, B2-17, B2-18, B2-19. A lower percentage of LILRB2 reporter cells were labeled with clones B2-8, B2-10, B2-12, B2-24, B2-25. Other clones did not have binding ability to LILRB2 reporter cells (FIGS. 1A-B). Because members of LILRAs and LILRBs exhibit high sequence homology, the inventors detected the potential cross-reactivity of B2-7, B2-15, B2-16, B2-17, B2-18, B2-19, B2-8, B2-10, B2-12, B2-24 and B2-25 to LILRBAs and LILRBs. The inventors generated LILRBAs and LILRBs reporters stably transduced with each receptor's extracellular domain (ECD). Flow cytometry analysis showed that B2-7, B2-15, B2-16, B2-17, B2-18, B2-19, B2-8, B2-24, B2-25 did not cross-react with LILRAs and other LILRBs except LILRB2. B2-10, B2-12 and B2-18 nonspecifically bound to LILRA1 (FIGS. 1C-D and FIG. 29). Therefore, these were eight antibodies identified as specific monoclonal antibodies for LILRB2. In addition, the inventors demonstrated that B2-7, B2-15, B2-16, B2-17 and B2-19 only bind myeloid cells in samples of human peripheral blood (FIG. 30), thereby further confirming binding on cells expressing endogenous LILRB2. The inventors also confirmed that B2-7, B2-15, B2-16, B2-17 and B2-19 bind HEK293 cells stably expressing full length LILRB2 (HEK293_LILRB2) (FIG. 31) and primary monocytes (FIG. 32) in a dose-dependent manner. The binding $EC_{50}$ values range from 0.101 to 0.277 µg/mL in HEK293_LILRB2 (FIG. 31) and from 0.056 to >10 µg/mL in primary monocytes (FIG. 32).

Screening potential antagonistic and agonistic antibodies for LILRB2. Typically, receptor blocking antibodies are targeted to the ligand-binding site and compete with the ligand and/or block the interaction of receptor with its ligand. LILRB2 ligands include angiopoietin-like proteins (ANGPTLs), semaphorin 4A (SEMA4A), TIM-3, CD-1 molecules, amyloid-β (AB) oligomer, classical human leukocyte antigen (HLA) class I molecules (HLA-A, HLA-B. HLA-C) and non-classical HLA-class I molecules (HLA-E, HLA-F, HLA-G, and HLA-H). The LILRB2 reporter system has provided a powerful tool to screen the potential antagonistic antibody for LILRB2. When the chimeric receptor is activated by ligand binding to the ECD of LILRB2, ZAP70 or Syk kinase is recruited to the immunoreceptor tyrosine-based activation motif of the adaptor DAP12 and activates NFATs to promote GFP expression driven by the NFAT-responsive promoter. An antibody that significantly decreased GFP signaling was consider potential antagonistic antibody.

Figure 3C:
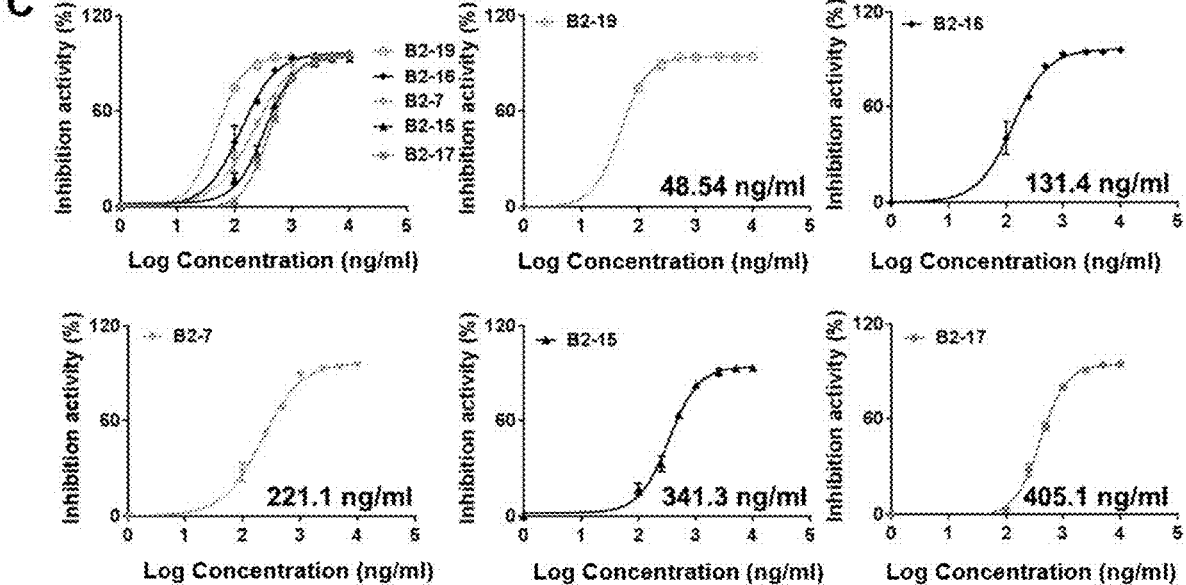
Figure 4A:
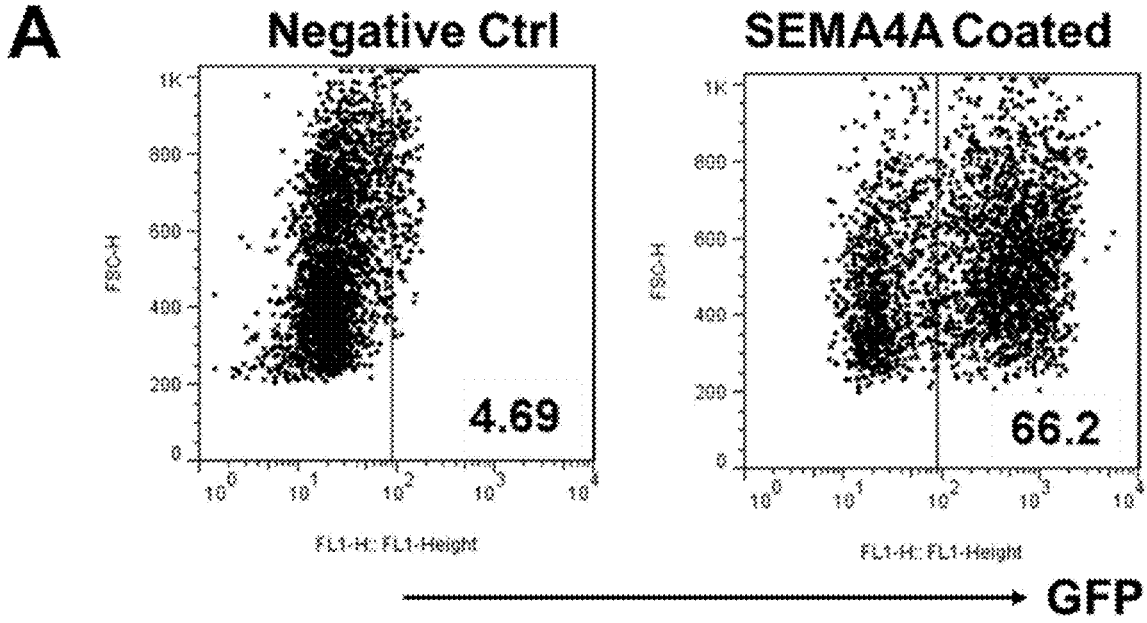
FIGS. 4A-C. Antibodies B2-7, B-15, B2-16, B2-17 and B2-19 block GFP signaling of LILRB2 reporter cells activated by coated SEMA4A.
Figure 4B:
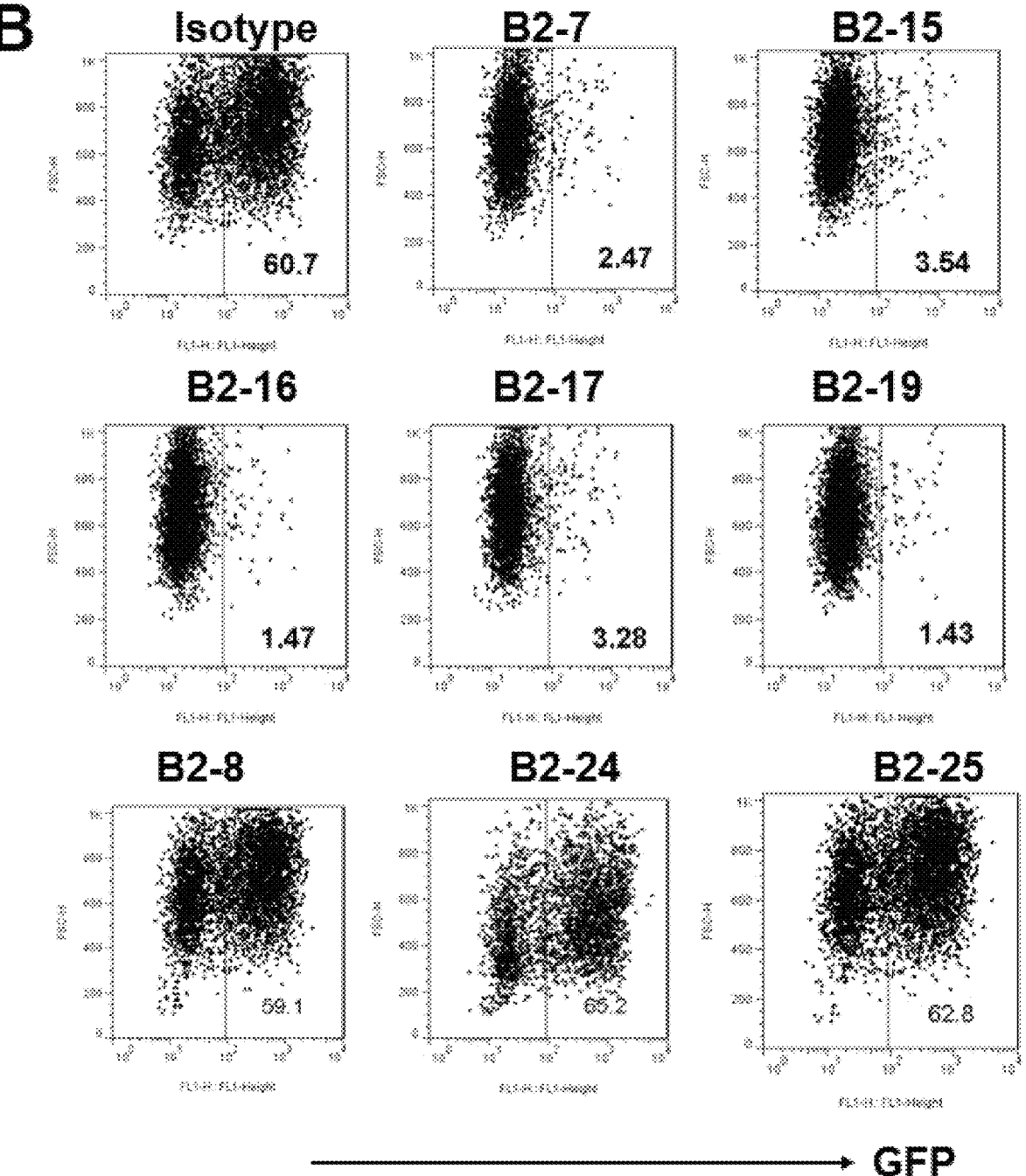
Figure 4C:
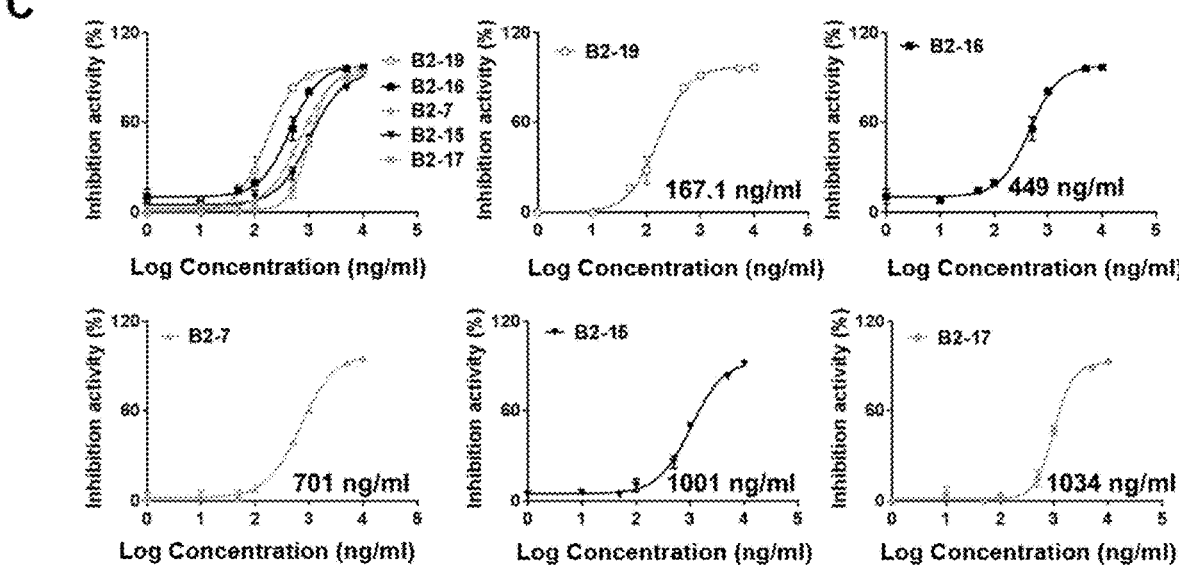
Figure 5C:
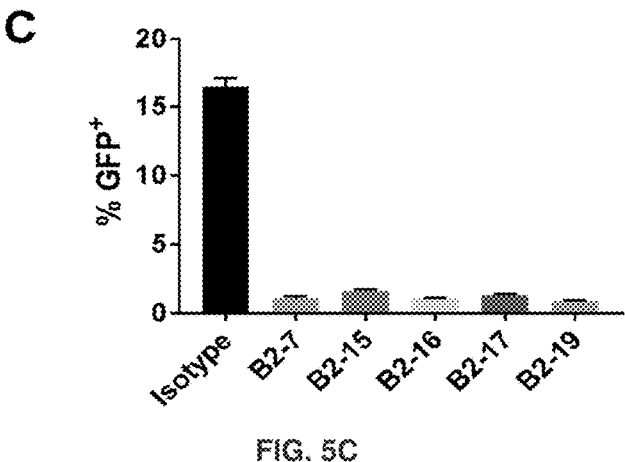

The functions of LILRB2 mAbs to block the activation of LILRB2 reporter cells stimulated by coated ANGPTL2 (FIGS. 3A-C; FIG. 51) and SEMA4A (FIGS. 4A-C) were tested. The results showed that B2-7, B2-15, B2-16, B2-17, and B2-19 could prevent the activation of LILRB2 reporter cells by the coated ligands in a dose-dependent manner. B2-19 antibody was also able to block the activation of LILRB2 reporter cells stimulated by coated CD1d (FIG. 52). The LILRB2 reporter cells were also cocultured with K562 cells overexpressed with HLA-G and then treated with LILRB2 mAbs. The results also showed that these LILRB2 mAbs blocked the activation of LILRB2 reporter cells stimulated by HLA-G on K562 cells (FIGS. 5A-C). LILRB2 antibodies were also shown to block binding of HLA-G and SEMA4A to HEK293 cells expressing full length LILRB2 in a dose-dependent manner (FIG. 33 and FIG. 34, respectively). These data proved that B2-7, B2-15, B2-16, B2-17, and B2-19 are antagonistic LILRB2 mAbs.

Contrastingly, several LILRB2 mAbs (B2-8, B2-24, B2-25, B2-10, B2-12 and B2-18) can activate the LILRB2 reporter cells when added into cell culture medium (FIG. 2A) or the cocultured with K562 (FIG. 2B), demonstrating that these LILRB2 mAbs are agonistic antibodies.

Figure 6A:
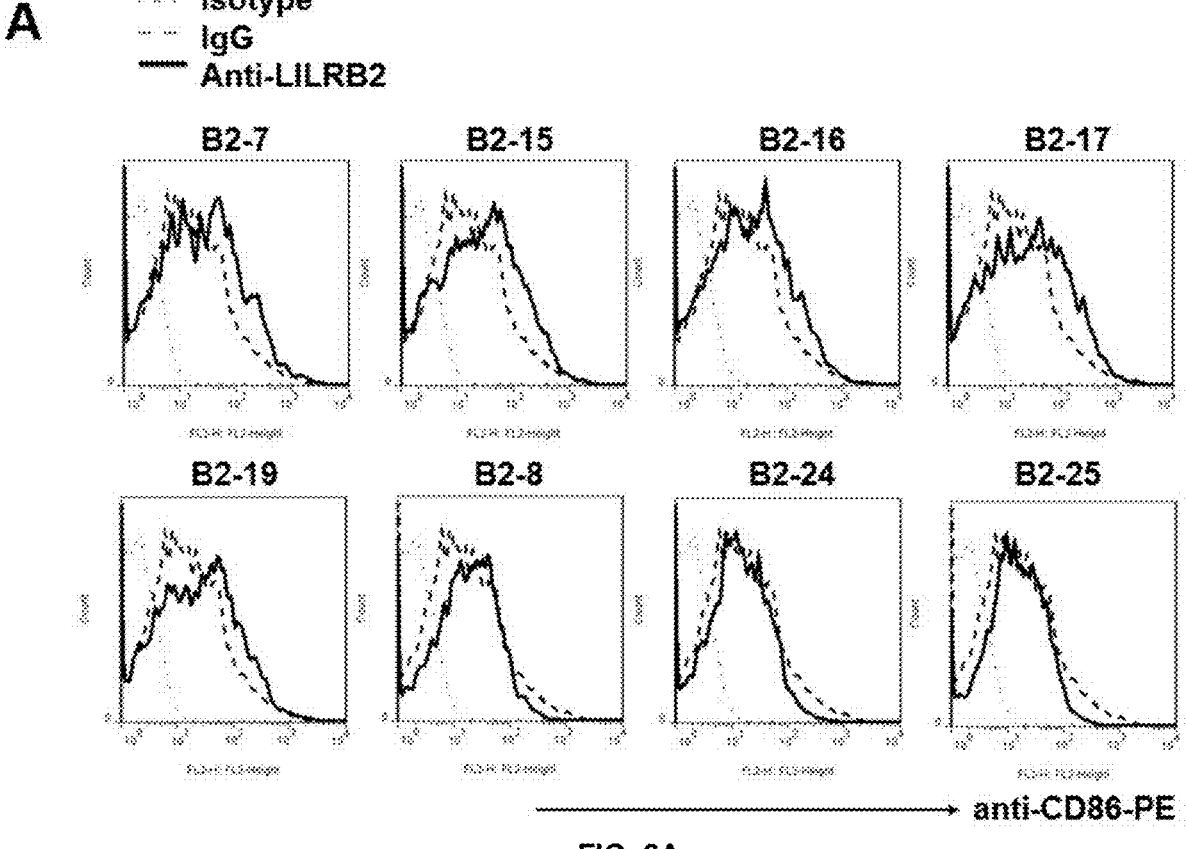

The effect of anti-LILRB2 antibodies on LPS response in primary human monocytes. LILRB2 is expressed on hematopoietic stem cells, monocytes, macrophages, dendritic cells, basophils in some individuals, decidual macrophages, mast cell progenitors, endothelial cells and osteoclasts but not on lymphoid cells. LILRB2 is classified as an immune inhibitory receptor and associated with down modulation of immune response. To determine the function of screened anti-LILRB2 antibodies, peripheral blood mononuclear cell (PBMC) based functional assays were conducted to assess whether screened antibodies could amplify or inhibit monocyte activation. B2-7, B2-15, B2-16, B2-17 and B2-19 could enhance CD86 and TNFα levels in the presence of LPS. B2-8, B2-24 and B2-25 seemed has no effect on TNFα levels, even though showed an inhibition on CD86 levels with LPS stimulation (FIGS. 6A-C). B2-7, B2-16 and B2-19 could enhance IFN-γ (FIG. 35) and TNF-α (FIG. 36) secretion from PBMC stimulated with LPS. B2-19 could also enhance secretion of IL-12p40 from PBMC stimulated with LPS (FIG. 37). The inventors identified B2-7, B2-15, B2-16, B2-17 and B2-19 LILRB2-specific antibodies that enhanced monocyte inflammatory potential in response to LPS stimulation. All these antibodies are functional antagonistic antibodies. B2-8, B2-24 and B2-25 are potential active antibodies for LILRB2.

The effect of anti-LILRB2 antibodies on PBMC stimulated by anti-CD3 activating antibody. The inventors evaluated the indirect effect of LILRB2 blockade on T cell activation by an activating anti-CD3 antibody. B2-7 and B2-19 antibodies were able to enhance the secretion of IFN-γ (FIG. 38), TNF-α (FIG. 39), GM-CSF (FIG. 40), IL-1a (FIG. 41), IL-1B (FIG. 42), IL-6 (FIG. 43) and CXCL2 (FIG. 44). B2-19 was also able to enhance the cell surface expression of CD25 on CD8$^+$ T cells (FIG. 46). The inventors identified B2-7 and B2-19 LILRB2-specific antibodies that enhanced T cell activation.

The effect of anti-LILRB2 antibodies on monocyte derived M2a macrophages. The inventors evaluated the effect of B2-19 on the phenotype of M2a macrophages in vitro. In M2a macrophages differentiated from monocytes of several donors, B2-19 decreased the expression of CD64, CD163 and CD14 (FIG. 45). The inventors identified B2-19 as a LILRB2-specific antibody capable of modulating the phenotype of M2a macrophages.

Figure 7A:
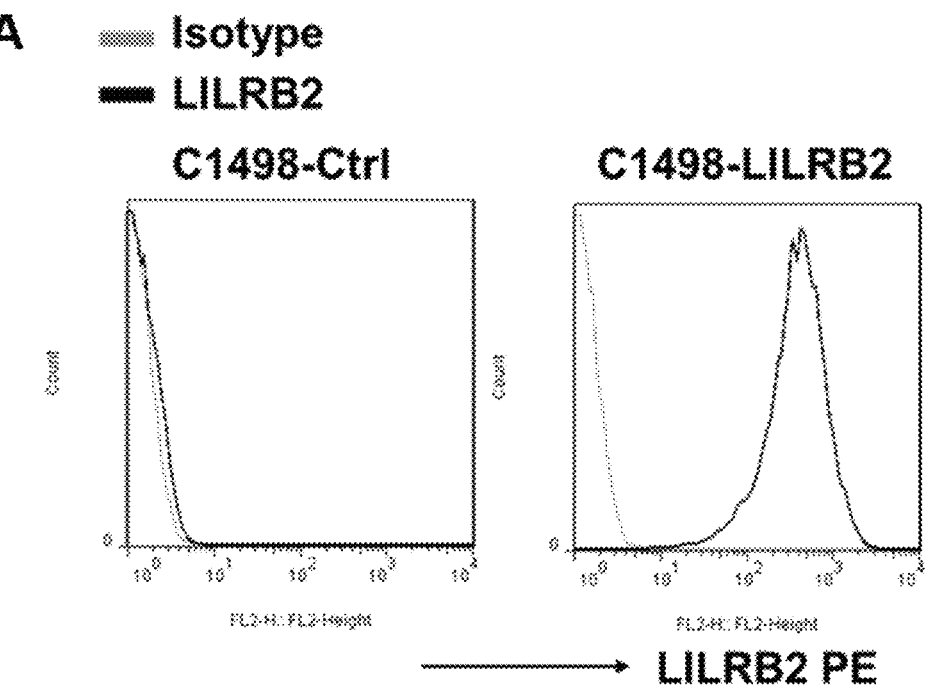
FIGS. 7A-J. Antagonistic LILRB2 mAbs inhibit the development of leukemia cells in C1498-LILRB2 tumor-bearing model.
Figure 7B:
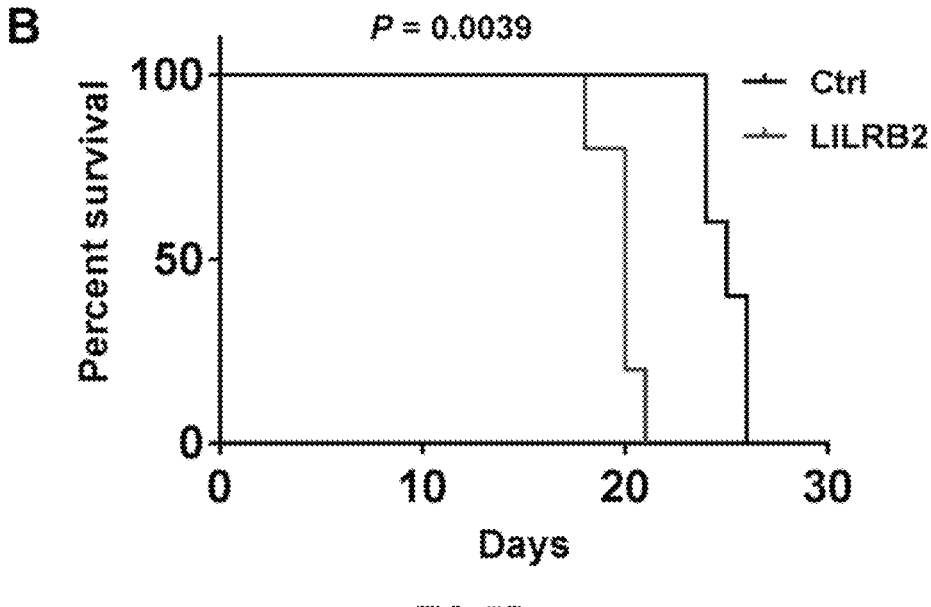
Figure 7C:
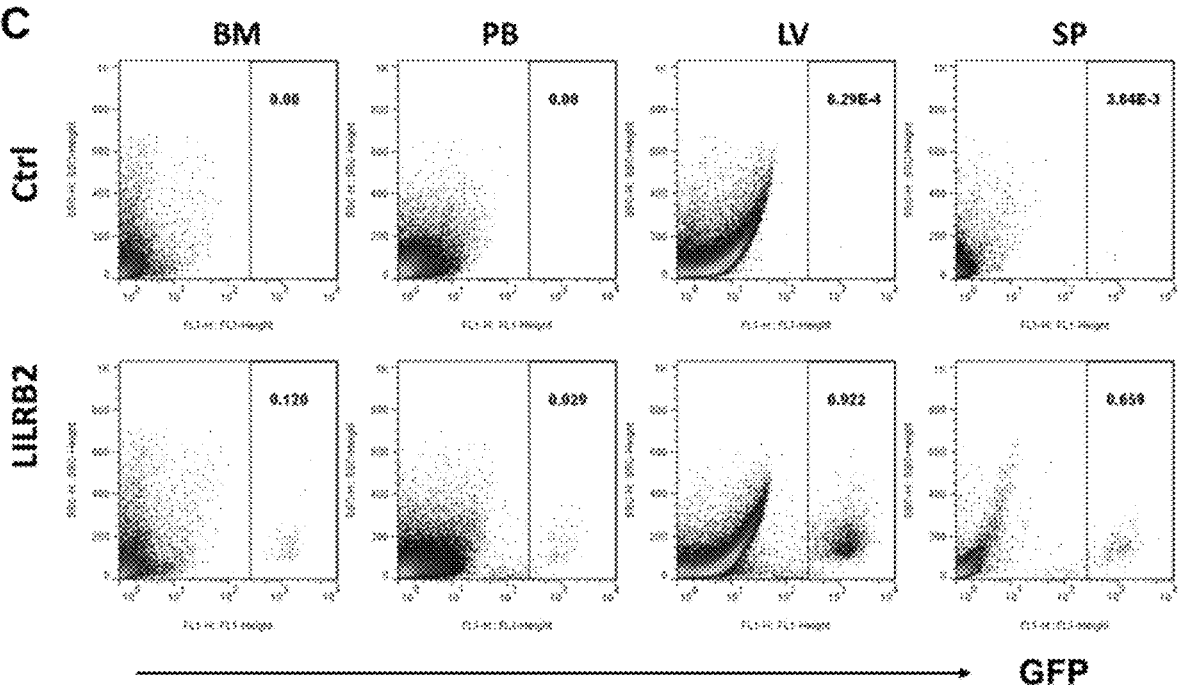
Figure 7D:
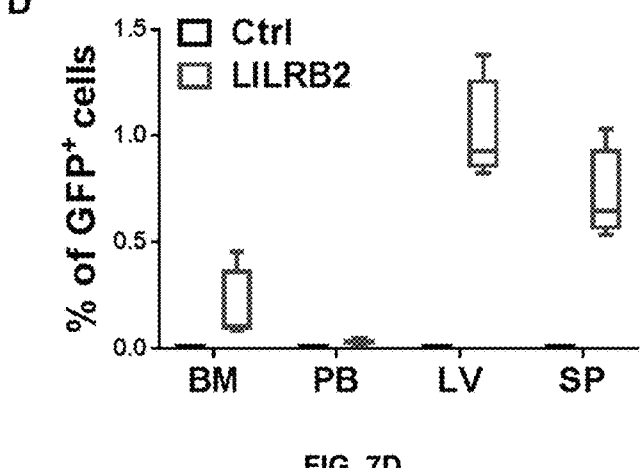
Figure 7E:
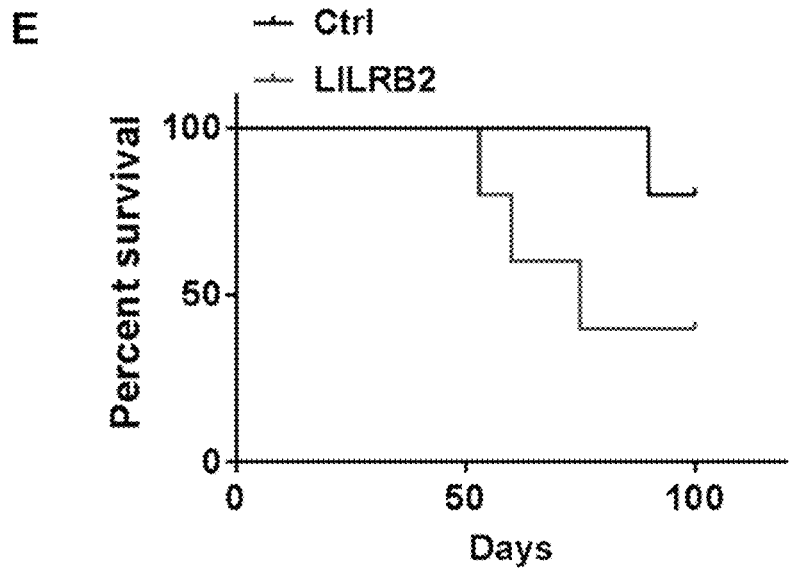
Figure 7F:
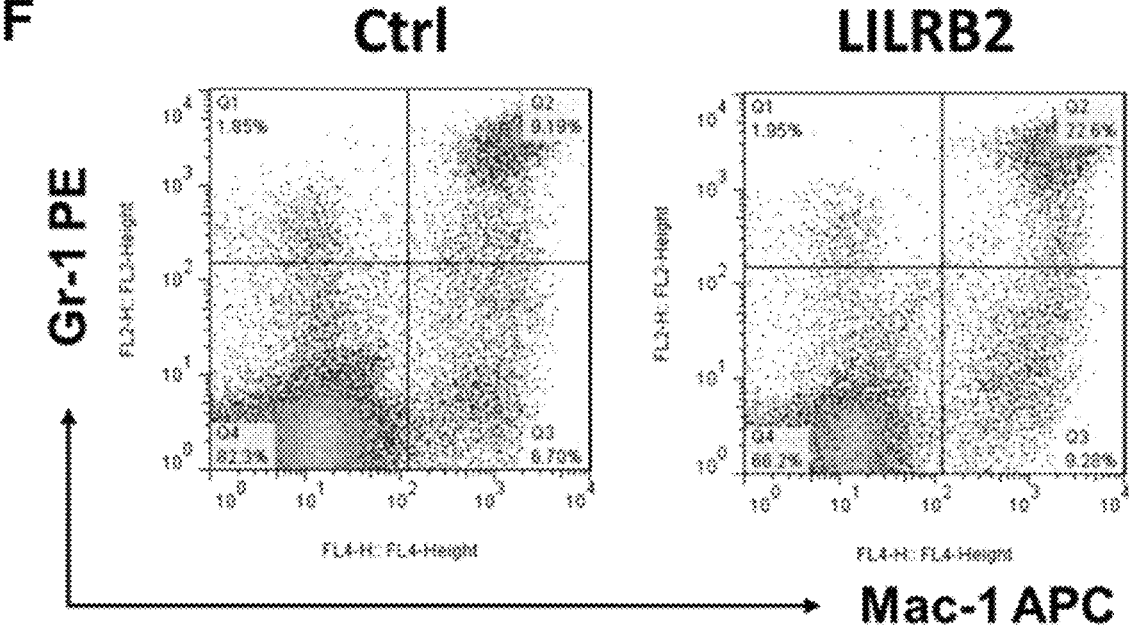
Figure 7G:
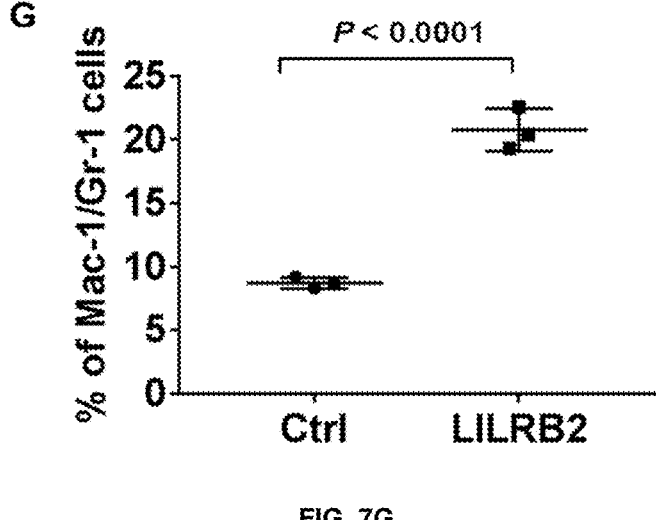
Figure 7H:
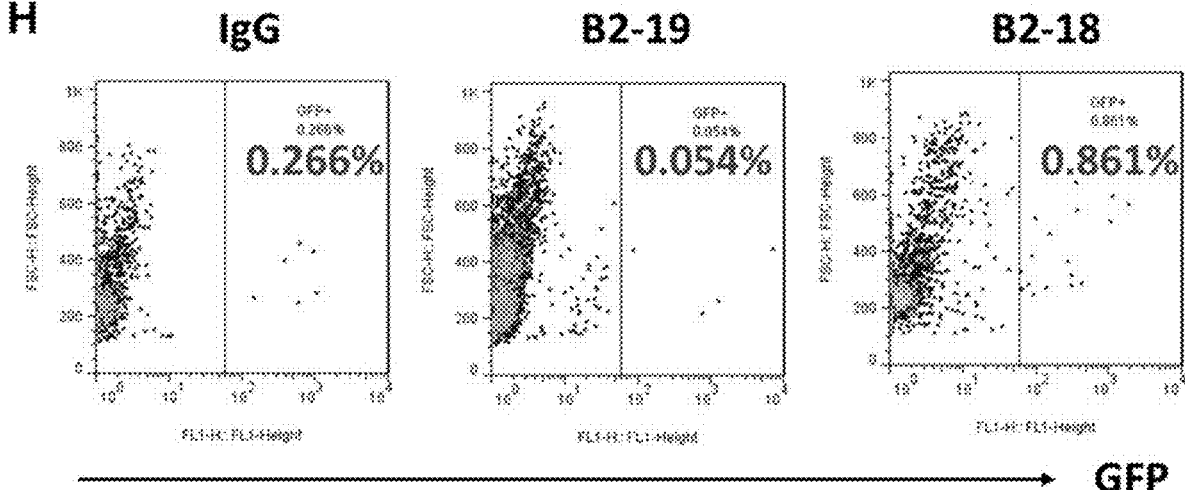
Figure 7I:
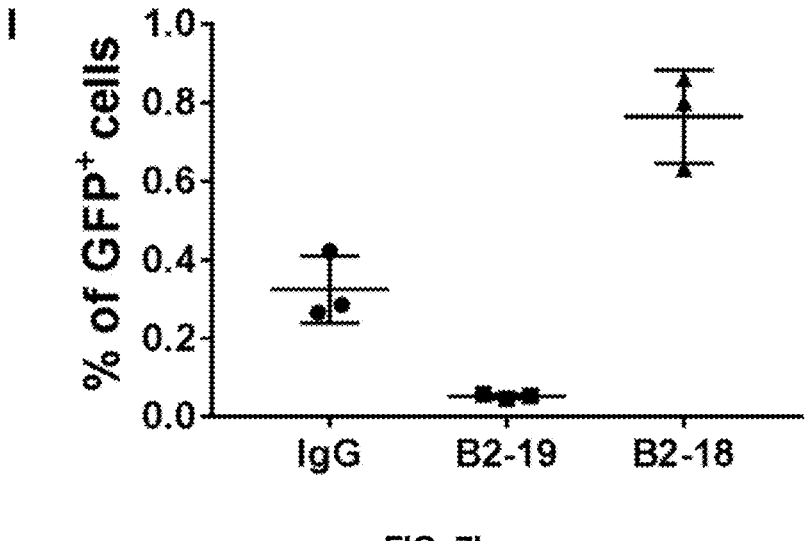
Figure 7J:
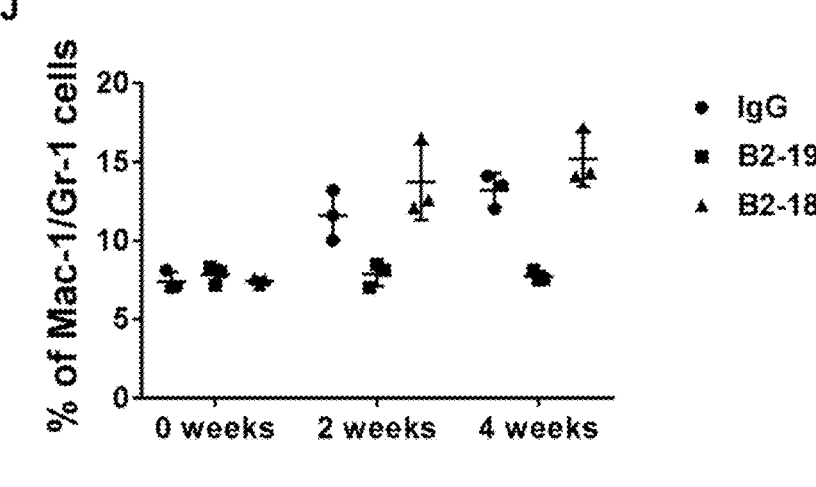

Anti-LILRB2 antibodies inhibit the development of leukemia cells in C1498-LILRB2 tumor-bearing model. The inventors evaluated whether LILRB2 blockade could inhibit tumor progression in a C1498 leukemia model. A C1498 subline overexpressing human LILRB2 (C1498-LILRB2) was generated by retroviral transduction. LILRB2 is stably expressed on C1498-LILRB2 (FIG. 7A). LILRB2 could promote leukemia development. Overexpressed LILRB2 promoted the leukemia development in NSG mice (FIG. 7B). LILRB2 overexpression have worse leukemia infiltration (FIG. 7C-D), survival curve (FIG. 7E) and myoid cell infiltration (FIG. 7G). Furthermore, LALAPG variants of B2-7 and B2-19 containing Fc mutations were generated to eliminate complement binding and fixation as well as Fc-γ dependent antibody-dependent cell-mediated cytotoxicity (ADCC) in both murine IgG2a and human IgG1. Treatment with LALAPG mutant antagonistic antibody significantly suppressed myeloid leukemia growth ((FIG. 7H-J).

Figure 8A:
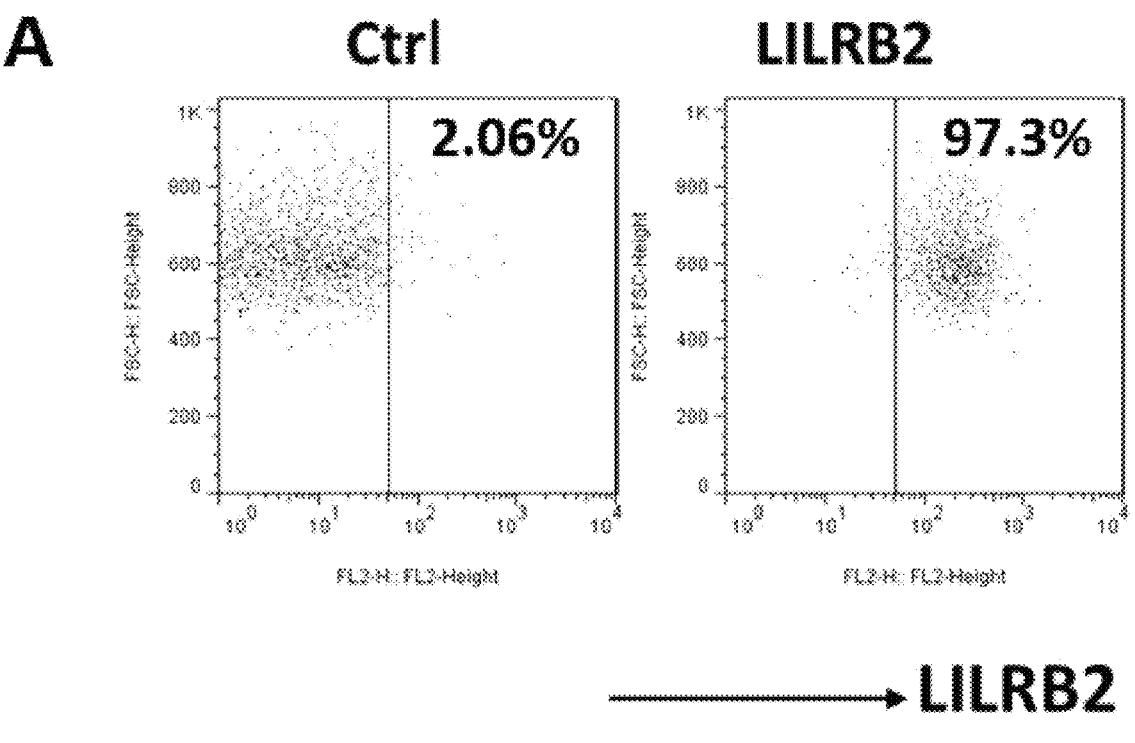
FIGS. 8A-F. Antagonistic LILRB2 mAbs inhibit the development of leukemia cells in MLL-AF9 leukemia model.
Figure 8B:
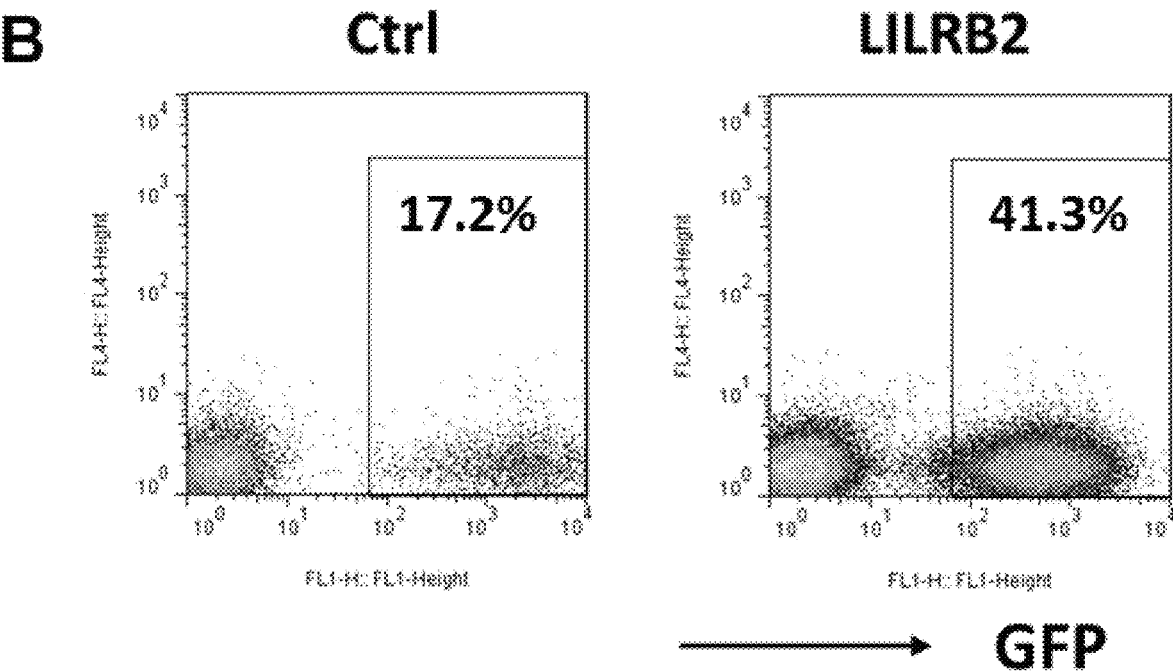
Figures 8C, 8D:
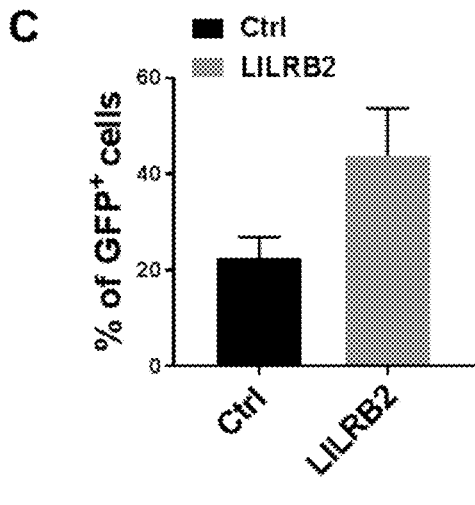
Figure 8E:
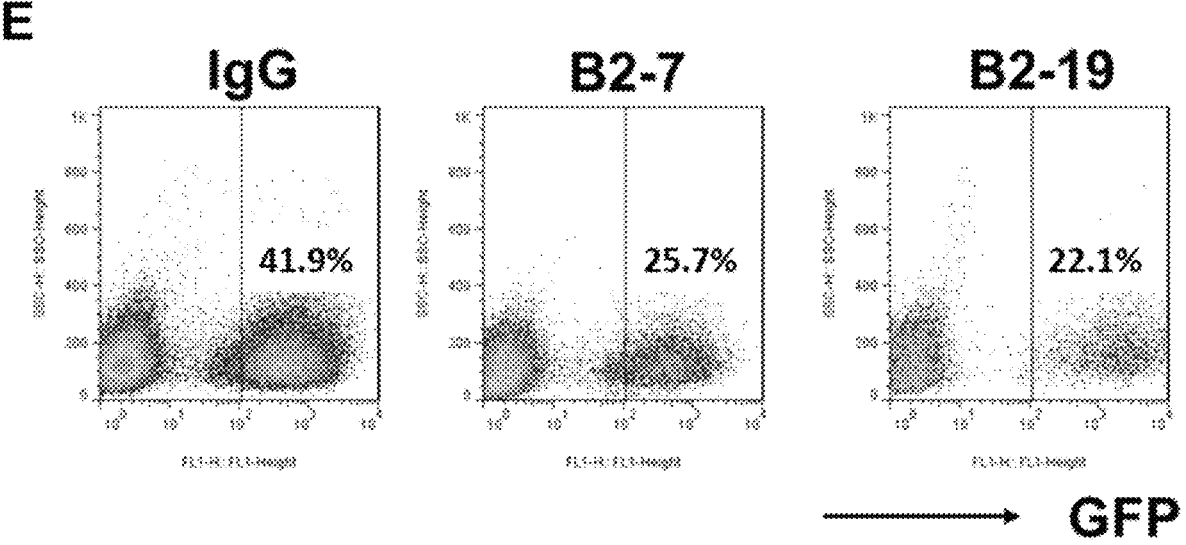
Figure 8F:
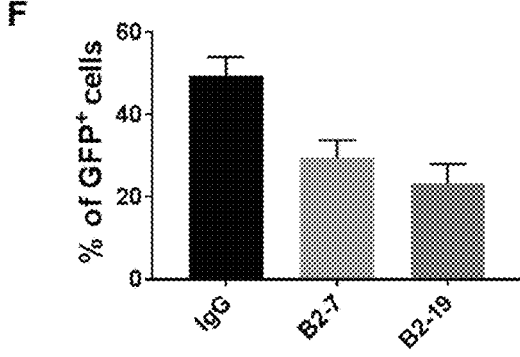

Anti-LILRB2 antibodies inhibit the development of leukemia cells in MLL-AF9 model. The inventors evaluated whether LILRB2 blockade could inhibit tumor progression in an MLL-AF9 leukemia model. A PirB-KO MLL-AF9 leukemia subline overexpressing human LILRB2 (LILRB2) was generated by retroviral transduction and mouse transplantation. Expression of LILRB2 could be detected on PirB-KO MLL-AF9 LILRB2 or control (Ctrl) leukemia cells (FIG. 8A). In this MLL-AF9 model, LILRB2 overexpression have worse leukemia infiltration (FIG. 8B-C), survival curve (FIG. 8D). Furthermore, treatment with LALAPG mutant antagonistic antibody significantly suppressed leukemia infiltration (FIG. 8E-F).

LILRB2 blockage inhibits the migration and infiltration of AML cells. LILRB2 plays various roles in cancer biology as well. Expression of LILRB2 could be detected on THP-1, a human leukemia cell line (FIG. 9A). The inventors used humanized mouse xenograft model to test LILRB2 function on leukemia. Blockage of LILRB2 reduced homing and engraftment of leukemia cells to hematopoietic organs (FIGS. 9B-C), resulting in delayed body weight loss (FIG. 9D), less severe infiltration of myeloid leukemia cells into liver (FIGS. 9E-F), prolonged survival of xenografted mice. Together, blockade of LILRB2 reduced leukemia migration and infiltration.

Antagonistic LILRB2 mAbs inhibit the development of leukemia cells in patient-derived xenograft (PDX) model. Flow cytometry analysis showed that of LILRB2 expressed on some cases of primary monocytic AML (M5) (FIG. 10A). In TCGA database, LILRB2 mRNA level was negatively correlated with the AML patient survival (FIG. 10B). In PDX model, LALAPG mutant antagonistic antibodies B2-7 and B2-19 significantly suppressed leukemia infiltration (FIG. 10C). In vitro culture system, LALAPG mutant antagonistic antibody promoted the differentiation of AML-M5 leukemia cells (FIG. 10D-E).

Antagonistic LILRB2 mAbs can prevent the T cell suppressive function of Myeloid-Derived Suppressor Cells (MDSC) in vitro and polarize CD14$^+$ cells from cancer-derived ascites towards a pro-inflammatory phenotype. The function of antagonistic LILRB2 antibodies in T cell suppressive function of MDSC was tested in vitro. Paired MDSC and T cells from the same tumor patient were cocultured and treated with antagonistic LILRB2 antibodies.

The treatment of B2-7 and B2-19 antibodies significantly attenuated the inhibition of T cell proliferation induced by MDSC, possibly by converting immune suppressive myeloid cells to proinflammatory myeloid cells (FIGS. 11A-E and FIG. 11G). B2-7, B2-15, B2-16, B2-17 and B2-19 were also able to decrease anti-inflammatory markers CD163 and CD206 and increase pro-inflammatory marker CD86 in primary CD14$^+$ cells isolated from cancer-derived ascites (FIG. 11F).

Example 2

Figure 12A:
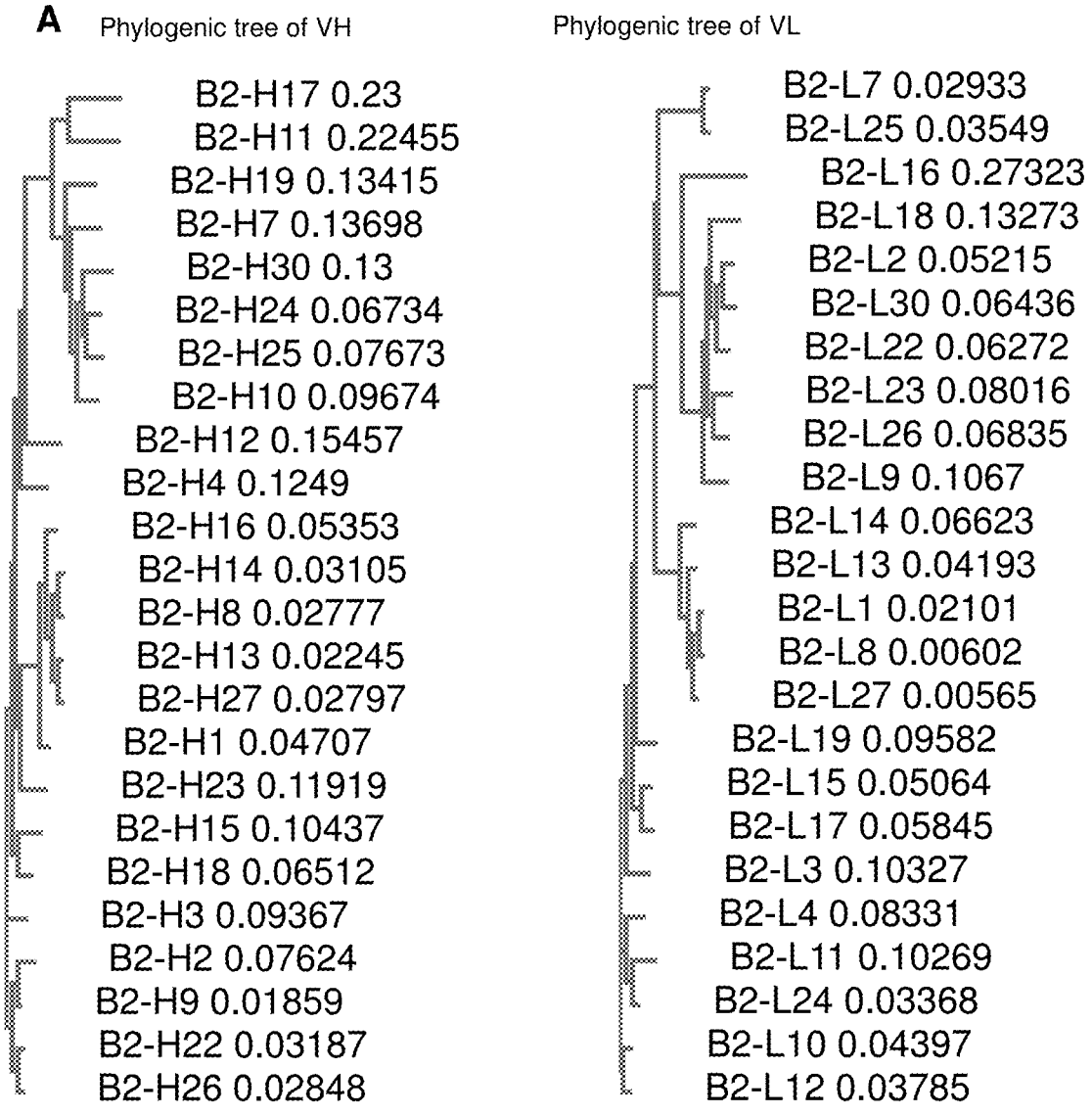
FIGS. 12A-B. Antibody sequence analysis of positive phages.
Figure 12B:
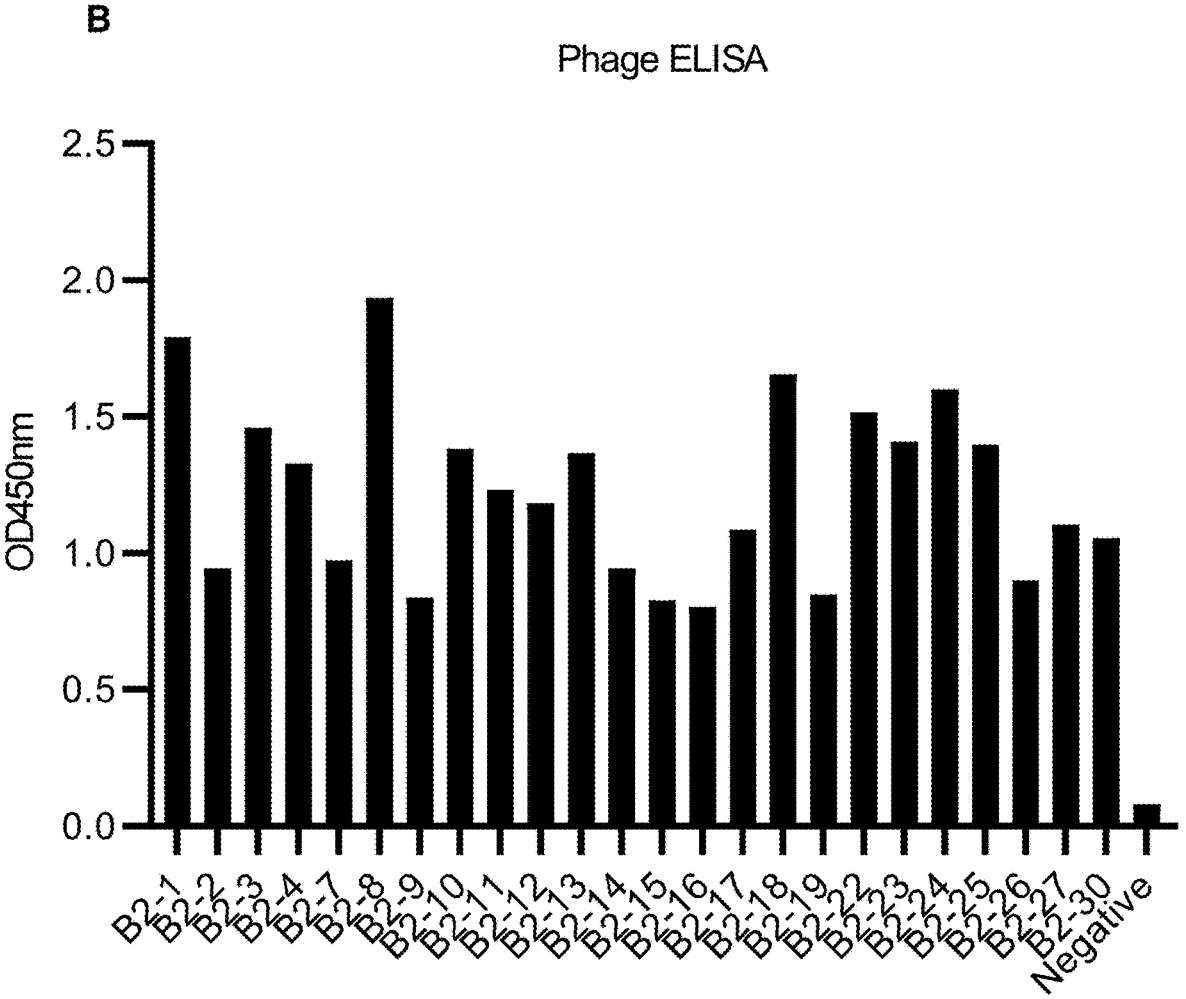
Figure 24A:
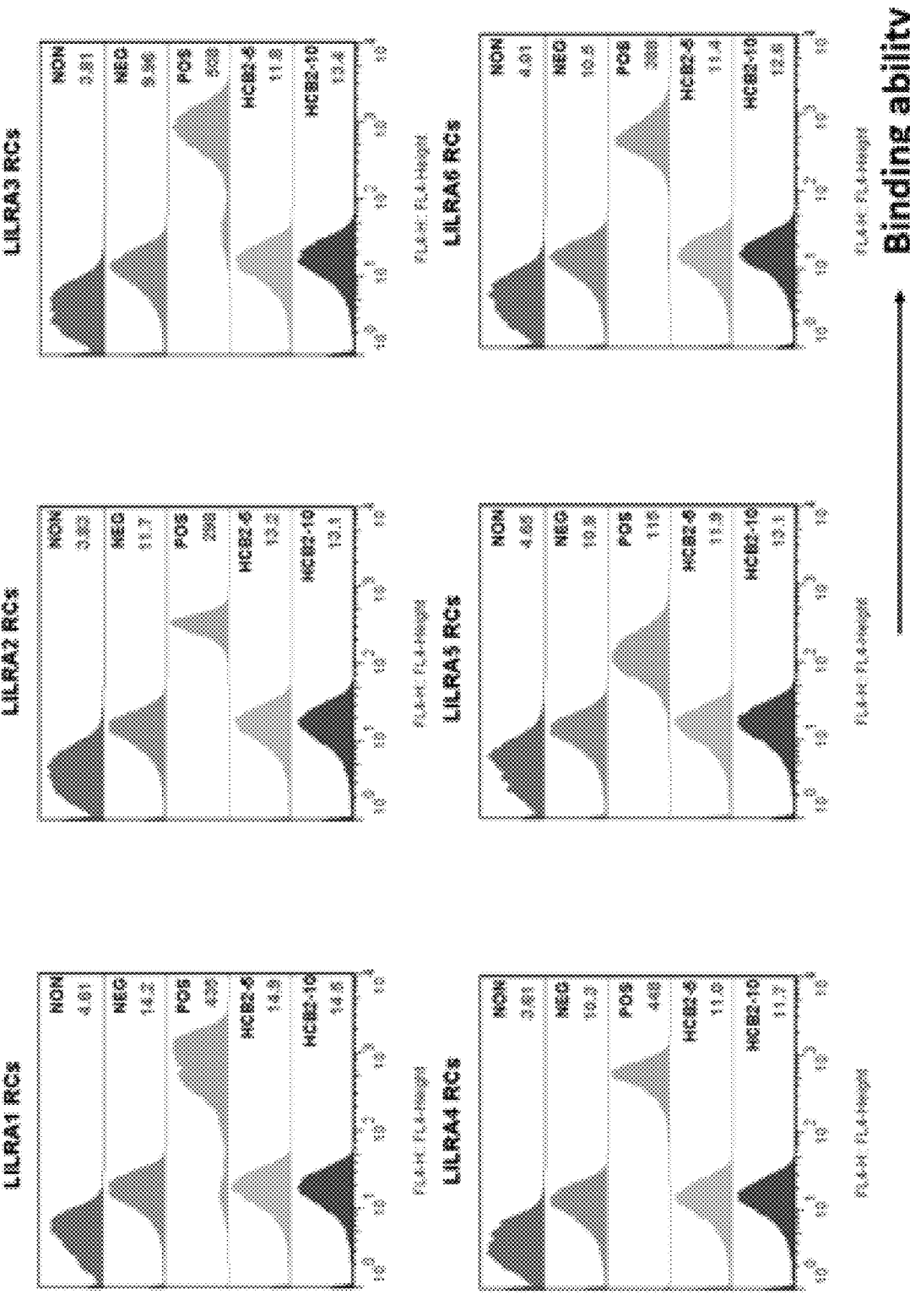
FIGS. 24A-B. Specific binding of LILRB2 by LILRB2 monoclonal antibodies.
Figure 24B:
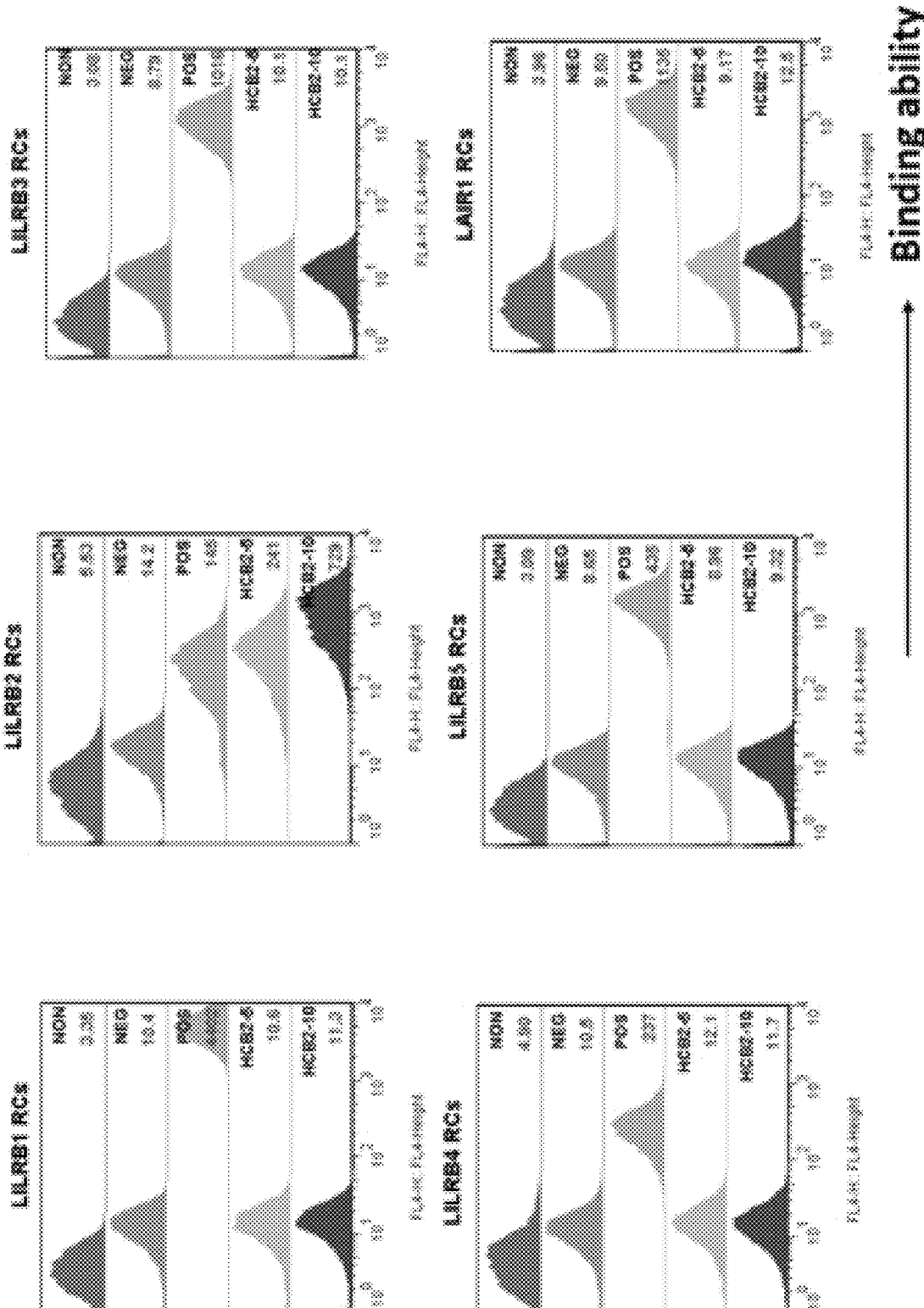
Figures 25A, 25B:
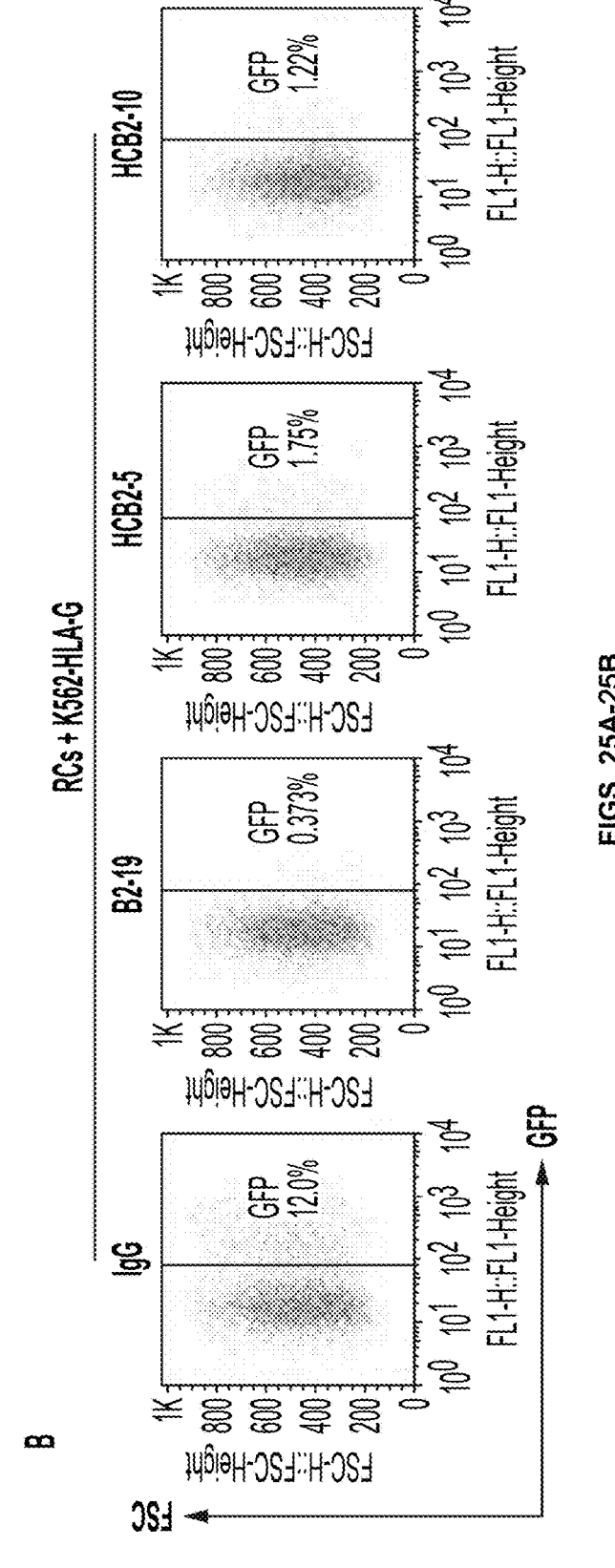
FIGS. 25A-B. Blocking activity of LILRB2 antibodies assayed in GFP signaling of LILRB2 reporter cells activated by HLA-G overexpressed on K562 cells.
Figures 26A, 26B:
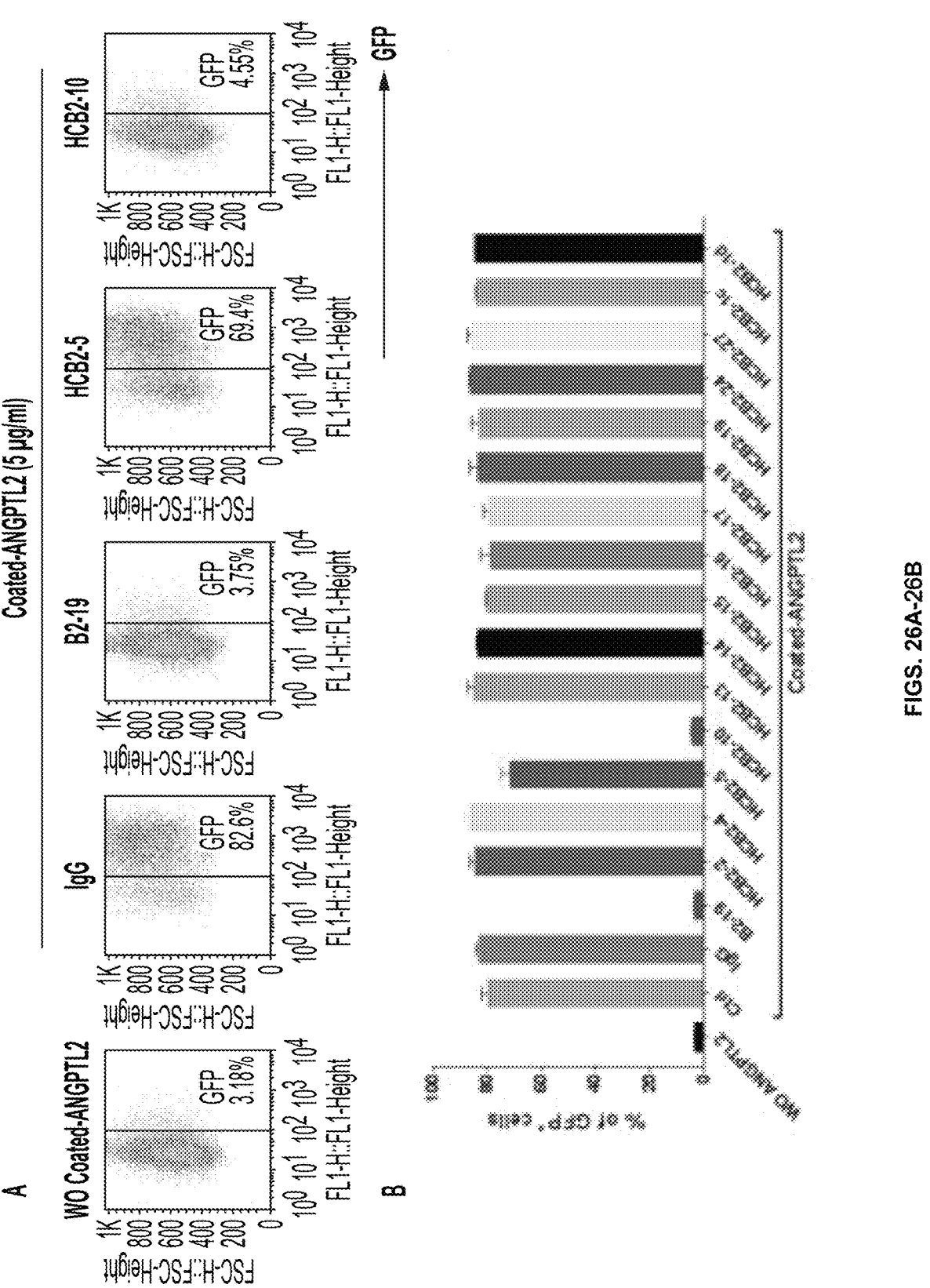
Figures 27A, 27B:
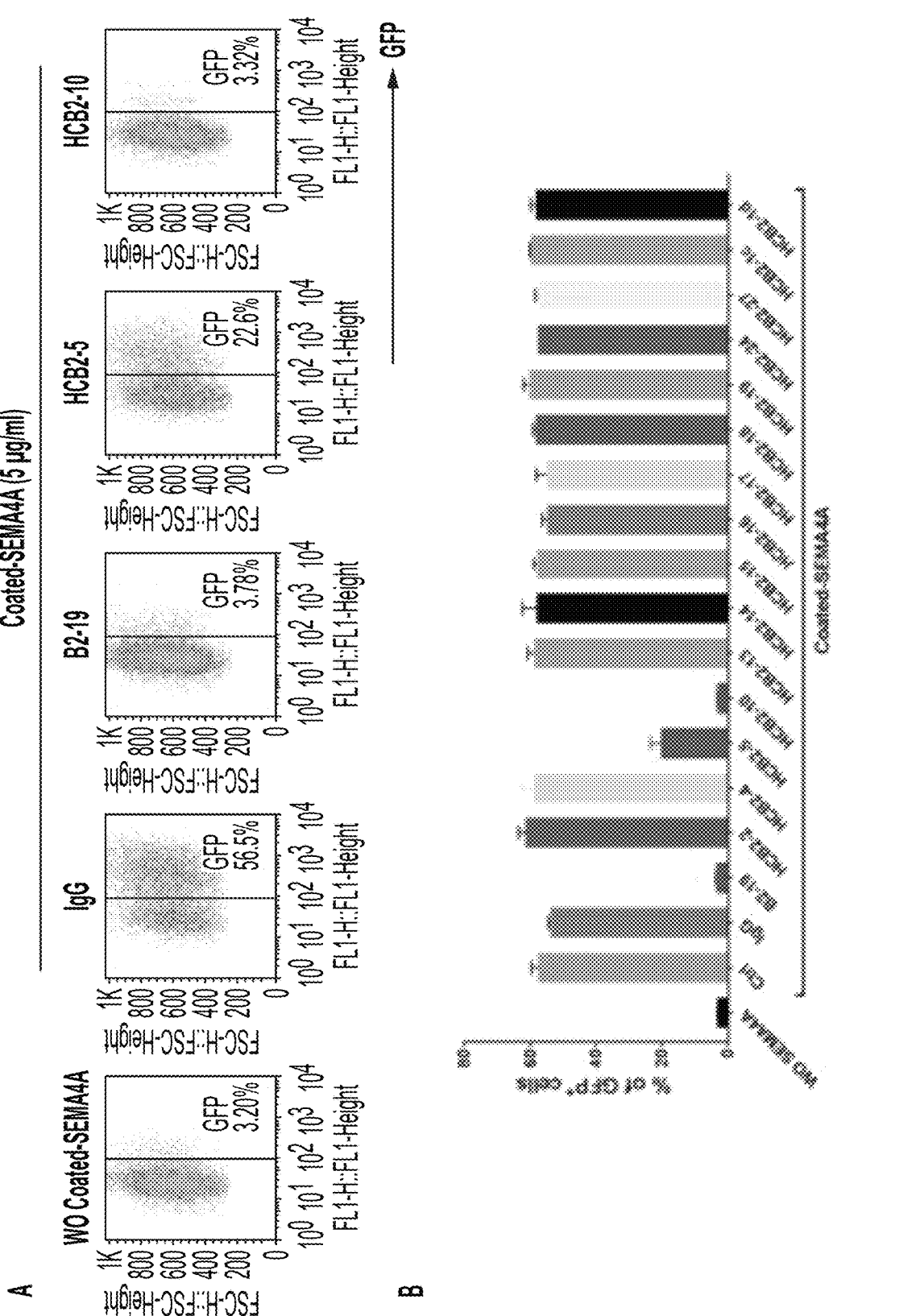
FIGS. 27A-C. Blocking activity of HCB2-5 and HCB2-10 assayed in GFP signaling of LILRB2 reporter cells activated by coated SEMA4A.
Figure 27C:
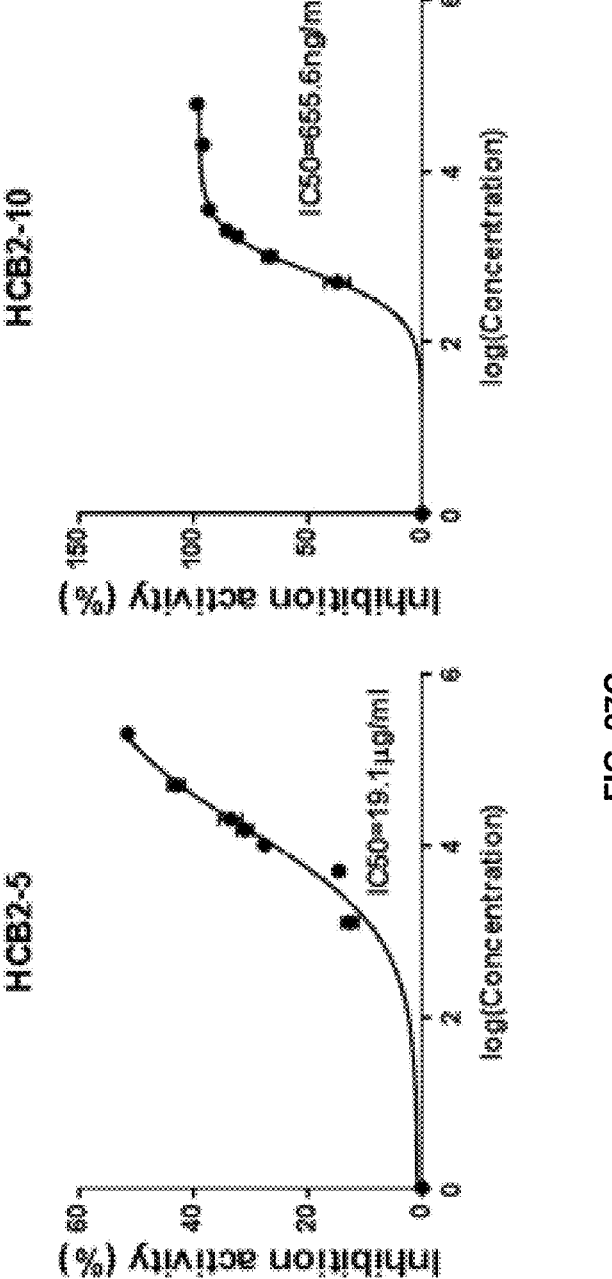

Generation and characterization of LILRB2 antibodies. LILRB2 antibodies were generated by panning phage displayed human antibody scFv library. The LILRB2-His antigen was coated on solid phase for 3 rounds of panning. In each round of phage panning, the LILRB1-His antigen was used for de-selection. After phage panning, single bacterial colonies were picked for phage ELISA testing. The positive ones in phage ELSIA were sequenced and analyzed of theirs scFv region. As shown in FIG. 12A, 24 unique antibody sequences were obtained. The phages presenting the scFv showed binding to LILRB2 antigen in phage ELISA (FIG. 12B). These 24 scFvs were then converted to full human IgG1 for further analysis.

Figures 13A, 13B:
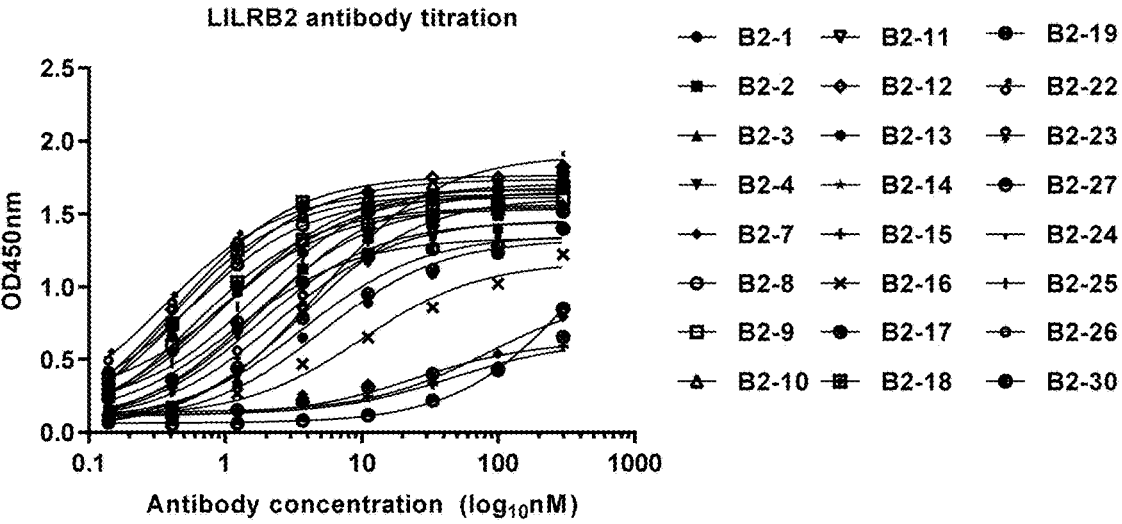
FIGS. 13A-B. ELISA binding $EC_{50}$ to LILRB2.

ELISA binding EC$_{50}$ of LILRB2 antibodies. The ELISA binding EC$_{50}$ of these 24 antibodies were measured by indirect ELISA. Briefly, ELISA plates were coated with LILRB2-His antigen. Serially diluted antibodies were incubated with antigen coated pates. After incubation, HRP-conjugated goat anti-human Fc secondary antibody was incubated with the plates. The TMB substrate was added for color development and measurement of absorbance at 450 nm. As shown in FIGS. 13A-B, these antibodies bind to LILRB2 in a dose-dependent manner (FIG. 13A) and their EC$_{50}$ values range from 0.355 to 46.49 nM (FIG. 13B).

Figure 14A:
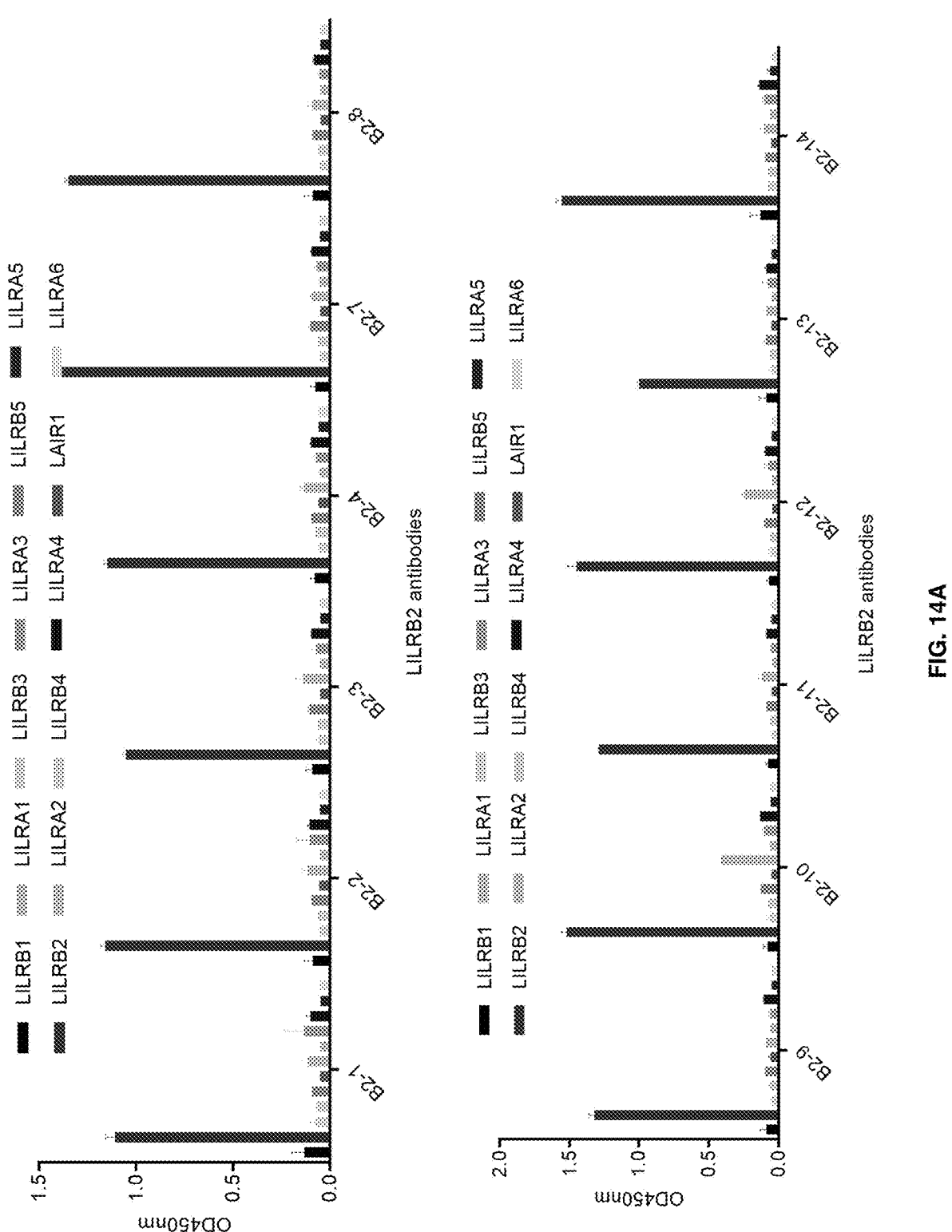
Figure 14B:
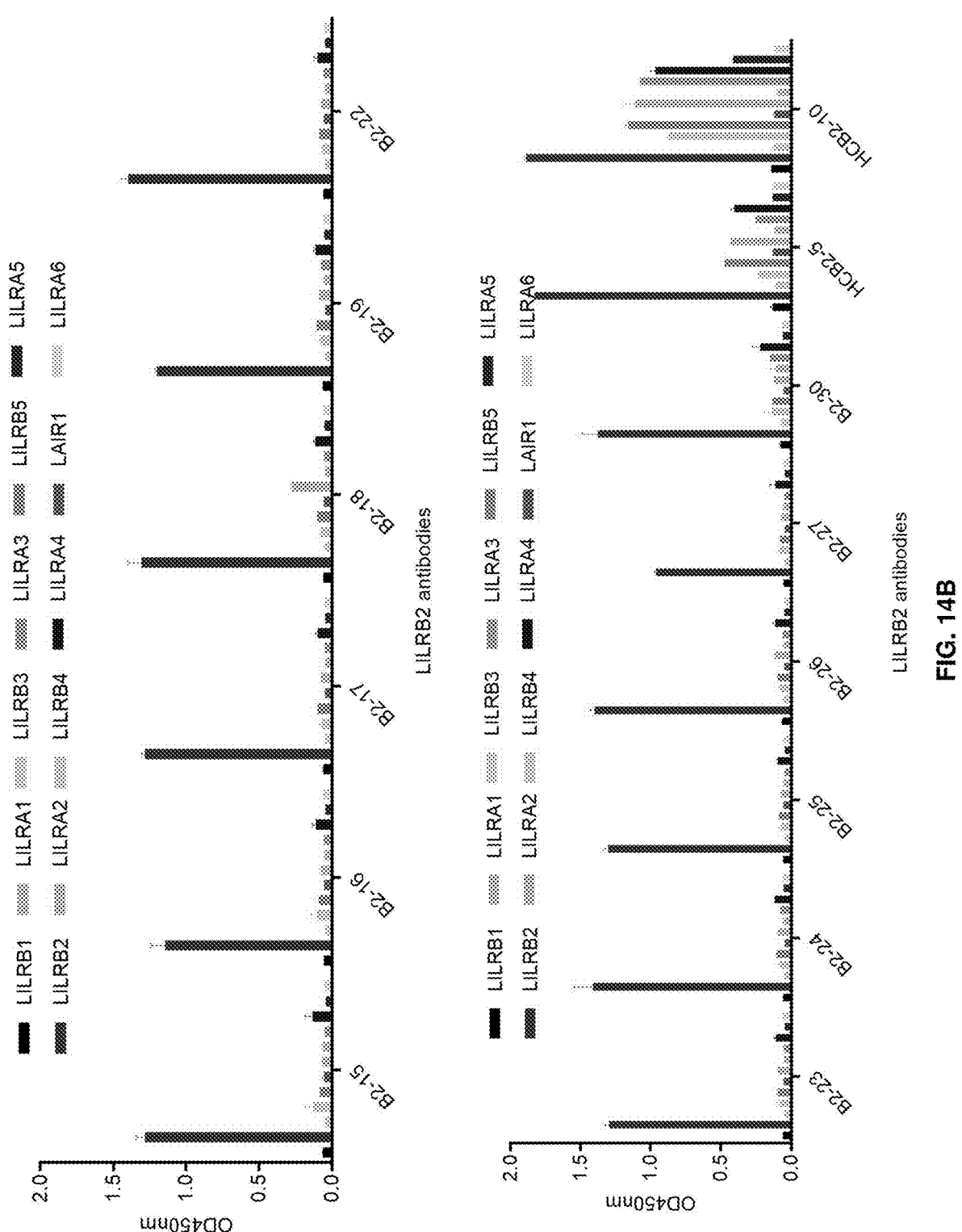

Binding specificity of LILRB2 antibodies. The binding specificity of the LILRB2 antibodies were evaluated by determining their ELISA binding activities with antigens for the other members of LILR family. As shown in FIGS. 14A-B, of the 24 antibodies, 21 showed very specific binding to LILRB2, 3 antibodies (B2-10, -12, -18) showed weak cross binding to LILRA1. A further titration of these 3 antibodies with LILRB2 and LILRA1 antigen showed that the binding abilities of these three antibodies to LILRB2 are much more potent (>100 times) than to LILRA1 (FIG. 14C).

Epitope binning of LILRB2 antibodies. Epitope binning was performed for 22 antibodies on OctetRED96 system by a sandwich format. Each antibody was cross-binned with the rest of antibodies to determine whether they could compete with each other. As shown in FIG. 15, these antibodies can be divided into 3 bins. In each bin, the antibodies compete with each other for LILRB2 binding. Antibodies in bin 1 and bin 2 showed overlap for their blocking profile.

Domain mapping of LILRB2 antibodies. LILRB2 has four Ig-like domains (D1, D2, D3 and D4) and a juxta membrane domain (JM). To determine the binding domain of LILRB2 antibodies, the full extracellular domain (ECD) or the truncated ECD of LILRB2 were fused to Fc fragment of mouse IgG2a for recombinant protein expression (FIGS. 16A-B). The binding abilities of LILRB2 antibodies to these domain proteins were then determined. Deletion of D1 domain resulted in loss of binding to antibodies B2-7, -15, -16, -17 and -19, but not to other antibodies, indicating these antibodies bind to the D1 domain of LILRB2 (FIG. 16C). Similarly, the binding domains of other antibodies were determined and summarized (FIG. 16D).

Key residues for antibody binding. To fine map the key residues for antibody binding, a series of mutant B2-ECD proteins were produced for determining antibody binding. Because most antibodies bind to the D1 or D4 domain, the inventors designed mutations only on D1 or D4 domain and the mutations were based on two criteria: 1) residues that are different between LILRB2 and LILRB1; (2) residues that are exposed and locate in the flexible loop region. As shown in FIGS. 17A-C, four regions on D1 domain of LILRB2 were mutated to the correspondent sequences on LILRB1. Similarly, four regions on D4 domain of LILRB2 were also mutated (FIGS. 17B-D). The four D1 mutants were used to test binding with the 5 antibodies (B2-7, -15, -16, -17 and -19) that bind to the D1 domain, and the antibody B2-18, which binds to the D4 region, was used as a control. As shown in FIG. 17E, D1M4 and D1M2 mutants completely abolished binding by antibodies B2-7, -15 and -17, indicating that the two regions are key to the binding activities of these antibodies; D1M4 completely, while D1M2 partially, abolished binding by antibodies B2-16 and -19, indicating that the M4 region is key to the binding activities of the two antibodies. As a control, none of these mutants abolished binding by antibody B2-18. By similar method, key regions to the binding activities of other antibodies on the D4 domain were determined (FIG. 17F).

Figure 18:
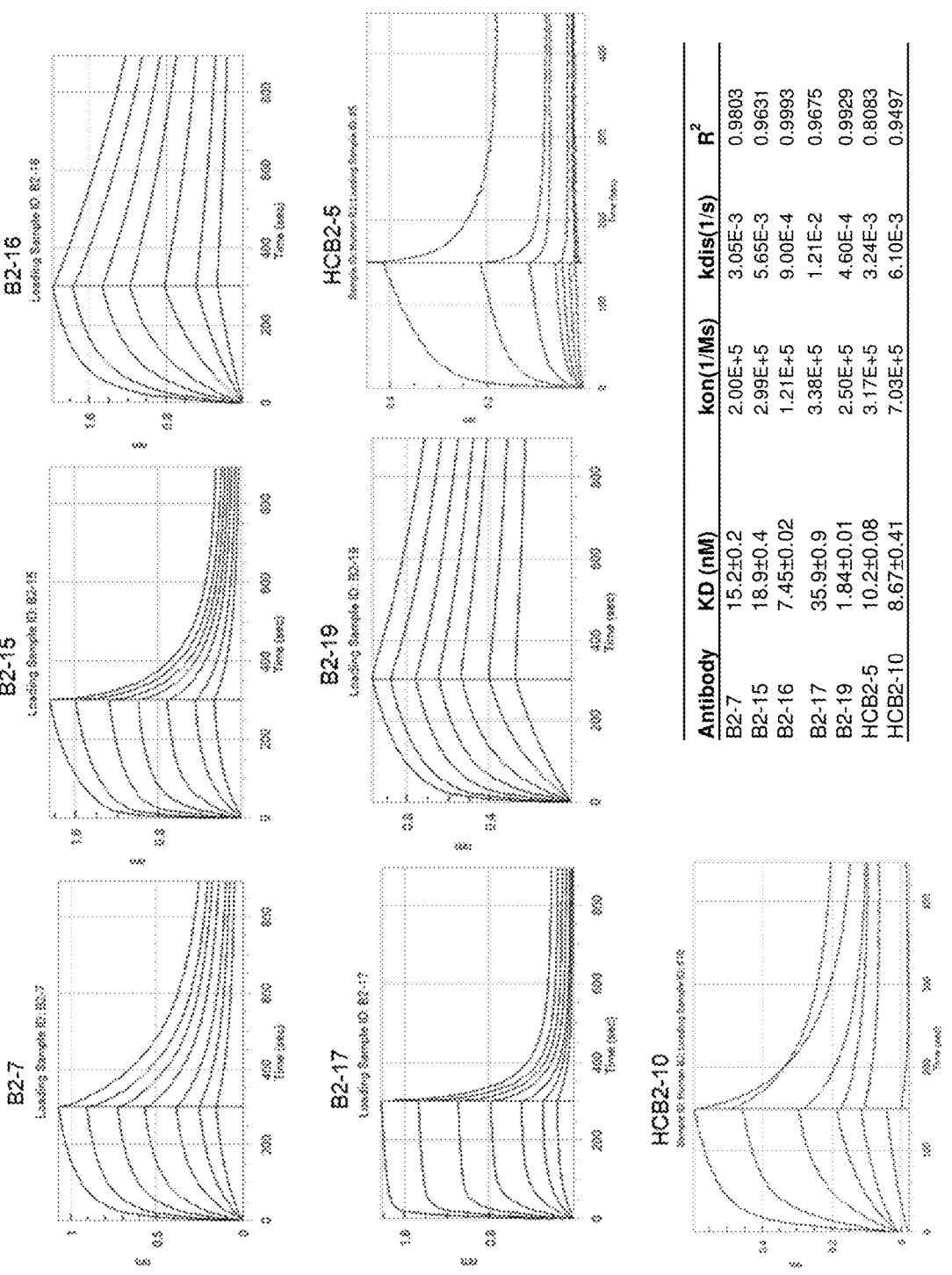
FIG. 18. Affinities of blocking antibodies. Antibodies were captured on protein A biosensors. The sensors were dipped in serially diluted LILRB2 solution for 300 secs to allow association and then dipped into kinetic buffer for 600 secs to allow dissociation. The association and dissociation curves are shown in blue solid lines and the two phases are divided by dotted lines.
Figure 21A:
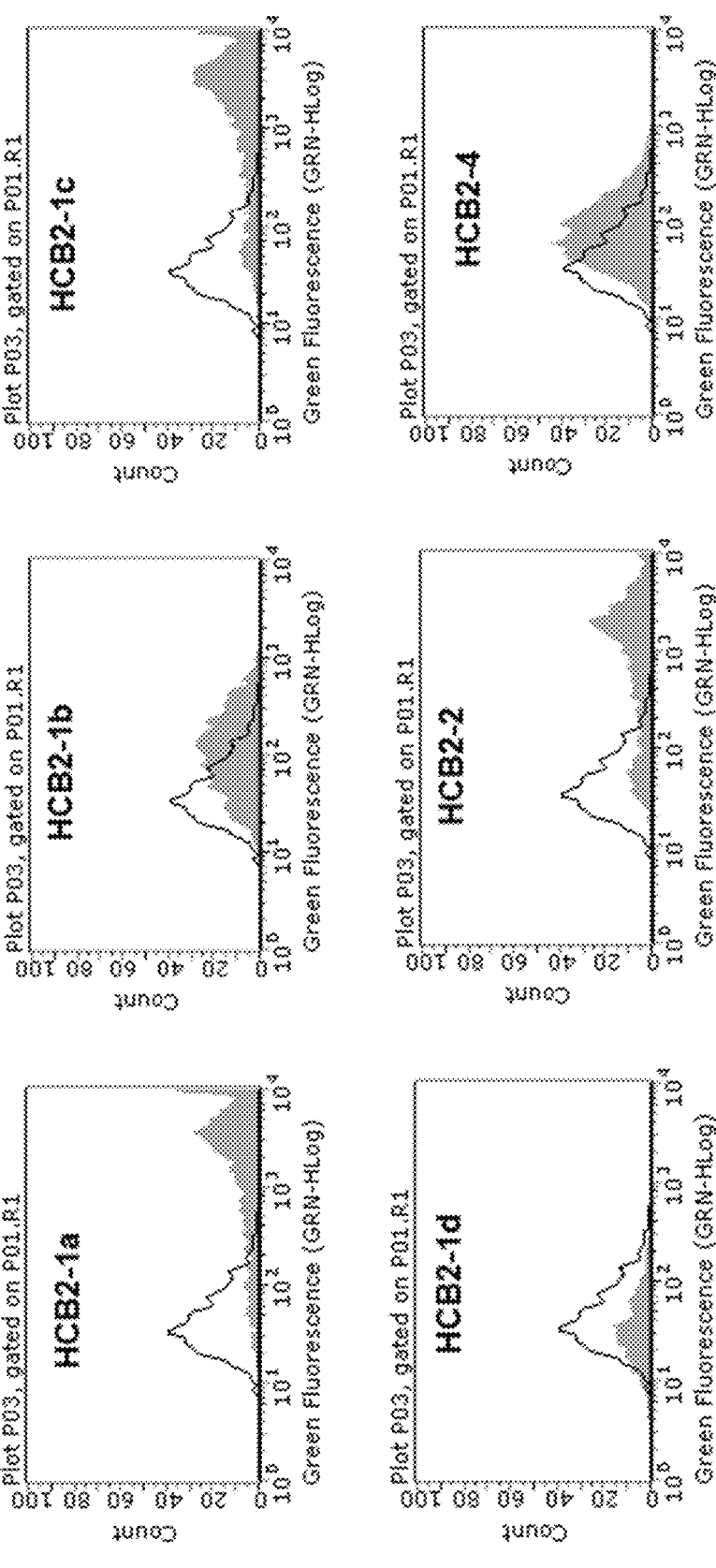
FIGS. 21A-B. Detection of LILRB2 antibodies binding to cyno-LILRB2 expressed on cell surface. HEK293 cells stably expressing full length cyno-LILRB2 with N-terminus FLAG tag was used to detect antibody binding by flow cytometry. An isotype human IgG1 was used as control shown as black line and solid peaks indicate the binding of the LILRB2 antibody to cyno-LILRB2 on cell surface. Mouse-anti-Flag monoclonal antibody was used for detection by flow cytometry.
Figure 21B:
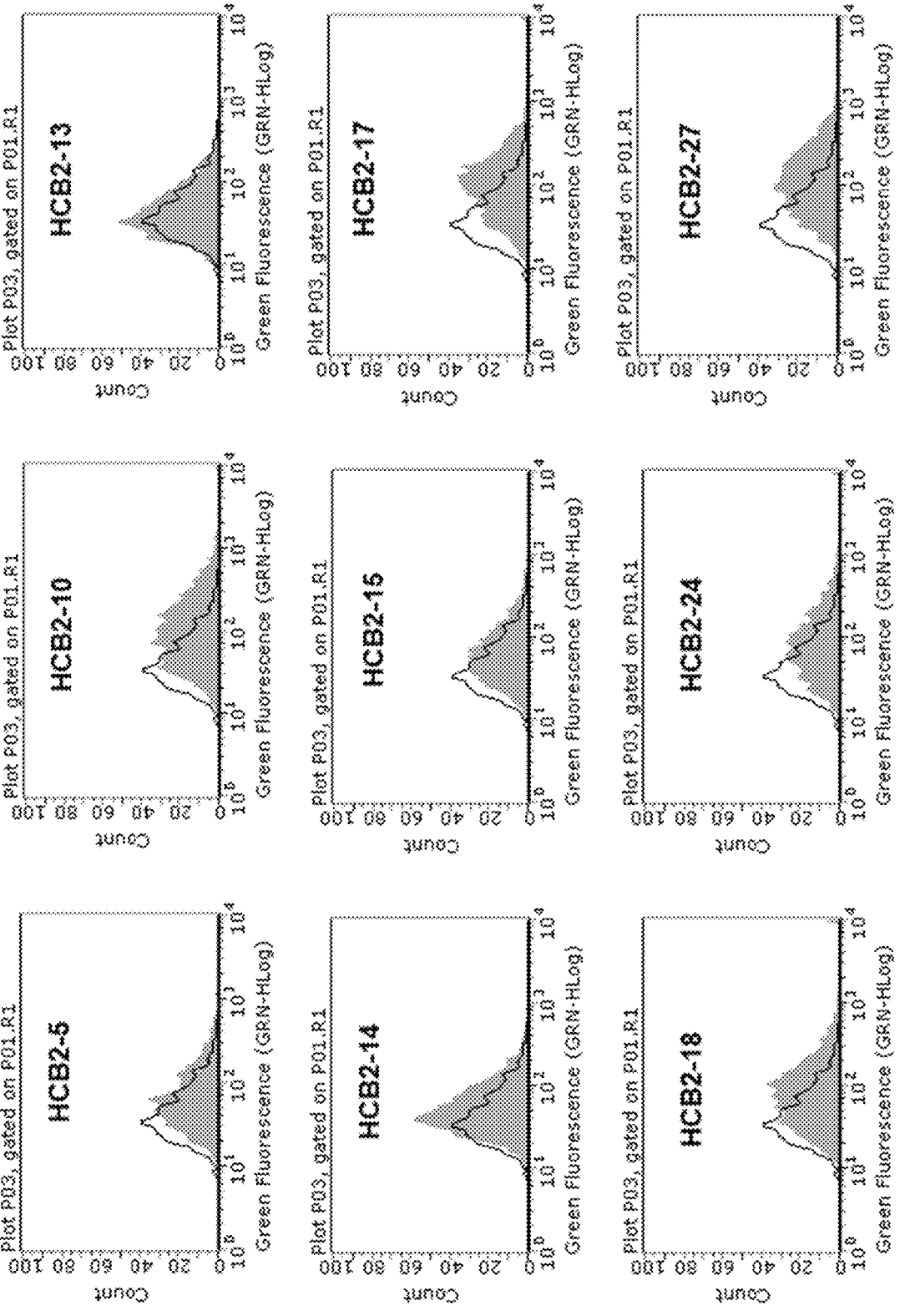
Figure 22A:
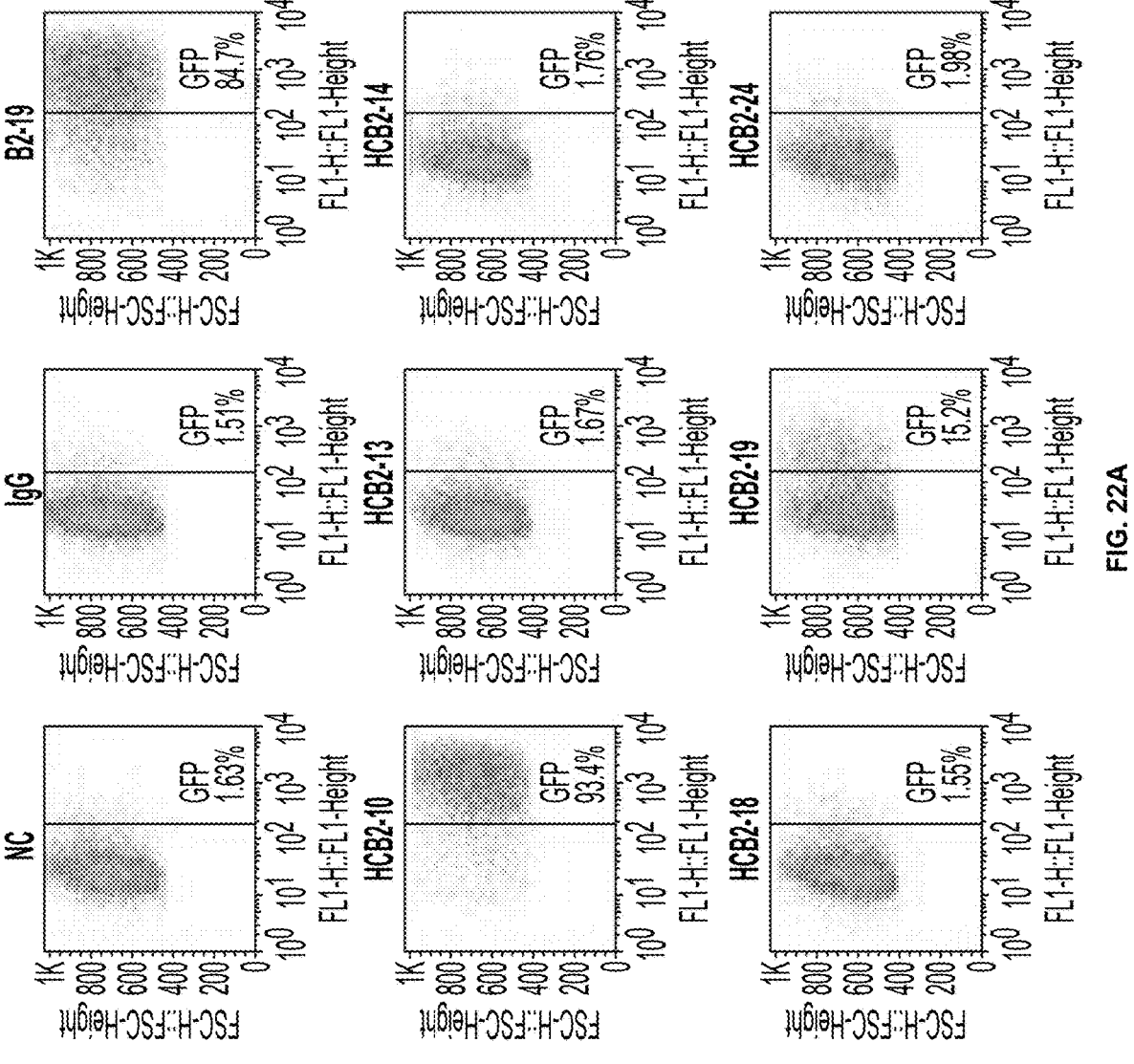
FIGS. 22A-22B. Determination of engagement of GFP reporter signaling by immobilized LILRB2 antibodies. NC, negative control and IgG for isotype control.
Figure 22B:
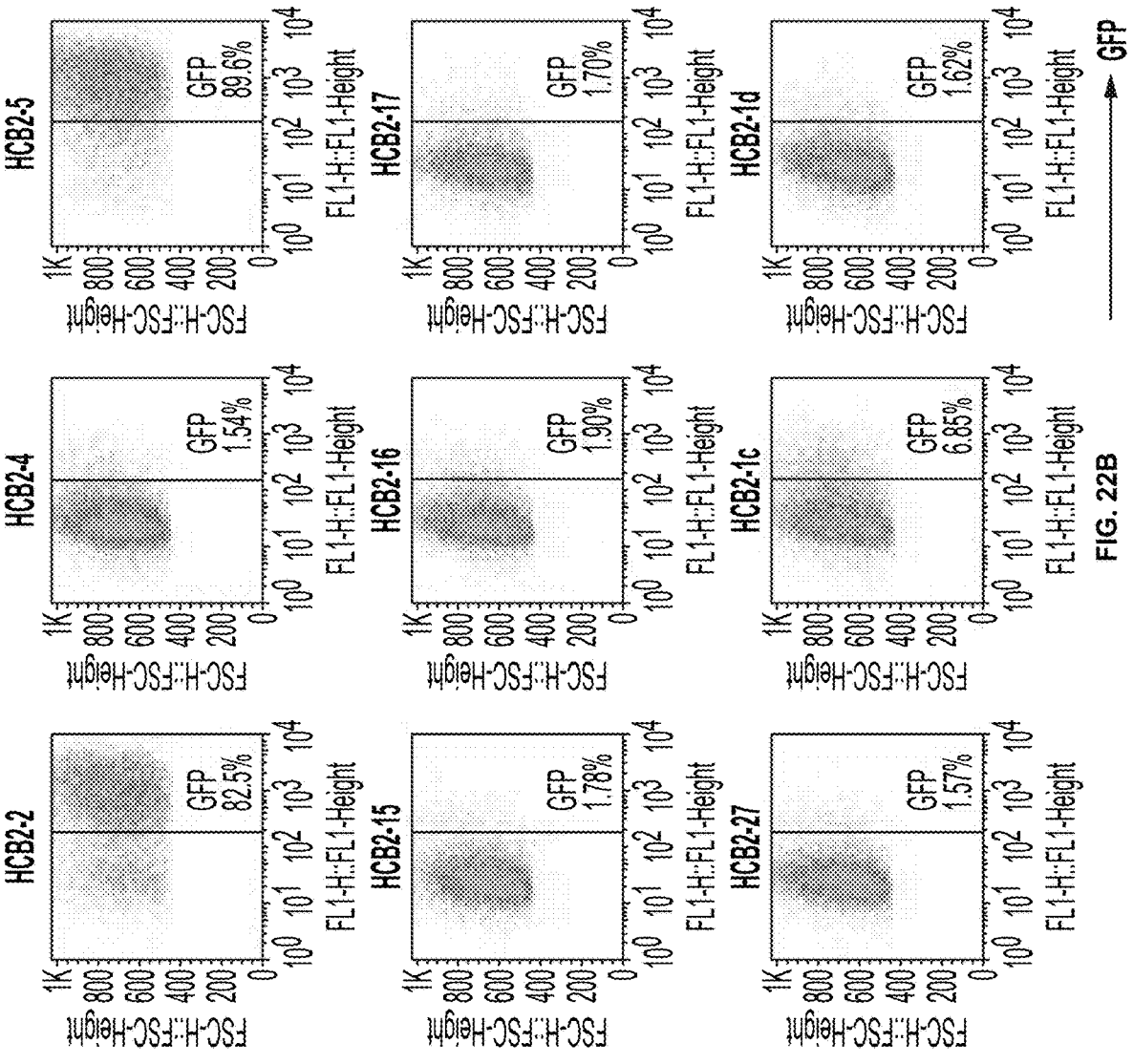

Affinity measurement of blocking antibodies. Affinities of the 5 blocking antibodies were measured on Octet RED 96 system. As shown in FIG. 18 and Table 1, the affinities range from 1.87 to 35.9 nM.

Example 3

Classical monocytes isolated from PBMC of apparently healthy donors were differentiated into immature DC for 6 days using 50 ng/mL GM-CSF and 35 ng/mL IL-4. On day 6, DC were treated with 40 ng/ml IL-10 (as a tolerogenic stimulus) and with 10 μg/mL B2-19 or its isotype control. After 48 hours, the levels of cytokines and chemokines were measured in the culture media supernatant, using a Luminex assay (R&D Systems). B2-19 triggered enhanced production of the pro-inflammatory cytokine IL-6 and of chemokines known to recruit monocytes (CCL2) and neutrophils (CXCL8) (FIG. 47).

Classical monocytes isolated from PBMC prepared from apparently healthy donors were differentiated into immature DC for 6 days using 50 ng/ml GM-CSF and 35 ng/ml IL-4. On day 6, DC were treated with 100 ng/mL LPS (as a maturation stimulus) and with 10 μg/mL B2-19 or its isotype control. After 48 hours, the expression levels of several cell surface markers were measured by flow cytometry. B2-19 increased the expression of CD83 (a DC maturation marker), CD86 (a co-stimulatory molecule), HLA-DR (antigen presentation). On the other hand, B2-19 decreased the expression levels of the inhibitory receptors LILRB4 and CD209. Altogether, these data indicate that B2-19 further promotes a pro-inflammatory phenotype in LPS-stimulated DC (FIG. 48).

The pharmacokinetics of B2-19 were evaluated in wild-type mice (no LILRB2 expression). Nine C57BL/6J mice received a single 5 mg/kg intravenous dose of B2-19 and were randomized into groups of 3 for blood sampling at alternated time points. Sera were prepared from blood samples and B2-19 concentration determined using ELISA. The antibody in sera was captured by plate-coated antigen (LILRB2-ECD, R&D Systems) and detected using an HRP-conjugated goat-anti-human IgG Fc antibody (Jackson ImmunoResearch) and TMB substrate. The results indicate that B2-19 antibody presents the expected pharmacokinetics profile (CL and half-life) of human IgG4 in C57BL/6J wildtype mice dosed at 5 mg/kg. Since the ELISA format measures active antibody, these results demonstrate that B2-19 in vivo exposure (in mice) does not decrease its binding activity.

The anti-tumor efficacy of B2-19 antibody was evaluated in humanized NSG-SGM3 mice xenografted with SK-MEL-5 melanoma cell line. NSG-SGM3 mice (The Jackson Laboratory, stock No. 013062) were humanized with $1 \times 10^5$ CD34$^+$ hematopoietic cells isolated from umbilical cord blood of individual donors. Six weeks after humanization, mice were implanted subcutaneously with $1 \times 10^6$ SK-MEL-5 cells. When the mean tumor size reached 70-80 mm$^3$ (29 days following tumor implantation), mice were randomized into 2 treatment groups with 6 mice per group, based on the following criteria: % human CD45$^+$CD14$^+$ cells in blood, tumor volume and donor (2 mice from each CD34$^+$ donor per treatment cohort). Mice were treated intravenously with 20 mg/kg B2-19 or its isotype control every 3 days for 3 doses. Compared to its isotype control, B2-19 monotherapy decreased tumor growth rate and caused a 29% reduction in tumor size (FIGS. 50A-B). These data demonstrate that B2-19 antibody monotherapy displays anti-tumor efficacy in a mouse model of solid tumor.

TABLE 1

Affinities of LILRB2 blocking antibodies

| Antibody | KD (nM) | Kon (1/Ms) | Kdis (1/s) | R$^2$ |
|---|---|---|---|---|
| B2-7 | 15.2 ± 0.2 | 2.00E+5 | 3.05E−3 | 0.9803 |
| B2-15 | 18.9 ± 0.4 | 2.99E+5 | 5.65E−3 | 0.9631 |
| B2-16 | 7.45 ± 0.02 | 1.21E+5 | 9.00E−4 | 0.9993 |
| B2-17 | 35.9 ± 0.9 | 3.38E+5 | 1.21E−2 | 0.9675 |
| B2-19 | 1.84 ± 0.01 | 2.50E+5 | 4.60E−4 | 0.9929 |
| HCB2-5 | 10.2 ± 0.08 | 3.17E+5 | 3.24E−3 | 0.8083 |
| HCB2-10 | 8.67 ± 0.41 | 7.03E+5 | 6.10E−3 | 0.9497 |

TABLE 2

Amino acid sequences of CDRs for LILRB2 antibodies

| Heavy chain | CDR1 | SEQ ID NO: | CDR2 | SEQ ID NO: | CDR3 | Light chain | SEQ ID NO: | CDR1 | SEQ ID NO: | CDR2 | SEQ ID NO: | CDR3 | SEQ ID NO: |
|---|---|---|---|---|---|---|---|---|---|---|---|---|---|
| B2-19_HC | GFTFSNAW | 97 | IKSKTDGGTT | 98 | TTDRYSSSWYSPAFDI | B2-19_LC | 99 | SSNIGNNV | 100 | YDD | 101 | ATWDDSLNGPV | 102 |
| B2-1_HC | GGTFSSYA | 1 | IIPIFGTA | 2 | ARGNQGDTAFDI | B2-1_LC | 3 | SSDVGGYNY | 4 | DVS | 5 | SSYTSSSTPYV | 6 |
| B2-2_HC | GYTFSDYG | 7 | ISGYNGNT | 8 | ARLLLGYYGMDV | B2-2_LC | 9 | QSIGNY | 10 | AAS | 11 | QQSFSIPPIT | 12 |
| B2-3_HC | GYTFSSYG | 13 | ISGNTGNT | 14 | ARDRGIAAGRAFDI | B2-3_LC | 15 | SSNIGTNP | 16 | NNN | 17 | SSWDDSLSAWV | 18 |
| B2-4_HC | GYPFTSNG | 19 | ISTNSGNT | 20 | ARDVQYRMDV | B2-4_LC | 21 | RSNIGSNP | 22 | SNN | 23 | AAWDDNVHGV | 24 |
| B2-7_HC | GFTISSYG | 25 | ISYDGSNK | 26 | AKDLLLRYFDWSPKYYNGMDV | B2-7_LC | 27 | NIGSKS | 28 | DDS | 29 | QVWDSSDHPGV | 30 |
| B2-8_HC | GGTFSSYA | 31 | IIPIFGTA | 32 | ARVAVADTFFDY | B2-8_LC | 33 | SSDVGGYNY | 34 | DVS | 35 | SSYTSSSTPYV | 36 |
| B2-9_HC | GYTFTSYG | 37 | ISAYNGNT | 38 | ARDGYGMDV | B2-9_LC | 39 | HTVNSY | 40 | AAS | 41 | QQSYRTPLT | 42 |
| B2-10_HC | GFTFSSYA | 43 | INDSGGST | 44 | AKDHITIFGVAPFDY | B2-10_LC | 45 | SSNIGGNP | 46 | YND | 47 | ATWDDSLNGWV | 48 |
| B2-11_HC | GDSVSNSAA | 49 | TYYRSKWYN | 50 | ARQDESAADDAFDI | B2-11_LC | 51 | KSNVGNNF | 52 | SNL | 53 | AAWDSLPGWV | 54 |
| B2-12_HC | GYTFPDNG | 55 | INVDTGYT | 56 | AREIEGVWTA | B2-12_LC | 57 | SSNIGSNP | 58 | NNN | 59 | AAWDDSLNGWV | 60 |
| B2-13_HC | GGTFSSYA | 61 | IIPIFGTA | 62 | ARSDYGDSYFDY | B2-13_LC | 63 | SSDVGGFNY | 64 | DVS | 65 | SSYTSSTAPYV | 66 |
| B2-14_HC | GGTFSSYA | 67 | IIPIFGTA | 68 | ARASMVETYFDY | B2-14_LC | 69 | SSDVGGYNY | 70 | EVS | 71 | SSYAGGYTPYV | 72 |
| B2-15_HC | GYTFTNYG | 73 | ISGDAGDT | 74 | ARDGEYIPMFRGFDNYYGLDV | B2-15_LC | 75 | NANIGSNP | 76 | SNN | 77 | EGWDDSLNGYV | 78 |
| B2-16_HC | GGTFSSYA | 79 | IIPIFGTA | 80 | ASGIIPDNPYGMDV | B2-16_LC | 81 | QSLVYSDGNTY | 82 | KVS | 83 | MQGTHWPVT | 84 |

TABLE 2-continued

Amino acid sequences of CDRs for LILRB2 antibodies

| Heavy chain | SEQ ID NO: | CDR1 | SEQ ID NO: | CDR2 | SEQ ID NO: | CDR3 | SEQ ID NO: | Light chain | SEQ ID NO: | CDR1 | SEQ ID NO: | CDR2 | SEQ ID NO: | CDR3 | SEQ ID NO: |
|---|---|---|---|---|---|---|---|---|---|---|---|---|---|---|---|
| B2-17_HC | 85 | GVSTSSTHW | 86 | ILHNGNT | 87 | ASASPNWGASGAFDA | | B2-17_LC | 88 | SSNIGSNP | 89 | SDN | 90 | STWDDSLNGLV | |
| B2-18_HC | 91 | GYTFTRYG | 92 | ISGYNGNT | 93 | ARDRGSGYLEY | | B2-18_LC | 94 | QGIYSS | 95 | GTS | 96 | QQHYNLPIT | |
| B2-22_HC | 103 | GYTFTSYG | 104 | ISAYNGNT | 105 | ARVGSYGDY | | B2-22_LC | 106 | QGISNY | 107 | AAS | 108 | QKYNSAPLT | |
| B2-23_HC | 109 | GYTFTHSY | 110 | INPVGGST | 111 | ARAGGDGYNPYFDY | | B2-23_LC | 112 | QSISSW | 113 | KAS | 114 | QQYNSYLT | |
| B2-24_HC | 115 | GFTFSDYY | 116 | ISSSSSYT | 117 | ARVGDLDAFDI | | B2-24_LC | 118 | SSNIGSNY | 119 | RNN | 120 | AAWDDSLSGWV | |
| B2-25_HC | 121 | GFTFSDHY | 122 | ITTTGSTM | 123 | ARDSIHVDGAFDI | | B2-25_LC | 124 | NIGSKS | 125 | DDS | 126 | QVWDSSSDHWV | |
| B2-26_HC | 127 | GYTFTSYG | 128 | ISAYNGNT | 129 | ARDRGGWFDP | | B2-26_LC | 130 | QSISNF | 131 | GAS | 132 | QQGYSVPLT | |
| B2-27_HC | 133 | GGTFSSYA | 134 | IIPIFGTA | 135 | ARESYSSSSFDY | | B2-27_LC | 136 | SSDVGGYNY | 137 | DVS | 138 | SSYTSSSTPYV | |
| B2-30_HC | 139 | GFTFSSYD | 140 | IGTAGDT | 141 | ARAKEYCSGGSCQDAFDI | | B2-30_LC | 142 | QSIRTY | 143 | AAT | 144 | QQSYSAPVFT | |
| HCB2-1c_HC | 145 | GYTFTDYY | 146 | VNANGGDT | 147 | ARDWYYYSSGSFPFDY | | HCB2-1c_LC | 148 | QSISSF | 149 | GAS | 150 | QQSYSIPIT | |
| HCB2-1d_HC | 151 | GYTFTDYY | 152 | VNANGGDT | 153 | ARDWYYYSSGSFPFDY | | HCB2-1d_LC | 154 | QDVSIA | 155 | SAS | 156 | QQHYITPLT | |
| HCB2-2_HC | 157 | GYIFNTYG | 158 | TNVYNSNT | 159 | ARDPGSAIFDM | | HCB2-2_LC | 160 | QSISSF | 161 | GAS | 162 | QQSYSIPIT | |
| HCB2-4_HC | 163 | GDAIKDKY | 164 | ISNSGST | 165 | ARGSGYTAFDI | | HCB2-4_LC | 166 | QSISSY | 167 | AAS | 168 | QQSYSTPPT | |
| HCB2-5_HC | 169 | GFTFSSYA | 170 | ISGSGGST | 171 | AKDVDPYSSGYFDY | | HCB2-5_LC | 172 | QGIGSW | 173 | VAS | 174 | QQANSFPLT | |
| HCB2-10_HC | 175 | GFTFSNVA | 176 | ISGSSIST | 177 | ASSGFGSFDY | | HCB2-10_LC | 178 | SSNIGDNS | 179 | LDD | 180 | ATWDDSLNGVV | |
| HCB2-13_HC | 181 | GFTLSSYA | 182 | INSGGST | 183 | AKAKSYSSDLDH | | HCB2-13_LC | 184 | QSLLNSGNQKTY | 185 | GAS | 186 | QNDHSYPFT | |
| HCB2-14_HC | 187 | GFTFSSYA | 188 | ISGSGGST | 189 | AKDLLGDSGSYPAFDI | | HCB2-14_LC | 190 | QSISSY | 191 | AAS | 192 | QQSYSTPYT | |

TABLE 2-continued

Amino acid sequences of CDRs for LILRB2 antibodies

| Heavy chain | CDR1 | SEQ ID NO: | CDR2 | SEQ ID NO: | CDR3 | SEQ ID NO: | Light chain | CDR1 | SEQ ID NO: | CDR2 | SEQ ID NO: | CDR3 | SEQ ID NO: |
|---|---|---|---|---|---|---|---|---|---|---|---|---|---|
| HCB2-15_HC | GFPPFADYA | 193 | IKSKTRDGTT | 194 | ALGGAAAL | | HCB2-15_LC | SSNIGAGYG | 195 | GDN | 196 | QSYDSLGVGV | 197 | 198 |
| HCB2-17_HC | GGTFSSYA | 199 | IIPIFGTA | 200 | AISSGYYYN PFDY | | HCB2-17_LC | QSISSY | 201 | AAS | 202 | QQSYSTPLT | 203 | 204 |
| HCB2-18_HC | GGTFSSYA | 205 | IIPIFGTA | 206 | ARGGYQPLD Y | | HCB2-18_LC | QSISSY | 207 | AAS | 208 | QQSYSTPFT | 209 | 210 |
| HCB2-24_HC | GGTFSSYA | 211 | IIPIFGTA | 212 | ARAGGIHYY DSLDY | | HCB2-24_LC | QSISSY | 213 | AAS | 214 | QQSYSTPLT | 215 | 216 |
| HCB2-27_HC | GFTFANAW | 217 | IKPSSSGGRT | 218 | CVTGRRVAK TFDF | | HCB2-27_LC | QSISSY | 219 | AAS | 220 | QQSYSTPRT | 221 | 222 |

TABLE 3

DNA sequences of CDRs for LILRB2 antibodies

| Heavy chain | CDR1 | SEQ ID NO: | CDR2 | SEQ ID NO: | CDR3 | SEQ ID NO: | Light chain | CDR1 | SEQ ID NO: | CDR2 | SEQ ID NO: | CDR3 | SEQ ID NO: |
|---|---|---|---|---|---|---|---|---|---|---|---|---|---|
| B2-19_HC | ggattcact tcagtaac gcctgg | 319 | attaaaagcaa aactgatggtg ggacaaca | 320 | accacagatcga tatacgcagc tggtactcccct gctttgatatc | 321 | B2-19_LC | agctccaacat cggaaataatg tt | 322 | tatgatgat | 323 | gcaacatggg atgacagcct gaatggccct gta | 324 |
| B2-1_HC | ggaggcacc ttcagcagc tatgct | 223 | atcatccctat cttggtacag ca | 224 | gcgaggggaat caggggatacg gctttgatatc | 225 | B2-1_LC | agcagtgacgt tggtggttata actat | 226 | gatgtcagt | 227 | agtcatata caagcagcag cactccttat gtc | 228 |
| B2-2_HC | ggttacacc tttagcgac tatggt | 229 | atcagtggtta caatggtaac ca | 230 | gcgagattgctg ctgggttactac ggtatggacgtc | 231 | B2-2_LC | cagagcattgg caactat | 232 | gctgcatcc | 233 | caacagagtt tcagtatccc cccgataact | 234 |
| B2-3_HC | ggttacacg tttagcagc tatggt | 235 | atcagtggtaa cactggtaaca ca | 236 | gcgagagatcgt ggtatacggca ggccgtgctttt gatatc | 237 | B2-3_LC | agtccaacat cggaactaatc ct | 238 | aataataat | 239 | tcgtcatggg acgacagcct gagtcgtgg gtg | 240 |
| B2-4_HC | ggttacccc tttagcagc aatggt | 241 | atcagcactaa cagcggaaaca ca | 242 | gcgagagatgtt caatatcgtatg gacgtc | 243 | B2-4_LC | agtccaacat cggaagtaatc ct | 244 | agtaataat | 245 | gcagcgtggg atgacaacgt gcacggagtt | 246 |
| B2-7_HC | ggattcacc atcagcagt tatggc | 247 | atatcatatga tggaagtaata | 248 | gcgaaagatctc ttattacgatat tttgactggag cccaaatactac tacaacggtatg gacgtc | 249 | B2-7_LC | aacattggaag taaaagt | 250 | gatgatagc | 251 | caggtgtggg atagtagtag tgatcatcccg ggggtc | 252 |
| B2-8_HC | ggaggcacc ttcagcagc tatgct | 253 | atcatccctat cttggtacag ca | 254 | gcgagagtggca gtggctgacacc ttccttgactac | 255 | B2-8_LC | agcagtgacgt tggtggttata actat | 256 | gatgtcagt | 257 | agtcatata caagcagcag caccccttat gtc | 258 |
| B2-9_HC | ggttacacc tttagcagc tatggt | 259 | atcagcgctta caatggtaac ca | 260 | gcgagagacggc tacggtatggac gtc | 261 | B2-9_LC | cacaccgttaa cagctat | 262 | gctgcatcc | 263 | caacagagtt acagaacccc tctcact | 264 |
| B2-10_HC | ggattcacc tttagcagc tatgcc | 265 | attaatgatag tggtggtaaca ca | 266 | gcgaaagatcat attacgatttt ggagtggcccg tttgactac | 267 | B2-10_LC | agtccaacat cggaggtaatc ct | 268 | tataatgat | 269 | gcaacatggg atgacagcct gaatggtagg gtg | 270 |

TABLE 3-continued

DNA sequences of CDRs for LILRB2 antibodies

| Heavy chain | CDR1 | SEQ ID NO: | CDR2 | SEQ ID NO: | CDR3 | SEQ ID NO: | Light chain | CDR1 | SEQ ID NO: | CDR2 | SEQ ID NO: | CDR3 | SEQ ID NO: |
|---|---|---|---|---|---|---|---|---|---|---|---|---|---|
| B2-11_HC | gggacagt gtcttagc aacagtgct gct | 271 | acatactacag gtccaagtggt ataat | 272 | gcaagacaagat gaatcggcagcc gatgatgcttt gatatc | 273 | B2-11_LC | aagtccaacgt cggaaataatt tt | 274 | agcaatctt | 275 | gcagcatggg atgacagcct gcccggttgg gtg | 276 |
| B2-12_HC | ggttacacg tttcccgac aacggt | 277 | atcaacgttga cactggataca cc | 278 | gcgagagaaatc gaggagtgtgg acagct | 279 | B2-12_LC | agctccaacat cggaagtaatc ct | 280 | aataaatat | 281 | gcggcatggg atgacagcct gaatggttgg gtg | 282 |
| B2-13_HC | ggaggcacc ttcagcagc tatgct | 283 | atcatccctat cttggtacag ca | 284 | gcgaggtcggac tacggtgactcc tacttgactac | 285 | B2-13_LC | agcagtgacgt tgtggtttta actat | 286 | gatgtcagt | 287 | agctcatta caagcagcac cgctccttat gtc | 288 |
| B2-14_HC | ggaggcacc ttcagcagc tatgct | 289 | atcatccctat cttggtacag ca | 290 | gcgagagccctct atggtcgagact tacttgactac | 291 | B2-14_LC | agcagtgatgt tgtggtttata actat | 292 | gaggtcagt | 293 | tcctccatg caggcgggta cacccctat gtc | 294 |
| B2-15_HC | ggttacacc tttaccaac tatggt | 295 | atcagcggtga cgctggtgaca ca | 296 | gcgagagatggg gaatatattcct atgttcgggga tttgacaactac tacggtctggac gtc | 297 | B2-15_LC | aacgccaacat cggaagtaatc ct | 298 | agtaatat | 299 | gaaggatggg atgacagcct gaatggctat gtc | 300 |
| B2-16_HC | ggaggcacc ttcagcagc tatgct | 301 | atcatccctat cttggtacag ca | 302 | gcgacgcggatt ataacctgataat ccctacggtatg gacgtc | 303 | B2-16_LC | caaagccccgt atacagtgatg gaaacacctac | 304 | aaggtttct | 305 | atgcaaggta cacactggcc ggtcacc | 306 |
| B2-17_HC | ggtgttccc accagcagt actcattgg | 307 | atccttcataa tggaaacacc | 308 | gcgtcagctcg cctacgggga gctacgggggct tttgatgcc | 309 | B2-17_LC | agctccaacat cggaagtaatc ct | 310 | agtgataat | 311 | tcaactatgg atgacagcct gaatggctt gtc | 312 |
| B2-18_HC | ggttacacc tttaccagg tatggt | 313 | atcagcggtta caatggtaata ca | 314 | gcgagagatccgg ggtagtggttat cttgaatac | 315 | B2-18_LC | caggggcattta cagtct | 316 | ggtacgtcg | 317 | caacacatt acaatctacc catcacc | 318 |
| B2-22_HC | ggttacacc tttaccagc tatggt | 325 | atcagcgctta caatggtaaca ca | 326 | gcgagagtggggc agctatggtgac tac | 327 | B2-22_LC | caggggcattag caattat | 328 | gctgcatccc | 329 | caaaagtata acagtgcccc gctcact | 330 |

TABLE 3-continued

DNA sequences of CDRs for LILRB2 antibodies

| Heavy chain | CDR1 | SEQ ID NO: | CDR2 | SEQ ID NO: | CDR3 | SEQ ID NO: | Light chain | CDR1 | SEQ ID NO: | CDR2 | SEQ ID NO: | CDR3 | SEQ ID NO: |
|---|---|---|---|---|---|---|---|---|---|---|---|---|---|
| B2-23_HC | gggtacaccttcaccactcctat | 331 | atcaaccctgttggtagcaca | 332 | gctagagcggggggagatggctacaatccttactttgactac | 333 | B2-23_LC | cagagtattagtagctgg | 334 | aaggcgtct | 335 | caacagtataatagttatctcact | 336 |
| B2-24_HC | ggattcaccttcagtgactactac | 337 | attagtagtagtagtgttacaca | 338 | gcgagagtcggagatcttgatgcttttgatatc | 339 | B2-24_LC | agctccaacatcggaagtaattat | 340 | aggaataat | 341 | gcagcatgggatgacgcctgagtggttgggtg | 342 |
| B2-25_HC | ggattcaccttcagtgaccactac | 343 | attactactactggtgtaccatg | 344 | gcgagagattccatacatgtggatggtgctttgatatt | 345 | B2-25_LC | aacattggaagtaaaagt | 346 | gatgatagc | 347 | caggttggggatagtgtagtgatcattgggtg | 348 |
| B2-26_HC | ggttacacctttaccagctatggt | 349 | atcagcgcttacaatggtaacaca | 350 | gcgagagatcggggaggggtggttcgacccc | 351 | B2-26_LC | cagagcataagcaacttt | 352 | ggtgcatcc | 353 | caacaggttacagtgtcccactcact | 354 |
| B2-27_HC | ggaggcaccttcagcagctatgct | 355 | atcatccctatcttggtacagca | 356 | gcgagagtcgtatagcagctcgtcctttgactac | 357 | B2-27_LC | agcagtgacgttggtggttataactat | 358 | gatgtcagt | 359 | agctcatatacaagcagcagcactccctatgtc | 360 |
| B2-30_HC | ggattcaccttcagtagctacgac | 361 | attgtactgctggtgacaca | 362 | gcaagggcgaaggaatattgagtggtggtagctgccaagatgcttttgatatc | 363 | B2-30_LC | cagagcattaggacctac | 364 | gctgccaac | 365 | caacagagttacagtgcccccgtgttcact | 366 |
| HCB2-1c_HC | gggtacaccttcaccgactattat | 367 | gtcaacgctaatggtggtgacaca | 368 | gctagagattgtattactattcttcgggggagtttcccttttgactac | 369 | HCB2-1c_LC | cagagcattagcagcttt | 370 | ggtgcatcc | 371 | caacagagttacagtatcccgatcacc | 372 |
| HCB2-1d_HC | gggtacaccttcaccgactattat | 373 | gtccaacgctaatggtggtgacaca | 374 | gctagagattgtattactattcttcgggggagtttcccttttgactac | 375 | HCB2-1d_LC | caagagatgtccatcgcc | 376 | tccgccagc | 377 | cagcagcactacataccctttaaca | 378 |
| HCB2-2_HC | ggttacatcttcaacacctatggt | 379 | accacgtttacaatagtaacaca | 380 | gcgagagacccgggctcggccatttttgatatg | 381 | HCB2-2_LC | cagagcattagcagcttt | 382 | ggtgcatcc | 383 | caacagagttacagtatcccgatcacc | 384 |

TABLE 3-continued

DNA sequences of CDRs for LILRB2 antibodies

| Heavy chain | SEQ ID NO: | CDR1 | SEQ ID NO: | CDR2 | SEQ ID NO: | CDR3 | Light chain | SEQ ID NO: | CDR1 | SEQ ID NO: | CDR2 | SEQ ID NO: | CDR3 | SEQ ID NO: |
|---|---|---|---|---|---|---|---|---|---|---|---|---|---|---|
| HCB2-4_HC | 385 | ggtgacgc catcaaag ataagtac | 386 | atcctaaca gtggaagcac c | 387 | gcgagaggcag cggtatactg ctttgatatc | HCB2-4_LC | 388 | cagagcatta gcagctat | 389 | gctgcatc c | 390 | caacagagt tacagtacc ccgcccact |
| HCB2-5_HC | 391 | ggattcac cttagca gctatgcc | 392 | attagtggta gtggtggtag caca | 393 | gcgaaagatgt cgaccctata gtagtggttat tttgactac | HCB2-5_LC | 394 | cagggtattg gcagtgg | 395 | gttgcatc c | 396 | caacagct aacagttc ccgtcact |
| HCB2-10_HC | 397 | ggattcac cttagca actatgcc | 398 | attagtggta gtagtattag caca | 399 | gcgtcctcggg tttcggtcct ttgactac | HCB2-10_LC | 400 | agctccaata tcggagataa ttct | 401 | cttgatga t | 402 | gcaacatgg gatgacagc ctgaacggt gtggtt |
| HCB2-13_HC | 403 | ggattcac cttagta gctatgcc | 404 | attaatagtg gtggtagcac a | 405 | gcgaaagcgaa gagtatagca gtgaccttgac cac | HCB2-13_LC | 406 | cagagtctgt taacagtgg aaatcaaaag acctac | 407 | ggggcatc c | 408 | cagaatgat catagttat ccattcacg |
| HCB2-14_HC | 409 | ggattcac cttagca gctatgcc | 410 | attagtggta gtggtggtag caca | 411 | gcgaaagatct tctcggggata gtgggagctac cctgctttga tatc | HCB2-14_LC | 412 | cagagcatta gcagctat | 413 | gctgcatc c | 414 | caacagagt tacagtacc ccgtacact |
| HCB2-15_HC | 415 | ggattccc ctttgcgg actatgct | 416 | attaaaagca agactagaga tgggacaaca | 417 | gccctcggggg agcagcagtc ta | HCB2-15_LC | 418 | agctccaaca tcggggcagg ttatggt | 419 | ggtgacaa c | 420 | cagtcctat gacagcagc ctggggggt ggtgtg |
| HCB2-17_HC | 421 | ggaggcac cttcagca gctatgct | 422 | atcatcccta tctttggtac agca | 423 | gcgattagtag tggttattatt ataacccattt gactac | HCB2-17_LC | 424 | cagagcatta gcagctat | 425 | gctgcatc c | 426 | caacagagt tacagtacc cccctcact |
| HCB2-18_HC | 427 | ggaggcac cttcagca gctatgct | 428 | atcatcccta tctttggtac agca | 429 | gcgagagggggg ataccagccac tggattac | HCB2-18_LC | 430 | cagagcatta gcagctat | 431 | gctgcatc c | 432 | caacagagt tacagtacc ccattcact |
| HCB2-24_HC | 433 | ggaggcac cttcagca gctatgct | 434 | atcatcccta tctttggtac agca | 435 | gcgagagctgg ggaatccatt actatgatagt ttagactac | HCB2-24_LC | 436 | cagagcatta gcagctat | 437 | gctgcatc c | 438 | caacagagt tacagtacc cctctgacg |

TABLE 3-continued

DNA sequences of CDRs for LILRB2 antibodies

| Heavy chain | CDR1 | SEQ ID NO: | CDR2 | SEQ ID NO: | CDR3 | SEQ ID NO: | Light chain | CDR1 | SEQ ID NO: | CDR2 | SEQ ID NO: | CDR3 | SEQ ID NO: |
|---|---|---|---|---|---|---|---|---|---|---|---|---|---|
| HCB2-27_HC | ggattcac cttcgcga atgcctgg | 439 | attaagccca gttctagcgg cgggaggaca | 440 | tgtgtcacagg aagaagggtcg cgaagactttt gattc | 441 | HCB2-27_LC | cagagcatta gcagctat | 442 | gctgcatc c | 443 | caacagagt tacagtacc cctcggacg | 444 |

TABLE 4

DNA sequences of antibody heavy chains (HC)

>B2-19_HC (SEQ ID NO: 461)
CAGGTGCAGCTGGTGCAGTCTGGGGGAGGCTTGGTAAAGCCTGGGGGGTCCCTTAGACTCTCCTGTGCAGCCTCT
GGATTCACTTTCAGTAACGCCTGGATGAGCTGGGTCCGCCAGGCTCCAGGGAAGGGGCTGGAGTGGGTTGGCCGT
ATTAAAAGCAAAACTGATGGTGGGACAACAGACTACGCTGCACCCGTGAAAGGCAGATTCACCATCTCAAGAGAT
GATTCAAAAAACACGCTGTATCTGCAAATGAACAGCCTGAAAACCGAGGACACAGCCGTGTATTACTGTACCACA
GATCGATATAGCAGCAGCTGGTACTCCCCTGCTTTTGATATCTGGGGCCAAGGGACAACGGTCAGCGTCTCCTCA

>B2-1_HC (SEQ ID NO: 445)
GAGGTGCAGCTGGTGCAGTCTGGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACAAATCC
ACGAGCACAGCCTACATGGAGCTGAGCAGCCTGAGATCTGAGGACACGGCCGTGTATTACTGTGCGAGGGGGAAT
CAGGGGGATACGGCTTTTGATATCTGGGGCCAAGGGACCACGGTCATCGTCTCCTCA

>B2-2_HC (SEQ ID NO: 446)
CAGGTGCAGCTGGTGCAGTCTGGAGCTGAGGTGAAGAAGCCTGGGGCCTCAGTGAAGGTCTCCTGCAAGGCTTCT
GGTTACACCTTTAGCGACTATGGTTTCAGCTGGGTGCGACAGGCCCCTGGACAAGGGCTTGAGTGGATGGGATGG
ATCAGTGGTTACAATGGTAACACAAACTATGCACAGAAGTTCCAGGGCAGAGTCACCATGACCATAGACGCATCC
ACGAGCACAGCCTACATGGAGCTGAGGAGCCTGAAATCTGACGACACGGCCGTGTATTACTGTGCGAGATTGCTG
CTGGGTTACTACGGTATGGACGTCTGGGGCCAAGGGACCACGGTCACCGTCTCCTCA

>B2-3_HC (SEQ ID NO: 447)
CAGGTGCAGCTGGTGCAGTCTGGAGCTGAGGTGAAGAAGCCTGGGGCCTCAGTGAAGGTCTCCTGCAGGACTTCT
GGTTACACGTTTAGCAGCTATGGTATCAGCTGGGTGCGACAGGCCCCTGGACAAGGGCTTGAGTGGATGGGATGG
ATCAGTGGTAACACTGGTAACACAAAGTATACACCGAAGCTCCAAGGCAGAGTCACCATGACCACAGACACATCC
ACGAGCACAGCCTACATGGAGCTGAGGAGCCTGAGATCTGACGACACGGCCGTGTATTACTGTGCGAGAGATCGT
GGTATAGCGGCAGGCCGTGCTTTTGATATCTGGGGCCAAGGGACAATGGTCACCGTCTCTTCA

>B2-4_HC (SEQ ID NO: 448)
CAGGTGCAGCTGGTGCAGTCTGGACCCACGGTGAGGAAGCCTGGGGCCTCAGTGAGGGTCTCCTGCAAGGCTTCT
GGTTACCCCTTTACCAGCAATGGTATGAGCTGGGTGCGGCAGGCCCCTGGACAAGGACTTGAGTGGATGGGATGG
ATCAGCACTAACAGCGGAAACACAAACTATGCGCAGAAATTTCAGGGCAGAGTCACCTTGACCACAGACACATCC
TCGACCACTACGTACCTGGATCTGAGGAGCCTGACATCTGACGACACGGCCATATATTACTGTGCGAGAGATGTT
CAATATCGTATGGACGTCTGGGGCCAAGGGACCACGGTCACCGTCTCTTCA

>B2-7_HC (SEQ ID NO: 449)
GAGGTGCAGCTGGTGGAGTCTGGGGGAGGCGTGGTCCAGCCCGGGAGGTCCCTGAGACTCTCCTGTGCAGCCTCT
GGATTCACCATCAGCAGTTATGGCATGCACTGGGTCCGCCAGGCTCCAGGCAAGGGGCTGGAGTGGGTGGCAGTT
ATATCATATGATGGAAGTAATAAATACTATGCAGACTCCGTGAAGGGCCGATTCACCATCTCCAGAGACAATTCC
AAGAACACGCTGTATCTGCAAATGAACAGCCTGAGAGTTGAGGACACGGCTGTGTATTACTGTGCGAAAGATCTC
TTATTACGATATTTTGACTGGAGCCCCAAATACTACTACAACGGTATGGACGTCTGGGGCCAAGGGACAATGGTC
ACCGTCTCCTCA

>B2-8_HC (SEQ ID NO: 450)
CAGGTGCAGCTGGTGCAATCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACGAATCC
ACGAGCACAGCCTACATGGAGCTGAGCAGCCTGAGATCTGAGGACACGGCCGTGTATTACTGTGCGAGAGTGGCA
GTGGCTGACACCTTCTTTGACTACTGGGGCCAGGGAACCCTGGTCACCGTCTCCTCA

>B2-9_HC (SEQ ID NO: 451)
CAGGTGCAGCTGGTGCAGTCTGGAGCTGAGGTGAAGAAGCCTGGGGCCTCAGTGAAGGTCTCCTGCAAGGCTTCT
GGTTACACCTTTACCAGCTATGGTATCAGCTGGGTGCGACAGGCCCCTGGACAAGGGCTTGAGTGGATGGGATGG
ATCAGCGCTTACAATGGTAACACAAACTATGCACAGAAGCTCCAGGGCAGAGTCACCATGACCACAGACACATCC
ACGAGCACAGCCTACATGGAGCTGAGGAGCCTGAGATCTGACGACACGGCCGTGTATTACTGTGCGAGAGACGGC
TACGGTATGGACGTCTGGGGCCAAGGGACCACGGTCACCGTCTCCTCA

>B2-10_HC (SEQ ID NO: 452)
CAGGTGCAGCTGGTGCAGTCTGGGGGAGGCTTGGTCCAGCCTGGGGGGTCCCTGAGACTCTCCTGTGCAGCCTCT
GGATTCACCTTTAGCAGCTATGCCATGAGCTGGGTCCGCCAGGCTCCAGGGAAGGGGCTGGAGTGGGTCTCAACT
ATTAATGATAGTGGTGGTAGCACATACTACGCAGACTCCGTGAAGGGCCGGTTCACCATCTCCAGAGACAATTCC
AAGAACACGCTGTATCTGCAAATGAACAGCCTGAGAGCCGAGGACACGGCCGTATATTACTGTGCGAAAGATCAT
ATTACGATTTTTGGAGTGGCCCCGTTTGACTACTGGGGCCTGGGAACCCTGGTCACCGTCTCCTCA

>B2-11_HC (SEQ ID NO: 453)
CAGGTGCAGCTACAGCAGTCAGGTCCAGGACTGGTGAAGCCCTCGCAGACCCTCTCACTCACCTGTGCCATCTCC
GGGGACAGTGTCTCTAGCAACAGTGCTGCTTGGAACTGGATCAGGCAGTCCCCATCGAGAGGCCTTGAGTGGCTG
GGAAGGACATACTACAGGTCCAAGTGGTATAATGATTATGCAGTATCTGTGAAAAGTCGAATAACCATCAACCCA
GACACATCCAAGAACCAGTTCTCCCTGCAGCTGAACTCTGTGACTCCCGAGGACACGGCTGTGTATTACTGTGCA
AGAGACAAGATGAATCGGCAGCCGATGATGCTTTTGATATCTGGGGCCAAGGAACCCTGGTCATCGTCTCCTCA

>B2-12_HC (SEQ ID NO: 454)
CAGGTGCAGCTGGTGCAGTCTGGAGATGAGGTGAAGAAGGCTGGGGCCTCAGTGAGGGTCTCCTGCAAGGCTTCT
GGTTACACGTTTCCCGACAACGGTATCAGTTGGGTGCGACAGGCCCCTGGACACGGGCTTGAGTGGATGGGTTGG
ATCAACGTTGACACTGGATACACCCACTATGCACAGAGGGTCCAGGACAGAGTCGTCATGACCACAGACACGTCC
ACGAACACACTCCACATGACATTGAGGAGCCTGACAACGGACGACACGGCCGTTTATTATTGTGCGAGAGAAATC
GAGGGAGTGTGGACAGCTTGGGGCCAGGGAACCCTGGTCATCGTCTCCTCA

TABLE 4-continued

DNA sequences of antibody heavy chains (HC)

>B2-13_HC (SEQ ID NO: 455)
CAGGTGCAGCTGGTGCAGTCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACGAATCC
ACGAGCACAGCCTACATGGAGCTGAGCAGCCTGAGATCTGAGGACACGGCCGTGTATTACTGTGCGAGGTCGGAC
TACGGTGACTCCTACTTTGACTACTGGGGCCAGGGAACCCTGGTCAGCGTCTCCTCA

>B2-14_HC (SEQ ID NO: 456)
CAGGTGCAGCTGGTGCAGTCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACGAATCC
ACGAGCACAGCCTACATGGAGCTGAGCAGCCTGAGATCTGAGGACACGGCCGTGTATTACTGTGCGAGAGCCTCT
ATGGTCGAGACTTACTTTGACTACTGGGGCCAGGGAACCATGGTCACCGTCTCTTCA

>B2-15_HC (SEQ ID NO: 457)
GAGGTGCAGCTGGTGCAGTCTGGAGCTGAGGTGAAGAAGTCTGGGGCCTCAGTGAAGGTCTCCTGCAAGTCTTCT
GGTTACACCTTTACCAACTATGGTATCAGTTGGGTGCGACAAGCCCCGGGACAAGGGCTTGAGTGGATGGGCTGG
ATCAGCGGTGACGCTGGTGACACAAAATTTGCACAGAAGTTCCAGGGCAGAGTCACCATGACGACAGACACATCC
ACGACTACAACGTACATGGAGCTGAGGAGCCTGAGATCTGACGACACGGCCGTGTATTACTGTGCGAGAGATGGG
GAATATATTCCTATGTTTCGGGGATTTGACAACTACTACGGTCTGGACGTCTGGGGCCAAGGGACCCTGGTCAGC
GTCTCCTCA

>B2-16_HC (SEQ ID NO: 458)
CAGGTGCAGCTGGTGCAGTCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACGAATCC
ACGAGCACAGCCTACATGGAGCTGAGCAGCCTGAGATCTGAGGACACGGCCGTGTATTACTGTGCGAGCGGGATT
ATACCTGATAATCCCTACGGTATGGACGTCTGGGGCCAAGGGACAATGGTCAGCGTCTCCTCA

>B2-17_HC (SEQ ID NO: 459)
GAGGTGCAGCTGTTGGACTCGGGCCCACGACTGTTGAAGCCTTCGGAGACCCTGTCCCTCACCTGCGGTGTGTCA
GGTGTCTCCACCAGCAGTACTCATTGGTGGAGTTGGGTCCGCCAGACCCCAGGGAAGGGGCTGGAGTGGATTGGT
GAAATCCTTCATAATGGAAACACCAACTCCAATCCGTCCCTCAAGAGTCGAGTCTCCATGTCGATTGACAAGTCG
AGGAACCAATTCTCCCTACAACTGAAGTCTATGACCGCCGCGGACACGGCCGTCTACTACTGTGCGTCAGCGTCG
CCTAACTGGGGAGCTAGCGGGGCTTTTGATGCCTGGGCCCAAGGGACAATGGTCACCGTCTCCTCA

>B2-18_HC (SEQ ID NO: 460)
CAGGTGCAGCTGGTGCAGTCTGGAGCTGAGGTGAAGAAGCCTGGGGCCTCAGTGAAGGTCTCCTGCAAGGCTTCT
GGTTACACCTTTACCAGGTATGGTTTCAGCTGGGTGCGACAGGCCCCTGGACAAGGGCTTGAGTGGATGGGATGG
ATCAGCGGTTACAATGGTAATACAAAGTATGCACAGAAGTTCCAGGGCAGAGTCACCATGACTACAGACACATCT
ACGAGCACAGCCTACATGGAGCTGAGGAGCCTAACATCTAACGACACGGCCGTTTATTACTGTGCGAGAGATCGG
GGTAGTGGTTATCTTGAATACTGGGGCCCGGGAACCCTGGTCACCGTCTCTTCA

>B2-22_HC (SEQ ID NO: 462)
CAGGTGCAGCTGGTGCAGTCTGGAGCTGAGGTGAAGAAGCCTGGGGCCTCAGTGAAGGTCTCCTGCAAGGCTTCT
GGTTACACCTTTACCAGCTATGGTATCAGCTGGGTGCGACAGGCCCCTGGACAAGGGCTTGAGTGGATGGGATGG
ATCAGCGCTTACAATGGTAACACAAACTATGCACAGAAGCTCCAGGGCAGAGTCACCATGACCACAGACACATCC
ACGAGCACAGCCTACATGGAGCTGAGGAGCCTGAGATCTGACGACACGGCCGTGTATTACTGTGCGAGAGTGGGC
AGCTATGGTGACTACTGGGGCCAGGGAACCCTGGTCACCGTCTCCTCA

>B2-23_HC (SEQ ID NO: 463)
CAGGTGCAGCTGGTGCAGTCTGGGGCTGAGGTGAAGAAGCCTGGGGCCTCAGTGAAGGTTTCCTGCAAGGCATCT
GGGTACACCTTCACCCACTCCTATATACACTGGGTGCGCCAGGCCCCTGGACAAGGGCTTGAGTGGATGGGAGTA
ATCAACCCTGTTGGTGGTAGCACAACCTACGCACAGAGGTTCCAGGGCAGAGTCACCATGACCAGGGACACGTCC
ACGAGCACAGTCTACATGGAGCTGAGCAGCCTGAGATCTGAGGACACGGCCGTGTATTACTGTGCTAGAGCGGGG
GGAGATGGCTACAATCCTTACTTTGACTACTGGGGCCAGGGAACCCTGGTCACCGTCTCCTCA

>B2-24_HC (SEQ ID NO: 464)
CAGGTGCAGCTGGTGGAGTCTGGGGGAGGCTTGGTCAAGCCTGGAGGGTCCCTGAGACTCTCCTGTGCAGCCTCT
GGATTCACCTTCAGTGACTACTACATGAGCTGGATCCGCCAGGCTCCAGGGAAGGGGCTGGAGTGGGTTTCATAC
ATTAGTAGTAGTAGTAGTTACACAAACTACGCAGACTCTGTGAAGGGCCGATTCACCATCTCCAGAGACAACGCC
AAGAACTCACTGTATCTGCAAATGAACAGCCTGAGAGCCGAGGACACGGCCGTGTATTACTGTGCGAGAGTCGGA
GATCTTGATGCTTTTGATATCTGGGGCCAAGGGACAATGGTCACCGTCTCTTCA

>B2-25_HC (SEQ ID NO: 465)
CAGGTGCAGCTGGTGGAGTCTGGGGGAGGCTTGGTCAAGCCTGGAGGGTCCCTGAGACTCTCCTGTGCAGCCTCT
GGATTCACCTTCAGTGACCACTACATGAGCTGGATCCGCCAGGCTCCAGGAAAGGGGCTGGAGTGGGTTTCATAC
ATTACTACTACTGGTAGTACCATGTCCTACGCAGACTCTGTGAAGGGCCGCTTCACCATTTCCAGGGACAACTCC
AAGAACTCACTGCATCTGCAATTGAGCAGCCTGAGAGCCGAGGACACGGCCGTATATTACTGTGCGAGAGATTCC
ATACATGTGGATGGTGCTTTTGATATTTGGGGCCAAGGGACAATGGTCACCGTCTCCTCA

>B2-26_HC (SEQ ID NO: 466)
CAGGTGCAGCTGGTGCAGTCTGGAGCTGAGGTGAAGAAGCCTGGGGCCTCAGTGAAGGTCTCCTGCAAGGCTTCT
GGTTACACCTTTACCAGCTATGGTATCAGCTGGGTGCGACAGGCCCCTGGACAAGGGCTTGAGTGGATGGGATGG
ATCAGCGCTTACAATGGTAACACAAACTATGCACAGAAGCTCCAGGGCAGAGTCACCATGACCACAGACACATCC
ACGAGCACAGCCTACATGGAGCTGAGGAGCCTGAGATCTGACGACACGGCCGTGTATTACTGTGCGAGAGATCGG
GGAGGGTGGTTCGACCCCTGGGGCCAGGGAACCCTGGTCATCGTCTCCTCA

TABLE 4-continued

DNA sequences of antibody heavy chains (HC)

>B2-27_HC (SEQ ID NO: 467)
CAGGTGCAGCTGGTGCAGTCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACGAATCC
ACGAGCACAGCCTACATGGAGCTGAGCAGCCTGAGATCTGAGGACACGGCCGTGTATTACTGTGCGAGAGAGTCG
TATAGCAGCTCGTCCTTTGACTACTGGGGCCAGGGAACCACGGTCAGCGTCTCCTCA

>B2-30_HC (SEQ ID NO: 468)
CAGGTGCAGCTGGTGGAGTCTGGGGGAGGCTTGGTACAGCCTGGGGGGTCCCTGAGACTCTCCTGTGCAGCCTCT
GGATTCACCTTCAGTAGCTACGACATGCACTGGGTCCGCCAAGCTACAGGGAAAAGGTCTGGAGTGGGTCTCAGCT
ATTGGTACTGCTGGTGACACATACTATCCAGGCTCCGTGAAGGGCCGATTCACCATCTCCAGAGAAAATGCCAAG
AACTCCTTGTATCTTCAAATGAACAGCCTGAGAGCCGGGGACACGGCTGTGTATTACTGTCAAGGGCGAAGGAA
TATTGTAGTGGTGGTAGCTGCCAAGATGCTTTTGATATCTGGGGCCAAGGGACAATGGTCAGCGTCTCCTCA

>HCB2-1c_HC (SEQ ID NO: 469)
GAAGTGCAGCTGGTGCAGTCTGGGGCTGAGGTGAAGAAGCCTGGGGCCTCAGTGAAGGTTGCCTGCAAGGCATCT
GGGTACACCTTCACCGACTATTATATACACTGGGTGCGACAGGCCCCTGGACAAGGGCTTGAGTGGATGGGAATA
GTCAACGCTAATGGTGGTGACACAAACTACGCACAACAGTTCCAGGGCAGAGTCACCATGACCAGGGACACGTCC
ACGAGCACAGTCTATTTGGAGTTGACCAGCCTGAGATCTGACGACACGGCCGTATATTACTGTGCTAGAGATTGG
TATTACTATTCTTCGGGGAGTTTCCCTTTTGACTACTGGGGCCAGGGAACCCTGGTCAGCGTCTCCTCA

>HCB2-1d_HC (SEQ ID NO: 470)
GAAGTGCAGCTGGTGCAGTCTGGGGCTGAGGTGAAGAAGCCTGGGGCCTCAGTGAAGGTTGCCTGCAAGGCATCT
GGGTACACCTTCACCGACTATTATATACACTGGGTGCGACAGGCCCCTGGACAAGGGCTTGAGTGGATGGGAATA
GTCAACGCTAATGGTGGTGACACAAACTACGCACAACAGTTCCAGGGCAGAGTCACCATGACCAGGGACACGTCC
ACGAGCACAGTCTATTTGGAGTTGACCAGCCTGAGATCTGACGACACGGCCGTATATTACTGTGCTAGAGATTGG
TATTACTATTCTTCGGGGAGTTTCCCTTTTGACTACTGGGGCCAGGGAACCCTGGTCAGCGTCTCCTCA

>HCB2-2_HC (SEQ ID NO: 471)
CAGGTGCAGCTGGTGCAGTCTGGAGCTGAGGTGAAGAAGCCTGGGGCCTCAGTGAAGGTCTCCTGCAAGGCTTCT
GGTTACATCTTCAACACCTATGGTATCAGTTGGGTGCGACAGGCCCCTGGACAAGGACTTGAGTGGATGGGATGG
ACCAACGTTTACAATAGTAACACAGACAGTGGACACAAGTTCCAGGGCAGAGTCACCATGACCACAGACACATCC
ACGGACACAGCCTACATGGAACTGAGGGAGCCTGAGATCTGACGACACGGCCGTGTATTACTGTGCGAGAGACCCG
GGCTCGGCTATTTTTGATATGTGGGGCCAAGGGACAATGGTCACCGTCTCCTCA

>HCB2-4_HC (SEQ ID NO: 472)
CAGGTGGAGCTGCAGGAGTCGGGCCCAGGACTGGTGAAGCCTTCGGAGACCCTGTCCCTCACTTGCACTGTCTCT
GGTGACGCCATCAAAGATAAGTACTGGAGTTGGGTCCGGCAGCCCCCAGGGAAGGGACTGGAGTGGATTGGCTAC
ATCTCTAACAGTGGAAGCACCAACTACAACCCCTCCCTCAAGAGTCGAGTCAGTCTATCAGTAGACACGTCCAAG
AATCAGTTCTCCCTGAAGCAGACCTCTGTGACCGCTGCGGACACGGCCACATATTACTGTGCGAGAGGCAGCGGT
TATACTGCTTTTGATATCTGGGGCCAAGGGACAATGGTCACCGTCTCCTCA

>HCB2-5_HC (SEQ ID NO: 473)
CAGGTGCAGCTGGTGGAGTCTGGGGGAGGCTTGGTACAGCCTGGGGGGTCCCTGAGACTCTCCTGTGCAGCCTCT
GGATTCACCTTTAGCAGCTATGCCATGAGCTGGGTCCGCCAGGCTCCAGGGAAGGGGCTGGAGTGGGTCTCAGCT
ATTAGTGGTAGTGGTGGTAGCACATACTACGCAGACTCCGTGAAGGGCCGGTTCACCATCTCCAGAGACAATTCC
AAGAACACGCTGTATCTGCAAATGAACAGCCTGAGAGCCGAGGACACGGCCGTATATTACTGTGCGAAAGATGTC
GACCCCTATAGTAGTGGTTATTTTGACTACTGGGGCCAGGGAACCCTGGTCATCGTCTCCTCA

>HCB2-10_HC (SEQ ID NO: 474)
CAGGTGCAGCTGGTGGAGTCTGGGGGAGGCTTGGTACAGCCTGGGGGGTCCCTGAGACTCTCCTGTGCAGCCTCT
GGATTCACCTTTAGCAACTATGCCATGAGCTGGGTCCGCCAGGCTCCAGGGAAGGGGCTGGAGTGGGTCTCAGCC
ATTAGTGGTAGTAGTATTAGCACATACTACGCAGACTCCGTGAAGGGCCGGTTCACCATCTCCAGAGACAATTCC
AAGAACACGCTTTATCTGCAAATGAACAGCCTGAGAGCCGAGGACACGGCCGTATATTACTGTGCGTCCTCGGGT
TTCGGGTCCTTTGACTACTGGGGCCAGGGCACCCTGGTCACCGTCTCTTCA

>HCB2-13_HC (SEQ ID NO: 475)
CAGGTGCAGCTGGTGGAGTCTGGGGGAGGCTTGGTACAGCCTGGGGGGTCCCTGAGACTCTCCTGTGCAGCCTCT
GGATTCACCTTAAGTAGCTATGCCATGAGCTGGGTCCGCCAGGCTCCAGGGGAGGGGCTGGAGTGGGTCTCAAGT
ATTAATAGTGGTGGTAGCACATACTACGCAGGCTCCGTGAGGGGCCGGTTCACCATCTCCAGAGACAATTCCAAG
AACACGTTGTATCTGCAAATGAACAGCCTGAGAGCCGAGGACACGGCCGTATATTACTGTGCGAAAGCGAAGAGT
TATAGCAGTGACCTTGACCACTGGGGCCAGGGAACCACGGTCACCGTCTCTTCA

>HCB2-14_HC (SEQ ID NO: 476)
CAGGTGCAGATGGTGGAGTCTGGGGGAGGCTTGGTACAGCCTGGGGGGTCCCTGAGACTCTCCTGTGCAGCCTCT
GGATTCACCTTTAGCAGCTATGCCATGAGCTGGGTCCGCCAGGCTCCAGGGAAGGGGCTGGAGTGGGTCTCAGCT
ATTAGTGGTAGTGGTGGTAGCACATACTACGCAGACTCCGTGAAGGGCCGGTTCACCATCTCCAGAGACAATTCC
AAGAACACGCTGTATCTGCAAATGAACAGCCTGAGAGCCGAGGACACGGCCGTATATTACTGTGCGAAAGATCTT
CTCGGGGATAGTGGGAGCTACCCTGCTTTTGATATCTGGGGCCAAGGGACAATGGTCACCGTCTCTTCA

>HCB2-15_HC (SEQ ID NO: 477)
CAGGTGCAGATGGTGGAGTCTGGGGGAGACTTGGTACAGCCAGGGCAATCCCTGAGACTCTCCTGTGTAACTTCT
GGATTCCCCTTTGCGGACTATGCTATGAGCTGGTTCCGCCAGGCTCCAGGGCAGCGGCCGGAGTGGATAGGTTAC
ATTAAAAGCAAGACTAGAGATGGGACAACAAAATACGCCGAGTCTCTGCGAGGCAGATTCACCATCTCAAGAGAT
GATTCCAAAAGCATCGCCTATCTACAAATGAACAACTTAAAAAGGGAAGACACAGCCGTCTATTACTGTGCCCTC
GGGGGAGCAGCAGCTCTATGGGGCCCGGGAACCCTGGTCAGCGTCTCCTCA

TABLE 4-continued

DNA sequences of antibody heavy chains (HC)

>HCB2-17_HC (SEQ ID NO: 478)
CAGGTGCAGCTGGTGCAGTCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACGAATCC
ACGAGCACAGCCTACATGGAGCTGAGCAGCCTGAGATCTGAGGACACGGCCGTGTATTACTGTGCGATTAGTAGT
GGTTATTATTATAACCCATTTGACTACTGGGGCCAGGGAACCCTGGTCACCGTCTCCTCA

>HCB2-18_HC (SEQ ID NO: 479)
CAGGTGCAGCTGGTGCAGTCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACGAATCC
ACGAGCACAGCCTACATGGAGCTGAGCAGCCTGAGATCTGAGGACACGGCCGTGTATTACTGTGCGAGAGGGGGA
TACCAGCCACTGGATTACTGGGGCCAGGGAACCCTGGTCATCGTCTCCTCA

>HCB2-24_HC (SEQ ID NO: 480)
CAAATGCAGCTGGAGCAGTCTGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAGGG
ATCATCCCTATCTTTGGTACAGCAAACTACGCACAGAAGTTCCAGGGCAGAGTCACGATTACCGCGGACAAATCC
ACGAGCACAGCCTACATGGAGCTGAGCAGCCTGAGATCTGAGGACACGGCCGTGTATTACTGTGCGAGAGCTGGG
GGAATCCATTACTATGATAGTTTAGACTACTGGGGCCAGGGAACCCTGGTCACCGTCTCCTCA

>HCB2-27_HC (SEQ ID NO: 481)
CAGGTGCAGCTGGTGGAGTCTGGGGGAGGCTTGGTAAAGCCGGGGGGGTCTCTAAGACTCTCCTGTGCAGCCTCT
GGATTCACCTTCGCGAATGCCTGGATGGGCTGGGTTCGCCAGGCTCCAGGGAAGGGGCTGCAGTGGGTATCCCAT
ATTAAGCCCAGTTCTAGCGGCGGGAGGACAACAGACTACGATGCACCCGTGAAAGGCCGATTCACCATCTCAAGA
GATGATTCAAACGACACGGTGTATCTGCAAATGAACAGCCTCAAGACCGAAGACACAGGCGTCTATTACTGTGTC
ACAGGAAGAAGGGTCGCGAAGACTTTTGATTTCTGGGGCCAGGGGACAACGGTCAGCGTCTCCTCA

TABLE 5

Amino acid sequences of antibody heavy chains (HC)

>82-19_HC (SEQ ID NO: 498)
QVQLVQSGGGLVKPGGSLRLSCAASGFTFSNAWMSWVRQAPGKGLEWVGRIKSKTDGGTTDYAAPVKGRFTISRD
DSKNTLYLQMNSLKTEDTAVYYCTTDRYSSSWYSPAFDIWGQGTTVSVSS

>B2-1_HC (SEQ ID NO: 482)
EVQLVQSGAEVKKPGSSVKVSCKASGGTFSSYAISWVRQAPGQGLEWMGGIIPIFGTANYAQKFQGRVTITADKS
TSTAYMELSSLRSEDTAVYYCARGNQGDTAFDIWGQGTTVIVSS

>82-2_HC (SEQ ID NO: 483)
QVQLVQSGAEVKKPGASVKVSCKASGYTFSDYGFSWVRQAPGQGLEWMGWISGYNGNTNYAQKFQGRVTMTIDAS
TSTAYMELRSLKSDDTAVYYCARLLLGYYGMDVWGQGTTVTVSS

>B2-3_HC (SEQ ID NO: 484)
QVQLVQSGAEVKKPGASVKVSCRTSGYTFSSYGISWVRQAPGQGLEWMGWISGNTGNTKYTPKLQGRVTMTTDTS
TSTAYMELRSLRSDDTAVYYCARDRGIAAGRAFDIWGQGTMVTVSS

>82-4_HC (SEQ ID NO: 485)
QVQLVQSGPTVRKPGASVRVSCRASGYPFTSNGMSWVRQAPGQGLEWMGWTSTNSGNTNY
AQKFQGRVTLTTDTSSTTTYLDLRSLTSDDTAIYYCARDVQYRMDVWGQGTTVTVSS

>82-7_HC (SEQ ID NO: 486)
EVQLVESGGGVVQPGRSLRLSCAASGFTISSYGMHWVRQAPGKGLEWVAVISYDGSNKYYADSVKGRFTISRDNS
KNTLYLQMNSLRVEDTAVYYCAKDLLLRYFDWSPKYYYNGMDVWGQGTMVTVSS

>B2-8_HC (SEQ ID NO: 487)
QVQLVQSGAEVKKPGSSVKVSCKASGGTFSSYAISWVRQAPGQGLEWMGGIIPIFGTANYAQKFQGRVTITADES
TSTAYMELSSLKSEDIAV Y YCARVAVADTFFDYWGQGTLVTVSS

>82-9_HC (SEQ ID NO: 488)
QVQLVQSGAEVKKPGASVAVSCKASGYTFTSYGISWVRQAPGQGLEWMGWISAYNGNTNYAQKLQGRVTMTTDTS
TSTAYMELRSLRSDDTAVYYCARDGYGMDVWGQGTTVTVSS

>82-10_HC (SEQ ID NO: 489)
QVQLVQSGGGLVQPGGSLRLSCAASGFTFSSYAMSWVRQAPGKGLEWVSTINDSGGSTYYADSVKGRFTISRDNS
KNTLYLQMNSLRAEDTAVYYCAKDHITIFGVAPFDYWGLGTLVTVSS

>B2-11_HC (SEQ ID NO: 490)
QVQLQQSGPGLVKPSQTLSLTCAISGDSVSSNSAAWNWIRQSPSRGLEWLGRTYYRSKWYNDYAVSVKSRITINP
DTSKNQFSLQLNSVTPEDTAVYYCARQDESAADDAFDIWGQGTLVIVSS

>82-12_HC (SEQ ID NO: 491)
QVQLVQSGDEVKKAGASVRVSCKASGYTFPDNGISWVRQAPGHGLEWMGWTNVDTGYTHYAQRVQDRVVMTTDTS
TNTLHMTLRSLTTDDTAVYYCAREIEGVWTAWGQGTLVIVSS

TABLE 5-continued

Amino acid sequences of antibody heavy chains (HC)

>B2-13_HC (SEQ ID NO: 492)
QVQLVQSGAEVKKPGSSVKVSCKASGGTFSSYAISWVRQAPGQGLEWMGGIIPIFGTANYAQRFQGRVTITADES
TSTAYMELSSLRSEDTAVYYCARSDYGDSYFDYWGQGTLVSVSS

>B2-14_HC (SEQ ID NO: 493)
QVQLVQSGAEVKKPGSSVKVSCKASGGTFSSYAISWVRQAPGQGLEWMGGIIPIFGTANYAQKFQGRVTITADES
TSTAYMELSSLRSEDTAVYYCARASMVETYFDYWGQGTMVTVSS

>82-15_HC (SEQ ID NO: 494)
EVQLVQSGAEVKKSGASVKVSCKSSGYTFTNYGISWVRQAPGQGLEWMGWISGDAGDTKFAQKFQGRVIMTTDTS
TTTTYMELRSLRSDDTAVYYCARDGEYIPMFRGFDNYYGLDVWGQGTLVSVSS

>B2-16_HC (SEQ ID NO: 495)
QVQLVQSGAEVKKPGSSVKVSCKASGGTFSSYAISWVRQAPGQGLEWMGGIIPIFGTANYAQKFQGRVTITADES
TSTAYMELSSLRSEDTAVYYCASGIIPDNPYGMDVWGQGTMVSVSS

>82-17_HC (SEQ ID NO: 496)
EVQLLDSGPRLLKPSETLSLTCGVSGVSTSSTHWWSWVRQTPGKGLEWIGEILHNGNTNSNPSLKSRVSMSIDKS
RNQFSLQLKSMTAADTAVYYCASASPNWGASGAFDAWAQGTMVTVSS

>82-18_HC (SEQ ID NO: 497)
QVQLVQSGAEVKKPGASVKVSCKASGYTFTRYGFSWVRQAPGQGLEWMGWISGYNGNTKYAQKFQGRVTMTTDTS
TSTAYMELRSLTSNDTAVYYCARDRGSGYLEYWGPGTLVTVSS

>B2-22_HC (SEQ ID NO: 499)
QVQLVQSGAEVKKPGASVKVSCKASGYTFTSYGISWVRQAPGQGLEWMGWISAYNGNTNYAQKLQGRVTMTTDTS
TSTAYMELRSLRSDDTAVYYCARVGSYGDYWGQGTLVTVSS

>82-23_HC (SEQ ID NO: 500)
QVQLVQSGAEVKKPGASVKVSCRASGYTFTHSYIHWVRQAPGQGLEWMGVINPVGGSTTYAQRFQGRVTMTRDTS
TSTVYMELSSLRSEDTAVYYCARAGGDGYNPYFDYWGQGTLVTVSS

>B2-24_HC (SEQ ID NO: 501)
QVQLVESGGGLVKPGGSLRLSCAASGFTFSDYYMSWIRQAPGKGLEWVSYISSSSSYTNYADSVKGRFTISRDNA
KNSLYLQMNSLRAEDTAVYYCARVGDLDAFDIWGQGTMVTVSS

>82-25_HC (SEQ ID NO: 502)
QVQLVESGGGLVKPGGSLRLSCAASGFTFSDHYMSWIRQAPGKGLEWVSYITTTGSTMSYADSVKGRFTISRDNS
KNSLHLQLSSLRAEDTAVYYCARDSIHVDGAFDIWGQGTMVTVSS

>82-26_HC (SEQ ID NO: 503)
QVQLVQSGAEVKKPGASVKVSCKASGYTFTSYGISWVRQAPGQGLEWMGWISAYNGNTNYAQKLQGRVTMTTDTS
TSTAYMELRSLRSDDTAVYYCARDRGGWFDPWGQGTLVIVSS

>B2-27_HC (SEQ ID NO: 504)
QVQLVQSGAEVKKPGSSVKVSCKASGGTFSSYAISWVRQAPGQGLEWMGGIIPIFGTANYAQKFQGRVTITADES
TSTAYMELSSLRSEDTAVYYCARESYSSSSFDYWGQGTTVSVSS

>82-30_HC (SEQ ID NO: 505)
QVQLVESGGGLVQPGGSLRLSCAASGFTFSSYDMHWVRQALGKGLEWVSALGIAGDIYYPGSVKGRFTISRENAK
NSLYLQMNSLRAGDTAVYYCARAKEYCSGGSCQDAFDIWGQGTMVSVSS

>HCB2-1c_HC (SEQ ID NO: 506)
EVQLVQSGAEVKKPGASVKVACKASGYTFTDYYIHWVRQAPGQGLEWMGIVNANGGDTNYAQQFQGRVTMTRDTS
TSTVYLELTSLRSDDTAVYYCARDWYYYSSGSFPFDYWGQGTLVSVSS

>HCB2-1d_HC (SEQ ID NO: 507)
EVQLVQSGAEVKKPGASVKVACKASGYTFTDYYIHWVRQAPGQGLEWMGIVNANGGDTNYAQQFQGRVTMTRDTS
TSTVYLELTSLRSDDTAVYYCARDWYYYSSGSFPFDYWGQGTLVSVSS

>HCB2-2_HC (SEQ ID NO: 508)
QVQLVQSGAEVKKPGASVKVSCKASGYIFNTYGISWVRQAPGQGLEWMGWTNVYNSNTDSGHKFQGRVTMTTDTS
TDTAYMELRSLRSDDTAVYYCARDPGSAIFDMWGQGTMVTVSS

>HCB2-4_HC (SEQ ID NO: 509)
QVELQESGPGLVKPSETLSLTCTVSGDAIKDKYWSWVRQPPGKGLEWIGYISNSGSTNYNPSLKSRVSLSVDTSK
NQFSLKQTSVTAADTATYYCARGSGYTAFDIWGQGTMVTVSS

>HCB2-5_HC (SEQ ID NO: 510)
QVQLVESGGGLVQPGGSLRLSCAASGFFFSSYAMSWVRQAPGKGLEWVSAISGSGGSFYYADSVKGRFFISRDNS
KNFLYLQMNSLRAEDFAVYYCAKDVDPYSSGYFDYWGQGFLVIVSS

>HCB2-10_HC (SEQ ID NO: 511)
QVQLVESGGGLVQPGGSLRLSCAASGFFFSNYAMSWVRQAPGKGLEWVSAISGSSISFYYADSVKGRFFISRDNS
KNFLYLQMNSLRAEDFAVYYCASSGFGSFDYWGQGFLVFVSS

TABLE 5-continued

Amino acid sequences of antibody heavy chains (HC)

>HCB2-13_HC (SEQ ID NO: 512)
QVQLVESGGGLVQPGGSLRLSCAASGFTLSSYAMSWVRQAPGEGLEWVSSINSGGSTYYAGSVRGRFTISRDNSK
NTLYLQMNSLRAEDTAVYYCAKAKSYSSDLDHWGQGTTVTVSS

>HCB2-14_HC (SEQ ID NO: 513)
QVQMVESGGGLVQPGGSLRLSCAASGFTFSSYAMSWVRQAPGKGLEWVSAISGSGGSTYYADSVKGRFTISRDNS
KNTLYLQMNSLRAEDTAVYYCAKDLLGDSGSYPAFDIWGQGTMVTVSS

>HCB2-15_HC (SEQ ID NO: 514)
QVQMVESGGDLVQPGQSLRLSCVTSGFPFADYAMSWFRQAPGQRPEWIGYIKSKTRDGTTKYAESLRGRFTISRD
DSKSIAYLQMNNLKREDTAVYYCALGGAAALWGPGTLVSVSS

>HCB2-17_HC (SEQ ID NO: 515)
QVQLVQSGAEVKKPGSSVKVSCKASGGTFSSYAISWVRQAPGQGLEWMGGIIPIFGTANYAQKFQGRVTIFADES
TSTAYMELSSLRSEDTAVYYCAISSGYYYNPFDYWGQGTLVTVSS

>HCB2-18_HC (SEQ ID NO: 516)
QVQLVQSGAEVKKPGSSVKVSCKASGGTFSSYAISWVRQAPGQGLEWMGGIIPIFGTANYAQKFQGRVTIFADES
FSFAYMELSSLRSEDFAVYYCARGGYQPLDYWGQGFLVIVSS

>HCB2-24_HC (SEQ ID NO: 517)
QMQLEQSGAEVKKPGSSVKVSCKASGGFFSSYAISWVRQAPGQGLEWMGGIIPIFGFANYAQKFQGRVFIFADKS
FSFAYMELSSLRSEDFAVYYCARAGGIHYYDSLDYWGQGFLVFVSS

>HCB2-27_HC (SEQ ID NO: 518)
QVQLVESGGGLVKPGGSLRLSCAASGFFFANAWMGWVRQAPGKGLQWVSHIKPSSSGGRFFDYDAPVKGRFFISR
DDSNDFVYLQMNSLKFEDFGVYYCVFGRRVAKFFDFWGQGFFVSVSS

TABLE 6

DNA sequences of LILRB2 antibody light chains (LC)

>B2-19_LC (SEQ ID NO: 535)
CAGCCTGTGCTGACTCAGCCACCCTCAGTGTCTGAAGCCCCCAGGCAGAGGGTCACCATCTCCTGTTCTGGAAGC
AGCTCCAACATCGGAAATAATGTTGTAAACTGGTACCAGCAGCTCCCAGGAAAGGCTCCCAAACTCCTCATCTAT
TATGATGATCTGCTGCCCTCAGGGGTCTCTGACCGATTCTCTGGCTCCAAGTCTGGCACCTCAGCCTCCCTGGCC
ATCAGTGGGCTCCAGTCTGAGGATGAGGCTGATTATTACTGTGCAACATGGGATGACAGCCTGAATGGCCCTGTA
TTCGGCGGAGGGACCAAGCTGACCGTCCTA

>B2-1_LC (SEQ ID NO: 519)
CAGTCTGCCCTGAATCAGCCTGCCTCCGTGTCTGGGTCTCCTGGACAGTCGATCACCATCTCCTGCACTGGAACC
AGCAGTGACGTTGGTGGTTATAACTATGTCTCCTGGTACCAACAACACCCAGGCAAAGCCCCCAAACTCATGATT
TATGATGTCAGTAATCGGCCCTCAGGGGTTTCTAATCGCTTCTCTGGCTCCAAGTCTGGCAACACGGCCTCCCTG
ACCATCTCTGGGCTCCAGGCTGAGGACGAGGCTGATTATTACTGCAGCTCATATACAAGCAGCAGCACTCCTTAT
GTCTTCGGAACTGGGACCAAGGTCACCGTCCTA

>B2-2_LC (SEQ ID NO: 520)
GACATCGTGATGACCCAGTCTCCATCCTCCCTGTCTGCATCTGTAGGAGACAGAGTCACCCTCACTTGCCGGGCA
AGTCAGAGCATTGGCAACTATTTAAATTGGTATCAACAGAAACCAGGGAAAGCCCCTAACCTCCTGATCTATGCT
GCATCCAGTTTGCAAAGTGGGGTCCCATCAAGGTTCAGTGGCAGTGGATCTGGGACAGATTTCACTCTCACCATC
AGCAGTCTGCAGCCTGAAGATTTTGCAACTTACTACTGTCAACAGAGTTTCAGTATCCCCCCGATAACTTTCGGC
CAAGGGACACGACTGGAGATTAAA

>B2-3_LC (SEQ ID NO: 521)
CAGCCTGTGCTGACTCAGCCACCCTCAGCGTCTGGGACCCCCGGCCAGAGGGTCACCATCTCTTGTTCTGGAAGC
AGCTCCAACATCGGAACTAATCCTGTAAACTGGTACCAGCAAGTCCCAGGAACGGGCCCCAAACTCCTCATCTAT
AATAATAATCAGTGGCCCTCAGGGGTCCCTGACCGATTCTCTGGCTCCAAGTCTGCCACCTCAGCCTCCCTGGCC
ATCTATGGGCTCCAGTCTGGGGATGAGGCTCATTATTACTGTTCGTCATGGGACGACAGCCTGAGTGCGTGGGTG
TTCGGCGGAGGGACCAAGGTCACCGTCCTA

>B2-4_LC (SEQ ID NO: 522)
CAGTCTGTGCTGACTCAGCCACCCTCAGCGTCTGGGACCCCCGGGCAGAGGGTCACCATCTCTTGTTCTGGAAGC
AGGTCCAACATCGGAAGTAATCCTGTAAACTGGTATCAGCACCTCCCAGGAACGGCCCCCAAACTCCTCGTCTAT
AGTAATAATCGGCGGCCCTCAGGGGTCCCTGACCGATTCTCTGGCTCCAAGTCTGGCACCTCAGCCTCCCTGTCC
ATCAGTGGGCTCCAGTCTGAGGATGAAGGTGTTTATTACTGTGCAGCGTGGGATGACAACGTGCACGGAGTTTTC
GGCGGAGGGACCAAGGTCACCGTCCTA

>B2-7_LC (SEQ ID NO: 523)
CAGTCTGTGCTGACTCAGCCACCCTCGGTGTCAGTGGCCCCAGGAAAGACGGCCAGGATTACCTGTGGGGGAAAC
AACATTGGAAGTAAAAGTGTGCACTGGTACCAGCAGAAGCCAGGCCAGGCCCCTGTGCTGGTCGTCTATGATGAT
AGCGACCGGCCCTCAGGGATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAGTGATCATCCGGGGGTCTTC
GGAACTGGGACCAAGGTCACCGTCCTA

TABLE 6-continued

DNA sequences of LILRB2 antibody light chains (LC)

>B2-8_LC (SEQ ID NO: 524)
CAGCCTGTGCTGACTCAGCCTGCCTCCGTGTCTGGGTCTCCTGGACAGTCGATCACCATCTCCTGCACTGGAACC
AGCAGTGACGTTGGTGGTTATAACTATGTCTCCTGGTACCAACAACACCCAGGCAAAGCCCCCAAACTCATGATT
TATGATGTCAGTAATCGGCCCTCAGGGGTTTCTAATCGCTTCTCTGGCTCCAAGTCTGGCAACACGGCCTCCCTG
ACCATCTCTGGGCTCCAGGCTGAGGACGAGGCTGATTATTACTGCAGCTCATATACAAGCAGCAGCACCCCTTAT
GTCTTCGGAACTGGGACCAAGGTCACCGTCCTA

>B2-9_LC (SEQ ID NO: 525)
CAGTCTCCATCCTCCCTGTCTGCATCTGTAGGCGACAGAGTCACCATCACTTGCCGGACAAGTCACACCGTTAAC
AGCTATCTAAATTGGTATCAACAAGAACCAGGGAAAGCCCCTAAACTCCTGATCTATGCTGCATCCAATTTGCAA
AGTGGGGTCCCGTCAAGGTTCAGTGGCAGTGGATCTGGGACAGATTTCTCTCTCACCATCCACAATCTGCAACCT
GAAGATTTTGCAACTTACTACTGTCAACAGAGTTACAGAACCCCTCTCACTTTTGGCCAGGGGACCAAAGTGGAT
ATCAAA

>B2-10_LC (SEQ ID NO: 526)
CAGTCTGTGCTGACTCAGCCACCCTCAGCGTCTGGAACCCCCGGGCAGAGGGTCACCATCTCTTGTTCTGGAAGC
AGCTCCAACATCGGAGGTAATCCTGTAAACTGGTACCAGCACCTCCCAGGAACGGCCCCCAAGCTCCTCATCTAT
TATAATGATCAGCGGCCTTCAGGGGTCCCTGACCGATTCTCTGGCTCCAAGTCTGGCACCTCAGCCTCCCTGGCC
ATCAGTGGACTCCAGTCTGAGGATGAGACTGATTATTACTGTGCAACATGGGATGACAGCCTGAATGGTTGGGTG
TTTGGCGGAGGGACCCAGCTGACCGTCCTA

>B2-11_LC (SEQ ID NO: 527)
CAGTCTGTGCTGACTCAGCCACCCTCAGCGTCTGGCACCCCCGGGCAGAGGGTCACCATCTCTTGTTCTGGAAGC
AAGTCCAACGTCGGAAATAATTTTGTACATTGGTACCAGCAACTCCCAGGGACGGCCCCCAAACTCCTCCTCTAT
AGCAATCTTGAGCGGTCCTCAGGGGTCCCTGAGCGATTCTCTGGCTCCAAGTCTGGCACCTCAGCCTACCTGGCC
ATCAGTGGGCTCCGGTCCGACGATGAGGCTGATTATTACTGTGCAGCATGGGATGACAGCCTGCCCGGTTGGGTG
TTCGGCGGAGGGACCAAGCTGACCGTCCTA

>B2-12_LC (SEQ ID NO: 528)
CAGCCTGTGCTGACTCAGCCACCCTCAGCGTCTGGGACCCCCGGGCAGAGGGTCACCATCTCTTGTTCTGGAAGC
AGCTCCAACATCGGAAGTAATCCTCTAAACTGGTACCAGCAACTCCCAGGAACGGCCCCCAAACTCCTCATCTAT
AATAATAATCAGCGGCCCTCAGGGGTCCCTGACCGATTCTCTGGCTCCAAGTCTGGCACCTCAGCCTCCCTGGCC
ATCAGTGGACTCCAGTCTGAGGATGAGGCTGATTATTACTGTGCGGCATGGGATGACAGCCTGAATGGTTGGGTG
TTCGGCGGAGGGACCCAGCTGACCGTCCTA

>B2-13_LC (SEQ ID NO: 529)
CAGGCTGTGGTGACTCAGCCTGCCTCCGTGTCTGGGTCTCCTGGACAGTCGGTCAGCATCTCCTGCACTGGAACC
AGCAGTGACGTTGGTGGTTTTAACTATGTCTCCTGGTATCAACAACACCCAGGCAAAGCCCCCAAACTCATGATT
TATGATGTCAGTAATCGGCCCTCAGGGGTTTCTAATCGCTTCTCTGGCTCCAAGTCTGGCAACACGGCCTCCCTG
ACCATCTCTGGGCTCCAGGCTGAGGACGAGGCTGATTATTACTGCAGCTCATATACAAGCAGCACCGCTCCTTAT
GTCTTCGGAACTGGGACCAAGGTCACCGTCCTA

>B2-14_LC (SEQ ID NO: 530)
CAGTCTGTGCTGACTCAGCCTCGCTCAGTGTCCGGGTCTCCTGGACAGTCAGTCACCATCTCCTGCACTGGAACC
AGCAGTGATGTTGGTGGTTATAACTATGTCTCCTGGTACCAACAACACCCAGGCAAAGCCCCCAAACTCATGATT
TCTGAGGTCAGTAAGCGGCCCTCAGGGGTCCCTGATCGCTTCTCTGGCTCCAAGTCTGGCAACACGGCCTCCCTG
ACCGTCTCTGGGCTCCAGGCTGAGGATGAGGCTGATTATTACTGCTCCTCATATGCAGGCGGGTACACCCCCTAT
GTCTTCGGAACTGGGACCAAGGTCACCGTCCTA

>B2-15_LC (SEQ ID NO: 531)
CAGTCTGTGCTGACTCAGCCACCCTCAGCGTCTGCGACCCCCGGGCAGAGGGTCACCATCTCTTGTTCTGGAAGA
AACGCCAACATCGGAAGTAATCCTGTAAACTGGTACCAGCAGCTCCCAGGAACGGCCCCCAGACTCGTCATGTAT
AGTAATAATCAGCGGCCCTCAGGGGTCCCTGACCGATTCTCTCGGCTCCAAGTCTGGCACCTCAGCCTCCCTGGCC
ATCAGTGGGCTCCAGTCTGAGGACGAGGCTGATTATTACTGTGAAGGATGGGATGACAGCCTGAATGGCTATGTC
TTCGGAACTGGGACCAAGGTCACCGTCCTA

>B2-16_LC (SEQ ID NO: 532)
GATATTGTGATGACTCAGTCTCCACTCTCCCTGCCCGTCACCCTTGGACAGCCGGCCTCCATCTCCTGCACGTCT
AGTCAAAGCCTCGTATACAGTGATGGAAACACCTACTTGAATTGGTTTCACCAGAGGCCAGGCCAGTCTCCAAGG
CGCCTATTTTATAAGGTTTCTAACCGGGCCTCTGGGGTCCCAGACAGATTCAGCGGCAGTGGGTCAGGCACTGAT
TTCACACTGAAAATCAGCAGGGTGGAGGCTGAGGATCTTGGGGTTTATTACTGCATGCAAGGTACACACTGGCCG
GTCACCTTCGGCCAAGGGACACGACTGGAGATTAAA

>B2-17_LC (SEQ ID NO: 533)
CAGTCTGTGCTGACTCAGCCACCCTCAGCGTCTGCGACCCCCGGGCAGAGGGTCACCATCTCTTGTTCTGGAAGC
AGCTCCAACATCGGAAGTAATCCTGTAAACTGGTATCAGCAGGTCCCAGGAATGGCCCCCGACTCGTCATGTAT
AGTGATAATCAGCGGCCCTCAGGGGTCCCTGACCGATTCTCTCGGCTCCAACTCTGGCACCTCAGCCTCCCTGGCC
ATCAGTGGCCTCCAGTCTGAGGATGAGGCTGATTATTACTGTTCAACATGGGATGACAGCCTGAATGGTCTTGTC
TTCGGAACTGGGACCAAGGTCACCGTCCTA

>B2-18_LC (SEQ ID NO: 534)
GACGTCCAGATGACCCAGTCTCCATCCTCCCTGTCTGCATCTGTAGGAGAGAGAGTCACCCTCACTTGCCGGGCG
AGTCAGGGCATTTACAGTTCTTTAGCCTGGTATCAGCAAAAACCAGGTAAAGCCCCTAAACTCCTACTATATGGT
ACGTCGCAATTGGAACGTGGGGTCCCATCCAGATTCAGTGGCAGTGGATCTGGGACGGATTACACTCTCACCATC
AGCAGCCTGCAGCCTGAAGATTCTGCAACTTATTATTGTCAACAACATTACAATCTACCCATCACCTTCGGCCAA
GGGACACGACTGGAGATTAAA

TABLE 6-continued

DNA sequences of LILRB2 antibody light chains (LC)

>B2-22_LC (SEQ ID NO: 536)
CAGTCTCCATCCTCCCTGTCTGCATCTGTAGGAGACAGAGTCACCATCACTTGCCGGGCGAGTCAGGGCATTAGC
AATTATTTAGCCTGGTATCAGCAGAAACCAGGGAAAGTTCCTAAGCTCCTGATCTATGCTGCATCCACTTTGCAA
TCAGGGGTCCCATCTCGGTTCAGTGGCAGTGGATCTGGGACAGATTTCACTCTCACCATCAGCAGCCTGCAGCCT
GAAGATGTTGCAACTTATTACTGTCAAAAGTATAACAGTGCCCCGCTCACTTTCGGCGGAGGGACCAAGCTGGAG
ATCAAA

>B2-23_LC (SEQ ID NO: 537)
CAGTCTCCTTCCACCCTGTCTGCATCTGTAGGAGACAGAGTCACCATCACTTGCCGGGCCAGTCAGAGTATTAGT
AGCTGGTTGGCCTGGTATCAGCAGAAACCAGGGAAAGCCCCTAAGCTCCTGATCTATAAGGCGTCTAGTTTAGAA
AGTGGGGTCCCATCAAGGTTCAGCGGCAGTGGATCTGGGACAGAATTCACTCTCACCATCAGCAGCCTGCAGCCT
GATGATTTTGCAACTTATTACTGCCAACAGTATAATAGTTATCTCACTTTCGGCGGAGGGACCAAAGTGGATATC
AAA

>B2-24_LC (SEQ ID NO: 538)
CAGTCTGTGCTGACTCAGCCACCCTCAGCGTCTGGGACCCCCGGGCAGAGGGTCACCATCTCTTGTTCTGGAAGC
AGCTCCAACATCGGAAGTAATTATGTATACTGGTACCAGCAGCTCCCAGGAACGGCCCCCAAACTCCTCATCTAT
AGGAATAATCAGCGGCCCTCAGGGGTCCCTGACCGATTCTCTGGCTCCAAGTCTGGCACCTCAGCCTCCCTGGCC
ATCAGTGGGCTCCGGTCCGAGGATGAGGCTGATTATTACTGTGCAGCATGGGATGACAGCCTGAGTGGTTGGGTG
TTCGGCGGAGGGACCAAGGTCACCGTCCTA

>B2-25_LC (SEQ ID NO: 539)
TCCTATGAGCTGACTCAGCCACCCTCGGTGTCAGTGGCCCCAGGACAGACGGCCAGGATTACCTGTGGGGGAAAC
AACATTGGAAGTAAAAGTGTGCACTGGTACCAGCAGAAGCCAGGCCAGGCCCCTGTGCTGGTCGTCTATGATGAT
AGCGACCGGCCCTCAGGGATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAGTGATCATTGGGTGTTCGGC
GGAGGGACCAAGCTGACCGTCCTA

>B2-26_LC (SEQ ID NO: 540)
CAGTCTCCATCCTCCCTGTCTGCATCTGTAGGAGACAGAGTCACCATCACTTGCCGGGCAAGTCAGAGCATAAGC
AACTTTGTAAATTGGTATCAGCAGAAACCAGGGAAGTCCCTAAGCTCCTGATCTACGGTGCATCCAGTTTGCAG
AGTGGGGTCCCATCAAGGTTCAGTGGCAGTGGATCTGGGACGGATTTCACTCTCACCATCAGCAGTCTGCAACCT
GAAGATTTTGCGACTTACTACTGTCAACAGGGTTACAGTGTCCCACTCACTTTCGGCGGAGGGACTACAGTGGAT
ATCAAA

>B2-27_LC (SEQ ID NO: 541)
CAGCCTGTGCTGACTCAGCCTGCCTCCGTGTCTGGGTCTCCTGGACAGTCGATCACCATCTCCTGCACTGGAACC
AGCAGTGACGTTGGTGGTTATAACTATGTCTCCTGGTACCAACAACACCCAGGCAAAGCCCCCAAACTCATGATT
TATGATGTCAGTAATCGGCCCTCGGGGGTTTCTAATCGCTTCTCTGGCTCCAAGTCTGGCAACTCGGCCTCCCTG
ACCATCTCTGGGCTCCAGGCTGAGGACGAGGCTGATTATTACTGCAGCTCATATACAAGCAGCAGCACTCCCTAT
GTCTTCGGAACTGGGACCAAGGTCACCGTCCTA

>B2-30_LC (SEQ ID NO: 542)
CAGTCTCCATCCTCCTTGTCTGCATCTGTAGGAGACAGAGTCACCATCACTTGCCGGGCAAGTCAGAGCATTAGG
ACCTACTTAAATTGGTATCAGCAGAAACCAGGCAAAGACCCTGAACTCCTGATCTATGCTGCAACCAGTTTGCAA
AGTGGGGTCCCATCAAGGTTCACTGGCAGCGGATCTGGGACAGACTTCACTCTCACCATCAGCAGTCTGCAGCCT
GAAGATTTTGCAACTTATTACTGTCAACAGAGTTACAGTGCCCCCGTGTTCACTTTTGGCCAGGGGACCAAGCTG
GAGATCAAA

>HCB2-1c_LC (SEQ ID NO: 543)
GCCATCCAGATGACCCAGTCTCCATCCTCCCTGTCTGCATCTGTAGGAGACAGAGTCTCCATCACTTGCCGGGCA
AGTCAGAGCATTAGCAGCTTTTTAAATTGGTATCAGCAGAAACCAGGGAAAGCCCCTGAGCTCCTGATCTATGGT
GCATCCAGCTTGCAAAGTGGGGTCCCATCAAGGTTCAGTGGCAGTGGATCTGGGACAGATTTCACTCTCACCATC
AGTAGTCTGCAACCTGAAGATTTTGCAACTTACTACTGTCAACAGAGTTACAGTATCCCGATCACCTTCGGCCAA
GGGACACAGCTGGAGATCAAA

>HCB2-1d_LC (SEQ ID NO: 544)
GACGTCCAGATGACCCAGTCCCCTTCCTCTTTATCCGCTAGCGTGGGCGATCGTGTGTCCATCACTTGTAAGGCC
TCCCAAGATGTGTCCATCGCCGTGGCTTGGTACCAGCAGAAGCCCGGCAAGGCCCCCAAGCTGCTGATCTACTCC
GCCAGCTATCGTTACACCGGCGTGCCCGATCGTTTCTCCGGCTCCGGATCCGGCACCGACTTCACTTTAACCATC
TCCTCTTTACAGCCCGAGGACTTCGCCGTCTACTACTGCCAGCAGCACTACATCACCCCTTTAACATTCGGCGCC
GGCACCAAGCTGGAGATCAAA

>HCB2-2_LC (SEQ ID NO: 545)
GACGTCCAGATGACCCAGTCTCCATCCTCCCTGTCTGCATCTGTAGGAGACAGAGTCTCCATCACTTGCCGGGCA
AGTCAGAGCATTAGCAGCTTTTTAAATTGGTATCAGCAGAAACCAGGGAAAGCCCCTGAGCTCCTGATCTATGGT
GCATCCAGCTTGCAAAGTGGGGTCCCATCAAGGTTCAGTGGCAGTGGATCTGGGACAGATTTCACTCTCACCATC
AGTAGTCTGCAACCTGAAGATTTTGCAACTTACTACTGTCAACAGAGTTACAGTATCCCGATCACCTTCGGCCAA
GGGACACGACTGGAGATCAAA

>HCB2-4_LC (SEQ ID NO: 546)
AACATCCAGATGACCCAGTCTCCATCCTCCCTGTCTGCATCTGTAGGAGACAGAGTCACCATCACTTGCCGGGCA
AGTCAGAGCATTAGCAGCTATTTAAATTGGTATCAGCAGAAACCAGGGAAAGCCCCTAAGCTCCTGATCTATGCT
GCATCCAGTTTGCAAAGTGGGGTCCCATCAAGGTTCAGTGGCAGTGGATCTGGGACAGATTTCACTCTCACCATC
AGCAGTCTGCAACCTGAAGATTTTGCAACTTACTACTGTCAACAGAGTTACAGTACCCCGCCCACTTTCGGCGGA
GGGACTACAGTGGAGATCAAA

TABLE 6-continued

_____

DNA sequences of LILRB2 antibody light chains (LC)
_____

>HCB2-5_LC (SEQ ID NO: 547)
GCCATCCAGATGACCCAGTCTCCATCTTCCGTGTCTGCATCTGTAGGAGACAGAGTCACCATCACTTGTCGGGCG
AGTCAGGGTATTGGCAGCTGGTTAGCCTGGTATCAGCAGAAACCAGGGAAAGCCCCTAAGCTCCTGATCTCTGTT
GCATCCAGTTTGCAAAGTGGGGTCCCATCAAGGTTCAGCGGCAGTGGATCTGGGACAGATTTCACTCTCACCATC
AGCAGCCTGCAGCCTGAAGATTTTGCAACTTACTATTGTCAACAGGCTAACAGTTTCCCGCTCACTTTTGGCGGA
GGGACTACAGTGGAGATCAAA

>HCB2-10_LC (SEQ ID NO: 548)
CAGCCACCCTCGGTGTCTGCAGCCCCCAGGCAGAGGGTCACCATCTCCTGTTCTGGAAGCAGCTCCAATATCGGA
GATAATTCTGTTAACTGGTACCAGCAGCTCCCAGGAAAGGCTCCCAAACTCCTCATTTATCTTGATGATCTCCTG
CCCTCAGGGGTCTCTGGCCGATTCTCTGGCTCCAAGTCTGGCACCTCAGCCTCCCTGGTCATCAGTGGCCTCCAG
TCTGAGGATGAGGCTGATTATTACTGTGCAACATGGGATGACAGCCTGAACGGTGTGGTTTTCGGCGGAGGGACC
AAGGTCACCGTCCTA

>HCB2-13_LC (SEQ ID NO: 549)
GATGTTGTGATGACGCAGTCTCCATCCTCCCTGAGTGTGTCAGCAGGAGAGAAGGTCACTATGAGCTGCAAGTCC
AGTCAGAGTCTGTTAAACAGTGGAAATCAAAAGACCTACTTGGCCTGGTACCAGCAGAAACCAGGGCAGCCTCCT
AAACTGTTGATCTACGGGGCATCCACTAGGGAATCTGGGGTCCCTGATCGCTTCACAGGCAGTGGATCTGGAACC
GATTTCACTCTTACCATCAGCAGTGTGCAGGCTGAAGACCTGGCAGTTTATTACTGTCAGAATGATCATAGTTAT
CCATTCACGTTCGGCTCGGGGACAAAGGTGGAAATCAAA

>HCB2-14_LC (SEQ ID NO: 550)
AACATCCAGATGACCCAGTCTCCATCCTCCCTGTCTGCATCTGTAGGAGACAGAGTCACCATCACTTGCCGGGCA
AGTCAGAGCATTAGCAGCTATTTAAATTGGTATCAGCAGAAACCAGGGAAAGCCCCTAAGCTCCTGATCTATGCT
GCATCCAGTTTGCAAAGTGGGGTCCCATCAAGGTTCAGTGGCAGTGGATCTGGGACAGATTTCACTCTCACCATC
AGCAGTCTGCAACCTGAAGATTTTGCAACTTACTACTGTCAACAGAGTTACAGTACCCCGTACACTTTTGGCCAG
GGGACCAAGCTGGAGATCAAA

>HCB2-15_LC (SEQ ID NO: 551)
CAGCCGCCCTCGGTGTCTGGGGCCCCAGGGCAGAGGGTCACCATCTCCTGCGCTGGGAGCAGCTCCAACATCGGG
GCAGGTTATGGTGTGCACTGGTATCAACACCTTCCAGGAACAGCCCCCAAACTCCTCATCTATGGTGACAACAAT
CGGCCCTCAGGGGTCCCTTACCGATTCTCTGGGTCCAAGTCTGGCACCTCAGCCTCCCTGGCCATCACTGGACTC
CAGGCTGAGGATGAGGCTGATTATTTCTGCCAGTCCTATGACAGCAGCCTGGGGGTTGGTGTGTTCGGCGGAGGG
ACCAAGGTCACCGTCCTAC

>HCB2-17_LC (SEQ ID NO: 552)
GCCATCCAGTTGACCCAGTCTCCATCCTCCCTGTCTGCATCTGTAGGAGACAGAGTCACCATCACTTGCCGGGCA
AGTCAGAGCATTAGCAGCTATTTAAATTGGTATCAGCAGAAACCAGGGAAAGCCCCTAAGCTCCTGATCTATGCT
GCATCCAGTTTGCAAAGTGGGGTCCCATCAAGGTTCAGTGGCAGTGGATCTGGGACAGATTTCACTCTCACCATC
AGCAGTCTGCAACCTGAAGATTTTGCAACTTACTACTGTCAACAGAGTTACAGTACCCCCCTCACTTTCGGCGGA
GGGACCAAGCTGGAGATCAAA

>HCB2-18_LC (SEQ ID NO: 553)
GACATCGTGATGACCCAGTCTCCATCCTCCCTGTCTGCATCTGTAGGAGACAGAGTCACCATCACTTGCCGGGCA
AGTCAGAGCATTAGCAGCTATTTAAATTGGTATCAGCAGAAACCAGGGAAAGCCCCTAAGCTCCTGATCTATGCT
GCATCCAGTTTGCAAAGTGGGGTCCCATCAAGGTTCAGTGGCAGTGGATCTGGGACAGATTTCACTCTCACCATC
AGCAGTCTGCAACCTGAAGATTTTGCAACTTACTACTGTCAACAGAGTTACAGTACCCCATTCACTTTCGGCCCT
GGGACCAAGCTGGAGATCAAA

>HCB2-24_LC (SEQ ID NO: 554)
GACGTCCAGATGACCCAGTCTCCATCCTCCCTGTCTGCATCTGTAGGAGACAGAGTCACCATCACTTGCCGGGCA
AGTCAGAGCATTAGCAGCTATTTAAATTGGTATCAGCAGAAACCAGGGAAAGCCCCTAAGCTCCTGATCTATGCT
GCATCCAGTTTGCAAAGTGGGGTCCCATCAAGGTTCAGTGGCAGTGGATCTGGGACAGATTTCACTCTCACCATC
AGCAGTCTGCAACCTGAAGATTTTGCAACTTACTACTGTCAACAGAGTTACAGTACCCCTCTGACGTTCGGCCAA
GGGACCAAGCTGGAGATCAAA

>HCB2-27_LC (SEQ ID NO: 555)
AACATCCAGATGACCCAGTCTCCATCCTCCCTGTCTGCATCTGTAGGAGACAGAGTCACCATCACTTGCCGGGCA
AGTCAGAGCATTAGCAGCTATTTAAATTGGTATCAGCAGAAACCAGGGAAAGCCCCTAAGCTCCTGATCTATGCT
GCATCCAGTTTGCAAAGTGGGGTCCCATCAAGGTTCAGTGGCAGTGGATCTGGGACAGATTTCACTCTCACCATC
AGCAGTCTGCAACCTGAAGATTTTGCAACTTACTACTGTCAACAGAGTTACAGTACCCCTCGGACGTTCGGCCAA
GGGACTACGGTGGAAATCAAA

_____

TABLE 7

_____

Amino acid sequences of LILRB2 antibody light chains (LC)
_____

>82-19_LC (SEQ ID NO: 572)
QPVLTQPPSVSEAPRQRVTISCSGSSSNIGNNVVNWYQQLPGKAPRLLIYYDDLLPSGVSDRFSGSKSGTSASLA
ISGLQSEDEADYYCATWDDSLNGPVFGGGTKLTVL

>B2-1_LC (SEQ ID NO: 556)
QSALNQPASVSGSPGQSITISCTGTSSDVGGYNYVSWYQQHPGKAPKLMIYDVSNRPSGVSNRFSGSKSGNTASL
TISGLQAEDEADYYCSSYTSSSTPYVFGTGTKVTVL

TABLE 7-continued

Amino acid sequences of LILRB2 antibody light chains (LC)

>82-2_LC (SEQ ID NO: 557)
DIVMTQSPSSLSASVGDRVTLTCRASQSIGNYLNWYQQKPGKAPNLLIYAASSLQSGVPSRFSGSGSGTDFTLTI
SSLQPEDFATYYCQQSFSIPPITFGQGTRLEIK

>B2-3_LC (SEQ ID NO: 558)
QPVLTQPPSASGTPGQRVTISCSGSSSNIGTNPVNWYQQVPGTGPKLLIYNNNQWPSGVPDRFSGSKSATSASLA
IYGLQSGDEAHYYCSSWDDSLSAWVFGGGTKVTVL

>82-4_LC (SEQ ID NO: 559)
QSVLTQPPSASGTPGQRVTTSCSGSRSNIGSNPVNWYQHLPGTAPKLLVYSNNRRPSGVPDRFSGSKSGTSASLS
ISGLQSEDEGVYYCAAWDDNVHGVFGGGTRVTVL

>82-7_LC (SEQ ID NO: 560)
QSVLTQPPSVSVAPGKTARITCGGNNIGSKSVHWYQQKPGQAPVLVVYDDSDRPSGIPERFSGSNSGNTATLTIS
RVEAGDEADYYCQVWDSSSDHPGVFGTGTKVTVL

>B2-8_LC (SEQ ID NO: 561)
QPVLTQPASVSGSPGQSITISCTGTSSDVGGYNYVSWYQQHPGKAPKLMIYDVSNRPSGVSNRFSGSKSGNTASL
TISGLQAEDEADYYCSSYTSSSTPYVFGTGTKVTVL

>82-9_LC (SEQ ID NO: 562)
QSPSSLSASVGDRVTITCRTSHTVNSYLNWYQQEPGKAPKLLIYAASNLQSGVPSRFSGSGSGTDFSLTIHNLQP
EDFATYYCQQSYRTPLTFGQGTKVDIK

>82-10_LC (SEQ ID NO: 563)
QSVLTQPPSASGTPGQRVTISCSGSSSNIGGNPVNWYQHLPGTAPKLLIYYNDQRPSGVPDRFSGSKSGTSASLA
ISGLQSEDETDYYCATWDDSLNGWVFGGGTQLTVL

>B2-11_LC (SEQ ID NO: 564)
QSVLTQPPSASGTPGQRVTISCSGSKSNVGNNFVHWYQQLPGTAPKLLLYSNLERSSGVPERFSGSKSGTSAYLA
ISGLRSDDEADYYCAAWDDSLPGWVFGGGTKLTVL

>82-12_LC (SEQ ID NO: 565)
QPVLTQPPSASGTPGQRVTISCSGSSSNIGSNPLNWYQQLPGTAPKLLIYNNNQRPSGVPDRFSGSKSGTSASLA
ISGLQSEDEADYYCAAWDDSLNGWVFGGGTQLTVL

>B2-13_LC (SEQ ID NO: 566)
QAVVTQPASVSGSPGQSVSISCTGTSSDVGGFNYVSWYQQHPGKAPKLMIYDVSNRPSGVSNRFSGSKSGNTASL
TISGLQAEDEADYYCSSYTSSTAPYVFGTGTKVTVL

>B2-14_LC (SEQ ID NO: 567)
QSVLTQPRSVSGSPGQSVTISCTGTSSDVGGYNYVSWYQQHPGKAPKLMISEVSKRPSGVPDRFSGSKSGNTASL
TVSGLQAEDEADYYCSSYAGGYTPYVFGTGTKVTVL

>82-15_LC (SEQ ID NO: 568)
QSVLTQPPSASATPGQRVTISCSGRNANIGSNPVNWYQQLPGTAPRLVMYSNNQRPSGVPDRFSGSKSGTSASLA
ISGLQSEDEADYYCEGWDDSLNGYVFGTGTKVTVL

>B2-16_LC (SEQ ID NO: 569)
DIVMTQSPLSLPVTLGQPASISCTSSQSLVYSDGNTYLNWFHQRPGQSPRRLFYKVSNRASGVPDRFSGSGSGTD
FTLKISRVEAEDLGVYYCMQGTHWPVTFGQGTRLEIK

>82-17_Lc (SEQ ID NO: 570)
QSVLTQPPSASATPGQRVTISCSGSSSNIGSNPVNWYQQVPGMAPELVMYSDNQRPSGVPDRFSGSNSGTSASLA
ISGLQSEDEADYYCSTWDDSLNGLVFGTGTKVTVL

>82-18_LC (SEQ ID NO: 571)
DVQMTQSPSSLSASVGERVTLTCRASQGIYSSLAWYQQKPGKAPKLLLYGTSQLERGVPSRFSGSGSGTDYTLTI
SSLQPEDSATYYCQQHYNLPITFGQGTRLEIK

>82-22_LC (SEQ ID NO: 573)
QSPSSLSASVGDRVTITCRASQGISNYLAWYQQKPGKVPKLLIYAASTLQSGVPSRFSGSGSGTDFTLTISSLQP
EDVATYYCQKYNSAPLTFGGGTKLEIK

>82-23_LC (SEQ ID NO: 574)
QSPSTLSASVGDRVTITCRASQSISSWLAWYQQKPGKAPKLLIYKASSLESGVPSRFSGSGSGTEFTLTISSLQP
DDFATYYCQQYNSYLTFGGGTKVDIK

>B2-24_LC (SEQ ID NO: 575)
QSVLTQPPSASGTPGQRVTISCSGSSSNIGSNYVYWYQQLPGTAPKLLIYRNNQRPSGVPDRFSGSKSGTSASLA
ISGLRSEDEADYYCAAWDDSLSGWVFGGGTKVTVL

>82-25_LC (SEQ ID NO: 576)
SYELTQPPSVSVAPGQTARITCGGNNIGSKSVHWYQQKPGQAPVLVVYDDSDRPSGIPERFSGSNSGNTATLTIS
RVEAGDEADYYCQVWDSSSDHWVFGGGTKLTVL

TABLE 7-continued

Amino acid sequences of LILRB2 antibody light chains (LC)

```
>82-26_LC (SEQ ID NO: 577)
QSPSSLSASVGDRVTITCRASQSISNFVNWYQQKPGEVPKLLIYGASSLQSGVPSRFSGSGSGTDFTLTISSLQP
EDFATYYCQQGYSVPLTFGGGTTVDIK

>B2-27_LC (SEQ ID NO: 578)
QPVLTQPASVSGSPGQSITISCTGTSSDVGGYNYVSWYQQHPGKAPKLMIYDVSNRPSGVSNRFSGSKSGNSASL
TISGLQAEDEADYYCSSYTSSSTPYVFGTGTKVTVL

>82-30_LC (SEQ ID NO: 579)
QSPSSLSASVGDRVTITCRASQSIRTYLNWYQQKPGKDPELLIYAATSLQSGVPSRFTGSGSGTDFTLTISSLQP
EDFATYYCQQSYSAPVFTFGQGTKLEIK

>HCB2-1c_LC (SEQ ID NO: 580)
AIQMTQSPSSLSASVGDRVSITCRASQSISSFLNWYQQRPGKAPELLIYGASSLQSGVPSRFSGSGSGTDFTLTI
SSLQPEDFATYYCQQSYSIPITFGQGTQLEIK

>HCB2-1d_LC (SEQ ID NO: 581)
DVQMTQSPSSLSASVGDRVSITCKASQDVSIAVAWYQQKPGKAPKLLIYSASYRYTGVPDRFSGSGSGTDFTLTI
SSLQPEDFAVYYCQQHYITPLTFGAGTKLEIK

>HCB2-2_LC (SEQ ID NO: 582)
DVQMTQSPSSLSASVGDRVSITCRASQSISSFLNWYQQRPGKAPELLIYGASSLQSGVPSRFSGSGSGTDFTLTI
SSLQPEDFATYYCQQSYSIPITFGQGTRLEIK

>HCB2-4_LC (SEQ ID NO: 583)
NIQMTQSPSSLSASVGDRVTITCRASQSISSYLNWYQQKPGKAPKLLIYAASSLQSGVPSRFSGSGSGTDFTLTI
SSLQPEDFATYYCQQSYSTPPTFGGGTTVEIK

>HCB2-5_LC (SEQ ID NO: 584)
AIQMTQSPSSVSASVGDRVTITCRASQGIGSWLAWYQQKPGKAPKLLISVASSLQSGVPSRFSGSGSGTDFTLTI
SSLQPEDFATYYCQQANSFPLTFGGGTTVEIK

>HCB2-10_LC (SEQ ID NO: 585)
QPPSVSAAPRQRVTISCSGSSSNIGDNSVNWYQQLPGKAPKLLIYLDDLLPSGVSGRFSGSKSGTSASLVISGLQ
SEDEADYYCATWDDSLNGVVFGGGTKVTVL

>HCB2-13_LC (SEQ ID NO: 586)
DVVMTQSPSSLSVSAGEKVTMSCKSSQSLLNSGNQKTYLAWYQQKPGQPPKLLIYGASTRESGVPDRFTGSGSGT
DFTLTISSVQAEDLAVYYCQNDHSYPFTFGSGTKVEIKRTVAA

>HCB2-14_LC (SEQ ID NO: 587)
NIQMTQSPSSLSASVGDRVTITCRASQSISSYLNWYQQKPGKAPKLLIYAASSLQSGVPSRFSGSGSGTDFTLTI
SSLQPEDFATYYCQQSYSTPYTFGQGTKLEIK

>HCB2-15_LC (SEQ ID NO: 588)
QPPSVSGAPGQRVTISCAGSSSNIGAGYGVHWYQHLPGTAPKLLIYGDNNRPSGVPYRFSGSKSGTSASLAITGL
QAEDEADYFCQSYDSSLGVGVFGGGTKVTVL

>HCB2-17_LC (SEQ ID NO: 589)
AIQLTQSPSSLSASVGDRVTITCRASQSISSYLNWYQQKPGKAPKLLIYAASSLQSGVPSRFSGSGSGTDFTLTI
SSLQPEDFATYYCQQSYSTPLTFGGGTKLEIK

>HCB2-18_LC (SEQ ID NO: 590)
DIVMTQSPSSLSASVGDRVTITCRASQSISSYLNWYQQKPGKAPKLLIYAASSLQSGVPSRFSGSGSGTDFTLTI
SSLQPEDFATYYCQQSYSTPFTFGPGTKLEIK

>HCB2-24_LC (SEQ ID NO: 591)
DVQMTQSPSSLSASVGDRVTITCRASQSISSYLNWYQQKPGKAPKLLIYAASSLQSGVPSRFSGSGSGTDFTLTI
SSLQPEDFATYYCQQSYSTPLTFGQGTKLEIK

>HCB2-27_LC (SEQ ID NO: 592)
NIQMTQSPSSLSASVGDRVTITCRASQSISSYLNWYQQKPGKAPKLLIYAASSLQSGVPSRFSGSGSGTDFTLTI
SSLQPEDFATYYCQQSYSTPRTFGQGTTVEIK
```

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

101                                                             102

REFERENCES

The following references, to the extent that they provide exemplary procedural or other details supplementary to those set forth herein, are specifically incorporated herein by reference.

Swerdlow, S., Campo, E., Harris, N. L., Jaffe, E. S., Pileri, S. A., Stein, H., Thiele, J., Arber, D., Hasserjian, R., and Le Beau, M. (2017). WHO classification of tumors of haematopoietic and lymphoid tissues (WHO).

Schuler, E., Schroeder, M., Neukirchen, J., Strupp, C., Xicoy, B., Kundgen, A., Hildebrandt, B., Haas, R., Gattermann, N., and Germing, U. (2014). Refined medullary blast and white blood cell count based classification of chronic myelomonocytic leukemias. Leuk Res 38, 1413-1419.

What is claimed is:

1. An isolated monoclonal antibody or an antigen-binding fragment thereof that binds to LILRB2 comprising a heavy chain (HC) variable region (VH) and a light chain (LC) variable region (VL) comprising heavy chain complementarity determining regions 1-3 (HCDR1-3) and light chain complementarity determining regions 1-3 (LCDR1-3) as set out below:

HCDR1 comprising SEQ ID NO: 97,
HCDR2 comprising SEQ ID NO: 98,
HCDR3 comprising SEQ ID NO: 99,
LCDR1 comprising SEQ ID NO: 100,
LCDR2 comprising SEQ ID NO: 101, and
LCDR3 comprising SEQ ID NO: 102.

2. The isolated monoclonal antibody or an antigen binding fragment thereof of claim 1, wherein the isolated monoclonal antibody is a murine, a rodent, a rabbit, or a chimeric antibody.

3. The isolated monoclonal antibody or an antigen-binding fragment thereof of claim 1, wherein the antigen-binding fragment is a recombinant (single chain fragment variable (ScFv) antibody, Fab fragment, F(ab')2 fragment, or Fv fragment.

4. The isolated monoclonal antibody or an antigen binding fragment thereof of claim 1, wherein the isolated monoclonal antibody is a humanized antibody.

5. The isolated monoclonal antibody or an antigen-binding fragment thereof of claim 1, wherein the VH and VL chains have amino acid sequences at least 90% or 95% identical to SEQ ID NO: 498 and SEQ ID NO: 572, respectively.

6. The isolated monoclonal antibody or an antigen-binding fragment thereof of claim 1, wherein the VH and VL chains are encoded by nucleic acid sequences at least 80% or 90% identical to SEQ ID NO: 461 and SEQ ID NO: 535, respectively.

7. The isolated monoclonal antibody or an antigen-binding fragment thereof of claim 5, wherein the VH and VL chains have amino acid sequences identical to SEQ ID NO: 498 and SEQ ID NO: 572, respectively.

8. The isolated monoclonal antibody or an antigen binding fragment thereof of claim 5, wherein the VH and VL chains are encoded by nucleic acid sequences identical to SEQ ID NO: 461 and SEQ ID NO: 535, respectively.

9. The isolated monoclonal antibody or an antigen binding fragment thereof of claim 1, wherein the antibody is a chimeric antibody.

10. A pharmaceutical composition comprising the isolated monoclonal antibody or an antigen-binding fragment thereof according to claim 1, and a pharmaceutically acceptable carrier.

11. An isolated nucleic acid that encodes the isolated monoclonal antibody according to claim 1.

12. A vector comprising the isolated nucleic acid of claim 11.

13. A host cell comprising the vector of claim 12.

14. The host cell of claim 13, wherein the host cell is a mammalian cell.

15. The host cell of claim 13, wherein the host cell is a CHO cell.

16. An engineered cell encoding and/or producing the isolated monoclonal antibody according to claim 1.

17. A process of producing an antibody, comprising culturing the host cell of claim 13 under conditions suitable for expressing the antibody, and recovering the antibody.

18. A chimeric antigen receptor (CAR) protein comprising an antigen-binding fragment according to claim 1.

19. An isolated nucleic acid that encodes a CAR protein of claim 18.

20. A vector comprising the isolated nucleic acid of claim 19.

21. An engineered cell comprising the isolated nucleic acid of claim 19.

22. The engineered cell of claim 21, wherein the cell is a T cell, NK cell, or macrophage.

23. A method of treating or ameliorating the effect of an LILRB2-expressing cancer in a subject, the method comprising administering to the subject a therapeutically effective amount of the antibody or an antigen-binding fragment thereof according to claim 1.

24. A method of detecting an LILRB2-expressing cancer cell or an LILRB2-expressing cancer stem cell in a sample or subject comprising:

(a) contacting a subject or a sample from the subject with the antibody or an antigen-binding fragment thereof according to claim 1; and (b) detecting binding of said antibody to a cancer cell or cancer stem cell in said subject or sample.

25. A method for enhancing T cell activation in a subject, the method comprising administering to the subject the antibody or an antigen-binding fragment thereof according to claim 1.

26. A method for modulating M2a macrophage phenotype in a subject, the method comprising administering to the subject the antibody or an antigen-binding fragment thereof according to claim 1.

* * * * *